United States Patent [19]

Barnette et al.

[11] Patent Number: 4,789,465

[45] Date of Patent: Dec. 6, 1988

[54] HERBICIDAL PYRIDINE N-OXIDE SULFONYLUREAS

[75] Inventors: William E. Barnette, West Chester; Thomas R. Dean, Wilmington; Wallace C. Petersen, Hockessin; Barry A. Wexler, Wilmington, all of Del.

[73] Assignee: E. I. Du Pont de Nemours and Company, Wilmington, Del.

[21] Appl. No.: 91,497

[22] Filed: Aug. 31, 1987

Related U.S. Application Data

[63] Continuation of Ser. No. 929,980, Nov. 12, 1986, abandoned.

[51] Int. Cl.$^4$ ................. C07D 401/12; C07D 401/14; A01N 43/54
[52] U.S. Cl. ........................................... 71/90; 71/92; 544/320; 544/321; 544/331; 544/296; 544/324
[58] Field of Search ............... 544/320, 321, 331, 296, 544/332, 324, 323; 71/92, 90

[56] References Cited

U.S. PATENT DOCUMENTS

| | | | |
|---|---|---|---|
| 4,339,267 | 7/1982 | Levitt | 71/92 |
| 4,342,587 | 8/1982 | Levitt | 71/92 |
| 4,421,550 | 12/1983 | Selby et al. | 71/92 |
| 4,425,155 | 1/1984 | Dumas | 71/93 |
| 4,435,206 | 3/1984 | Levitt | 71/92 |
| 4,456,469 | 6/1984 | Adams, Jr. | 71/93 |
| 4,487,626 | 12/1984 | Zimmerman | 71/90 |
| 4,496,392 | 1/1985 | Levitt | 71/93 |
| 4,579,583 | 4/1986 | Fory et al. | 71/92 |

FOREIGN PATENT DOCUMENTS

| | | |
|---|---|---|
| 13480 | 7/1980 | European Pat. Off. |
| 84224 | 7/1983 | European Pat. Off. |
| 125864 | 11/1984 | European Pat. Off. |
| 155767 | 9/1985 | European Pat. Off. |
| 161905 | 11/1985 | European Pat. Off. |
| 164269 | 12/1985 | European Pat. Off. |
| 171286 | 2/1986 | European Pat. Off. |
| 187489 | 7/1986 | European Pat. Off. |
| 201345 | 11/1986 | European Pat. Off. |
| 870436 | 7/1987 | South Africa |

*Primary Examiner*—John M. Ford

[57] ABSTRACT

This invention relates to pyridine N-oxide sulfonylurea herbicides, agriculturally suitable compositions containing them and their method-of-use as preemergent and/or postemergent herbicides or plant growth regulants.

25 Claims, No Drawings

HERBICIDAL PYRIDINE N-OXIDE SULFONYLUREAS

RELATED APPLICATION

This application is a continuation-in-part of copending application U.S. Ser. No. 929,980, filed Nov. 12, 1986, abandoned.

BACKGROUND OF THE INVENTION

EP-A-No. 13,480 discloses herbicidal sulfonamides of the formula

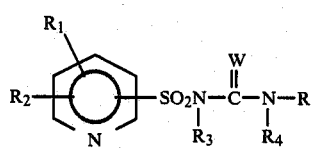

wherein
$R_1$ is H, Cl, Br, F, $C_1$-$C_4$ alkyl, $C_1$-$C_4$ alkoxy, $C_1$-$C_4$ alkylthio, $NO_2$ or $CO_2R_5$.

U.S. Pat. No. 4,339,267 discloses herbicidal sulfonamides of the formula

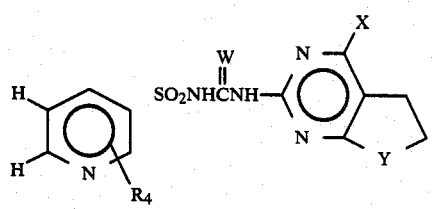

wherein
$R_4$ is H, Cl, Br, F, $C_1$-$C_4$ alkyl, $C_1$-$C_4$ alkoxy, $NO_2$, $CO_2R_6$ or $SR_{13}$.

U.S. Pat. No. 4,342,587 discloses herbicidal sulfonamides of the formula

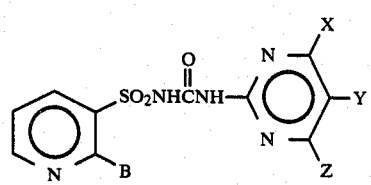

wherein
B is Cl or Br.

U.S. Pat. No. 4,456,469 discloses herbicidal sulfonamides of the formula

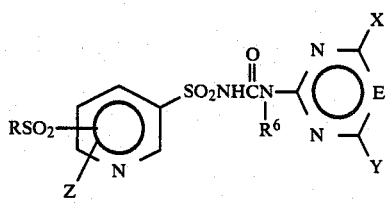

wherein
R is $C_1$-$C_6$ alkyl, $C_3$-$C_6$ alkenyl, $C_2$-$C_4$ alkoxyalkyl, $C_5$-$C_6$ cycloalkyl, R'OCH$_2$CH$_2$OCH$_2$, R'OCH$_2$CH$_2$OCH$_2$CH$_2$,

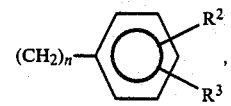

$CF_3$, $CF_3CH_2$, HGLCCF$_2$ or HCF$_2$; and
Z is H, F, Cl, Br, $CH_3$, $OCH_3$ or $SCH_3$.

U.S. Pat. No. 4,487,626 discloses herbicidal sulfonamides of the formula

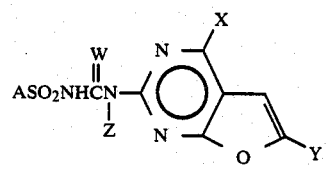

wherein
A is

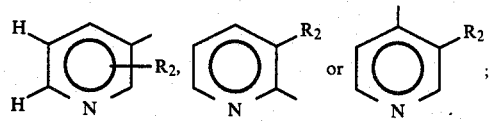

and
$R_2$ is H, F, Cl, Br, $C_1$-$C_4$ alkyl, $C_1$-$C_4$ alkoxy, $NO_2$, $CO_2R_{15}$, $S(O)_mR_{16}$, $SO_2NR_{18}R_{19}$ or $SO_2N(OCH_3)CH_3$.

U.S. Pat. No. 4,421,550 discloses herbicidal sulfonamides of the formula

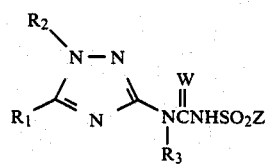

wherein
Z is

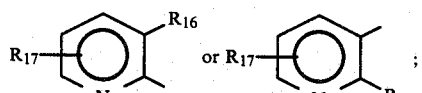

and
$R_{16}$ is H, $C_1$-$C_4$ alkyl, $C_1$-$C_4$ alkoxy, F, Cl, Br, $CF_3$, $CO_2R_{20}$, $SO_2NR_{10}R_{11}$, $SO_2N(OCH_3)CH_3$ or $S(O)_nR_{13}$.

U.S. Pat. No. 4,496,392 discloses herbicidal sulfonamides of the formula

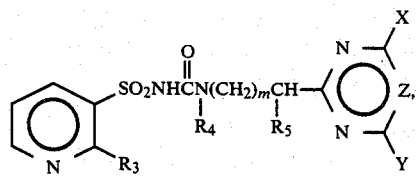

wherein $R_3$ is Cl, $SO_2CH_3$ or $SO_2N(CH_3)_2$.

EP-A-No. 84,224 discloses herbicidal sulfonamides of the formula

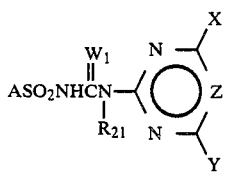

wherein
A is

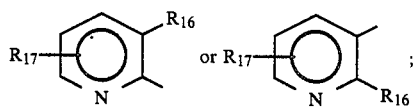

and
$R_{16}$ is H, $C_1$-$C_4$ alkyl, $C_1$-$C_4$ alkoxy, F, Cl, Br, $CF_3$, $CO_2R_9$, $SO_2NR_{10}R_{11}$, $SO_2N(OCH_3)CH_3$ or $S(O)_nR_{13}$.

EP-A-No. 125,846 discloses herbicidal sulfonamides of the formula

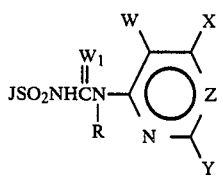

wherein
J is

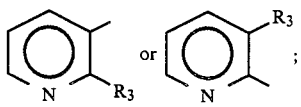

and
R is Cl, $SO_2CH_3$, $SO_2N(CH_3)_2$, $OCH_3$, $NO_2$ or $N(CH_3)_2$.

EP-A-No. 155,767 discloses herbicidal sulfonamides of the formula

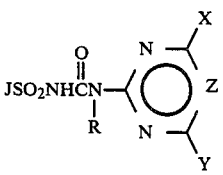

wherein
J is

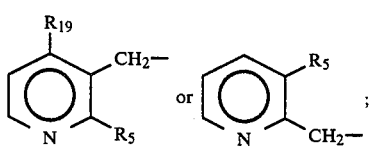

and
$R_5$ is H, $CH_3$, Cl, Br, $CO_2R_{15}$, $C(O)NR_{16}R_{17}$, $SO_2NR_{16}R_{17}$, $SO_2N(OCH_3)CH_3$, $SO_2R_{18}$ or $NO_2$.

EP-A-No. 161,905 discloses herbicidal sulfonamides of the formula

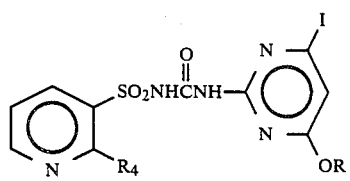

wherein
$R_4$ is $CH_3$, $CH_2CH_3$, $OCH_3$, $OCH_2CH_3$, F, Cl, Br, $SO_2NR_{16}R_{17}$, $SO_2N(OCH_3)CH_3$, $S(O)_nR_{19}$, $C_3$-$C_4$ alkenyloxy or $C_3$-$C_4$ alkynyloxy.

EP-A-No. 164,269 discloses herbicidal sulfonamides of the formula

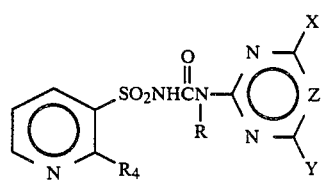

wherein
$R_4$ is $CH_3$, $CH_2CH_3$, $OCH_3$, $OCH_2CH_3$, F, Cl, Br, $SO_2NR_{11}R_{12}$, $SO_2N(OCH_3)CH_3$ or $S(O)_nR_{13}$.

EP-A-No. 171,286 discloses herbicidal sulfonamides of the formula

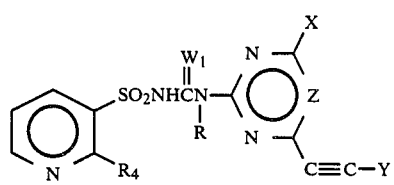

wherein
$R_4$ is $CH_3$, $CH_2CH_3$, $OCH_3$, $OCH_2CH_3$, F, Cl, Br, $SO_2NR_{18}R_{19}$, $SO_2N(OCH_3)CH_3$, $S(O)_nR_{21}$, $C_3$-$C_4$ alkenyloxy, $CH_2OCH_3$ or $CH_2OCH_2CH_3$.

EP-A-No. 187,489 discloses herbicidal sulfonamides of the formula

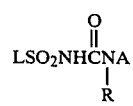

wherein
L is

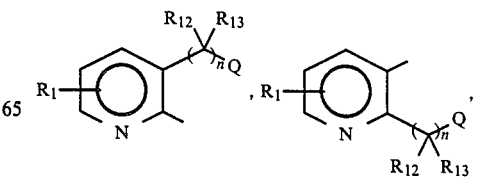

-continued

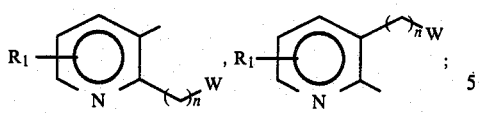

Q is an optionally substituted 3- or 4-membered ring; and
W is substituted alkenyl or alkynyl.

SUMMARY OF THE INVENTION

This application pertains to novel compounds of Formula I, agriculturally suitable compositions containing them and their method-of-use as preemergent and/or postemergent herbicides or plant growth regulants.

wherein
J is

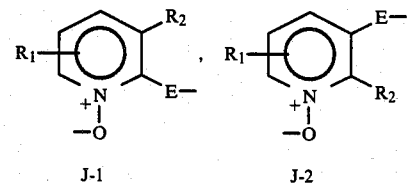

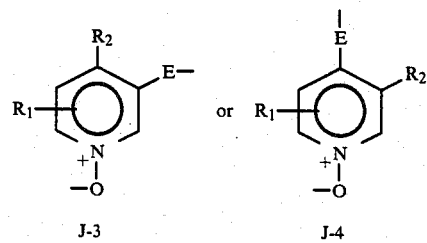

wherein
R is H or $CH_3$;
E is a single bond or $CH_2$;
W is O, S or $NR_x$;
$R_x$ is H, $C_1$–$C_3$ alkyl or $C_1$–$C_3$ alkoxy;
$R_1$ is H, F, Cl, Br, $C_1$–$C_3$ alkyl, $C_1$–$C_3$ haloalkyl, $C_1$–$C_3$ alkoxy, $C_1$–$C_3$ haloalkoxy or $C_1$–$C_3$ thioalkyl;
$R_2$ is H, Cl, Br, F, $C_1$–$C_4$ alkyl, $C_1$–$C_4$ haloalkyl, cyclopropyl optionally substituted by 1–4 halogen, cyclobutyl optionally substituted by 1–4 halogen, $C_2$–$C_4$ alkenyl optionally substituted by halogen, $C_2$–$C_4$ alkynyl optionally substituted by halogen, $C_1$–$C_4$ alkoxy, $C_1$–$C_4$ haloalkoxy, $C_3$–$C_4$ alkenyloxy, $C_3$–$C_4$ alkynyloxy, $NO_2$, $CO_2R_3$, $NR_4R_5$, $S(O)_nR_6$, $SO_2NR_7R_8$, $C(O)NR_9R_{10}$,

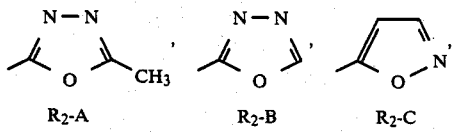

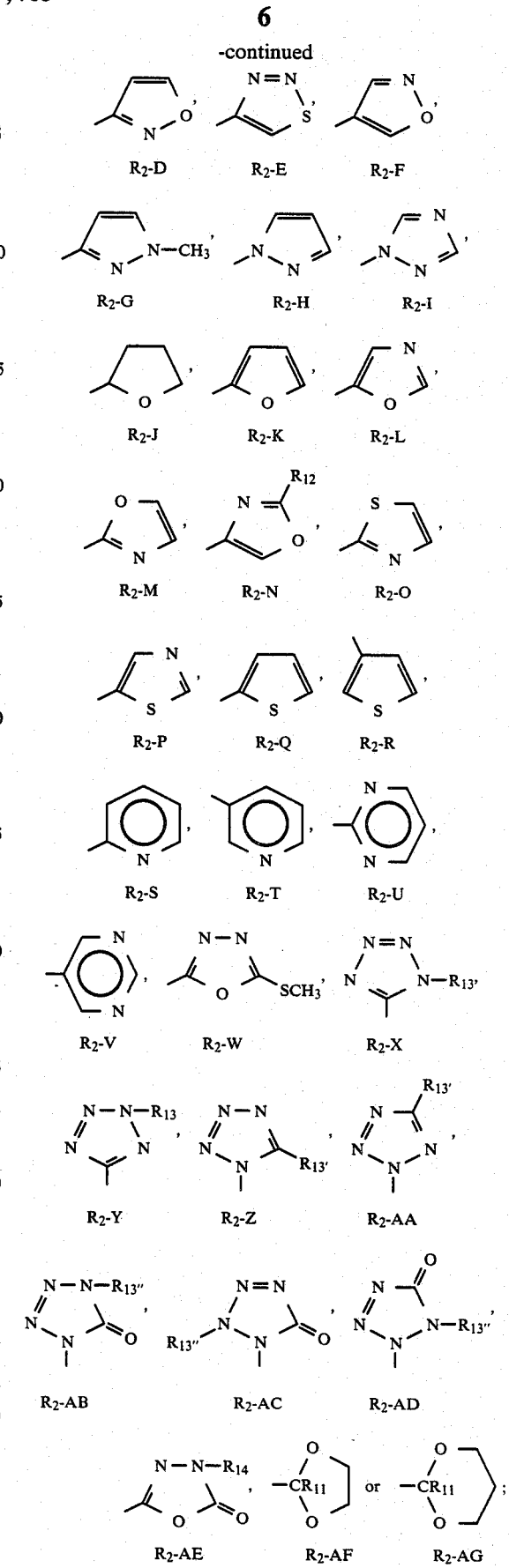

n is 0, 1 or 2;

$R_3$ is $C_1-C_3$ alkyl, $C_2-C_3$ haloalkyl, $C_1-C_3$ alkoxy, $C_3-C_4$ alkenyl, $CH_2(C_3-C_5$ cycloalkyl) or $C_3-C_4$ alkynyl;

$R_4$ is H or $C_1-C_2$ alkyl;

$R_5$ is $C_1-C_2$ alkyl;

$R_6$ is $C_1-C_4$ alkyl, $C_3-C_4$ alkenyl, $C_2-C_4$ alkoxyalkyl or $C_1-C_3$ haloalkyl;

$R_7$ is H or $C_1-C_2$ alkyl;

$R_8$ is $C_1-C_2$ alkyl or $C_1-C_2$ alkoxy;

$R_9$ is H or $C_1-C_3$ alkyl;

$R_{10}$ is $C_1-C_3$ alkyl;

$R_{11}$ is H or $CH_3$;

$R_{12}$ is H or $CH_3$;

$R_{13}$ is H, $C_1-C_3$ alkyl, allyl, $C_1-C_3$ haloalkyl or $C_1-C_3$ alkyl substituted with $C_1-C_2$ alkoxy;

$R_{13}'$ is H, $C_1-C_3$ alkyl, $C_1-C_3$ haloalkyl, allyl, $C_1-C_2$ alkoxy, $C_1-C_2$ haloalkoxy or $C_1-C_2$ alkylthio;

$R_{13}''$ is H, $C_1-C_3$ alkyl, allyl or $C_1-C_3$ haloalkyl;

$R_{14}$ is $C_1-C_3$ alkyl, $CH_2OCH_3$ or $CH_2CN$;

A is

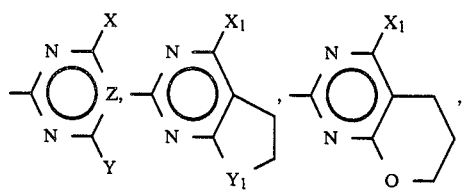

A-1    A-2    A-3

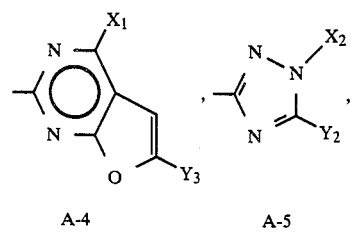

A-4    A-5

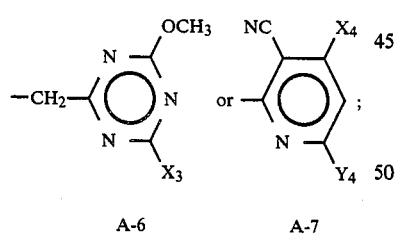

A-6    A-7

X is H, $C_1-C_4$ alkyl, $C_1-C_4$ alkoxy, $C_1-C_4$ haloalkoxy, $C_1-C_4$ haloalkyl, $C_1-C_4$ haloalkylthio, $C_1-C_4$ alkylthio, halogen, $C_2-C_5$ alkoxyalkyl, $C_2-C_5$ alkoxyalkoxy, amino, $C_1-C_3$ alkylamino or di($C_1-C_3$ alkyl)amino;

Y is H, $C_1-C_4$ alkyl, $C_1-C_4$ alkoxy, $C_1-C_4$ haloalkoxy, $C_1-C_4$ haloalkylthio, $C_1-C_4$ alkylthio, $C_2-C_5$ alkoxyalkyl, $C_2-C_5$ alkoxyalkoxy, amino, $C_1-C_3$ alkylamino, di($C_1-C_3$ alkyl)amino, $C_3-C_4$ alkenyloxy, $C_3-C_4$ alkynyloxy, $C_2-C_5$ alkylthioalkyl, $C_2-C_5$ alkylsulfinylalkyl, $C_2-C_5$ alkylsulfonylalkyl, $C_1-C_4$ haloalkyl, $C_2-C_4$ alkynyl, $C_3-C_5$ cycloalkyl, azido, cyano,

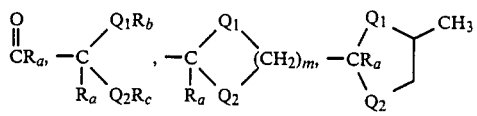

or $N(OCH_3)CH_3$;

m is 2 or 3;

$Q_1$ and $Q_2$ are independently O or S;

$R_a$ is H or $C_1-C_3$ alkyl;

$R_b$ and $R_c$ are independently $C_1-C_3$ alkyl;

Z is CH, N, $CCH_3$, $CC_2H_5$, CCl or CBr;

$Y_1$ is O or $CH_2$;

$X_1$ is $CH_3$, $OCH_3$, $OC_2H_5$ or $OCF_2H$;

$X_2$ is $CH_3$, $C_2H_5$ or $CH_2CF_3$;

$Y_2$ is $OCH_3$, $OC_2H_5$, $SCH_3$, $SC_2H_5$, $CH_3$ or $CH_2CH_3$;

$X_3$ is $CH_3$ or $OCH_3$;

$Y_3$ is H or $CH_3$;

$X_4$ is $CH_3$, $OCH_3$, $OC_2H_5$, $CH_2OCH_3$ or Cl;

$Y_4$ is $CH_3$, $OCH_3$, $OC_2H_5$ or Cl;

and their agriculturally suitable salts; provided that (1) when X is halogen, then Z is CH and Y is $OCH_3$, $OC_2H_5$, $NH_2$, $NHCH_3$, $N(CH_3)_2$, $OCF_2H$, $OCF_2Br$ or $N(OCH_3)CH_3$;

(2) when X or Y is $C_1$ haloalkoxy, then Z is CH;

(3) when W is S, then R is H, E is a single bond, A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

;

(4) when the total number of carbon atoms of X and Y is greater than four, then the combined number of carbons of $R_1$ and $R_2$ is less than or equal to six; and (5) $X_4$ and $Y_4$ are not simultaneously Cl.

In the above definitions, the term "alkyl", used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

The term "halogen", either alone or in compound words such as "haloalkyl", denotes fluorine, chlorine, bromine or iodine. Further, when used in compound words such as "haloalkyl" said alkyl may be monohalogenated or fully substituted with halogen atoms, which may be the same or different. Examples of haloalkyl include $CH_2CH_2F$, $CF_2CF_3$ and $CH_2CHFCl$.

Similarly, the terms haloalkoxy and haloalkylthio would include groups which are mono- or poly-substituted with halogen atoms, which may be the same or different.

The total number of carbon atoms in a substituent group is indicated by the $C_i$–$C_j$ prefix where i and j are numbers from 1 to 5. For example, $C_2$–$C_4$ alkenyl would designate ethenyl through butenyl.

Preferred for reasons of increased ease of synthesis and/or greater herbicidal efficacy are:

1. Compounds of Formula I where
   X is $C_1$–$C_2$ alkyl, $C_1$–$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
   Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $C(O)R_a$, $$-\underset{R_a}{\overset{Q_1R_b}{\underset{|}{\overset{|}{C}}}}-Q_2R_c \;,\; -\underset{R_a}{\overset{Q_1}{\underset{|}{\overset{|}{C}}}}\underset{Q_2}{\overset{}{\diagdown\diagup}}(CH_2)_m, \; CR_a \underset{Q_2}{\overset{Q_1}{\diagup\diagdown}} CH_3 \;,$$

$OCF_2H$, $SCF_2H$, $OCF_2Br$, cyclopropyl, $C\equiv CH$ or $C\equiv CCH_3$;
   Z is CH or N; and
   $R_a$ is H or $CH_3$.
2. Compounds of Preferred 1 where
   E is a single bond;
   W is O; and
   $R_1$ is H, F, Cl, Br, $CH_3$, $C_1$ haloalkyl or $OCH_3$.
3. Compounds of Preferred 1 where
   E is $CH_2$;
   W is O; and
   $R_1$ is H, F, Cl, Br, $CH_3$ or $OCH_3$.
4. Compounds of Preferred 2 where
   $R_2$ is H, Cl, Br, F, $C_1$–$C_2$ alkyl, $C_1$–$C_2$ haloalkyl, cyclopropyl, $C_1$–$C_2$ alkoxy, $C_1$–$C_2$ haloalkoxy, CF=CFCl, CF=CFCF$_3$, $NO_2$, $CO_2R_3$, $NR_4R_5$, $S(O)_nR_6$, $SO_2NR_7R_8$, $SO_2N(OCH_3)CH_3$, $C(O)NR_9R_{10}$, $R_2$-A, $R_2$-B, $R_2$-E, $R_2$-J, $R_2$-N, $R_2$-Q, $R_2$-R, $R_2$-X, $R_2$-Y, $R_2$-AB, $R_2$-AC or $R_2$-AD;
   $R_3$ is $CH_3$, $CH_2CH_3$, $CH_2CH_2OCH_3$ or $CH_2CH_2Cl$;
   $R_4$ is H or $CH_3$;
   $R_6$ is $C_1$–$C_3$ alkyl, $C_1$–$C_3$ haloalkyl or allyl;
   $R_7$ is H or $CH_3$;
   $R_8$ is $C_1$–$C_2$ alkyl
   $R_9$ is H or $CH_3$;
   $R_{10}$ is $CH_3$ or $CH_2CH_3$;
   $R_{13}$ is H, $CH_3$, $CH_2CH_3$ or $CH_2CH_2OCH_3$; and
   $R_{13}''$ is H, $CH_3$ or $CH_2CH_3$.
5. Compounds of Preferred 4 where
   X is $CH_3$, $OCH_3$, $OCH_2CH_3$, Cl, $OCF_2H$ or $OCH_2CF_3$;
   Y is $CH_3$, $OCH_3$, $CH_2CH_3$, $CH_2OCH_3$, $NHCH_3$ or $CH(OCH_3)_2$.
6. Compounds of Preferred 5 where
   J is $J_1$; and
   A is A-1.
7. Compounds of Preferred 5 where
   J is $J_2$; and
   A is A-1.
8. Compounds of Preferred 5 where
   J is $J_3$; and
   A is A-1.
9. Compounds of Preferred 5 where
   J is $J_4$; and
   A is A-1.

Specifically preferred for reasons of greatest ease of synthesis and/or greatest herbicidal efficacy are:

N[(4,6-dimethoxypyrimidin-2-yl)aminocarbonyl]-3-methyl-2-pyridinesulfonamide-1-oxide, m.p. 155°–157° C.; and N[(4-methoxy-6-methyl-1,3,5-triazin-2-yl)aminocarbonyl]-2-pyridinesulfonamide-1-oxide, m.p. 172°–176° C.

DETAILED DESCRIPTION OF THE INVENTION

Synthesis

Compounds of Formula I can be prepared by one or more of the procedures shown in Equations 1, 4, and 5. J, R, and A are as previously defined.

Equation 1

$$JSO_2N=C=W + HNA \xrightarrow{\;\;\;} I$$
$$\hspace{3.2cm} | $$
$$\hspace{3.2cm} R$$
$$\;\;\;II \hspace{1.5cm} III$$

The reaction of Equation 1 is best carried out in an inert aprotic organic solvent such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent, to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

Sulfonyl isocyanates (II, W is O) are known in the art and are prepared from the corresponding sulfonamides (IV) by one of the following two general methods.

Equation 2

$$JSO_2NH_2 \xrightarrow[\;COCl_2,\;cat.\;]{CH_3(CH_2)_3NCO} II,\; W\;is\;O$$

IV

The sulfonamide IV is reacted with an alkyl isocyanate (e.g., n-butyl isocyanate) in a solvent whose boiling point is above 135° C., such as xylene. The reaction can optionally be carried out in the presence of a catalytic amount of 1,4-diaza[2.2.2]bicyclooctane (DABCO). The reaction mixture is heated to 135°–140° C. and held at that temperature for 5–60 minutes, after which phosgene is slowly added at such a rate that the temperature remains between 133 and 135° C. When the consumption of phosgene has ceased, the mixture is cooled and filtered to remove insoluble material. Finally, the solvent, alkyl isocyanate, and excess phosgene are evaporated, leaving the sulfonyl isocyanate (II).

If desired, the alkyl isocyanate-sulfonamide adduct can be made and isolated before reaction with the phosgene. In this case the sulfonamide (IV), alkyl isocyanate, and anhydrous base (e.g, $K_2CO_3$) in a polar, aprotic solvent (e.g. acetone, butanone, or acetonitrile) are mixed and heated under reflux for 1 to 6 hours. The reaction mixture is then diluted with water, and the pH is adjusted to about 3 with acid (e.g. HCl, H$_2$SO$_4$). The adduct is filtered out and dried, and then reacted with phosgene as described above. This procedure modification is especially useful when sulfonamide (IV) is high melting and has low solubility in the phosgenation solvent.

Sulfonyl isocyanates (II, W is O) can also be prepared by the following method.

Equation 3

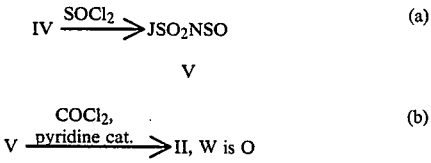

The sulfonamide (IV) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (V) (Equation 3a).

The thionyl chloride is evaporated and the residue is treated with an inert solvent (e.g. toluene) containing at least one equivalent (typically 2-3 equivalents) of phosgene. A catalytic amount of pyridine (typically 0.1 equivalent) is added, and the mixture is heated to about 60°–140° C., with 80°–100° C. preferred. Conversion to the isocyanate (II, W is O) is usually substantially complete within 15 minutes to 3 hours (Equation 3b). The mixture is then cooled and filtered, and the solvent is evaporated, leaving the sulfonyl isocyanate (II, W is O).

Sulfonyl isothiocyanates (II, W is S) are known in the art and are prepared from the corresponding sulfonamides (IV) by reaction with carbon disulfide and potassium hydroxide followed by treatment of the resulting dipotassium salt VI with phosgene. Such a procedure is described in Arch. Pharm. 299, 174 (1966).

Many of the compounds of Formula I can be prepared by the procedure shown in Equation 4.

Equation 4

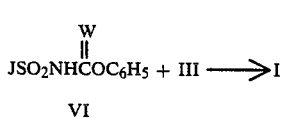

The reaction of Equation 4 is carried out by contacting phenylcarbamates or phenylthiocarbamates of Formula VI with aminoheterocycles of Formula III in an inert organic solvent such as dioxane or tetrahydrofuran at temperatures of about 20°–100° C. for a period of about one-half to twenty-four hours. The product can be isolated by evaporation of the reaction solvent and purified by methods previously described.

Phenylcarbamates and phenylthiocarbamates of Formula VI can be prepared by the methods described, or modifications thereof known to those skilled in the art, in U.S. Pat. No. 4,443,243.

Alternatively, many of the compounds of Formula I can be prepared by the method described in Equation 5.

Equation 5

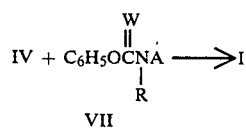

The reaction of Equation 5 can be carried out by contacting equimolar amounts of a sulfonamide of Formula IV with a heterocyclic phenylcarbamate or phenylthiocarbamate of Formula VII in the presence of a base such as 1,8-diazabicyclo[5.4.0]undec-7-ene (DBU), by methods analogous to those described in South African Patent Application 83/0441. The phenylcarbamates and phenylthiocarbamates of Formula VII can be prepared by methods, or modifications thereof known to those skilled in the art, described in South African Patent Application No. 82/5671 and South African Patent Application No. 82/5045.

The sulfonamides IV of this invention may be prepared in a variety of ways, some of which are described in Equations 6 through 13.

For example, pyridine sulfonamides such as 1 may be oxidized directly to the corresponding N-oxide 2, using a variety of oxidants. Some of the oxidants of choice are m-chloroperoxybenzoic acid, CF$_3$CO$_3$H, H$_2$O$_2$, etc. This is outlined in Equation 6.

Equation 6

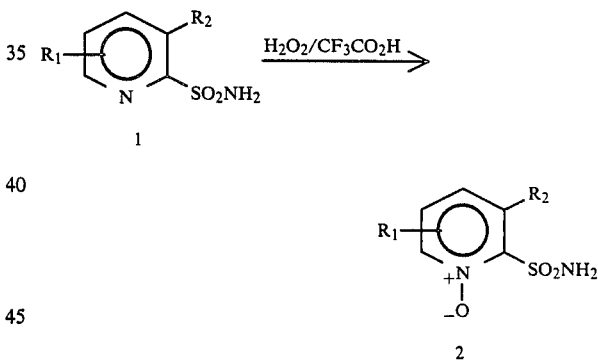

In Equation 6, R$_1$ and R$_2$ are as previously defined, with the exception that R$_2$ cannot be a group which will react with a strong oxidant (i.e., thioalkyl, alkenyl, etc.). In addition, isomers of sulfonamide 2, that is sulfonamides such as 3, 4 and 5 may also be prepared in the same manner as outlined in Equation 6.

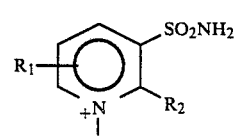

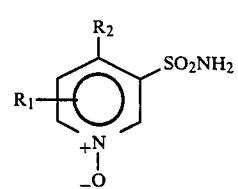

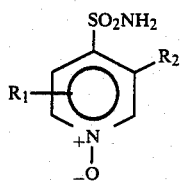

Preparation of pyridine sulfonamides such as 1 (and its isomers) is well known to one skilled in the art. For further details pertaining to the preparation of pyridine sulfonamides see, U.S. Pat No. 4,544,401 (3-pyridine sulfonamides), U.S. Pat. No. 4,435,206 (2-pyridine sulfonamides), U.S. Pat. Nos. 4,456,469, 4,342,587 and EP-A-No. 165,753.

Preparation of sulfonamides such as 2, 3, 4 and 5 may also be accomplished utilizing organo lithium chemistry as outlined in Equations 7 through 10.

Equation 7

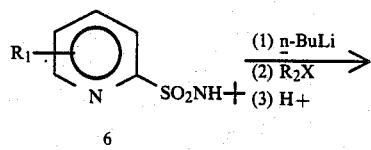

Equation 8

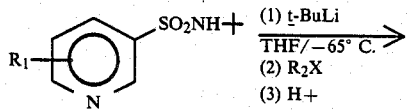

Equation 9

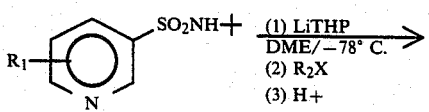

Equation 10

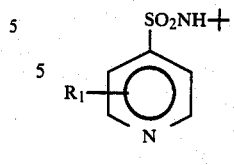

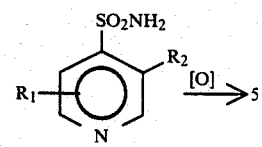

The methodology outlined in Equations 7–10 is applicable to a wide variety of derivatives where $R_1$ and $R_2$ are compatible with organo metallic conditions. For example, sulfonamide 2a where $R_1$ is H and $R_2$ is $CO_2CH_3$ may be prepared as outlined in Equation 11.

Equation 11

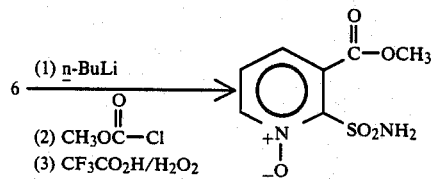

An alternate synthesis of sulfonamides such as 2, (also applicable to other isomers) is to introduce the n-oxide functionality into the pyridine ring at the beginning of the synthetic scheme rather than the end of the synthesis. This is outlined in Equation 12.

Equation 12

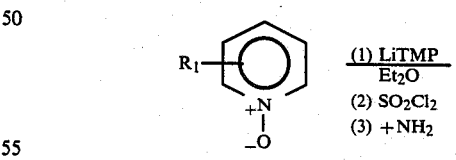

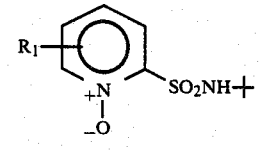

Preparation of sulfonamides such as 2 where $R_2$ is incompatible with reagents such as BuLi or LDA may be carried out in a variety of ways. For example, preparation of sulfonamides 10 and 12 utilizing fluoride 11 is outlined in Equation 13.

Equation 13

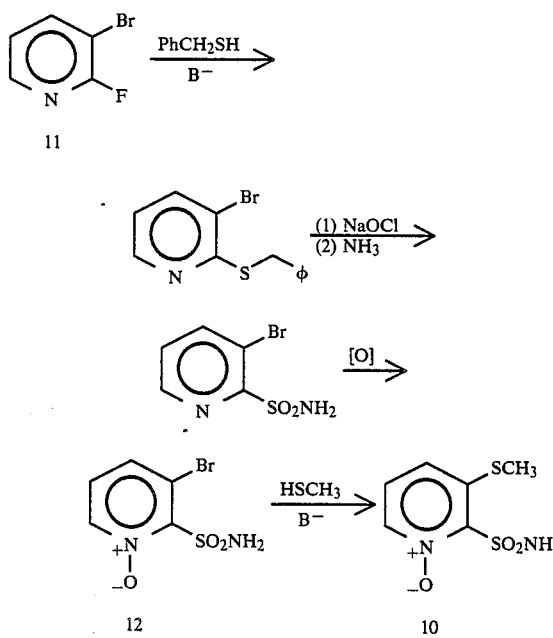

In Equation 13, introduction of the N-oxide functionality may be strategically done at any point of the synthesis. This then allows for the introduction of a functionality in $R_2$ which is sensitive to strong oxidants (i.e., thioalkyl, alkenyl, etc.) as discussed in Equation 6.

For further details pertaining to lithiations of pyridine ring systems see, Epsztarjn et al., *Tetrahedron Lett.*, 4739 (1980); Snieckus et al., *J. Am. Chem. Soc.*, 102, 1457 (1980); Kuraishi et al., *Tet. Lett.*, 2049 (1983); Meyers et al., *J. Org. Chem.*, 47, 2633 (1982); Taylor et al., *J. Org. Chem.*, 48, 4156 (1983) and Breant et al., *Synthesis*, 822 (1983).

For further details pertaining to the oxidation of pyridines to pyridine N-oxides see, Evans et al., *Rec. Trav.*, 78, 408 (1959).

For a general treatment of pyridines and pyridine N-oxides see, Katritzky, A. R., and Rees, C. W., "Comprehensive Heterocyclic Chemistry", Vol. 2, Pergamon Press, Oxford, New York, Part 2A, 1984.

The synthesis of heterocyclic amines such as those represented by Formula III has been reviewed in "The Chemistry of Heterocyclic Compounds," a series published by Interscience Publ., New York and London. Aminopyrimidines are described by D. J. Brown in "The Pyrimidines," Vol. XVI of the series mentioned above which is herein incorporated by reference. The 2-amino-1,3,5-triazines of Formula III, where A is A-1 and Z is N, can be prepared according to methods described by E. M. Smolin and L. Rapaport in "s-Triazines and Derivatives," Vol. XIII.

Pyrimidines of Formula III, where A is A-1 and Y is an acetal or thioacetal substituent, can be prepared by methods taught in European Patent Application No. 84,224 (published July 27, 1983).

Pyrimidines of Formula III, where A is A-1 and Y is cyclopropyl or $OCF_2H$ can be synthesized according to the methods taught in U.S. Pat. No. 4,515,626 and U.S. Pat. No. 4,540,782, respectively.

Compounds of Formula III, where A is A-2 or A-3, can be prepared by procedures disclosed in U.S. Pat. No. 4,339,267.

Compounds of Formula III, where A is A-4, can be prepared by methods taught in U.S. Pat. No. 4,487,626.

Additional references dealing with the synthesis of bicyclic pyrimidines of Formula III, where A is A-2, A-3, or A-4 are Braker, Sheehan, Spitzmiller and Lott, *J. Am. Chem. Soc.*, 69, 3072 (1947); Mitler and Bhattachanya, Quart. *J. Indian Chem. Soc.*, 4, 152 (1927); Shrage and Hitchings, *J. Org. Chem.*, 16, 1153 (1951); Caldwell, Kornfeld and Donnell, *J. Am. Chem. Soc.*, 63, 2188 (1941); and Fissekis, Myles and Brown, *J. Org. Chem.*, 29, 2670 (1964).

Compounds of Formula III, where A is A-5, can be prepared by methods taught in U.S. Pat. No. 4,421,550.

Compounds of Formula III, where A is A-6, can be prepared by methods taught in the U.S. Pat. No. 4,496,392.

Compounds of Formula III, where A is A-7 can be prepared by methods taught in EP-A-No. 125,864.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by simlar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also beeffected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

Preparation of 3-Methyl-2-(phenylmethylthio)pyridine

To a solution of NaH (2.4 g, 99 mmol) in 100 mL of DMF cooled to 0° C. is added benzylmercaptan (12.3 g, 99 mmol). The solution was allowed to warm to room temperature then recooled to 0° C. 2-Fluoro-3-methylpyridine in 10 mL DMF was added dropwise and stirred at room temperature overnight. The solution was diluted with $H_2O$, extracted twice with $Et_2O$, twice with EtOAc, and the combined organics washed twice with saturated $NaHCO_3$, dried and concentrated. The resulting oil was flash chromatographed (10% $Et_2O$/- hexane (v/v)) to yield 16.3 g of the desired product. NMR (200 MHz, CDCl$_3$) δ 2.24 (s, 3H), 4.50 (s, 2H), 6.9 (dd, 1H), 7.2 (m, 5H), 7.4 (d, 1H) and 8.3 (d, 1H).

EXAMPLE 2

Preparation of N-(1,1-Dimethylethyl)-3-methyl-2-pyridinesulfonamide

To a vigorously stirring mixture of 3-methyl-2-(phenylmethylthio)pyridine (25 g, 116 mmol) CH$_2$Cl$_2$ (500 mL) and H$_2$O (260 mL) cooled to 0° C. was added 45 mL concentrated HCl. Chlorox ® (500 mL) was then added dropwise between 0° to −5° C. The reaction was stirred 1 hour at 0° C. and then extracted with CH$_2$Cl$_2$. The organic extracts were cooled to −70° C. and tert-butylamine (50 mL) was added dropwise. The solution was allowed to slowly warm to room temperature, diluted with H$_2$O and extracted with CH$_2$Cl$_2$. The organics were dried and concentrated to an oil. The oil was triturated with Et$_2$O/hexane to afford 10 g of the desired product, m.p. 107°–110° C.; NMR (200 MHz, CDCl$_3$) δ 1.27 (s, 9H), 2.68 (s, 3H), 5.138 (br s, 1H), 7.35 (dd, 1H), 7.62 (d, 1H) and 8.4 (d, 1H).

EXAMPLE 3

Preparation of N-(1,1-Dimethylethyl)-3-methyl-2-pyridinesulfonamide-1-oxide

To a stirring solution of 3-methyl-2-tert-butyl-pyridinesulfonamide (3.2 g, 14.0 mmol) in 100 mL of CH$_2$Cl$_2$ was added m-chloroperoxybenzoic acid (2.8 g, 14.0 mmol). The solution was stirred overnight at room temperature, washed once with brine, twice with saturated NaHCO$_3$, dried and concentrated. The resulting oil was flash chromatographed (25% EtOAc/hexane (v/v)) to yield 3.0 g of the desired product, m.p. 124°–126° C. NMR (200 MHz, CDCl$_3$) δ 1.25 (s, 9H), 2.7 (s, 3H), 7.1 (br s, 1H), 7.26 (m, 2H) and 8.2 (d, 1H).

EXAMPLE 4

Preparation of 3-Methyl-2-pyridinesulfonamide-1-oxide

A mixture of the N-oxide of N-(1,1-dimethylethyl)-3-methyl-2-pyridinesulfonamide (2.5 g, 8.2 mmol) and 50 mL of CF$_3$CO$_2$H were stirred for 6 hours. The CF$_3$CO$_2$H was removed under vacuum and the resulting solids were washed with butyl chloride to afford 1 g of the desired product, m.p. 233°–235° C., (M+ = 188, expected, 188).

EXAMPLE 5

Preparation of N-[(4,6-Dimethylpyrimidin-2-yl)aminocarbonyl]-3-methyl-2-pyridinesulfonamide-1-oxide To a stirring solution of the N-oxide of 3-methyl-2-pyridinesulfonamide (150 mg, 0.79 mmol) and the phenylcarbamate of 4,6-dimethyl-2-aminopyridine (194 mg, 0.79 mmol) in 3 mL of CH$_3$CN was added DBU (121 mg, 0.79 mmol). The solution was stirred for 15 minutes. Three mL of H$_2$O, then 3 mL of 5% HCl was added to the reaction and the resulting solid was collected, m.p. 161°–163° C. NMR (200 MHz, d$_6$-DMSO) δ 2.36 (s, 6H), 2.59 (s, 3H), 6.97 (s, 1H), 7.4 (d, 1H), 7.5 (d, 1H), 8.3 (d, 1H), 10.6 (br s, 1H) and 13.3 (br s, 1H).

EXAMPLE 6

Preparation of 3-Chloro-2-pyridinesulfonamide-1-oxide

To a stirring solution of 3-chloro-2-pyridinesulfonamide (2.5 g, 13.0 mmol) in 35 mL of trifluoroacetic acid was added 30% H$_2$O$_2$ (1.2 g, 35.1 mmol). The solution was concentrated to ~15 mL, diluted with ethyl acetate, washed twice with brine, dried and concentrated. The resulting solid was flash chromatographed with EtOAc to afford the desired product, m.p. 195°–197° C.

EXAMPLE 7

Preparation of 3-Chloro-N-[(4,6-dimethoxypyrimidin-2-yl)aminocarbonyl]-2-pyridinesulfonamide-1-oxide To a stirring solution of the N-oxide of 3-chloro-2-pyridinesulfonamide (85 mg, 0.4 mmol) and the phenyl carbamate of 4,6-dimethoxy-2-aminopyrimidine (114 mg, 0.40 mmol) in acetonitrile was added DBU (62 mg, 0.40 mmol). Addition of H$_2$O followed by 5% HCl caused a precipitate to form which was collected, m.p. 144°–147° C. NMR (200 MHz, d$_6$-DMSO) δ 3.91 (s, 6H), 5.998 (s, 1H), 7.7 (m, 2H), 8.4 (d, 1H), 10.8 (br s, 1H) and 13.1 (br s, 1H); IR (nujol) 1710 (s) cm$^{-1}$; mass spectrum m/e 390 (M+, calc. for C$_{12}$H$_{12}$ClN$_5$O$_6$S 389+1).

EXAMPLE 8

Preparation of 6-methylthio-3-carboxy-2-pyridinesulfonamide-1-oxide methyl ester To a stirring solution of n-butyllithium in 150 ml of tetrahydrofuran cooled to −78° C. was added 6-methylthio-2-pyridine-t-butylsulfonamide-1-oxide (30 g, 10.9 mmol) dropwise. The solution was stirred for one hour at −78° C. followed by dropwise addition of methylchloroformate (5.1 g, 53.4 mmol). The solution was warmed to 0° C. and quenched with brine. The organic layer was separated, dryed and concentrated to an oil. The resulting oil was subjected to MPLC with a 25% EtOAc-hexane (v/v) to afford 710 mg of product. This was then submitted to trifluroacetic acid (25 ml) for 24 hours. Removal of the acid and triteration with BuCl afforded 400 mg of the desired sulfonamide: m.p. 199°–202; NMR (200 MHz, DMSO) δ 2.48 (s, 3H), 3.78 (s, 3H), 7.60 (br s, 2H); mass spectrum m/e 279 (M+, calc. for C$_8$H$_{10}$NO$_5$S$_2$ 278+1).

COMPOUND TABLES

Structure of J Substituent in Tables I–IV

Table I

J is J-1

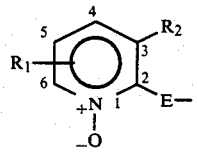

Table II

J is J-2

COMPOUND TABLES-continued

Structure of J Substituent in Tables I–IV

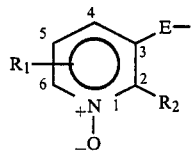

Table III
J is J-3

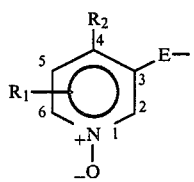

COMPOUND TABLES-continued

Structure of J Substituent in Tables I–IV

Table IV
J is J-4

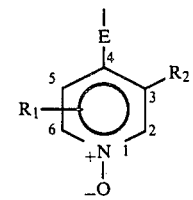

TABLE I

| R | A | E | W | R₁ | R₂ | X | Y | Z | m.p.(°C.) |
|---|---|---|---|----|----|---|---|---|-----------|
| H | A-1 | — | O | H | H | CH₃ | CH₃ | CH | 169–172 |
| H | A-1 | — | O | H | H | CH₃ | OCH₃ | CH | 173–175 |
| H | A-1 | — | O | H | H | OCH₃ | OCH₃ | CH | 179–183 |
| H | A-1 | — | O | H | H | CH₃ | CH₃ | N | 149–166 |
| H | A-1 | — | O | H | H | CH₃ | OCH₃ | N | 172–176 |
| H | A-1 | — | O | H | H | OCH₃ | OCH₃ | N | 167–170 |
| H | A-1 | — | O | H | H | Cl | OCH₃ | CH | |
| H | A-1 | — | O | H | Cl | CH₃ | CH₃ | CH | 147–149 |
| H | A-1 | — | O | H | Cl | CH₃ | OCH₃ | CH | |
| H | A-1 | — | O | H | Cl | OCH₃ | OCH₃ | CH | 144–147 |
| H | A-1 | — | O | H | Cl | CH₃ | CH₃ | N | |
| H | A-1 | — | O | H | Cl | CH₃ | OCH₃ | N | 130–132 |
| H | A-1 | — | O | H | Cl | OCH₃ | OCH₃ | N | |
| H | A-1 | — | O | H | Cl | Cl | OCH₃ | CH | 162–164 |
| H | A-1 | — | O | H | Br | CH₃ | CH₃ | CH | |
| H | A-1 | — | O | H | Br | CH₃ | OCH₃ | CH | |
| H | A-1 | — | O | H | Br | OCH₃ | OCH₃ | CH | |
| H | A-1 | — | O | H | Br | CH₃ | CH₃ | N | |
| H | A-1 | — | O | H | Br | CH₃ | OCH₃ | N | |
| H | A-1 | — | O | H | Br | OCH₃ | OCH₃ | N | |
| H | A-1 | — | O | H | Br | Cl | OCH₃ | CH | |
| H | A-1 | — | O | H | F | CH₃ | CH₃ | CH | |
| H | A-1 | — | O | H | F | CH₃ | OCH₃ | CH | |
| H | A-1 | — | O | H | F | OCH₃ | OCH₃ | CH | |
| H | A-1 | — | O | H | F | CH₃ | CH₃ | N | |
| H | A-1 | — | O | H | F | CH₃ | OCH₃ | N | |
| H | A-1 | — | O | H | F | OCH₃ | OCH₃ | N | |
| H | A-1 | — | O | H | F | Cl | OCH₃ | CH | |
| H | A-1 | — | O | H | CH₃ | CH₃ | CH₃ | CH | 161–163 |
| H | A-1 | — | O | H | CH₃ | CH₃ | OCH₃ | CH | 150–152 |
| H | A-1 | — | O | H | CH₃ | OCH₃ | OCH₃ | CH | 155–157 |
| H | A-1 | — | O | H | CH₃ | CH₃ | CH₃ | N | |
| H | A-1 | — | O | H | CH₃ | CH₃ | OCH₃ | N | 130–132 |
| H | A-1 | — | O | H | CH₃ | OCH₃ | OCH₃ | N | 156–158 |
| H | A-1 | — | O | H | CH₃ | Cl | OCH₃ | CH | 160–162 |
| H | A-1 | — | O | H | CH₂CH₃ | CH₃ | CH₃ | CH | 147–150 |
| H | A-1 | — | O | H | CH₂CH₃ | CH₃ | OCH₃ | CH | 158–160 |
| H | A-1 | — | O | H | CH₂CH₃ | OCH₃ | OCH₃ | CH | 175–178 |
| H | A-1 | — | O | H | CH₂CH₃ | CH₃ | CH₃ | N | |
| H | A-1 | — | O | H | CH₂CH₃ | CH₃ | OCH₃ | N | 179–181 |
| H | A-1 | — | O | H | CH₂CH₃ | OCH₃ | OCH₃ | N | 183–185 |
| H | A-1 | — | O | H | CH₂CH₃ | Cl | OCH₃ | CH | 181–183 |
| H | A-1 | — | O | H | CH(CH₃)₂ | CH₃ | CH₃ | CH | 143–147 |
| H | A-1 | — | O | H | CH(CH₃)₂ | CH₃ | OCH₃ | CH | |
| H | A-1 | — | O | H | CH(CH₃)₂ | OCH₃ | OCH₃ | CH | 189–191 |
| H | A-1 | — | O | H | CH(CH₃)₂ | CH₃ | CH₃ | N | |
| H | A-1 | — | O | H | CH(CH₃)₂ | CH₃ | OCH₃ | N | |
| H | A-1 | — | O | H | CH(CH₃)₂ | OCH₃ | OCH₃ | N | |
| H | A-1 | — | O | H | CH(CH₃)₂ | Cl | OCH₃ | CH | |
| H | A-1 | — | O | H | CH₂CH₂CH₃ | CH₃ | CH₃ | CH | |
| H | A-1 | — | O | H | CH₂CH₂CH₃ | CH₃ | OCH₃ | CH | |
| H | A-1 | — | O | H | CH(CH₃)CH₂CH₃ | OCH₃ | OCH₃ | CH | |
| H | A-1 | — | O | H | CH(CH₃)CH₂CH₃ | CH₃ | CH₃ | N | |
| H | A-1 | — | O | H | CH₂CH(CH₃)₂ | CH₃ | OCH₃ | N | |
| H | A-1 | — | O | H | CH₂CH(CH₃)₂ | OCH₃ | OCH₃ | N | |
| H | A-1 | — | O | H | CH₂CH(CH₃)₂ | Cl | OCH₃ | CH | |

TABLE I-continued

| | | | | | | | | | |
|---|---|---|---|---|---|---|---|---|---|
| H | A-1 | — | O | H | (CH₂)₄CH₃ | OCH₃ | OCH₃ | CH | 178–180 |
| H | A-1 | — | O | H | CH₂Cl | CH₃ | CH₃ | CH | |
| H | A-1 | — | O | H | CH₂Cl | CH₃ | OCH₃ | CH | |
| H | A-1 | — | O | H | CH₂Cl | OCH₃ | OCH₃ | CH | |
| H | A-1 | — | O | H | CH₂Cl | CH₃ | CH₃ | N | |
| H | A-1 | — | O | H | CH₂Br | CH₃ | OCH₃ | N | |
| H | A-1 | — | O | H | CH₂Br | OCH₃ | OCH₃ | N | |
| H | A-1 | — | O | H | CH₂F | Cl | OCH₃ | CH | |
| H | A-1 | — | O | H | CH(Cl)CH₃ | CH₃ | CH₃ | CH | |
| H | A-1 | — | O | H | CH(Cl)CH₃ | CH₃ | OCH₃ | CH | |
| H | A-1 | — | O | H | CH(Cl)CH₃ | OCH₃ | OCH₃ | CH | |
| H | A-1 | — | O | H | CH(Cl)CH₃ | CH₃ | CH₃ | N | |
| H | A-1 | — | O | H | CH(Cl)CH₃ | CH₃ | OCH₃ | N | |
| H | A-1 | — | O | H | CH(Cl)CH₃ | OCH₃ | OCH₃ | N | |
| H | A-1 | — | O | H | CH(Cl)CH₃ | Cl | OCH₃ | CH | |
| H | A-1 | — | O | H | CH(F)CH₃ | CH₃ | CH₃ | CH | |
| H | A-1 | — | O | H | CH(F)CH₃ | CH₃ | OCH₃ | CH | |
| H | A-1 | — | O | H | CH(F)CH₃ | OCH₃ | OCH₃ | CH | |
| H | A-1 | — | O | H | CH(F)CH₃ | CH₃ | CH₃ | N | |
| H | A-1 | — | O | H | CH(F)CH₃ | CH₃ | OCH₃ | N | |
| H | A-1 | — | O | H | CH(F)CH₃ | OCH₃ | OCH₃ | N | |
| H | A-1 | — | O | H | CH(F)CH₃ | Cl | OCH₃ | CH | |
| H | A-1 | — | O | H | CH(F)CH₂CH₃ | CH₃ | CH₃ | CH | |
| H | A-1 | — | O | H | CH(F)CH₂CH₃ | CH₃ | OCH₃ | CH | |
| H | A-1 | — | O | H | CH(F)CH₂CH₃ | OCH₃ | OCH₃ | CH | |
| H | A-1 | — | O | H | CH(F)CH₂CH₃ | CH₃ | CH₃ | N | |
| H | A-1 | — | O | H | CH(F)CH₂CH₃ | CH₃ | OCH₃ | N | |
| H | A-1 | — | O | H | CH(F)CH₂CH₃ | OCH₃ | OCH₃ | N | |
| H | A-1 | — | O | H | CH(F)CH₂CH₃ | Cl | OCH₃ | CH | |
| H | A-1 | — | O | H | CF₂CH₃ | CH₃ | CH₃ | CH | |
| H | A-1 | — | O | H | CF₂CH₃ | CH₃ | OCH₃ | CH | |
| H | A-1 | — | O | H | CF₂CH₃ | OCH₃ | OCH₃ | CH | |
| H | A-1 | — | O | H | CF₂CH₃ | CH₃ | CH₃ | N | |
| H | A-1 | — | O | H | CF₂CH₃ | CH₃ | OCH₃ | N | |
| H | A-1 | — | O | H | CF₂CH₃ | OCH₃ | OCH₃ | N | |
| H | A-1 | — | O | H | CF₂CH₃ | Cl | OCH₃ | CH | |
| H | A-1 | — | O | H | CF₂H | CH₃ | CH₃ | CH | |
| H | A-1 | — | O | H | CF₂H | CH₃ | OCH₃ | CH | |
| H | A-1 | — | O | H | CF₂H | OCH₃ | OCH₃ | CH | |
| H | A-1 | — | O | H | CF₂H | CH₃ | CH₃ | N | |
| H | A-1 | — | O | H | CF₂H | CH₃ | OCH₃ | N | |
| H | A-1 | — | O | H | CF₂H | OCH₃ | OCH₃ | N | |
| H | A-1 | — | O | H | CF₂H | Cl | OCH₃ | CH | |
| H | A-1 | — | O | H | CCl₂H | CH₃ | CH₃ | CH | |
| H | A-1 | — | O | H | CCl₂H | CH₃ | OCH₃ | CH | |
| H | A-1 | — | O | H | CCl₂H | OCH₃ | OCH₃ | CH | |
| H | A-1 | — | O | H | CCl₂H | CH₃ | CH₃ | N | |
| H | A-1 | — | O | H | CCl₂H | CH₃ | OCH₃ | N | |
| H | A-1 | — | O | H | CCl₂H | OCH₃ | OCH₃ | N | |
| H | A-1 | — | O | H | CCl₂H | Cl | OCH₃ | CH | |
| H | A-1 | — | O | H | CH₂CH(F)CH₃ | CH₃ | CH₃ | CH | |
| H | A-1 | — | O | H | CH₂CH(F)CH₃ | CH₃ | OCH₃ | CH | |
| H | A-1 | — | O | H | CH₂CH(F)CH₃ | OCH₃ | OCH₃ | CH | |
| H | A-1 | — | O | H | CH(CH₃)CH(Cl)CH₃ | CH₃ | CH₃ | N | |
| H | A-1 | — | O | H | CH(CH₃)CH(Cl)CH₃ | CH₃ | OCH₃ | N | |
| H | A-1 | — | O | H | CH(CH₃)CH₂Br | OCH₃ | OCH₃ | N | |
| H | A-1 | — | O | H | CH(CH₃)CH₂Br | Cl | OCH₃ | CH | |
| H | A-1 | — | O | H | cyclopropyl | CH₃ | CH₃ | CH | 167–169 |
| H | A-1 | — | O | H | cyclopropyl | CH₃ | OCH₃ | CH | 146–148 |
| H | A-1 | — | O | H | cyclopropyl | OCH₃ | OCH₃ | CH | 178–180 |
| H | A-1 | — | O | H | cyclopropyl | CH₃ | CH₃ | N | |
| H | A-1 | — | O | H | cyclopropyl | CH₃ | OCH₃ | N | |
| H | A-1 | — | O | H | cyclopropyl | OCH₃ | OCH₃ | N | 182–184 |
| H | A-1 | — | O | H | cyclopropyl | Cl | OCH₃ | CH | |
| H | A-1 | — | O | H | CH—CF₂—CH₂ (ring) | CH₃ | CH₃ | CH | |
| H | A-1 | — | O | H | CH—CF₂—CH₂ (ring) | CH₃ | OCH₃ | CH | |
| H | A-1 | — | O | H | CH—CF₂—CH₂ (ring) | OCH₃ | OCH₃ | CH | |
| H | A-1 | — | O | H | CH—CF₂—CH₂ (ring) | CH₃ | CH₃ | N | |

TABLE I-continued

| | | | | | | | | |
|---|---|---|---|---|---|---|---|---|
| H | A-1 | — | O | H | CH—CF$_2$—CH$_2$ (ring) | CH$_3$ | OCH$_3$ | N |
| H | A-1 | — | O | H | CH—CF$_2$—CH$_2$ (ring) | OCH$_3$ | OCH$_3$ | N |
| H | A-1 | — | O | H | CH—CF$_2$—CH$_2$ (ring) | Cl | OCH$_3$ | CH |
| H | A-1 | — | O | H | CH—CHF—CH$_2$ (ring) | CH$_3$ | CH$_3$ | CH |
| H | A-1 | — | O | H | CH—CHF—CH$_2$ (ring) | CH$_3$ | OCH$_3$ | CH |
| H | A-1 | — | O | H | CH—CHF—CH$_2$ (ring) | OCH$_3$ | OCH$_3$ | CH |
| H | A-1 | — | O | H | CH—CHF—CH$_2$ (ring) | CH$_3$ | CH$_3$ | N |
| H | A-1 | — | O | H | CH—CHF—CH$_2$ (ring) | CH$_3$ | OCH$_3$ | N |
| H | A-1 | — | O | H | CH—CHF—CH$_2$ (ring) | OCH$_3$ | OCH$_3$ | N |
| H | A-1 | — | O | H | CH—CHF—CH$_2$ (ring) | Cl | OCH$_3$ | CH |
| H | A-1 | — | O | H | CH—CHCl—CH$_2$ (ring) | CH$_3$ | CH$_3$ | CH |
| H | A-1 | — | O | H | CH—CHCl—CH$_2$ (ring) | CH$_3$ | OCH$_3$ | CH |
| H | A-1 | — | O | H | CH—CHCl—CH$_2$ (ring) | OCH$_3$ | OCH$_3$ | CH |
| H | A-1 | — | O | H | CH—CHCl—CH$_2$ (ring) | OCH$_3$ | OCH$_3$ | CH |
| H | A-1 | — | O | H | CH—CHCl—CH$_2$ (ring) | CH$_3$ | CH$_3$ | N |
| H | A-1 | — | O | H | CH—CHCl—CH$_2$ (ring) | CH$_3$ | OCH$_3$ | N |
| H | A-1 | — | O | H | CH—CHCl—CH$_2$ (ring) | OCH$_3$ | OCH$_3$ | N |
| H | A-1 | — | O | H | CH—CHCl—CH$_2$ (ring) | Cl | OCH$_3$ | CH |
| H | A-1 | — | O | H | cyclobutyl | CH$_3$ | CH$_3$ | CH |
| H | A-1 | — | O | H | cyclobutyl | CH$_3$ | OCH$_3$ | CH |
| H | A-1 | — | O | H | cyclobutyl | OCH$_3$ | OCH$_3$ | CH |
| H | A-1 | — | O | H | cyclobutyl | CH$_3$ | CH$_3$ | N |
| H | A-1 | — | O | H | cyclobutyl | CH$_3$ | OCH$_3$ | N |
| H | A-1 | — | O | H | cyclobutyl | OCH$_3$ | OCH$_3$ | N |
| H | A-1 | — | O | H | cyclobutyl | Cl | OCH$_3$ | CH |
| H | A-1 | — | O | H | CH$_2$—CH=CH$_2$ | CH$_3$ | CH$_3$ | CH |
| H | A-1 | — | O | H | CH$_2$—CH=CH$_2$ | CH$_3$ | OCH$_3$ | CH |
| H | A-1 | — | O | H | CH$_2$—CH=CH$_2$ | OCH$_3$ | OCH$_3$ | CH |
| H | A-1 | — | O | H | CH$_2$—CH=CH$_2$ | CH$_3$ | CH$_3$ | N |
| H | A-1 | — | O | H | CH$_2$—CH=CH$_2$ | CH$_3$ | OCH$_3$ | N |

TABLE I-continued

| | | | | | | | | |
|---|---|---|---|---|---|---|---|---|
| H | A-1 | — | O | H | CH$_2$—CH=CH$_2$ | OCH$_3$ | OCH$_3$ | N |
| H | A-1 | — | O | H | CH$_2$—CH=CH$_2$ | Cl | OCH$_3$ | CH |
| H | A-1 | — | O | H | CH=CH$_2$ | CH$_3$ | CH$_3$ | CH |
| H | A-1 | — | O | H | CH=CH$_2$ | CH$_3$ | OCH$_3$ | CH |
| H | A-1 | — | O | H | CH=CH$_2$ | OCH$_3$ | OCH$_3$ | CH |
| H | A-1 | — | O | H | CH=CH$_2$ | CH$_3$ | CH$_3$ | N |
| H | A-1 | — | O | H | CH=CH$_2$ | CH$_3$ | OCH$_3$ | N |
| H | A-1 | — | O | H | CH=CH$_2$ | OCH$_3$ | OCH$_3$ | N |
| H | A-1 | — | O | H | CH=CH$_2$ | Cl | OCH$_3$ | CH |
| H | A-1 | — | O | H | CH$_2$—CF=CH$_2$ | CH$_3$ | CH$_3$ | CH |
| H | A-1 | — | O | H | CH$_2$—CF=CH$_2$ | CH$_3$ | OCH$_3$ | CH |
| H | A-1 | — | O | H | CHF=CH$_2$ | OCH$_3$ | OCH$_3$ | CH |
| H | A-1 | — | O | H | CHF=CH$_2$ | CH$_3$ | CH$_3$ | N |
| H | A-1 | — | O | H | CHF=CH$_2$ | CH$_3$ | OCH$_3$ | N |
| H | A-1 | — | O | H | CHF=CH$_2$ | OCH$_3$ | OCH$_3$ | N |
| H | A-1 | — | O | H | CH$_2$—C=CH—CH$_3$ | Cl | OCH$_3$ | CH |
| H | A-1 | — | O | H | CH$_2$—C≡CH | CH$_3$ | CH$_3$ | CH |
| H | A-1 | — | O | H | CH$_2$—C≡CH | CH$_3$ | OCH$_3$ | CH |
| H | A-1 | — | O | H | CH$_2$—C≡CH | OCH$_3$ | OCH$_3$ | CH |
| H | A-1 | — | O | H | CH$_2$—C≡CH | CH$_3$ | CH$_3$ | N |
| H | A-1 | — | O | H | CH$_2$—C≡CH | CH$_3$ | OCH$_3$ | N |
| H | A-1 | — | O | H | CH$_2$—C≡CH | OCH$_3$ | OCH$_3$ | N |
| H | A-1 | — | O | H | CH$_2$—C≡CH | Cl | OCH$_3$ | CH |
| H | A-1 | — | O | H | C≡CH | CH$_3$ | CH$_3$ | CH |
| H | A-1 | — | O | H | C≡CH | CH$_3$ | OCH$_3$ | CH |
| H | A-1 | — | O | H | C≡CH | OCH$_3$ | OCH$_3$ | CH |
| H | A-1 | — | O | H | C≡CH | CH$_3$ | CH$_3$ | N |
| H | A-1 | — | O | H | C≡CH | CH$_3$ | OCH$_3$ | N |
| H | A-1 | — | O | H | C≡CH | OCH$_3$ | OCH$_3$ | N |
| H | A-1 | — | O | H | C≡C—CH$_2$F | Cl | OCH$_3$ | CH |
| H | A-1 | — | O | H | C≡C—CH$_2$F | CH$_3$ | CH$_3$ | CH |
| H | A-1 | — | O | H | C≡C—CH$_2$F | CH$_3$ | OCH$_3$ | CH |
| H | A-1 | — | O | H | C≡C—CH$_2$F | OCH$_3$ | OCH$_3$ | CH |
| H | A-1 | — | O | H | CH$_2$—C≡C—CH$_2$Cl | CH$_3$ | CH$_3$ | N |
| H | A-1 | — | O | H | CH$_2$—C≡C—CH$_2$Cl | CH$_3$ | OCH$_3$ | N |
| H | A-1 | — | O | H | CH$_2$—C≡C—CH$_2$Cl | OCH$_3$ | OCH$_3$ | N |
| H | A-1 | — | O | H | CH$_2$—C≡C—CH$_2$Cl | Cl | OCH$_3$ | CH |
| H | A-1 | — | O | H | OCH$_3$ | CH$_3$ | CH$_3$ | CH |
| H | A-1 | — | O | H | OCH$_3$ | CH$_3$ | OCH$_3$ | CH |
| H | A-1 | — | O | H | OCH$_3$ | OCH$_3$ | OCH$_3$ | CH |
| H | A-1 | — | O | H | OCH$_3$ | CH$_3$ | CH$_3$ | N |
| H | A-1 | — | O | H | OCH$_3$ | OCH$_3$ | OCH$_3$ | N |
| H | A-1 | — | O | H | OCH$_3$ | Cl | OCH$_3$ | CH |
| H | A-1 | — | O | H | OCH$_2$CH$_3$ | CH$_3$ | CH$_3$ | CH |
| H | A-1 | — | O | H | OCH$_2$CH$_3$ | OCH$_3$ | OCH$_3$ | CH |
| H | A-1 | — | O | H | OCH$_2$CH$_3$ | CH$_3$ | CH$_3$ | N |
| H | A-1 | — | O | H | OCH$_2$CH$_3$ | CH$_3$ | OCH$_3$ | N |
| H | A-1 | — | O | H | OCH$_2$CH$_3$ | OCH$_3$ | OCH$_3$ | N |
| H | A-1 | — | O | H | OCH$_2$CH$_3$ | Cl | OCH$_3$ | CH |
| H | A-1 | — | O | H | OCH(CH$_3$)$_2$ | CH$_3$ | CH$_3$ | CH |
| H | A-1 | — | O | H | OCH(CH$_3$)$_2$ | CH$_3$ | OCH$_3$ | CH |
| H | A-1 | — | O | H | OCH(CH$_3$)$_2$ | OCH$_3$ | OCH$_3$ | CH |
| H | A-1 | — | O | H | OCH(CH$_3$)$_2$ | CH$_3$ | CH$_3$ | N |
| H | A-1 | — | O | H | OCH(CH$_3$)$_2$ | CH$_3$ | OCH$_3$ | N |
| H | A-1 | — | O | H | OCH(CH$_3$)$_2$ | OCH$_3$ | OCH$_3$ | N |
| H | A-1 | — | O | H | OCH(CH$_3$)$_2$ | Cl | OCH$_3$ | CH |
| H | A-1 | — | O | H | OCH$_2$CH$_2$CH$_2$CH$_3$ | CH$_3$ | CH$_3$ | CH |
| H | A-1 | — | O | H | OCH$_2$CH$_2$CH$_2$CH$_3$ | CH$_3$ | OCH$_3$ | CH |
| H | A-1 | — | O | H | OCH$_2$CH$_2$CH$_2$CH$_3$ | OCH$_3$ | OCH$_3$ | CH |
| H | A-1 | — | O | H | OCH$_2$—CH(CH$_3$)$_2$ | CH$_3$ | CH$_3$ | N |
| H | A-1 | — | O | H | OCH$_2$—CH(CH$_3$)$_2$ | CH$_3$ | OCH$_3$ | N |
| H | A-1 | — | O | H | OCH$_2$—CH(CH$_3$)$_2$ | OCH$_3$ | OCH$_3$ | N |
| H | A-1 | — | O | H | OCH$_2$—CH(CH$_3$)$_2$ | Cl | OCH$_3$ | CH |
| H | A-1 | — | O | H | OCF$_2$H | CH$_3$ | CH$_3$ | CH |
| H | A-1 | — | O | H | OCF$_2$H | CH$_3$ | OCH$_3$ | CH |
| H | A-1 | — | O | H | OCF$_2$H | OCH$_3$ | OCH$_3$ | CH |
| H | A-1 | — | O | H | OCF$_2$H | CH$_3$ | CH$_3$ | N |
| H | A-1 | — | O | H | OCF$_2$H | CH$_3$ | OCH$_3$ | N |
| H | A-1 | — | O | H | OCF$_2$H | OCH$_3$ | OCH$_3$ | N |
| H | A-1 | — | O | H | OCF$_2$H | Cl | OCH$_3$ | CH |
| H | A-1 | — | O | H | OCH$_2$CH$_2$Cl | CH$_3$ | CH$_3$ | CH |
| H | A-1 | — | O | H | OCH$_2$CH$_2$Cl | CH$_3$ | OCH$_3$ | CH |
| H | A-1 | — | O | H | OCH$_2$CH$_2$Cl | OCH$_3$ | OCH$_3$ | CH |
| H | A-1 | — | O | H | OCH$_2$CH$_2$Cl | CH$_3$ | CH$_3$ | N |
| H | A-1 | — | O | H | OCH$_2$CH$_2$Cl | CH$_3$ | OCH$_3$ | N |
| H | A-1 | — | O | H | OCH$_2$CH$_2$Cl | OCH$_3$ | OCH$_3$ | N |
| H | A-1 | — | O | H | OCH$_2$CH$_2$Cl | Cl | OCH$_3$ | CH |
| H | A-1 | — | O | H | OCH$_2$CH$_2$F | CH$_3$ | CH$_3$ | CH |
| H | A-1 | — | O | H | OCH$_2$CH$_2$F | CH$_3$ | OCH$_3$ | CH |
| H | A-1 | — | O | H | OCH$_2$CH$_2$F | OCH$_3$ | OCH$_3$ | CH |

TABLE I-continued

| | | | | | | | | |
|---|---|---|---|---|---|---|---|---|
| H | A-1 | — | O | H | OCH₂CH₂F | CH₃ | CH₃ | N |
| H | A-1 | — | O | H | OCH₂CH₂F | CH₃ | OCH₃ | N |
| H | A-1 | — | O | H | OCH₂CH₂F | OCH₃ | OCH₃ | N |
| H | A-1 | — | O | H | OCH₂CH₂F | Cl | OCH₃ | CH |
| H | A-1 | — | O | H | OCH₂CF₃ | CH₃ | CH₃ | CH |
| H | A-1 | — | O | H | OCH₂CF₃ | CH₃ | OCH₃ | CH |
| H | A-1 | — | O | H | OCH₂CF₃ | OCH₃ | OCH₃ | CH |
| H | A-1 | — | O | H | OCH₂CF₃ | CH₃ | CH₃ | N |
| H | A-1 | — | O | H | OCH₂CF₃ | CH₃ | OCH₃ | N |
| H | A-1 | — | O | H | OCH₂CF₃ | OCH₃ | OCH₃ | N |
| H | A-1 | — | O | H | OCH₂CF₃ | Cl | OCH₃ | CH |
| H | A-1 | — | O | H | OCF₂CH₃ | CH₃ | CH₃ | CH |
| H | A-1 | — | O | H | OCF₂CH₃ | CH₃ | OCH₃ | CH |
| H | A-1 | — | O | H | OCF₂CH₃ | OCH₃ | OCH₃ | CH |
| H | A-1 | — | O | H | OCF₂CH₃ | CH₃ | CH₃ | N |
| H | A-1 | — | O | H | OCF₂CH₃ | CH₃ | OCH₃ | N |
| H | A-1 | — | O | H | OCF₂CH₃ | OCH₃ | OCH₃ | N |
| H | A-1 | — | O | H | OCF₂CH₃ | Cl | OCH₃ | CH |
| H | A-1 | — | O | H | OCH₂CH₂CH₂F | CH₃ | CH₃ | CH |
| H | A-1 | — | O | H | OCH₂CH₂CH₂F | CH₃ | OCH₃ | CH |
| H | A-1 | — | O | H | OCH₂CH₂CH₂F | OCH₃ | OCH₃ | CH |
| H | A-1 | — | O | H | OCH₂CH₂CH₂F | CH₃ | CH₃ | N |
| H | A-1 | — | O | H | OCH₂CH₂CH₂F | CH₃ | OCH₃ | N |
| H | A-1 | — | O | H | OCH₂CH₂CH₂F | OCH₃ | OCH₃ | N |
| H | A-1 | — | O | H | OCH₂CH₂CH₂F | Cl | OCH₃ | CH |
| H | A-1 | — | O | H | OCH₂CH₂Cl | CH₃ | CH₃ | CH |
| H | A-1 | — | O | H | OCH₂CH₂Cl | CH₃ | OCH₃ | CH |
| H | A-1 | — | O | H | OCH₂CH₂Cl | OCH₃ | OCH₃ | CH |
| H | A-1 | — | O | H | OCH₂CH₂Br | CH₃ | CH₃ | N |
| H | A-1 | — | O | H | OCH₂CH₂Br | CH₃ | OCH₃ | N |
| H | A-1 | — | O | H | OCH₂CH₂Br | OCH₃ | OCH₃ | N |
| H | A-1 | — | O | H | OCH₂CH₂Br | Cl | OCH₃ | CH |
| H | A-1 | — | O | H | OCH₂—C≡CH | CH₃ | CH₃ | CH |
| H | A-1 | — | O | H | OCH₂—C≡CH | CH₃ | OCH₃ | CH |
| H | A-1 | — | O | H | OCH₂—C≡CH | OCH₃ | OCH₃ | CH |
| H | A-1 | — | O | H | OCH₂—C≡CH | CH₃ | CH₃ | N |
| H | A-1 | — | O | H | OCH₂—C≡CH | CH₃ | OCH₃ | N |
| H | A-1 | — | O | H | OCH₂—C≡CH | OCH₃ | OCH₃ | N |
| H | A-1 | — | O | H | OCH₂—C≡CH | Cl | OCH₃ | CH |
| H | A-1 | — | O | H | OCH₂—CH=CH₂ | CH₃ | CH₃ | CH |
| H | A-1 | — | O | H | OCH₂—CH=CH₂ | CH₃ | OCH₃ | CH |
| H | A-1 | — | O | H | OCH₂—CH=CH₂ | OCH₃ | OCH₃ | CH |
| H | A-1 | — | O | H | OCH₂—CH=CH₂ | CH₃ | CH₃ | N |
| H | A-1 | — | O | H | OCH₂—CH=CH₂ | CH₃ | OCH₃ | N |
| H | A-1 | — | O | H | OCH₂—CH=CH₂ | OCH₃ | OCH₃ | N |
| H | A-1 | — | O | H | OCH₂—CH=CH₂ | Cl | OCH₃ | CH |
| H | A-1 | — | O | H | NO₂ | CH₃ | CH₃ | CH |
| H | A-1 | — | O | H | NO₂ | CH₃ | OCH₃ | CH |
| H | A-1 | — | O | H | NO₂ | OCH₃ | OCH₃ | CH |
| H | A-1 | — | O | H | NO₂ | CH₃ | CH₃ | N |
| H | A-1 | — | O | H | NO₂ | CH₃ | OCH₃ | N |
| H | A-1 | — | O | H | NO₂ | OCH₃ | OCH₃ | N |
| H | A-1 | — | O | H | NO₂ | Cl | OCH₃ | CH |
| H | A-1 | — | O | H | CO₂CH₃ | CH₃ | CH₃ | CH |
| H | A-1 | — | O | H | CO₂CH₃ | CH₃ | OCH₃ | CH |
| H | A-1 | — | O | H | CO₂CH₃ | OCH₃ | OCH₃ | CH |
| H | A-1 | — | O | H | CO₂CH₃ | CH₃ | CH₃ | N |
| H | A-1 | — | O | H | CO₂CH₃ | CH₃ | OCH₃ | N |
| H | A-1 | — | O | H | CO₂CH₃ | OCH₃ | OCH₃ | N |
| H | A-1 | — | O | H | CO₂CH₃ | Cl | OCH₃ | CH |
| H | A-1 | — | O | H | CO₂CH₂CH₃ | CH₃ | CH₃ | CH |
| H | A-1 | — | O | H | CO₂CH₂CH₃ | CH₃ | OCH₃ | CH |
| H | A-1 | — | O | H | CO₂CH₂CH₃ | OCH₃ | OCH₃ | CH |
| H | A-1 | — | O | H | CO₂CH₂CH₃ | CH₃ | CH₃ | N |
| H | A-1 | — | O | H | CO₂CH₂CH₃ | CH₃ | OCH₃ | N |
| H | A-1 | — | O | H | CO₂CH₂CH₃ | OCH₃ | OCH₃ | N |
| H | A-1 | — | O | H | CO₂CH₂CH₃ | Cl | OCH₃ | CH |
| H | A-1 | — | O | H | CO₂CH₂CH₂CH₃ | CH₃ | CH₃ | CH |
| H | A-1 | — | O | H | CO₂CH₂CH₂CH₃ | CH₃ | OCH₃ | CH |
| H | A-1 | — | O | H | CO₂CH₂CH₂CH₃ | OCH₃ | OCH₃ | CH |
| H | A-1 | — | O | H | CO₂CH₂CH₂CH₃ | CH₃ | CH₃ | N |
| H | A-1 | — | O | H | CO₂CH₂CH₂CH₃ | CH₃ | OCH₃ | N |
| H | A-1 | — | O | H | CO₂CH₂CH₂CH₃ | OCH₃ | OCH₃ | N |
| H | A-1 | — | O | H | CO₂CH₂CH₂CH₃ | Cl | OCH₃ | CH |
| H | A-1 | — | O | H | CO₂CH(CH₃)₂ | CH₃ | CH₃ | CH |
| H | A-1 | — | O | H | CO₂CH(CH₃)₂ | CH₃ | OCH₃ | CH |
| H | A-1 | — | O | H | CO₂CH(CH₃)₂ | OCH₃ | OCH₃ | CH |
| H | A-1 | — | O | H | CO₂CH(CH₃)₂ | CH₃ | CH₃ | N |
| H | A-1 | — | O | H | CO₂CH(CH₃)₂ | CH₃ | OCH₃ | N |
| H | A-1 | — | O | H | CO₂CH(CH₃)₂ | OCH₃ | OCH₃ | N |
| H | A-1 | — | O | H | CO₂CH(CH₃)₂ | Cl | OCH₃ | CH |
| H | A-1 | — | O | H | CO₂CH₂CH₂Cl | CH₃ | CH₃ | CH |

TABLE I-continued

| | | | | | | | | |
|---|---|---|---|---|---|---|---|---|
| H | A-1 | — | O | H | CO₂CH₂CH₂Cl | CH₃ | OCH₃ | CH |
| H | A-1 | — | O | H | CO₂CH₂CH₂Cl | OCH₃ | OCH₃ | CH |
| H | A-1 | — | O | H | CO₂CH₂CH₂Cl | CH₃ | CH₃ | N |
| H | A-1 | — | O | H | CO₂CH₂CH₂Cl | CH₃ | OCH₃ | N |
| H | A-1 | — | O | H | CO₂CH₂CH₂Cl | OCH₃ | OCH₃ | N |
| H | A-1 | — | O | H | CO₂CH₂CH₂Cl | Cl | OCH₃ | CH |
| H | A-1 | — | O | H | CO₂CH₂CH₂F | CH₃ | CH₃ | CH |
| H | A-1 | — | O | H | CO₂CH₂CH₂F | CH₃ | OCH₃ | CH |
| H | A-1 | — | O | H | CO₂CH₂CH₂F | OCH₃ | OCH₃ | CH |
| H | A-1 | — | O | H | CO₂CH₂CH₂F | CH₃ | CH₃ | N |
| H | A-1 | — | O | H | CO₂CH₂CH₂F | CH₃ | OCH₃ | N |
| H | A-1 | — | O | H | CO₂CH₂CH₂F | OCH₃ | OCH₃ | N |
| H | A-1 | — | O | H | CO₂CH₂CH₂F | Cl | OCH₃ | CH |
| H | A-1 | — | O | H | CO₂CH₂OCH₃ | CH₃ | CH₃ | CH |
| H | A-1 | — | O | H | CO₂CH₂OCH₃ | CH₃ | OCH₃ | CH |
| H | A-1 | — | O | H | CO₂CH₂OCH₃ | OCH₃ | OCH₃ | CH |
| H | A-1 | — | O | H | CO₂CH₂OCH₃ | CH₃ | CH₃ | N |
| H | A-1 | — | O | H | CO₂CH₂OCH₃ | CH₃ | OCH₃ | N |
| H | A-1 | — | O | H | CO₂CH₂OCH₃ | OCH₃ | OCH₃ | N |
| H | A-1 | — | O | H | CO₂CH₂OCH₃ | Cl | OCH₃ | CH |
| H | A-1 | — | O | H | CO₂CH₂CH₂OCH₃ | CH₃ | CH₃ | CH |
| H | A-1 | — | O | H | CO₂CH₂CH₂OCH₃ | CH₃ | OCH₃ | CH |
| H | A-1 | — | O | H | CO₂CH₂CH₂OCH₃ | OCH₃ | OCH₃ | CH |
| H | A-1 | — | O | H | CO₂CH₂CH₂OCH₃ | CH₃ | CH₃ | N |
| H | A-1 | — | O | H | CO₂CH₂CH₂OCH₃ | CH₃ | OCH₃ | N |
| H | A-1 | — | O | H | CO₂CH₂CH₂OCH₃ | OCH₃ | OCH₃ | N |
| H | A-1 | — | O | H | CO₂CH₂CH₂OCH₃ | Cl | OCH₃ | CH |
| H | A-1 | — | O | H | CO₂CH₂CH=CH₂ | CH₃ | CH₃ | CH |
| H | A-1 | — | O | H | CO₂CH₂CH=CH₂ | CH₃ | OCH₃ | CH |
| H | A-1 | — | O | H | CO₂CH₂CH=CH₂ | OCH₃ | OCH₃ | CH |
| H | A-1 | — | O | H | CO₂CH₂CH=CH₂ | CH₃ | CH₃ | N |
| H | A-1 | — | O | H | CO₂CH₂CH=CH₂ | CH₃ | OCH₃ | N |
| H | A-1 | — | O | H | CO₂CH₂CH=CH₂ | OCH₃ | OCH₃ | N |
| H | A-1 | — | O | H | CO₂CH₂CH=CH₂ | Cl | OCH₃ | CH |
| H | A-1 | — | O | H | CO₂CH₂—C≡CH | CH₃ | CH₃ | CH |
| H | A-1 | — | O | H | CO₂CH₂—C≡CH | CH₃ | OCH₃ | CH |
| H | A-1 | — | O | H | CO₂CH₂—C≡CH | OCH₃ | OCH₃ | CH |
| H | A-1 | — | O | H | CO₂CH₂—C≡CH | CH₃ | CH₃ | N |
| H | A-1 | — | O | H | CO₂CH₂—C≡CH | CH₃ | OCH₃ | N |
| H | A-1 | — | O | H | CO₂CH₂—C≡CH | OCH₃ | OCH₃ | N |
| H | A-1 | — | O | H | CO₂CH₂—C≡CH | Cl | OCH₃ | CH |
| H | A-1 | — | O | H | N(CH₃)₂ | CH₃ | CH₃ | CH |
| H | A-1 | — | O | H | N(CH₃)₂ | CH₃ | OCH₃ | CH |
| H | A-1 | — | O | H | N(CH₃)₂ | OCH₃ | OCH₃ | CH |
| H | A-1 | — | O | H | N(CH₃)₂ | CH₃ | CH₃ | N |
| H | A-1 | — | O | H | N(CH₃)₂ | CH₃ | OCH₃ | N |
| H | A-1 | — | O | H | N(CH₃)₂ | OCH₃ | OCH₃ | N |
| H | A-1 | — | O | H | N(CH₃)₂ | Cl | OCH₃ | CH |
| H | A-1 | — | O | H | NCH₂CH₃(CH₃) | CH₃ | CH₃ | CH |
| H | A-1 | — | O | H | NCH₂CH₃(CH₃) | CH₃ | OCH₃ | CH |
| H | A-1 | — | O | H | NCH₂CH₃(CH₃) | OCH₃ | OCH₃ | CH |
| H | A-1 | — | O | H | NCH₂CH₃(CH₃) | CH₃ | CH₃ | N |
| H | A-1 | — | O | H | NCH₂CH₃(CH₃) | CH₃ | OCH₃ | N |
| H | A-1 | — | O | H | NCH₂CH₃(CH₃) | OCH₃ | OCH₃ | N |
| H | A-1 | — | O | H | NCH₂CH₃(CH₃) | Cl | OCH₃ | CH |
| H | A-1 | — | O | H | SCH₃ | CH₃ | CH₃ | CH |
| H | A-1 | — | O | H | SCH₃ | CH₃ | OCH₃ | CH |
| H | A-1 | — | O | H | SCH₃ | OCH₃ | OCH₃ | CH |
| H | A-1 | — | O | H | SCH₃ | CH₃ | CH₃ | N |
| H | A-1 | — | O | H | SCH₃ | CH₃ | OCH₃ | N |
| H | A-1 | — | O | H | SCH₃ | OCH₃ | OCH₃ | N |
| H | A-1 | — | O | H | SCH₃ | Cl | OCH₃ | CH |
| H | A-1 | — | O | H | SCH₂CH₃ | CH₃ | CH₃ | CH |
| H | A-1 | — | O | H | SCH₂CH₃ | CH₃ | OCH₃ | CH |
| H | A-1 | — | O | H | SCH₂CH₃ | OCH₃ | OCH₃ | CH |
| H | A-1 | — | O | H | SCH₂CH₃ | CH₃ | CH₃ | N |
| H | A-1 | — | O | H | SCH₂CH₃ | CH₃ | OCH₃ | N |
| H | A-1 | — | O | H | SCH₂CH₃ | OCH₃ | OCH₃ | N |
| H | A-1 | — | O | H | SCH₂CH₃ | Cl | OCH₃ | CH |
| H | A-1 | — | O | H | SCH₂CH₂CH₃ | CH₃ | CH₃ | CH |
| H | A-1 | — | O | H | SCH₂CH₂CH₃ | CH₃ | OCH₃ | CH |
| H | A-1 | — | O | H | SCH₂CH₂CH₃ | OCH₃ | OCH₃ | CH |
| H | A-1 | — | O | H | SCH₂CH₂CH₃ | CH₃ | CH₃ | N |
| H | A-1 | — | O | H | SCH₂CH₂CH₃ | CH₃ | OCH₃ | N |
| H | A-1 | — | O | H | SCH₂CH₂CH₃ | OCH₃ | OCH₃ | N |
| H | A-1 | — | O | H | SCH₂CH₂CH₃ | Cl | OCH₃ | CH |
| H | A-1 | — | O | H | SCH₂—CH=CH₂ | CH₃ | CH₃ | CH |
| H | A-1 | — | O | H | SCH₂—CH=CH₂ | CH₃ | OCH₃ | CH |
| H | A-1 | — | O | H | SCH₂—CH=CH₂ | OCH₃ | OCH₃ | CH |
| H | A-1 | — | O | H | SCH₂—CH=CH₂ | CH₃ | CH₃ | N |
| H | A-1 | — | O | H | SCH₂—CH=CH₂ | CH₃ | OCH₃ | N |
| H | A-1 | — | O | H | SCH₂—CH=CH₂ | OCH₃ | OCH₃ | N |

TABLE I-continued

| | | | | | | | | |
|---|---|---|---|---|---|---|---|---|
| H | A-1 | — | O | H | SCH$_2$—CH=CH$_2$ | Cl | OCH$_3$ | CH |
| H | A-1 | — | O | H | SCH$_2$CH$_2$OCH$_3$ | CH$_3$ | CH$_3$ | CH |
| H | A-1 | — | O | H | SCH$_2$—C≡CH | CH$_3$ | OCH$_3$ | CH |
| H | A-1 | — | O | H | SCH(CH$_3$)$_2$ | OCH$_3$ | OCH$_3$ | CH |
| H | A-1 | — | O | H | SCH(CH$_3$)$_2$ | CH$_3$ | CH$_3$ | N |
| H | A-1 | — | O | H | SCH(CH$_3$)$_2$ | CH$_3$ | OCH$_3$ | N |
| H | A-1 | — | O | H | SCH(CH$_3$)$_2$ | OCH$_3$ | OCH$_3$ | N |
| H | A-1 | — | O | H | SCH(CH$_3$)$_2$ | Cl | OCH$_3$ | CH |
| H | A-1 | — | O | H | SOCH$_3$ | CH$_3$ | CH$_3$ | CH |
| H | A-1 | — | O | H | SOCH$_3$ | CH$_3$ | OCH$_3$ | CH |
| H | A-1 | — | O | H | SOCH$_3$ | OCH$_3$ | OCH$_3$ | CH |
| H | A-1 | — | O | H | SOCH$_3$ | CH$_3$ | CH$_3$ | N |
| H | A-1 | — | O | H | SOCH$_3$ | CH$_3$ | OCH$_3$ | N |
| H | A-1 | — | O | H | SOCH$_3$ | OCH$_3$ | OCH$_3$ | N |
| H | A-1 | — | O | H | SOCH$_3$ | Cl | OCH$_3$ | CH |
| H | A-1 | — | O | H | SO$_2$CH$_3$ | CH$_3$ | CH$_3$ | CH |
| H | A-1 | — | O | H | SO$_2$CH$_3$ | CH$_3$ | OCH$_3$ | CH |
| H | A-1 | — | O | H | SO$_2$CH$_3$ | OCH$_3$ | OCH$_3$ | CH |
| H | A-1 | — | O | H | SO$_2$CH$_3$ | CH$_3$ | CH$_3$ | N |
| H | A-1 | — | O | H | SO$_2$CH$_3$ | CH$_3$ | OCH$_3$ | N |
| H | A-1 | — | O | H | SO$_2$CH$_3$ | OCH$_3$ | OCH$_3$ | N |
| H | A-1 | — | O | H | SO$_2$CH$_3$ | Cl | OCH$_3$ | CH |
| H | A-1 | — | O | H | SOCH$_2$CH$_3$ | CH$_3$ | CH$_3$ | CH |
| H | A-1 | — | O | H | SOCH$_2$CH$_3$ | CH$_3$ | OCH$_3$ | CH |
| H | A-1 | — | O | H | SOCH$_2$CH$_3$ | OCH$_3$ | OCH$_3$ | CH |
| H | A-1 | — | O | H | SOCH$_2$CH$_3$ | CH$_3$ | CH$_3$ | N |
| H | A-1 | — | O | H | SOCH$_2$CH$_3$ | CH$_3$ | OCH$_3$ | N |
| H | A-1 | — | O | H | SOCH$_2$CH$_3$ | OCH$_3$ | OCH$_3$ | N |
| H | A-1 | — | O | H | SOCH$_2$CH$_3$ | Cl | OCH$_3$ | CH |
| H | A-1 | — | O | H | SO$_2$CH$_2$CH$_3$ | CH$_3$ | CH$_3$ | CH |
| H | A-1 | — | O | H | SO$_2$CH$_2$CH$_3$ | CH$_3$ | OCH$_3$ | CH |
| H | A-1 | — | O | H | SO$_2$CH$_2$CH$_3$ | OCH$_3$ | OCH$_3$ | CH |
| H | A-1 | — | O | H | SO$_2$CH$_2$CH$_3$ | CH$_3$ | CH$_3$ | N |
| H | A-1 | — | O | H | SO$_2$CH$_2$CH$_3$ | CH$_3$ | OCH$_3$ | N |
| H | A-1 | — | O | H | SO$_2$CH$_2$CH$_3$ | OCH$_3$ | OCH$_3$ | N |
| H | A-1 | — | O | H | SO$_2$CH$_2$CH$_3$ | Cl | OCH$_3$ | CH |
| H | A-1 | — | O | H | SOCH$_2$CH$_2$CH$_3$ | CH$_3$ | CH$_3$ | CH |
| H | A-1 | — | O | H | SOCH$_2$CH$_2$CH$_3$ | CH$_3$ | OCH$_3$ | CH |
| H | A-1 | — | O | H | SOCH$_2$CH$_2$CH$_3$ | OCH$_3$ | OCH$_3$ | CH |
| H | A-1 | — | O | H | SOCH$_2$CH$_2$CH$_3$ | CH$_3$ | CH$_3$ | N |
| H | A-1 | — | O | H | SOCH$_2$CH$_2$CH$_3$ | CH$_3$ | OCH$_3$ | N |
| H | A-1 | — | O | H | SOCH$_2$CH$_2$CH$_3$ | OCH$_3$ | OCH$_3$ | N |
| H | A-1 | — | O | H | SOCH$_2$CH$_2$CH$_3$ | Cl | OCH$_3$ | CH |
| H | A-1 | — | O | H | SO$_2$CH$_2$CH$_2$CH$_3$ | CH$_3$ | CH$_3$ | CH |
| H | A-1 | — | O | H | SO$_2$CH$_2$CH$_2$CH$_3$ | CH$_3$ | OCH$_3$ | CH |
| H | A-1 | — | O | H | SO$_2$CH$_2$CH$_2$CH$_3$ | OCH$_3$ | OCH$_3$ | CH |
| H | A-1 | — | O | H | SO$_2$CH$_2$CH$_2$CH$_3$ | CH$_3$ | CH$_3$ | N |
| H | A-1 | — | O | H | SO$_2$CH$_2$CH$_2$CH$_3$ | CH$_3$ | OCH$_3$ | N |
| H | A-1 | — | O | H | SO$_2$CH$_2$CH$_2$CH$_3$ | OCH$_3$ | OCH$_3$ | N |
| H | A-1 | — | O | H | SO$_2$CH$_2$CH$_2$CH$_3$ | Cl | OCH$_3$ | CH |
| H | A-1 | — | O | H | SO$_2$N(CH$_3$)$_2$ | CH$_3$ | CH$_3$ | CH |
| H | A-1 | — | O | H | SO$_2$N(CH$_3$)$_2$ | CH$_3$ | OCH$_3$ | CH |
| H | A-1 | — | O | H | SO$_2$N(CH$_3$)$_2$ | OCH$_3$ | OCH$_3$ | CH |
| H | A-1 | — | O | H | SO$_2$N(CH$_3$)$_2$ | CH$_3$ | CH$_3$ | N |
| H | A-1 | — | O | H | SO$_2$N(CH$_3$)$_2$ | CH$_3$ | OCH$_3$ | N |
| H | A-1 | — | O | H | SO$_2$N(CH$_3$)$_2$ | OCH$_3$ | OCH$_3$ | N |
| H | A-1 | — | O | H | SO$_2$N(CH$_3$)$_2$ | Cl | OCH$_3$ | CH |
| H | A-1 | — | O | H | SO$_2$N(CH$_2$CH$_3$)$_2$ | CH$_3$ | CH$_3$ | CH |
| H | A-1 | — | O | H | SO$_2$N(CH$_2$CH$_3$)$_2$ | CH$_3$ | OCH$_3$ | CH |
| H | A-1 | — | O | H | SO$_2$N(CH$_2$CH$_3$)$_2$ | OCH$_3$ | OCH$_3$ | CH |
| H | A-1 | — | O | H | SO$_2$N(CH$_2$CH$_3$)$_2$ | CH$_3$ | CH$_3$ | N |
| H | A-1 | — | O | H | SO$_2$N(CH$_2$CH$_3$)$_2$ | CH$_3$ | OCH$_3$ | N |
| H | A-1 | — | O | H | SO$_2$N(CH$_2$CH$_3$)$_2$ | OCH$_3$ | OCH$_3$ | N |
| H | A-1 | — | O | H | SO$_2$N(CH$_2$CH$_3$)$_2$ | Cl | OCH$_3$ | CH |
| H | A-1 | — | O | H | SO$_2$N(CH$_3$)CH$_2$CH$_3$ | CH$_3$ | CH$_3$ | CH |
| H | A-1 | — | O | H | SO$_2$N(CH$_3$)CH$_2$CH$_3$ | CH$_3$ | OCH$_3$ | CH |
| H | A-1 | — | O | H | SO$_2$N(CH$_3$)CH$_2$CH$_3$ | OCH$_3$ | OCH$_3$ | CH |
| H | A-1 | — | O | H | SO$_2$N(CH$_3$)CH$_2$CH$_3$ | CH$_3$ | CH$_3$ | N |
| H | A-1 | — | O | H | SO$_2$N(CH$_3$)CH$_2$CH$_3$ | CH$_3$ | OCH$_3$ | N |
| H | A-1 | — | O | H | SO$_2$N(CH$_3$)CH$_2$CH$_3$ | OCH$_3$ | OCH$_3$ | N |
| H | A-1 | — | O | H | SO$_2$N(CH$_3$)CH$_2$CH$_3$ | Cl | OCH$_3$ | CH |
| H | A-1 | — | O | H | SONHCH$_3$ | CH$_3$ | CH$_3$ | CH |
| H | A-1 | — | O | H | SO$_2$NHCH$_3$ | CH$_3$ | OCH$_3$ | CH |
| H | A-1 | — | O | H | SO$_2$NHCH$_3$ | OCH$_3$ | OCH$_3$ | CH |
| H | A-1 | — | O | H | SO$_2$NHCH$_3$ | CH$_3$ | CH$_3$ | N |
| H | A-1 | — | O | H | SO$_2$NHCH$_3$ | CH$_3$ | OCH$_3$ | N |
| H | A-1 | — | O | H | SO$_2$NHCH$_3$ | OCH$_3$ | OCH$_3$ | N |
| H | A-1 | — | O | H | SO$_2$NHCH$_3$ | Cl | OCH$_3$ | CH |
| H | A-1 | — | O | H | SO$_2$N(OCH$_3$)CH$_3$ | CH$_3$ | CH$_3$ | CH |
| H | A-1 | — | O | H | SO$_2$N(OCH$_3$)CH$_3$ | CH$_3$ | OCH$_3$ | CH |
| H | A-1 | — | O | H | SO$_2$N(OCH$_3$)CH$_3$ | OCH$_3$ | OCH$_3$ | CH |
| H | A-1 | — | O | H | SO$_2$N(OCH$_2$)CH$_3$ | CH$_3$ | CH$_3$ | N |

TABLE I-continued

| | | | | | | | | |
|---|---|---|---|---|---|---|---|---|
| H | A-1 | — | O | H | SO₂N(OCH₃)CH₃ | CH₃ | OCH₃ | N |
| H | A-1 | — | O | H | SO₂N(OCH₃)CH₃ | OCH₃ | OCH₃ | N |
| H | A-1 | — | O | H | SO₂N(OCH₃)CH₃ | Cl | OCH₃ | CH |
| H | A-1 | — | O | H | CON(CH₃)₂ | CH₃ | CH₃ | CH |
| H | A-1 | — | O | H | CON(CH₃)₂ | CH₃ | OCH₃ | CH |
| H | A-1 | — | O | H | CON(CH₃)₂ | OCH₃ | OCH₃ | CH |
| H | A-1 | — | O | H | CON(CH₃)₂ | CH₃ | CH₃ | N |
| H | A-1 | — | O | H | CON(CH₃)₂ | CH₃ | OCH₃ | N |
| H | A-1 | — | O | H | CON(CH₃)₂ | OCH₃ | OCH₃ | N |
| H | A-1 | — | O | H | CON(CH₃)₂ | Cl | OCH₃ | CH |
| H | A-1 | — | O | H | CONHCH₃ | CH₃ | CH₃ | CH |
| H | A-1 | — | O | H | CONHCH₃ | CH₃ | OCH₃ | CH |
| H | A-1 | — | O | H | CONHCH₃ | OCH₃ | OCH₃ | CH |
| H | A-1 | — | O | H | CONHCH₃ | CH₃ | CH₃ | N |
| H | A-1 | — | O | H | CONHCH₃ | CH₃ | OCH₃ | N |
| H | A-1 | — | O | H | CONHCH₃ | OCH₃ | OCH₃ | N |
| H | A-1 | — | O | H | CONHCH₃ | Cl | OCH₃ | CH |
| H | A-1 | — | O | H | CONHCH₂CH₃ | CH₃ | CH₃ | CH |
| H | A-1 | — | O | H | CON(CH₂CH₃)₂ | CH₃ | CH₃ | CH |
| H | A-1 | — | O | H | CON(CH₂CH₃)₂ | OCH₃ | OCH₃ | CH |
| H | A-1 | — | O | H | CON(CH₂CH₃)₂ | CH₃ | CH₃ | N |
| H | A-1 | — | O | H | CON(CH₂CH₃)₂ | CH₃ | OCH₃ | N |
| H | A-1 | — | O | H | CON(CH₂CH₃)₂ | OCH₃ | OCH₃ | N |
| H | A-1 | — | O | H | CON(CH₂CH₃)₂ | Cl | OCH₃ | CH |
| H | A-1 | — | O | H | oxadiazole-CH₃ | CH₃ | CH₃ | CH |
| H | A-1 | — | O | H | oxadiazole-CH₃ | CH₃ | OCH₃ | CH |
| H | A-1 | — | O | H | oxadiazole-CH₃ | OCH₃ | OCH₃ | CH |
| H | A-1 | — | O | H | oxadiazole-CH₃ | CH₃ | CH₃ | N |
| H | A-1 | — | O | H | oxadiazole-CH₃ | CH₃ | OCH₃ | N |
| H | A-1 | — | O | H | oxadiazole-CH₃ | OCH₃ | OCH₃ | N |
| H | A-1 | — | O | H | oxadiazole-CH₃ | Cl | OCH₃ | CH |
| H | A-1 | — | O | H | N-methylpyrazole | CH₃ | CH₃ | CH |
| H | A-1 | — | O | H | N-methylpyrazole | CH₃ | OCH₃ | CH |
| H | A-1 | — | O | H | N-methylpyrazole | OCH₃ | OCH₃ | CH |
| H | A-1 | — | O | H | N-methylpyrazole | CH₃ | CH₃ | N |

TABLE I-continued

| | | | | | | | |
|---|---|---|---|---|---|---|---|
| H | A-1 | — | O | H | 3-methyl-1-methylpyrazol-5-yl | CH₃ | OCH₃ | N |
| H | A-1 | — | O | H | 3-methyl-1-methylpyrazol-5-yl | OCH₃ | OCH₃ | N |
| H | A-1 | — | O | H | 3-methyl-1-methylpyrazol-5-yl | Cl | OCH₃ | CH |
| H | A-1 | — | O | H | 2-thienyl | CH₃ | CH₃ | CH |
| H | A-1 | — | O | H | 2-thienyl | CH₃ | OCH₃ | CH |
| H | A-1 | — | O | H | 2-thienyl | OCH₃ | OCH₃ | CH |
| H | A-1 | — | O | H | 2-thienyl | CH₃ | CH₃ | N |
| H | A-1 | — | O | H | 2-thienyl | CH₃ | OCH₃ | N |
| H | A-1 | — | O | H | 2-thienyl | OCH₃ | OCH₃ | N |
| H | A-1 | — | O | H | 2-thienyl | Cl | OCH₃ | CH |
| H | A-1 | — | O | H | 2-methyltetrazol-5-yl | CH₃ | CH₃ | CH |
| H | A-1 | — | O | H | 2-methyltetrazol-5-yl | CH₃ | OCH₃ | CH |
| H | A-1 | — | O | H | 2-methyltetrazol-5-yl | OCH₃ | OCH₃ | CH |
| H | A-1 | — | O | H | 2-methyltetrazol-5-yl | CH₃ | CH₃ | N |

TABLE I-continued
| | | | | | | | | |
|---|---|---|---|---|---|---|---|---|
| H | A-1 | — | O | H | 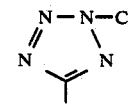 | CH₃ | OCH₃ | N |
| H | A-1 | — | O | H | 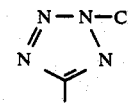 | OCH₃ | OCH₃ | N |
| H | A-1 | — | O | H | 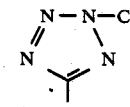 | Cl | OCH₃ | CH |
| H | A-1 | — | O | H | 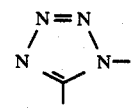 | CH₃ | CH₃ | CH |
| H | A-1 | — | O | H | 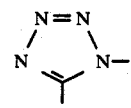 | CH₃ | OCH₃ | CH |
| H | A-1 | — | O | H | 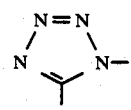 | OCH₃ | OCH₃ | CH |
| H | A-1 | — | O | H | 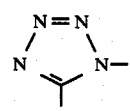 | CH₃ | CH₃ | N |
| H | A-1 | — | O | H | 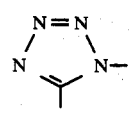 | CH₃ | OCH₃ | N |
| H | A-1 | — | O | H | 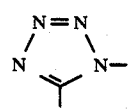 | OCH₃ | OCH₃ | N |
| H | A-1 | — | O | H | 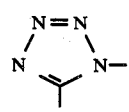 | Cl | OCH₃ | CH |
| H | A-1 | — | O | H | 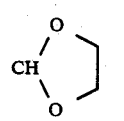 | CH₃ | CH₃ | CH |
| H | A-1 | — | O | H | 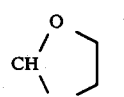 | CH₃ | OCH₃ | CH |
| H | A-1 | — | O | H | 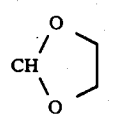 | OCH₃ | OCH₃ | CH |

TABLE I-continued
| | | | | | | | |
|---|---|---|---|---|---|---|---|
| H | A-1 | — | O | H | 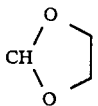 | CH₃ | CH₃ | N |
| H | A-1 | — | O | H | 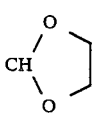 | CH₃ | OCH₃ | N |
| H | A-1 | — | O | H | 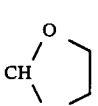 | OCH₃ | OCH₃ | N |
| H | A-1 | — | O | H | 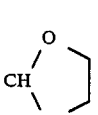 | Cl | OCH₃ | CH |
| H | A-1 | — | O | H | 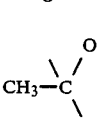 | CH₃ | CH₃ | CH |
| H | A-1 | — | O | H | 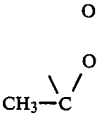 | CH₃ | OCH₃ | CH |
| H | A-1 | — | O | H | 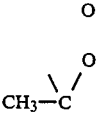 | OCH₃ | OCH₃ | CH |
| H | A-1 | — | O | H | 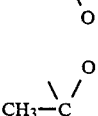 | CH₃ | CH₃ | N |
| H | A-1 | — | O | H | 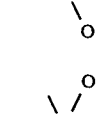 | CH₃ | OCH₃ | N |
| H | A-1 | — | O | H | 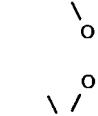 | OCH₃ | OCH₃ | N |
| H | A-1 | — | O | H | 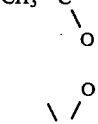 | Cl | OCH₃ | CH |
| H | A-1 | — | O | H | 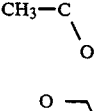 | CH₃ | CH₃ | CH |
| H | A-1 | — | O | H | 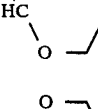 | CH₃ | OCH₃ | CH |

TABLE I-continued

| | | | | | R (substituent) | | | |
|---|---|---|---|---|---|---|---|---|
| H | A-1 | — | O | H | HC(OCH₂CH₂CH₂O) [1,3-dioxane] | OCH₃ | OCH₃ | CH |
| H | A-1 | — | O | H | HC(OCH₂CH₂CH₂O) | CH₃ | CH₃ | N |
| H | A-1 | — | O | H | HC(OCH₂CH₂CH₂O) | CH₃ | OCH₃ | N |
| H | A-1 | — | O | H | HC(OCH₂CH₂CH₂O) | OCH₃ | OCH₃ | N |
| H | A-1 | — | O | H | HC(OCH₂CH₂CH₂O) | Cl | OCH₃ | CH |
| CH₃ | A-1 | — | O | H | CH₃ | CH₃ | CH₃ | CH |
| CH₃ | A-1 | — | O | H | CH₃ | CH₃ | OCH₃ | CH |
| CH₃ | A-1 | — | O | H | CH₃ | OCH₃ | OCH₃ | CH |
| CH₃ | A-1 | — | O | H | CH₃ | CH₃ | CH₃ | N |
| CH₃ | A-1 | — | O | H | CH₃ | CH₃ | OCH₃ | N |
| CH₃ | A-1 | — | O | H | CH₃ | OCH₃ | OCH₃ | N |
| CH₃ | A-1 | — | O | H | CH₃ | Cl | OCH₃ | CH |
| CH₃ | A-1 | — | O | H | CH₂CH₃ | CH₃ | CH₃ | CH |
| CH₃ | A-1 | — | O | H | CH₂CH₃ | CH₃ | OCH₃ | CH |
| CH₃ | A-1 | — | O | H | CH₂CH₃ | OCH₃ | OCH₃ | CH |
| CH₃ | A-1 | — | O | H | CH₂CH₃ | CH₃ | CH₃ | N |
| CH₃ | A-1 | — | O | H | CH₂CH₃ | CH₃ | OCH₃ | N |
| CH₃ | A-1 | — | O | H | CH₂CH₃ | OCH₃ | OCH₃ | N |
| CH₃ | A-1 | — | O | H | CH₂CH₃ | Cl | OCH₃ | CH |
| CH₃ | A-1 | — | O | H | CH(CH₃)₂ | CH₃ | CH₃ | CH |
| CH₃ | A-1 | — | O | H | CH(CH₃)₂ | CH₃ | OCH₃ | CH |
| CH₃ | A-1 | — | O | H | CH(CH₃)₂ | OCH₃ | OCH₃ | CH |
| CH₃ | A-1 | — | O | H | CH(CH₃)₂ | CH₃ | CH₃ | N |
| CH₃ | A-1 | — | O | H | CH(CH₃)₂ | CH₃ | OCH₃ | N |
| CH₃ | A-1 | — | O | H | CH(CH₃)₂ | OCH₃ | OCH₃ | N |
| CH₃ | A-1 | — | O | H | CH(CH₃)₂ | Cl | OCH₃ | CH |
| CH₃ | A-1 | — | O | H | CH₂CH₂CH₃ | CH₃ | CH₃ | CH |
| CH₃ | A-1 | — | O | H | CH₂CH₂CH₃ | CH₃ | OCH₃ | CH |
| CH₃ | A-1 | — | O | H | CH(CH₃)CH₂CH₃ | OCH₃ | OCH₃ | CH |
| CH₃ | A-1 | — | O | H | CH(CH₃)CH₂CH₃ | CH₃ | CH₃ | N |
| CH₃ | A-1 | — | O | H | CH₂CH(CH₃)₂ | CH₃ | OCH₃ | N |
| CH₃ | A-1 | — | O | H | CH₂CH(CH₃)₂ | OCH₃ | OCH₃ | N |
| CH₃ | A-1 | — | O | H | CH₂CH(CH₃)₂ | Cl | OCH₃ | CH |
| CH₃ | A-1 | — | O | H | cyclopropyl | CH₃ | CH₃ | CH |
| CH₃ | A-1 | — | O | H | cyclopropyl | CH₃ | OCH₃ | CH |
| CH₃ | A-1 | — | O | H | cyclopropyl | OCH₃ | OCH₃ | CH |
| CH₃ | A-1 | — | O | H | cyclopropyl | CH₃ | CH₃ | N |
| CH₃ | A-1 | — | O | H | cyclopropyl | CH₃ | OCH₃ | N |
| CH₃ | A-1 | — | O | H | cyclopropyl | OCH₃ | OCH₃ | N |
| CH₃ | A-1 | — | O | H | cyclopropyl | Cl | OCH₃ | CH |
| CH₃ | A-1 | — | O | H | CH—CF₂—CH₂ (cyclic) | CH₃ | CH₃ | CH |
| CH₃ | A-1 | — | O | H | CH—CF₂—CH₂ (cyclic) | CH₃ | OCH₃ | CH |
| CH₃ | A-1 | — | O | H | CH—CF₂—CH₂ (cyclic) | OCH₃ | OCH₃ | CH |
| CH₃ | A-1 | — | O | H | CH—CF₂—CH₂ (cyclic) | CH₃ | CH₃ | N |

TABLE I-continued

| | | | | | | | | |
|---|---|---|---|---|---|---|---|---|
| CH₃ | A-1 | — | O | H | CH—CF₂—CH₂ (ring) | CH₃ | OCH₃ | N |
| CH₃ | A-1 | — | O | H | CH—CF₂—CH₂ (ring) | OCH₃ | OCH₃ | N |
| CH₃ | A-1 | — | O | H | CH—CF₂—CH₂ (ring) | Cl | OCH₃ | CH |
| CH₃ | A-1 | — | O | H | CH—CHF—CH₂ (ring) | CH₃ | CH₃ | CH |
| CH₃ | A-1 | — | O | H | CH—CHF—CH₂ (ring) | CH₃ | OCH₃ | CH |
| CH₃ | A-1 | — | O | H | CH—CHF—CH₂ (ring) | OCH₃ | OCH₃ | CH |
| CH₃ | A-1 | — | O | H | CH—CHF—CH₂ (ring) | CH₃ | CH₃ | N |
| CH₃ | A-1 | — | O | H | CH—CHF—CH₂ (ring) | CH₃ | OCH₃ | N |
| CH₃ | A-1 | — | O | H | CH—CHF—CH₂ (ring) | OCH₃ | OCH₃ | N |
| CH₃ | A-1 | — | O | H | CH—CHF—CH₂ (ring) | Cl | OCH₃ | CH |
| CH₃ | A-1 | — | O | H | CH—CHCl—CH₂ (ring) | CH₃ | CH₃ | CH |
| CH₃ | A-1 | — | O | H | CH—CHCl—CH₂ (ring) | CH₃ | OCH₃ | CH |
| CH₃ | A-1 | — | O | H | CH—CHCl—CH₂ (ring) | OCH₃ | OCH₃ | CH |
| CH₃ | A-1 | — | O | H | CH—CHCl—CH₂ (ring) | CH₃ | CH₃ | N |
| CH₃ | A-1 | — | O | H | CH—CHCl—CH₂ (ring) | CH₃ | OCH₃ | N |
| CH₃ | A-1 | — | O | H | CH—CHCl—CH₂ (ring) | OCH₃ | OCH₃ | N |
| CH₃ | A-1 | — | O | H | CH—CHCl—CH₂ (ring) | Cl | OCH₃ | CH |
| CH₃ | A-1 | — | O | H | OCH₂CH₂Cl | CH₃ | CH₃ | CH |
| CH₃ | A-1 | — | O | H | OCH₂CH₂Cl | CH₃ | OCH₃ | CH |
| CH₃ | A-1 | — | O | H | OCH₂CH₂Cl | OCH₃ | OCH₃ | CH |
| CH₃ | A-1 | — | O | H | OCH₂CH₂Cl | CH₃ | CH₃ | N |
| CH₃ | A-1 | — | O | H | OCH₂CH₂Cl | CH₃ | OCH₃ | N |
| CH₃ | A-1 | — | O | H | OCH₂CH₂Cl | OCH₃ | OCH₃ | N |
| CH₃ | A-1 | — | O | H | OCH₂CH₂Cl | Cl | OCH₃ | CH |
| CH₃ | A-1 | — | O | H | OCH₂CH₂F | CH₃ | CH₃ | CH |
| CH₃ | A-1 | — | O | H | OCH₂CH₂F | CH₃ | OCH₃ | CH |
| CH₃ | A-1 | — | O | H | OCH₂CH₂F | OCH₃ | OCH₃ | CH |
| CH₃ | A-1 | — | O | H | OCH₂CH₂F | CH₃ | CH₃ | N |
| CH₃ | A-1 | — | O | H | OCH₂CH₂F | CH₃ | OCH₃ | N |
| CH₃ | A-1 | — | O | H | OCH₂CH₂F | OCH₃ | OCH₃ | N |
| CH₃ | A-1 | — | O | H | OCH₂CH₂F | Cl | OCH₃ | CH |
| CH₃ | A-1 | — | O | H | OCH₂CF₃ | CH₃ | CH₃ | CH |

TABLE I-continued

| | | | | | | | | |
|---|---|---|---|---|---|---|---|---|
| CH₃ | A-1 | — | O | H | OCH₂CF₃ | CH₃ | OCH₃ | CH |
| CH₃ | A-1 | — | O | H | OCH₂CF₃ | OCH₃ | OCH₃ | CH |
| CH₃ | A-1 | — | O | H | OCH₂CF₃ | CH₃ | CH₃ | N |
| CH₃ | A-1 | — | O | H | OCH₂CF₃ | CH₃ | OCH₃ | N |
| CH₃ | A-1 | — | O | H | OCH₂CF₃ | OCH₃ | OCH₃ | N |
| CH₃ | A-1 | — | O | H | OCH₂CF₃ | Cl | OCH₃ | CH |
| CH₃ | A-1 | — | O | H | OCF₂CH₃ | CH₃ | CH₃ | CH |
| CH₃ | A-1 | — | O | H | OCF₂CH₃ | CH₃ | OCH₃ | CH |
| CH₃ | A-1 | — | O | H | OCF₂CH₃ | OCH₃ | OCH₃ | CH |
| CH₃ | A-1 | — | O | H | OCF₂CH₃ | CH₃ | CH₃ | N |
| CH₃ | A-1 | — | O | H | OCF₂CH₃ | CH₃ | OCH₃ | N |
| CH₃ | A-1 | — | O | H | OCF₂CH₃ | OCH₃ | OCH₃ | N |
| CH₃ | A-1 | — | O | H | OCF₂CH₃ | Cl | OCH₃ | CH |
| CH₃ | A-1 | — | O | H | NO₂ | CH₃ | CH₃ | CH |
| CH₃ | A-1 | — | O | H | NO₂ | CH₃ | OCH₃ | CH |
| CH₃ | A-1 | — | O | H | NO₂ | OCH₃ | OCH₃ | CH |
| CH₃ | A-1 | — | O | H | NO₂ | CH₃ | CH₃ | N |
| CH₃ | A-1 | — | O | H | NO₂ | CH₃ | OCH₃ | N |
| CH₃ | A-1 | — | O | H | NO₂ | OCH₃ | OCH₃ | N |
| CH₃ | A-1 | — | O | H | NO₂ | Cl | OCH₃ | CH |
| CH₃ | A-1 | — | O | H | CO₂CH₃ | CH₃ | CH₃ | CH |
| CH₃ | A-1 | — | O | H | CO₂CH₃ | CH₃ | OCH₃ | CH |
| CH₃ | A-1 | — | O | H | CO₂CH₃ | OCH₃ | OCH₃ | CH |
| CH₃ | A-1 | — | O | H | CO₂CH₃ | CH₃ | CH₃ | N |
| CH₃ | A-1 | — | O | H | CO₂CH₃ | CH₃ | OCH₃ | N |
| CH₃ | A-1 | — | O | H | CO₂CH₃ | OCH₃ | OCH₃ | N |
| CH₃ | A-1 | — | O | H | CO₂CH₃ | Cl | OCH₃ | CH |
| CH₃ | A-1 | — | O | H | CO₂CH₂CH₃ | CH₃ | CH₃ | CH |
| CH₃ | A-1 | — | O | H | CO₂CH₂CH₃ | CH₃ | OCH₃ | CH |
| CH₃ | A-1 | — | O | H | CO₂CH₂CH₃ | OCH₃ | OCH₃ | CH |
| CH₃ | A-1 | — | O | H | CO₂CH₂CH₃ | CH₃ | CH₃ | N |
| CH₃ | A-1 | — | O | H | CO₂CH₂CH₃ | CH₃ | OCH₃ | N |
| CH₃ | A-1 | — | O | H | CO₂CH₂CH₃ | OCH₃ | OCH₃ | N |
| CH₃ | A-1 | — | O | H | CO₂CH₂CH₃ | Cl | OCH₃ | CH |
| CH₃ | A-1 | — | O | H | CO₂CH₂CH₂CH₃ | CH₃ | CH₃ | CH |
| CH₃ | A-1 | — | O | H | CO₂CH₂CH₂CH₃ | CH₃ | OCH₃ | CH |
| CH₃ | A-1 | — | O | H | CO₂CH₂CH₂CH₃ | OCH₃ | OCH₃ | CH |
| CH₃ | A-1 | — | O | H | CO₂CH₂CH₂CH₃ | CH₃ | CH₃ | N |
| CH₃ | A-1 | — | O | H | CO₂CH₂CH₂CH₃ | CH₃ | OCH₃ | N |
| CH₃ | A-1 | — | O | H | CO₂CH₂CH₂CH₃ | OCH₃ | OCH₃ | N |
| CH₃ | A-1 | — | O | H | CO₂CH₂CH₂CH₃ | Cl | OCH₃ | CH |
| CH₃ | A-1 | — | O | H | CO₂CH₂CH₂OCH₃ | CH₃ | CH₃ | CH |
| CH₃ | A-1 | — | O | H | CO₂CH₂CH₂OCH₃ | CH₃ | OCH₃ | CH |
| CH₃ | A-1 | — | O | H | CO₂CH₂CH₂OCH₃ | OCH₃ | OCH₃ | CH |
| CH₃ | A-1 | — | O | H | CO₂CH₂CH₂OCH₃ | CH₃ | CH₃ | N |
| CH₃ | A-1 | — | O | H | CO₂CH₂CH₂OCH₃ | CH₃ | OCH₃ | N |
| CH₃ | A-1 | — | O | H | CO₂CH₂CH₂OCH₃ | OCH₃ | OCH₃ | N |
| CH₃ | A-1 | — | O | H | CO₂CH₂CH₂OCH₃ | Cl | OCH₃ | CH |
| CH₃ | A-1 | — | O | H | CO₂CH₂CH=CH₂ | CH₃ | CH₃ | CH |
| CH₃ | A-1 | — | O | H | CO₂CH₂CH=CH₂ | CH₃ | OCH₃ | CH |
| CH₃ | A-1 | — | O | H | CO₂CH₂CH=CH₂ | OCH₃ | OCH₃ | CH |
| CH₃ | A-1 | — | O | H | CO₂CH₂CH=CH₂ | CH₃ | CH₃ | N |
| CH₃ | A-1 | — | O | H | CO₂CH₂CH=CH₂ | CH₃ | OCH₃ | N |
| CH₃ | A-1 | — | O | H | CO₂CH₂CH=CH₂ | OCH₃ | OCH₃ | N |
| CH₃ | A-1 | — | O | H | CO₂CH₂CH=CH₂ | Cl | OCH₃ | CH |
| CH₃ | A-1 | — | O | H | CO₂CH₂—C≡CH | CH₃ | CH₃ | CH |
| CH₃ | A-1 | — | O | H | CO₂CH₂—C≡CH | CH₃ | OCH₃ | CH |
| CH₃ | A-1 | — | O | H | CO₂CH₂—C≡CH | OCH₃ | OCH₃ | CH |
| CH₃ | A-1 | — | O | H | CO₂CH₂—C≡CH | CH₃ | CH₃ | N |
| CH₃ | A-1 | — | O | H | CO₂CH₂—C≡CH | CH₃ | OCH₃ | N |
| CH₃ | A-1 | — | O | H | CO₂CH₂—C≡CH | OCH₃ | OCH₃ | N |
| CH₃ | A-1 | — | O | H | CO₂CH₂—C≡CH | Cl | OCH₃ | CH |
| CH₃ | A-1 | — | O | H | N(CH₃)₂ | CH₃ | CH₃ | CH |
| CH₃ | A-1 | — | O | H | N(CH₃)₂ | CH₃ | OCH₃ | CH |
| CH₃ | A-1 | — | O | H | N(CH₃)₂ | OCH₃ | OCH₃ | CH |
| CH₃ | A-1 | — | O | H | N(CH₃)₂ | CH₃ | CH₃ | N |
| CH₃ | A-1 | — | O | H | N(CH₃)₂ | CH₃ | OCH₃ | N |
| CH₃ | A-1 | — | O | H | N(CH₃)₂ | OCH₃ | OCH₃ | N |
| CH₃ | A-1 | — | O | H | N(CH₃)₂ | Cl | OCH₃ | CH |
| H | A-1 | — | O | 6-F | CH₃ | CH₃ | CH₃ | CH |
| H | A-1 | — | O | 6-F | CH₃ | CH₃ | OCH₃ | CH |
| H | A-1 | — | O | 6-F | CH₃ | OCH₃ | OCH₃ | CH |
| H | A-1 | — | O | 6-F | CH₃ | CH₃ | CH₃ | N |
| H | A-1 | — | O | 6-F | CH₃ | CH₃ | OCH₃ | N |
| H | A-1 | — | O | 6-F | CH₃ | OCH₃ | OCH₃ | N |
| H | A-1 | — | O | 6-F | CH₃ | Cl | OCH₃ | CH |
| H | A-1 | — | O | 6-F | CH₂CH₃ | CH₃ | CH₃ | CH |
| H | A-1 | — | O | 6-F | CH₂CH₃ | CH₃ | OCH₃ | CH |
| H | A-1 | — | O | 6-F | CH₂CH₃ | OCH₃ | OCH₃ | CH |
| H | A-1 | — | O | 6-F | CH₂CH₃ | CH₃ | CH₃ | N |
| H | A-1 | — | O | 6-F | CH₂CH₃ | CH₃ | OCH₃ | N |
| H | A-1 | — | O | 6-F | CH₂CH₃ | OCH₃ | OCH₃ | N |

TABLE I-continued

| | | | | | | | | |
|---|---|---|---|---|---|---|---|---|
| H | A-1 | — | O | 6-F | CH$_2$CH$_3$ | Cl | OCH$_3$ | CH |
| H | A-1 | — | O | 6-F | CH(CH$_3$)$_2$ | CH$_3$ | CH$_3$ | CH |
| H | A-1 | — | O | 6-F | CH(CH$_3$)$_2$ | CH$_3$ | OCH$_3$ | CH |
| H | A-1 | — | O | 6-F | CH(CH$_3$)$_2$ | OCH$_3$ | OCH$_3$ | CH |
| H | A-1 | — | O | 6-F | CH(CH$_3$)$_2$ | CH$_3$ | CH$_3$ | N |
| H | A-1 | — | O | 6-F | CH(CH$_3$)$_2$ | CH$_3$ | OCH$_3$ | N |
| H | A-1 | — | O | 6-F | CH(CH$_3$)$_2$ | OCH$_3$ | OCH$_3$ | N |
| H | A-1 | — | O | 6-F | CH(CH$_3$)$_2$ | Cl | OCH$_3$ | CH |
| H | A-1 | — | O | 6-F | CH$_2$CH$_2$CH$_3$ | CH$_3$ | CH$_3$ | CH |
| H | A-1 | — | O | 6-F | CH$_2$CH$_2$CH$_3$ | CH$_3$ | OCH$_3$ | CH |
| H | A-1 | — | O | 6-F | CH(CH$_3$)CH$_2$CH$_3$ | OCH$_3$ | OCH$_3$ | CH |
| H | A-1 | — | O | 6-F | CH(CH$_3$)CH$_2$CH$_3$ | CH$_3$ | CH$_3$ | N |
| H | A-1 | — | O | 6-F | CH$_2$CH(CH$_3$)$_2$ | CH$_3$ | OCH$_3$ | N |
| H | A-1 | — | O | 6-F | CH$_2$CH(CH$_3$)$_2$ | OCH$_3$ | OCH$_3$ | N |
| H | A-1 | — | O | 6-F | CH$_2$CH(CH$_3$)$_2$ | Cl | OCH$_3$ | CH |
| H | A-1 | — | O | 6-Cl | cyclopropyl | CH$_3$ | CH$_3$ | CH |
| H | A-1 | — | O | 6-Cl | cyclopropyl | CH$_3$ | OCH$_3$ | CH |
| H | A-1 | — | O | 6-Cl | cyclopropyl | OCH$_3$ | OCH$_3$ | CH |
| H | A-1 | — | O | 6-Cl | cyclopropyl | CH$_3$ | CH$_3$ | N |
| H | A-1 | — | O | 6-Cl | cyclopropyl | CH$_3$ | OCH$_3$ | N |
| H | A-1 | — | O | 6-Cl | cyclopropyl | OCH$_3$ | OCH$_3$ | N |
| H | A-1 | — | O | 6-Cl | cyclopropyl | Cl | OCH$_3$ | CH |
| H | A-1 | — | O | 6-Cl | CH—CF$_2$—CH$_2$ (ring) | CH$_3$ | CH$_3$ | CH |
| H | A-1 | — | O | 6-Cl | CH—CF$_2$—CH$_2$ (ring) | CH$_3$ | OCH$_3$ | CH |
| H | A-1 | — | O | 6-Cl | CH—CF$_2$—CH$_2$ (ring) | OCH$_3$ | OCH$_3$ | CH |
| H | A-1 | — | O | 6-Cl | CH—CF$_2$—CH$_2$ (ring) | CH$_3$ | CH$_3$ | N |
| H | A-1 | — | O | 6-Cl | CH—CF$_2$—CH$_2$ (ring) | CH$_3$ | OCH$_3$ | N |
| H | A-1 | — | O | 6-Cl | CH—CF$_2$—CH$_2$ (ring) | OCH$_3$ | OCH$_3$ | N |
| H | A-1 | — | O | 6-Cl | CH—CF$_2$—CH$_2$ (ring) | Cl | OCH$_3$ | CH |
| H | A-1 | — | O | 6-Cl | CH—CHF—CH$_2$ (ring) | CH$_3$ | CH$_3$ | CH |
| H | A-1 | — | O | 6-Cl | CH—CHF—CH$_2$ (ring) | CH$_3$ | OCH$_3$ | CH |
| H | A-1 | — | O | 6-Cl | CH—CHF—CH$_2$ (ring) | OCH$_3$ | OCH$_3$ | CH |
| H | A-1 | — | O | 6-Cl | CH—CHF—CH$_2$ (ring) | CH$_3$ | CH$_3$ | N |
| H | A-1 | — | O | 6-Cl | CH—CHF—CH$_2$ (ring) | CH$_3$ | OCH$_3$ | N |
| H | A-1 | — | O | 6-Cl | CH—CHF—CH$_2$ (ring) | OCH$_3$ | OCH$_3$ | N |
| H | A-1 | — | O | 6-Cl | CH—CHF—CH$_2$ (ring) | Cl | OCH$_3$ | CH |
| H | A-1 | — | O | 6-Cl | CH—CHCl—CH$_2$ (ring) | CH$_3$ | CH$_3$ | CH |

TABLE I-continued

| | | | | | | | | |
|---|---|---|---|---|---|---|---|---|
| H | A-1 | — | O | 6-Cl | CH—CHCl—CH₂ | CH₃ | OCH₃ | CH |
| H | A-1 | — | O | 6-Cl | CH—CHCl—CH₂ | OCH₃ | OCH₃ | CH |
| H | A-1 | — | O | 6-Cl | CH—CHCl—CH₂ | CH₃ | CH₃ | N |
| H | A-1 | — | O | 6-Cl | CH—CHCl—CH₂ | CH₃ | OCH₃ | N |
| H | A-1 | — | O | 6-Cl | CH—CHCl—CH₂ | OCH₃ | OCH₃ | N |
| H | A-1 | — | O | 6-Cl | CH—CHCl—CH₂ | Cl | OCH₃ | CH |
| H | A-1 | — | O | 6-CH₃ | OCH₂CH₂CH₂F | CH₃ | CH₃ | CH |
| H | A-1 | — | O | 6-CH₃ | OCH₂CH₂CH₂F | CH₃ | OCH₃ | CH |
| H | A-1 | — | O | 6-CH₃ | OCH₂CH₂CH₂F | OCH₃ | OCH₃ | CH |
| H | A-1 | — | O | 6-CH₃ | OCH₂CH₂CH₂F | CH₃ | CH₃ | N |
| H | A-1 | — | O | 6-CH₃ | OCH₂CH₂CH₂F | CH₂ | OCH₃ | N |
| H | A-1 | — | O | 6-CH₃ | OCH₂CH₂CH₂F | OCH₃ | OCH₃ | N |
| H | A-1 | — | O | 6-CH₃ | OCH₂CH₂CH₂F | Cl | OCH₃ | CH |
| H | A-1 | — | O | 6-CH₃ | OCH₂CH₂Cl | CH₃ | CH₃ | CH |
| H | A-1 | — | O | 6-CH₃ | OCH₂CH₂Cl | CH₃ | OCH₃ | CH |
| H | A-1 | — | O | 6-CH₃ | OCH₂CH₂Cl | OCH₃ | OCH₃ | CH |
| H | A-1 | — | O | 6-CH₃ | OCH₂CH₂Br | CH₃ | CH₃ | N |
| H | A-1 | — | O | 6-CH₃ | OCH₂CH₂Br | CH₃ | OCH₃ | N |
| H | A-1 | — | O | 6-CH₃ | OCH₂CH₂Br | OCH₃ | OCH₃ | N |
| H | A-1 | — | O | 6-CH₃ | OCH₂CH₂Br | Cl | OCH₃ | CH |
| H | A-1 | — | O | 6-CH₃ | OCH₂—C≡CH | CH₃ | CH₃ | CH |
| H | A-1 | — | O | 6-CH₃ | OCH₂—C≡CH | CH₃ | OCH₃ | CH |
| H | A-1 | — | O | 6-CH₃ | OCH₂—C≡CH | OCH₃ | OCH₃ | CH |
| H | A-1 | — | O | 6-CH₃ | OCH₂—C≡CH | CH₃ | CH₃ | N |
| H | A-1 | — | O | 6-CH₃ | OCH₂—C≡CH | CH₃ | OCH₃ | N |
| H | A-1 | — | O | 6-CH₃ | OCH₂—C≡CH | OCH₃ | OCH₃ | N |
| H | A-1 | — | O | 6-CH₃ | OCH₂—C≡CH | Cl | OCH₃ | CH |
| H | A-1 | — | O | 6-CH₃ | OCH₂—CH=CH₂ | CH₃ | CH₃ | CH |
| H | A-1 | — | O | 6-CH₃ | OCH₂—CH=CH₂ | CH₃ | OCH₃ | CH |
| H | A-1 | — | O | 6-CH₃ | OCH₂—CH=CH₂ | OCH₃ | OCH₃ | CH |
| H | A-1 | — | O | 6-CH₃ | OCH₂—CH=CH₂ | CH₃ | CH₃ | N |
| H | A-1 | — | O | 6-CH₃ | OCH₂—CH=CH₂ | CH₃ | OCH₃ | N |
| H | A-1 | — | O | 6-CH₃ | OCH₂—CH=CH₂ | OCH₃ | OCH₃ | N |
| H | A-1 | — | O | 6-CH₃ | OCH₂—CH=CH₂ | Cl | OCH₃ | CH |
| H | A-1 | — | O | 6-OCH₃ | NO₂ | CH₃ | CH₃ | CH |
| H | A-1 | — | O | 6-OCH₃ | NO₂ | CH₃ | OCH₃ | CH |
| H | A-1 | — | O | 6-OCH₃ | NO₂ | OCH₃ | OCH₃ | CH |
| H | A-1 | — | O | 6-OCH₃ | NO₂ | CH₃ | CH₃ | N |
| H | A-1 | — | O | 6-OCH₃ | NO₂ | CH₃ | OCH₃ | N |
| H | A-1 | — | O | 6-OCH₃ | NO₂ | OCH₃ | OCH₃ | N |
| H | A-1 | — | O | 6-OCH₃ | NO₂ | Cl | OCH₃ | CH |
| H | A-1 | — | O | 6-OCH₃ | CO₂CH₃ | CH₃ | CH₃ | CH |
| H | A-1 | — | O | 6-OCH₃ | CO₂CH₃ | CH₃ | OCH₃ | CH |
| H | A-1 | — | O | 6-OCH₃ | CO₂CH₃ | OCH₃ | OCH₃ | CH |
| H | A-1 | — | O | 6-OCH₃ | CO₂CH₃ | CH₃ | CH₃ | N |
| H | A-1 | — | O | 6-OCH₃ | CO₂CH₃ | CH₃ | OCH₃ | N |
| H | A-1 | — | O | 6-OCH₃ | CO₂CH₃ | OCH₃ | OCH₃ | N |
| H | A-1 | — | O | 6-OCH₃ | CO₂CH₃ | Cl | OCH₃ | CH |
| H | A-1 | — | O | 6-OCH₃ | CO₂CH₂CH₃ | CH₃ | CH₃ | CH |
| H | A-1 | — | O | 6-OCH₃ | CO₂CH₂CH₃ | CH₃ | OCH₃ | CH |
| H | A-1 | — | O | 6-OCH₃ | CO₂CH₂CH₃ | OCH₃ | OCH₃ | CH |
| H | A-1 | — | O | 6-OCH₃ | CO₂CH₂CH₃ | CH₃ | CH₃ | N |
| H | A-1 | — | O | 6-OCH₃ | CO₂CH₂CH₃ | CH₃ | OCH₃ | N |
| H | A-1 | — | O | 6-OCH₃ | CO₂CH₂CH₃ | OCH₃ | OCH₃ | N |
| H | A-1 | — | O | 6-OCH₃ | CO₂CH₂CH₃ | Cl | OCH₃ | CH |
| H | A-1 | — | O | 6-OCH₃ | CO₂CH₂CH₂CH₃ | CH₃ | CH₃ | CH |
| H | A-1 | — | O | 6-OCH₃ | CO₂CH₂CH₂CH₃ | CH₃ | OCH₃ | CH |
| H | A-1 | — | O | 6-OCH₃ | CO₂CH₂CH₂CH₃ | OCH₃ | OCH₃ | CH |
| H | A-1 | — | O | 6-OCH₃ | CO₂CH₂CH₂CH₃ | CH₃ | CH₃ | N |
| H | A-1 | — | O | 6-OCH₃ | CO₂CH₂CH₂CH₃ | CH₃ | OCH₃ | N |
| H | A-1 | — | O | 6-OCH₃ | CO₂CH₂CH₂CH₃ | OCH₃ | OCH₃ | N |
| H | A-1 | — | O | 6-OCH₃ | CO₂CH₂CH₂CH₃ | Cl | OCH₃ | CH |
| H | A-1 | — | O | 6-OCH₂CF₃ | CO₂CH(CH₃)₂ | CH₃ | CH₃ | CH |
| H | A-1 | — | O | 6-OCH₂CF₃ | CO₂CH(CH₃)₂ | CH₃ | OCH₃ | CH |
| H | A-1 | — | O | 6-OCH₂CF₃ | CO₂CH(CH₃)₂ | OCH₃ | OCH₃ | CH |

TABLE I-continued

| | | | | | | | | |
|---|---|---|---|---|---|---|---|---|
| H | A-1 | — | O | 6-OCH$_2$CF$_3$ | CO$_2$CH(CH$_3$)$_2$ | CH$_3$ | CH$_3$ | N |
| H | A-1 | — | O | 6-OCH$_2$CF$_3$ | CO$_2$CH(CH$_3$)$_2$ | CH$_3$ | OCH$_3$ | N |
| H | A-1 | — | O | 6-OCH$_2$CF$_3$ | CO$_2$CH(CH$_3$)$_2$ | OCH$_3$ | OCH$_3$ | N |
| H | A-1 | — | O | 6-OCH$_2$CF$_3$ | CO$_2$CH(CH$_3$)$_2$ | Cl | OCH$_3$ | CH |
| H | A-1 | — | O | 6-OCH$_2$CF$_3$ | CO$_2$CH$_2$CH$_2$Cl | CH$_3$ | CH$_3$ | CH |
| H | A-1 | — | O | 6-OCH$_2$CF$_3$ | CO$_2$CH$_2$CH$_2$Cl | CH$_3$ | OCH$_3$ | CH |
| H | A-1 | — | O | 6-OCH$_2$CF$_3$ | CO$_2$CH$_2$CH$_2$Cl | OCH$_3$ | OCH$_3$ | CH |
| H | A-1 | — | O | 6-OCH$_2$CF$_3$ | CO$_2$CH$_2$CH$_2$Cl | CH$_3$ | CH$_3$ | N |
| H | A-1 | — | O | 6-OCH$_2$CF$_3$ | CO$_2$CH$_2$CH$_2$Cl | CH$_3$ | OCH$_3$ | N |
| H | A-1 | — | O | 6-OCH$_2$CF$_3$ | CO$_2$CH$_2$CH$_2$Cl | OCH$_3$ | OCH$_3$ | N |
| H | A-1 | — | O | 6-OCH$_2$CF$_3$ | CO$_2$CH$_2$CH$_2$Cl | Cl | OCH$_3$ | CH |
| H | A-1 | — | O | 6-OCH$_2$CF$_3$ | CO$_2$CH$_2$CH$_2$F | CH$_3$ | CH$_3$ | CH |
| H | A-1 | — | O | 6-OCH$_2$CF$_3$ | CO$_2$CH$_2$CH$_2$F | CH$_3$ | OCH$_3$ | CH |
| H | A-1 | — | O | 6-OCH$_2$CF$_3$ | CO$_2$CH$_2$CH$_2$F | OCH$_3$ | OCH$_3$ | CH |
| H | A-1 | — | O | 6-OCH$_2$CF$_3$ | CO$_2$CH$_2$CH$_2$F | CH$_3$ | CH$_3$ | N |
| H | A-1 | — | O | 6-OCH$_2$CF$_3$ | CO$_2$CH$_2$CH$_2$F | CH$_3$ | OCH$_3$ | N |
| H | A-1 | — | O | 6-OCH$_2$CF$_3$ | CO$_2$CH$_2$CH$_2$F | OCH$_3$ | OCH$_3$ | N |
| H | A-1 | — | O | 6-OCH$_2$CF$_3$ | CO$_2$CH$_2$CH$_2$F | Cl | OCH$_3$ | CH |
| H | A-1 | — | O | 6-OCH$_2$CF$_3$ | CO$_2$CH$_2$OCH$_3$ | CH$_3$ | CH$_3$ | CH |
| H | A-1 | — | O | 6-OCH$_2$CF$_3$ | CO$_2$CH$_2$OCH$_3$ | CH$_3$ | OCH$_3$ | CH |
| H | A-1 | — | O | 6-OCH$_2$CF$_3$ | CO$_2$CH$_2$OCH$_3$ | OCH$_3$ | OCH$_3$ | CH |
| H | A-1 | — | O | 6-OCH$_2$CF$_3$ | CO$_2$CH$_2$OCH$_3$ | CH$_3$ | CH$_3$ | N |
| H | A-1 | — | O | 6-OCH$_2$CF$_3$ | CO$_2$CH$_2$OCH$_3$ | CH$_3$ | OCH$_3$ | N |
| H | A-1 | — | O | 6-OCH$_2$CF$_3$ | CO$_2$CH$_2$OCH$_3$ | OCH$_3$ | OCH$_3$ | N |
| H | A-1 | — | O | 6-OCH$_2$CF$_3$ | CO$_2$CH$_2$OCH$_3$ | Cl | OCH$_3$ | CH |
| H | A-1 | — | O | 4-OCH$_3$ | CO$_2$CH$_3$ | CH$_3$ | CH$_3$ | CH |
| H | A-1 | — | O | 4-OCH$_3$ | CO$_2$CH$_3$ | CH$_3$ | OCH$_3$ | CH |
| H | A-1 | — | O | 4-OCH$_3$ | CO$_2$CH$_3$ | OCH$_3$ | OCH$_3$ | CH |
| H | A-1 | — | O | 4-OCH$_3$ | CO$_2$CH$_3$ | CH$_3$ | CH$_3$ | N |
| H | A-1 | — | O | 4-OCH$_3$ | CO$_2$CH$_3$ | CH$_3$ | OCH$_3$ | N |
| H | A-1 | — | O | 4-OCH$_3$ | CO$_2$CH$_3$ | OCH$_3$ | OCH$_3$ | N |
| H | A-1 | — | O | 4-OCH$_3$ | CO$_2$CH$_3$ | Cl | OCH$_3$ | CH |
| H | A-1 | — | O | 4-OCH$_3$ | CO$_2$CH$_2$CH$_3$ | CH$_3$ | CH$_3$ | CH |
| H | A-1 | — | O | 4-OCH$_3$ | CO$_2$CH$_2$CH$_3$ | CH$_3$ | OCH$_3$ | CH |
| H | A-1 | — | O | 4-OCH$_3$ | CO$_2$CH$_2$CH$_3$ | OCH$_3$ | OCH$_3$ | CH |
| H | A-1 | — | O | 4-OCH$_3$ | CO$_2$CH$_2$CH$_3$ | CH$_3$ | CH$_3$ | N |
| H | A-1 | — | O | 4-OCH$_3$ | CO$_2$CH$_2$CH$_3$ | CH$_3$ | OCH$_3$ | N |
| H | A-1 | — | O | 4-OCH$_3$ | CO$_2$CH$_2$CH$_3$ | OCH$_3$ | OCH$_3$ | N |
| H | A-1 | — | O | 4-OCH$_3$ | CO$_2$CH$_2$CH$_3$ | Cl | OCH$_3$ | CH |
| H | A-1 | — | O | 4-OCH$_3$ | SO$_2$N(CH$_3$)$_2$ | CH$_3$ | CH$_3$ | CH |
| H | A-1 | — | O | 4-OCH$_3$ | SO$_2$N(CH$_3$)$_2$ | CH$_3$ | OCH$_3$ | CH |
| H | A-1 | — | O | 4-OCH$_3$ | SO$_2$N(CH$_3$)$_2$ | OCH$_3$ | OCH$_3$ | CH |
| H | A-1 | — | O | 4-OCH$_3$ | SO$_2$N(CH$_3$)$_2$ | CH$_3$ | CH$_3$ | N |
| H | A-1 | — | O | 4-OCH$_3$ | SO$_2$N(CH$_3$)$_2$ | CH$_3$ | OCH$_3$ | N |
| H | A-1 | — | O | 4-OCH$_3$ | SO$_2$N(CH$_3$)$_2$ | OCH$_3$ | OCH$_3$ | N |
| H | A-1 | — | O | 4-OCH$_3$ | SO$_2$N(CH$_3$)$_2$ | Cl | OCH$_3$ | CH |
| H | A-1 | — | O | 4-OCH$_3$ | SO$_2$CH$_3$ | CH$_3$ | CH$_3$ | CH |
| H | A-1 | — | O | 4-OCH$_3$ | SO$_2$CH$_3$ | CH$_3$ | OCH$_3$ | CH |
| H | A-1 | — | O | 4-OCH$_3$ | SO$_2$CH$_3$ | OCH$_3$ | OCH$_3$ | CH |
| H | A-1 | — | O | 4-OCH$_3$ | SO$_2$CH$_3$ | CH$_3$ | CH$_3$ | N |
| H | A-1 | — | O | 4-OCH$_3$ | SO$_2$CH$_3$ | CH$_3$ | OCH$_3$ | N |
| H | A-1 | — | O | 4-OCH$_3$ | SO$_2$CH$_3$ | OCH$_3$ | OCH$_3$ | N |
| H | A-1 | — | O | 4-OCH$_3$ | SO$_2$CH$_3$ | Cl | OCH$_3$ | CH |
| H | A-1 | — | O | 6-SOCH$_3$ | H | CH$_3$ | CH$_3$ | CH | 175–178 |
| H | A-1 | — | O | 6-SOCH$_3$ | H | CH$_3$ | OCH$_3$ | CH | 163–166 |
| H | A-1 | — | O | 6-SOCH$_3$ | H | OCH$_3$ | OCH$_3$ | CH | 214–217 |
| H | A-1 | — | O | 6-SOCH$_3$ | H | OCH$_3$ | CH$_3$ | N | 170–172 |
| H | A-1 | — | O | 6-SOCH$_3$ | H | OCH$_3$ | OCH$_3$ | N | |
| CH$_3$ | A-1 | — | O | 6-F | SCH$_2$—CH=CH$_2$ | CH$_3$ | CH$_3$ | CH |
| CH$_3$ | A-1 | — | O | 6-F | SCH$_2$—CH=CH$_2$ | CH$_3$ | OCH$_3$ | CH |
| CH$_3$ | A-1 | — | O | 6-F | SCH$_2$—CH=CH$_2$ | OCH$_3$ | OCH$_3$ | CH |
| CH$_3$ | A-1 | — | O | 6-F | SCH$_2$—CH=CH$_2$ | CH$_3$ | CH$_3$ | N |
| CH$_3$ | A-1 | — | O | 6-F | SCH$_2$—CH=CH$_2$ | CH$_3$ | OCH$_3$ | N |
| CH$_3$ | A-1 | — | O | 6-F | SCH$_2$—CH=CH$_2$ | OCH$_3$ | OCH$_3$ | N |
| CH$_3$ | A-1 | — | O | 6-F | SCH$_2$—CH=CH$_2$ | Cl | OCH$_3$ | CH |
| CH$_3$ | A-1 | — | O | 6-F | SCH$_2$CH$_2$OCH$_3$ | CH$_3$ | CH$_3$ | CH |
| CH$_3$ | A-1 | — | O | 6-F | SCH$_2$—C≡CH | CH$_3$ | OCH$_3$ | CH |
| CH$_3$ | A-1 | — | O | 6-F | SCH(CH$_3$)$_2$ | OCH$_3$ | OCH$_3$ | CH |
| CH$_3$ | A-1 | — | O | 6-F | SCH(CH$_3$)$_2$ | CH$_3$ | CH$_3$ | N |
| CH$_3$ | A-1 | — | O | 6-F | SCH(CH$_3$)$_2$ | CH$_3$ | OCH$_3$ | N |
| CH$_3$ | A-1 | — | O | 6-F | SCH(CH$_3$)$_2$ | OCH$_3$ | OCH$_3$ | N |
| CH$_3$ | A-1 | — | O | 6-F | SCH(CH$_3$)$_2$ | Cl | OCH$_3$ | CH |
| CH$_3$ | A-1 | — | O | 6-F | SOCH$_3$ | CH$_3$ | CH$_3$ | CH |
| CH$_3$ | A-1 | — | O | 6-F | SOCH$_3$ | CH$_3$ | OCH$_3$ | CH |
| CH$_3$ | A-1 | — | O | 6-F | SOCH$_3$ | OCH$_3$ | OCH$_3$ | CH |
| CH$_3$ | A-1 | — | O | 6-F | SOCH$_3$ | CH$_3$ | CH$_3$ | N |
| CH$_3$ | A-1 | — | O | 6-F | SOCH$_3$ | CH$_3$ | OCH$_3$ | N |
| CH$_3$ | A-1 | — | O | 6-F | SOCH$_3$ | OCH$_3$ | OCH$_3$ | N |
| CH$_3$ | A-1 | — | O | 6-F | SOCH$_3$ | Cl | OCH$_3$ | CH |
| CH$_3$ | A-1 | — | O | 6-F | SO$_2$CH$_3$ | CH$_3$ | CH$_3$ | CH |
| CH$_3$ | A-1 | — | O | 6-F | SO$_2$CH$_3$ | CH$_3$ | OCH$_3$ | CH |
| CH$_3$ | A-1 | — | O | 6-F | SO$_2$CH$_3$ | OCH$_3$ | OCH$_3$ | CH |

TABLE I-continued

| R | A | E | W | R₁ | R₂ | X₁ | Y₁ | | m.p.(°C.) |
|---|---|---|---|---|---|---|---|---|---|
| CH₃ | A-1 | — | O | 6-F | SO₂CH₃ | CH₃ | CH₃ | N | |
| CH₃ | A-1 | — | O | 6-F | SO₂CH₃ | CH₃ | OCH₃ | N | |
| CH₃ | A-1 | — | O | 6-F | SO₂CH₃ | OCH₃ | OCH₃ | N | |
| CH₃ | A-1 | — | O | 6-F | SO₂CH₃ | Cl | OCH₃ | CH | |
| H | A-1 | — | O | 6-SCH₃ | SCH₃ | CH₃ | CH₃ | CH | 174–176 |
| H | A-1 | — | O | 6-SCH₃ | SCH₃ | CH₃ | OCH₃ | CH | 169–171 |
| H | A-1 | — | O | 6-SCH₃ | H | CH₃ | CH₃ | CH | 203–205 |
| H | A-1 | — | O | 6-SCH₃ | H | CH₃ | OCH₃ | CH | 150–154 |
| H | A-1 | — | O | 6-SCH₃ | H | OCH₃ | OCH₃ | CH | 189–192 |
| H | A-1 | — | O | 6-SCH₃ | H | CH₃ | OCH₃ | N | 185–187 |
| H | A-1 | — | O | 6-SCH₃ | H | OCH₃ | OCH₃ | N | 180–182 |
| H | A-1 | — | O | 6-SCH₃ | H | Cl | OCH₃ | CH | 186–188 |

| R | A | E | W | R₁ | R₂ | X₁ | Y₁ | m.p.(°C.) |
|---|---|---|---|---|---|---|---|---|
| H | A-2 | — | O | H | CO₂CH₃ | CH₃ | O | |
| H | A-2 | — | O | H | CO₂CH₃ | CH₃ | CH₂ | |
| H | A-2 | — | O | H | CO₂CH₃ | OCH₃ | O | |
| H | A-2 | — | O | H | CO₂CH₃ | OCH₃ | CH₂ | |
| H | A-2 | — | O | H | CO₂CH₃ | OCH₂CH₃ | O | |
| H | A-2 | — | O | H | CO₂CH₃ | OCF₂H | CH₂ | |
| H | A-2 | — | O | H | SO₂N(CH₃)₂ | CH₃ | O | |
| H | A-2 | — | O | H | SO₂N(CH₃)₂ | OCH₃ | O | |
| H | A-2 | — | O | H | SO₂N(CH₃)₂ | OCF₂H | CH₂ | |
| H | A-3 | — | O | H | CO₂CH₃ | CH₃ | | |
| H | A-3 | — | O | H | CO₂CH₃ | OCH₃ | | |
| H | A-3 | — | O | H | CO₂CH₃ | OCH₂CH₃ | | |
| H | A-3 | — | O | H | CO₂CH₃ | OCF₂H | | |
| H | A-3 | — | O | H | Cl | CH₃ | | |
| H | A-3 | — | O | H | Cl | OCH₃ | | |
| H | A-3 | — | O | H | SO₂CH₃ | CH₃ | | |
| H | A-3 | — | O | H | SO₂CH₃ | OCH₃ | | |

| R | A | E | W | R₁ | R₂ | X₁ | Y₃ | m.p.(°C.) |
|---|---|---|---|---|---|---|---|---|
| H | A-4 | — | O | H | CO₂CH₃ | CH₃ | H | |
| H | A-4 | — | O | H | CO₂CH₃ | OCH₃ | H | |
| H | A-4 | — | O | H | CO₂CH₃ | OCH₂CH₃ | H | |
| H | A-4 | — | O | H | CO₂CH₃ | OCF₂H | H | |
| H | A-4 | — | O | H | CO₂CH₃ | CH₃ | CH₃ | |
| H | A-4 | — | O | H | CO₂CH₃ | OCH₃ | CH₃ | |
| H | A-4 | — | O | H | CO₂CH₃ | OCF₂H | CH₃ | |

| R | A | E | W | R₁ | R₂ | X₂ | Y₂ | m.p.(°C.) |
|---|---|---|---|---|---|---|---|---|
| H | A-5 | — | O | H | CO₂CH₃ | CH₃ | OCH₃ | |
| H | A-5 | — | O | H | CO₂CH₃ | CH₃ | OCH₂CH₃ | |
| H | A-5 | — | O | H | CO₂CH₃ | CH₃ | SCH₃ | |
| H | A-5 | — | O | H | CO₂CH₃ | CH₃ | SCH₂CH₃ | |
| H | A-5 | — | O | H | CO₂CH₃ | CH₃ | CH₃ | |
| H | A-5 | — | O | H | CO₂CH₃ | CH₃ | CH₂CH₃ | |
| H | A-5 | — | O | H | CO₂CH₃ | CH₂CH₃ | OCH₃ | |
| H | A-5 | — | O | H | CO₂CH₃ | CH₂CH₃ | SCH₃ | |
| H | A-5 | — | O | H | CO₂CH₃ | CH₂CH₃ | OCH₂CH₃ | |
| H | A-5 | — | O | H | CO₂CH₃ | CH₂CF₃ | OCH₃ | |

| R | A | E | W | R₁ | R₂ | X₃ | m.p.(°C.) |
|---|---|---|---|---|---|---|---|
| H | A-6 | — | O | H | CO₂CH₃ | CH₃ | |
| H | A-6 | — | O | H | CO₂CH₃ | OCH₃ | |
| H | A-6 | — | O | H | NO₂ | CH₃ | |
| H | A-6 | — | O | H | NO₂ | OCH₃ | |

| R | A | E | W | R₁ | R₂ | X₄ | Y₄ | m.p.(°C.) |
|---|---|---|---|---|---|---|---|---|
| H | A-7 | — | O | H | CO₂CH₃ | CH₃ | CH₃ | |
| H | A-7 | — | O | H | CO₂CH₃ | CH₃ | OCH₃ | |
| H | A-7 | — | O | H | CO₂CH₃ | CH₃ | OCH₂CH₃ | |
| H | A-7 | — | O | H | CO₂CH₃ | CH₃ | Cl | |
| H | A-7 | — | O | H | CO₂CH₃ | OCH₃ | CH₃ | |
| H | A-7 | — | O | H | CO₂CH₃ | OCH₃ | OCH₃ | |
| H | A-7 | — | O | H | CO₂CH₃ | OCH₂CH₃ | OCH₃ | |

| R | A | E | W | R₁ | R₂ | X | Y | Z | m.p.(°C.) |
|---|---|---|---|---|---|---|---|---|---|
| H | A-1 | — | O | H | CO₂CH₃ | CH₃ | OCH₂CH₃ | CH | |
| H | A-1 | — | O | H | CO₂CH₃ | CH₃ | OCF₂H | CH | |
| H | A-1 | — | O | H | CO₂CH₃ | CH₃ | SCF₂H | CH | |
| H | A-1 | — | O | H | CO₂CH₃ | CH₃ | SCH₃ | CH | |
| H | A-1 | — | O | H | CO₂CH₃ | CH₃ | CH₂OCH₃ | N | |
| H | A-1 | — | O | H | CO₂CH₃ | CH₃ | NHCH₃ | N | |
| H | A-1 | — | O | H | CO₂CH₃ | CH₃ | N(CH₃)₂ | N | |
| H | A-1 | — | O | H | CO₂CH₃ | CH₃ | CH₂F | CH | |
| H | A-1 | — | O | H | CO₂CH₃ | CH₃ | C≡CH | CH | |
| H | A-1 | — | O | H | CO₂CH₃ | CH₃ | cyclopropyl | CH | |
| H | A-1 | — | O | H | CO₂CH₃ | CH₃ | CN | CH | |
| H | A-1 | — | O | H | CO₂CH₃ | OCH₃ | CH₂CH₃ | CH | |
| H | A-1 | — | O | H | CO₂CH₃ | OCH₃ | OCH₂CH₃ | CH | |

TABLE I-continued

| | | | | | | | | |
|---|---|---|---|---|---|---|---|---|
| H | A-1 | — | O | H | CO₂CH₃ | OCH₃ | SCH₃ | CH |
| H | A-1 | — | O | H | CO₂CH₃ | OCH₃ | OCF₂H | CH |
| H | A-1 | — | O | H | CO₂CH₃ | OCH₃ | CH₂F | CH |
| H | A-1 | — | O | H | CO₂CH₃ | OCH₃ | N(CH₃)₂ | N |
| H | A-1 | — | O | H | CO₂CH₃ | OCH₃ | NHCH₃ | N |
| H | A-1 | — | O | H | CO₂CH₃ | OCH₃ | CN | CH |
| H | A-1 | — | O | H | CO₂CH₃ | OCF₂H | CH₃ | CH |
| H | A-1 | — | O | H | CO₂CH₃ | OCF₂H | OCH₂CH₃ | CH |
| H | A-1 | — | O | H | CO₂CH₃ | OCF₂H | CH₂CH₃ | CH |
| H | A-1 | — | O | H | CO₂CH₃ | OCF₂H | CH₂F | CH |
| H | A-1 | — | O | H | CO₂CH₃ | OCF₂H | SCH₃ | CH |
| H | A-1 | — | O | H | CO₂CH₃ | OCF₂H | N(CH₃)₂ | N |
| H | A-1 | — | O | H | CO₂CH₃ | OCF₂H | NHCH₃ | N |
| H | A-1 | — | O | H | CO₂CH₃ | CH₂OCH₃ | OCH₃ | CH |
| H | A-1 | — | O | H | CO₂CH₃ | CH₂OCH₃ | OCH₂CH₃ | CH |
| H | A-1 | — | O | H | CO₂CH₃ | CH₂OCH₃ | CH₃ | CH |
| H | A-1 | — | O | H | CO₂CH₃ | CH₂OCH₃ | CH₂F | CH |
| H | A-1 | — | O | H | CO₂CH₃ | CH₂OCH₃ | CH₂Cl | CH |
| H | A-1 | — | O | H | CO₂CH₃ | CH₂OCH₃ | CH₂Br | CH |
| H | A-1 | — | O | H | CO₂CH₃ | SCF₂H | OCH₂CH₃ | CH |
| H | A-1 | — | O | H | CO₂CH₃ | SCF₂H | CH₂CH₃ | CH |
| H | A-1 | — | O | H | CO₂CH₃ | SCF₂H | CH₂F | CH |
| H | A-1 | — | O | H | CO₂CH₃ | SCF₂H | NHCH₃ | N |
| H | A-1 | — | O | H | CO₂CH₃ | N(CH₃)₂ | OCH₂CH₃ | CH |
| H | A-1 | — | O | H | CO₂CH₃ | N(CH₃)₂ | CH₂CH₃ | CH |
| H | A-1 | — | O | H | CO₂CH₃ | N(CH₃)₂ | CH₂F | CH |
| H | A-1 | — | O | H | CO₂CH₃ | N(CH₃)₂ | CH₂OCH₃ | CH |
| H | A-1 | — | O | H | CO₂CH₃ | N(CH₃)₂ | cyclopropyl | CH |
| H | A-1 | — | O | H | CO₂CH₃ | C≡CH | CH₂CH₃ | CH |
| H | A-1 | — | O | H | CO₂CH₃ | C≡CH | OCH₃ | CH |
| H | A-1 | — | O | H | CO₂CH₃ | C≡CH | N(CH₃)₂ | N |
| H | A-1 | — | O | H | CO₂CH₃ | C≡CH | OCH₂CH₃ | CH |

TABLE II

| R | A | E | W | R₁ | R₂ | X | Y | Z | m.p. (°C.) |
|---|---|---|---|---|---|---|---|---|---|
| H | A-1 | — | O | H | H | CH₃ | CH₃ | CH | |
| H | A-1 | — | O | H | H | CH₃ | OCH₃ | CH | |
| H | A-1 | — | O | H | H | OCH₃ | OCH₃ | CH | |
| H | A-1 | — | O | H | H | CH₃ | CH₃ | N | |
| H | A-1 | — | O | H | H | CH₃ | OCH₃ | N | |
| H | A-1 | — | O | H | H | OCH₃ | OCH₃ | N | |
| H | A-1 | — | O | H | H | Cl | OCH₃ | CH | |
| H | A-1 | — | O | H | Cl | CH₃ | CH₃ | CH | |
| H | A-1 | — | O | H | Cl | CH₃ | OCH₃ | CH | |
| H | A-1 | — | O | H | Cl | OCH₃ | OCH₃ | CH | |
| H | A-1 | — | O | H | Cl | CH₃ | CH₃ | N | |
| H | A-1 | — | O | H | Cl | CH₃ | OCH₃ | N | |
| H | A-1 | — | O | H | Cl | OCH₃ | OCH₃ | N | |
| H | A-1 | — | O | H | Cl | Cl | OCH₃ | CH | |
| H | A-1 | — | O | H | Br | CH₃ | CH₃ | CH | |
| H | A-1 | — | O | H | Br | CH₃ | OCH₃ | CH | |
| H | A-1 | — | O | H | Br | OCH₃ | OCH₃ | CH | |
| H | A-1 | — | O | H | Br | CH₃ | CH₃ | N | |
| H | A-1 | — | O | H | Br | CH₃ | OCH₃ | N | |
| H | A-1 | — | O | H | Br | OCH₃ | OCH₃ | N | |
| H | A-1 | — | O | H | Br | Cl | OCH₃ | CH | |
| H | A-1 | — | O | H | F | CH₃ | CH₃ | CH | |
| H | A-1 | — | O | H | F | CH₃ | OCH₃ | CH | |
| H | A-1 | — | O | H | F | OCH₃ | OCH₃ | CH | |
| H | A-1 | — | O | H | F | CH₃ | CH₃ | N | |
| H | A-1 | — | O | H | F | CH₃ | OCH₃ | N | |
| H | A-1 | — | O | H | F | OCH₃ | OCH₃ | N | |
| H | A-1 | — | O | H | F | Cl | OCH₃ | CH | |
| H | A-1 | — | O | H | CH₃ | CH₃ | CH₃ | CH | |
| H | A-1 | — | O | H | CH₃ | CH₃ | OCH₃ | CH | |
| H | A-1 | — | O | H | CH₃ | OCH₃ | OCH₃ | CH | |
| H | A-1 | — | O | H | CH₃ | CH₃ | CH₃ | N | |
| H | A-1 | — | O | H | CH₃ | CH₃ | OCH₃ | N | |
| H | A-1 | — | O | H | CH₃ | OCH₃ | OCH₃ | N | |
| H | A-1 | — | O | H | CH₃ | Cl | OCH₃ | CH | |
| H | A-1 | — | O | H | CH₂CH₃ | CH₃ | CH₃ | CH | |
| H | A-1 | — | O | H | CH₂CH₃ | CH₃ | OCH₃ | CH | |
| H | A-1 | — | O | H | CH₂CH₃ | OCH₃ | OCH₃ | CH | |
| H | A-1 | — | O | H | CH₂CH₃ | CH₃ | CH₃ | N | |
| H | A-1 | — | O | H | CH₂CH₃ | CH₃ | OCH₃ | N | |
| H | A-1 | — | O | H | CH₂CH₃ | OCH₃ | OCH₃ | N | |
| H | A-1 | — | O | H | CH₂CH₃ | Cl | OCH₃ | CH | |
| H | A-1 | — | O | H | CH(CH₃)₂ | CH₃ | CH₃ | CH | |
| H | A-1 | — | O | H | CH(CH₃)₂ | CH₃ | OCH₃ | CH | |

TABLE II-continued

| | | | | | | | | |
|---|---|---|---|---|---|---|---|---|
| H | A-1 | — | O | H | CH(CH₃)₂ | OCH₃ | OCH₃ | CH |
| H | A-1 | — | O | H | CH(CH₃)₂ | CH₃ | CH₃ | N |
| H | A-1 | — | O | H | CH(CH₃)₂ | CH₃ | OCH₃ | N |
| H | A-1 | — | O | H | CH(CH₃)₂ | OCH₃ | OCH₃ | N |
| H | A-1 | — | O | H | CH(CH₃)₂ | Cl | OCH₃ | CH |
| H | A-1 | — | O | H | CH₂CH₂CH₃ | CH₃ | CH₃ | CH |
| H | A-1 | — | O | H | CH₂CH₂CH₃ | CH₃ | OCH₃ | CH |
| H | A-1 | — | O | H | CH(CH₃)CH₂CH₃ | OCH₃ | OCH₃ | CH |
| H | A-1 | — | O | H | CH(CH₃)CH₂CH₃ | CH₃ | CH₃ | N |
| H | A-1 | — | O | H | CH₂CH(CH₃)₂ | CH₃ | OCH₃ | N |
| H | A-1 | — | O | H | CH₂CH(CH₃)₂ | OCH₃ | OCH₃ | N |
| H | A-1 | — | O | H | CH₂CH(CH₃)₂ | Cl | OCH₃ | CH |
| H | A-1 | — | O | H | CH₂Cl | CH₃ | CH₃ | CH |
| H | A-1 | — | O | H | CH₂Cl | CH₃ | OCH₃ | CH |
| H | A-1 | — | O | H | CH₂Cl | OCH₃ | OCH₃ | CH |
| H | A-1 | — | O | H | CH₂Cl | CH₃ | CH₃ | N |
| H | A-1 | — | O | H | CH₂Br | CH₃ | OCH₃ | N |
| H | A-1 | — | O | H | CH₂Br | OCH₃ | OCH₃ | N |
| H | A-1 | — | O | H | CH₂F | Cl | OCH₃ | CH |
| H | A-1 | — | O | H | CH(Cl)CH₃ | CH₃ | CH₃ | CH |
| H | A-1 | — | O | H | CH(Cl)CH₃ | CH₃ | OCH₃ | CH |
| H | A-1 | — | O | H | CH(Cl)CH₃ | OCH₃ | OCH₃ | CH |
| H | A-1 | — | O | H | CH(Cl)CH₃ | CH₃ | CH₃ | N |
| H | A-1 | — | O | H | CH(Cl)CH₃ | CH₃ | OCH₃ | N |
| H | A-1 | — | O | H | CH(Cl)CH₃ | OCH₃ | OCH₃ | N |
| H | A-1 | — | O | H | CH(Cl)CH₃ | Cl | OCH₃ | CH |
| H | A-1 | — | O | H | CH(F)CH₃ | CH₃ | CH₃ | CH |
| H | A-1 | — | O | H | CH(F)CH₃ | CH₃ | OCH₃ | CH |
| H | A-1 | — | O | H | CH(F)CH₃ | OCH₃ | OCH₃ | CH |
| H | A-1 | — | O | H | CH(F)CH₃ | CH₃ | CH₃ | N |
| H | A-1 | — | O | H | CH(F)CH₃ | CH₃ | OCH₃ | N |
| H | A-1 | — | O | H | CH(F)CH₃ | OCH₃ | OCH₃ | N |
| H | A-1 | — | O | H | CH(F)CH₃ | Cl | OCH₃ | CH |
| H | A-1 | — | O | H | CH(F)CH₂CH₃ | CH₃ | CH₃ | CH |
| H | A-1 | — | O | H | CH(F)CH₂CH₃ | CH₃ | OCH₃ | CH |
| H | A-1 | — | O | H | CH(F)CH₂CH₃ | OCH₃ | OCH₃ | CH |
| H | A-1 | — | O | H | CH(F)CH₂CH₃ | CH₃ | CH₃ | N |
| H | A-1 | — | O | H | CH(F)CH₂CH₃ | CH₃ | OCH₃ | N |
| H | A-1 | — | O | H | CH(F)CH₂CH₃ | OCH₃ | OCH₃ | N |
| H | A-1 | — | O | H | CH(F)CH₂CH₃ | Cl | OCH₃ | CH |
| H | A-1 | — | O | H | CF₂CH₃ | CH₃ | CH₃ | CH |
| H | A-1 | — | O | H | CF₂CH₃ | CH₃ | OCH₃ | CH |
| H | A-1 | — | O | H | CF₂CH₃ | OCH₃ | OCH₃ | CH |
| H | A-1 | — | O | H | CF₂CH₃ | CH₃ | CH₃ | N |
| H | A-1 | — | O | H | CF₂CH₃ | CH₃ | OCH₃ | N |
| H | A-1 | — | O | H | CF₂CH₃ | OCH₃ | OCH₃ | N |
| H | A-1 | — | O | H | CF₂CH₃ | Cl | OCH₃ | CH |
| H | A-1 | — | O | H | CF₂H | CH₃ | CH₃ | CH |
| H | A-1 | — | O | H | CF₂H | CH₃ | OCH₃ | CH |
| H | A-1 | — | O | H | CF₂H | OCH₃ | OCH₃ | CH |
| H | A-1 | — | O | H | CF₂H | CH₃ | CH₃ | N |
| H | A-1 | — | O | H | CF₂H | CH₃ | OCH₃ | N |
| H | A-1 | — | O | H | CF₂H | OCH₃ | OCH₃ | N |
| H | A-1 | — | O | H | CF₂H | Cl | OCH₃ | CH |
| H | A-1 | — | O | H | CCl₂H | CH₃ | CH₃ | CH |
| H | A-1 | — | O | H | CCl₂H | CH₃ | OCH₃ | CH |
| H | A-1 | — | O | H | CCl₂H | OCH₃ | OCH₃ | CH |
| H | A-1 | — | O | H | CCl₂H | CH₃ | CH₃ | N |
| H | A-1 | — | O | H | CCl₂H | CH₃ | OCH₃ | N |
| H | A-1 | — | O | H | CCl₂H | OCH₃ | OCH₃ | N |
| H | A-1 | — | O | H | CCl₂H | Cl | OCH₃ | CH |
| H | A-1 | — | O | H | CH₂CH(F)CH₃ | CH₃ | CH₃ | CH |
| H | A-1 | — | O | H | CH₂CH(F)CH₃ | CH₃ | OCH₃ | CH |
| H | A-1 | — | O | H | CH₂CH(F)CH₃ | OCH₃ | OCH₃ | CH |
| H | A-1 | — | O | H | CH(CH₃)CH(Cl)CH₃ | CH₃ | CH₃ | N |
| H | A-1 | — | O | H | CH(CH₃)CH(Cl)CH₃ | CH₃ | OCH₃ | N |
| H | A-1 | — | O | H | CH(CH₃)CH₂Br | OCH₃ | OCH₃ | N |
| H | A-1 | — | O | H | CH(CH₃)CH₂Br | Cl | OCH₃ | CH |
| H | A-1 | — | O | H | cyclopropyl | CH₃ | CH₃ | CH |
| H | A-1 | — | O | H | cyclopropyl | CH₃ | OCH₃ | CH |
| H | A-1 | — | O | H | cyclopropyl | OCH₃ | OCH₃ | CH |
| H | A-1 | — | O | H | cyclopropyl | CH₃ | CH₃ | N |
| H | A-1 | — | O | H | cyclopropyl | CH₃ | OCH₃ | N |
| H | A-1 | — | O | H | cyclopropyl | OCH₃ | OCH₃ | N |
| H | A-1 | — | O | H | cyclopropyl | Cl | OCH₃ | CH |
| H | A-1 | — | O | H | 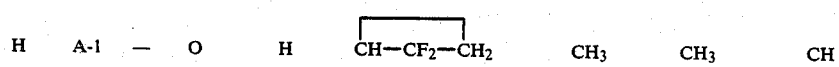 CH—CF₂—CH₂ | CH₃ | CH₃ | CH |
| H | A-1 | — | O | H | 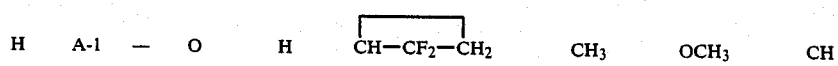 CH—CF₂—CH₂ | CH₃ | OCH₃ | CH |

| | | | | | | | | |
|---|---|---|---|---|---|---|---|---|
| H | A-1 | — | O | H | ⌐CH—CF₂—CH₂⌐ | OCH₃ | OCH₃ | CH |
| H | A-1 | — | O | H | ⌐CH—CF₂—CH₂⌐ | CH₃ | CH₃ | N |
| H | A-1 | — | O | H | ⌐CH—CF₂—CH₂⌐ | CH₃ | OCH₃ | N |
| H | A-1 | — | O | H | ⌐CH—CF₂—CH₂⌐ | OCH₃ | OCH₃ | N |
| H | A-1 | — | O | H | ⌐CH—CF₂—CH₂⌐ | Cl | OCH₃ | CH |
| H | A-1 | — | O | H | ⌐CH—CHF—CH₂⌐ | CH₃ | CH₃ | CH |
| H | A-1 | — | O | H | ⌐CH—CHF—CH₂⌐ | CH₃ | OCH₃ | CH |
| H | A-1 | — | O | H | ⌐CH—CHF—CH₂⌐ | OCH₃ | OCH₃ | CH |
| H | A-1 | — | O | H | ⌐CH—CHF—CH₂⌐ | CH₃ | CH₃ | N |
| H | A-1 | — | O | H | ⌐CH—CHF—CH₂⌐ | CH₃ | OCH₃ | N |
| H | A-1 | — | O | H | ⌐CH—CHF—CH₂⌐ | OCH₃ | OCH₃ | N |
| H | A-1 | — | O | H | ⌐CH—CHF—CH₂⌐ | Cl | OCH₃ | CH |
| H | A-1 | — | O | H | ⌐CH—CHCl—CH₂⌐ | CH₃ | CH₃ | CH |
| H | A-1 | — | O | H | ⌐CH—CHCl—CH₂⌐ | CH₃ | OCH₃ | CH |
| H | A-1 | — | O | H | ⌐CH—CHCl—CH₂⌐ | OCH₃ | OCH₃ | CH |
| H | A-1 | — | O | H | ⌐CH—CHCl—CH₂⌐ | CH₃ | CH₃ | N |
| H | A-1 | — | O | H | ⌐CH—CHCl—CH₂⌐ | CH₃ | OCH₃ | N |
| H | A-1 | — | O | H | CH—CHCl—CH₂ | OCH₃ | OCH₃ | N |
| H | A-1 | — | O | H | CH—CHCl—CH₂ | Cl | OCH₃ | CH |
| H | A-1 | — | O | H | cyclobutyl | CH₃ | CH₃ | CH |
| H | A-1 | — | O | H | cyclobutyl | CH₃ | OCH₃ | CH |
| H | A-1 | — | O | H | cyclobutyl | OCH₃ | OCH₃ | CH |
| H | A-1 | — | O | H | cyclobutyl | CH₃ | CH₃ | N |
| H | A-1 | — | O | H | cyclobutyl | CH₃ | OCH₃ | N |
| H | A-1 | — | O | H | cyclobutyl | OCH₃ | OCH₃ | N |
| H | A-1 | — | O | H | cyclobutyl | Cl | OCH₃ | CH |
| H | A-1 | — | O | H | CH₂—CH=CH₂ | CH₃ | CH₃ | CH |

TABLE II-continued

| | | | | | | | | |
|---|---|---|---|---|---|---|---|---|
| H | A-1 | — | O | H | $CH_2-CH=CH_2$ | $CH_3$ | $OCH_3$ | CH |
| H | A-1 | — | O | H | $CH_2-CH=CH_2$ | $OCH_3$ | $OCH_3$ | CH |
| H | A-1 | — | O | H | $CH_2-CH=CH_2$ | $CH_3$ | $CH_3$ | N |
| H | A-1 | — | O | H | $CH_2-CH=CH_2$ | $CH_3$ | $OCH_3$ | N |
| H | A-1 | — | O | H | $CH_2-CH=CH_2$ | $OCH_3$ | $OCH_3$ | N |
| H | A-1 | — | O | H | $CH_2-CH=CH_2$ | Cl | $OCH_3$ | CH |
| H | A-1 | — | O | H | $CH=CH_2$ | $CH_3$ | $CH_3$ | CH |
| H | A-1 | — | O | H | $CH=CH_2$ | $CH_3$ | $OCH_3$ | CH |
| H | A-1 | — | O | H | $CH=CH_2$ | $OCH_3$ | $OCH_3$ | CH |
| H | A-1 | — | O | H | $CH=CH_2$ | $CH_3$ | $CH_3$ | N |
| H | A-1 | — | O | H | $CH=CH_2$ | $CH_3$ | $OCH_3$ | N |
| H | A-1 | — | O | H | $CH=CH_2$ | $OCH_3$ | $OCH_3$ | N |
| H | A-1 | — | O | H | $CH=CH_2$ | Cl | $OCH_3$ | CH |
| H | A-1 | — | O | H | $CH_2-CF=CH_2$ | $CH_3$ | $CH_3$ | CH |
| H | A-1 | — | O | H | $CH_2-CF=CH_2$ | $CH_3$ | $OCH_3$ | CH |
| H | A-1 | — | O | H | $CHF=CH_2$ | $OCH_3$ | $OCH_3$ | CH |
| H | A-1 | — | O | H | $CHF=CH_2$ | $CH_3$ | $CH_3$ | N |
| H | A-1 | — | O | H | $CHF=CH_2$ | $CH_3$ | $OCH_3$ | N |
| H | A-1 | — | O | H | $CHF=CH_2$ | $OCH_3$ | $OCH_3$ | N |
| H | A-1 | — | O | H | $CH_2CH=CHCH_3$ | Cl | $OCH_3$ | CH |
| H | A-1 | — | O | H | $CH_2-C\equiv CH$ | $CH_3$ | $CH_3$ | CH |
| H | A-1 | — | O | H | $CH_2-C\equiv CH$ | $CH_3$ | $OCH_3$ | CH |
| H | A-1 | — | O | H | $CH_2-C\equiv CH$ | $OCH_3$ | $OCH_3$ | CH |
| H | A-1 | — | O | H | $CH_2-C\equiv CH$ | $CH_3$ | $CH_3$ | N |
| H | A-1 | — | O | H | $CH_2-C\equiv CH$ | $CH_3$ | $OCH_3$ | N |
| H | A-1 | — | O | H | $CH_2-C\equiv CH$ | $OCH_3$ | $OCH_3$ | N |
| H | A-1 | — | O | H | $CH_2-C\equiv CH$ | Cl | $OCH_3$ | CH |
| H | A-1 | — | O | H | $C\equiv CH$ | $CH_3$ | $CH_3$ | CH |
| H | A-1 | — | O | H | $C\equiv CH$ | $CH_3$ | $OCH_3$ | CH |
| H | A-1 | — | O | H | $C\equiv CH$ | $OCH_3$ | $OCH_3$ | CH |
| H | A-1 | — | O | H | $C\equiv CH$ | $CH_3$ | $CH_3$ | N |
| H | A-1 | — | O | H | $C\equiv CH$ | $CH_3$ | $OCH_3$ | N |
| H | A-1 | — | O | H | $C\equiv CH$ | $OCH_3$ | $OCH_3$ | N |
| H | A-1 | — | O | H | $C\equiv C-CH_2F$ | Cl | $OCH_3$ | CH |
| H | A-1 | — | O | H | $C\equiv C-CH_2F$ | $CH_3$ | $CH_3$ | CH |
| H | A-1 | — | O | H | $C\equiv C-CH_2F$ | $CH_3$ | $OCH_3$ | CH |
| H | A-1 | — | O | H | $C\equiv C-CH_2F$ | $OCH_3$ | $OCH_3$ | CH |
| H | A-1 | — | O | H | $CH_2-C\equiv C-CH_2Cl$ | $CH_3$ | $CH_3$ | N |
| H | A-1 | — | O | H | $CH_2-C\equiv C-CH_2Cl$ | $CH_3$ | $OCH_3$ | N |
| H | A-1 | — | O | H | $CH_2-C\equiv C-CH_2Cl$ | $OCH_3$ | $OCH_3$ | N |
| H | A-1 | — | O | H | $CH_2-C\equiv C-CH_2Cl$ | Cl | $OCH_3$ | CH |
| H | A-1 | — | O | H | $OCH_3$ | $CH_3$ | $CH_3$ | CH |
| H | A-1 | — | O | H | $OCH_3$ | $CH_3$ | $OCH_3$ | CH |
| H | A-1 | — | O | H | $OCH_3$ | $OCH_3$ | $OCH_3$ | CH |
| H | A-1 | — | O | H | $OCH_3$ | $CH_3$ | $CH_3$ | N |
| H | A-1 | — | O | H | $OCH_3$ | $CH_3$ | $OCH_3$ | N |
| H | A-1 | — | O | H | $OCH_3$ | $OCH_3$ | $OCH_3$ | N |
| H | A-1 | — | O | H | $OCH_3$ | Cl | $OCH_3$ | CH |
| H | A-1 | — | O | H | $OCH_2CH_3$ | $CH_3$ | $CH_3$ | CH |
| H | A-1 | — | O | H | $OCH_2CH_3$ | $CH_3$ | $OCH_3$ | CH |
| H | A-1 | — | O | H | $OCH_2CH_3$ | $OCH_3$ | $OCH_3$ | CH |
| H | A-1 | — | O | H | $OCH_2CH_3$ | $CH_3$ | $CH_3$ | N |
| H | A-1 | — | O | H | $OCH_2CH_3$ | $CH_3$ | $OCH_3$ | N |
| H | A-1 | — | O | H | $OCH_2CH_3$ | $OCH_3$ | $OCH_3$ | N |
| H | A-1 | — | O | H | $OCH_2CH_3$ | Cl | $OCH_3$ | CH |
| H | A-1 | — | O | H | $OCH(CH_3)_2$ | $CH_3$ | $CH_3$ | CH |
| H | A-1 | — | O | H | $OCH(CH_3)_2$ | $CH_3$ | $OCH_3$ | CH |
| H | A-1 | — | O | H | $OCH(CH_3)_2$ | $OCH_3$ | $OCH_3$ | CH |
| H | A-1 | — | O | H | $OCH(CH_3)_2$ | $CH_3$ | $CH_3$ | N |
| H | A-1 | — | O | H | $OCH(CH_3)_2$ | $CH_3$ | $OCH_3$ | N |
| H | A-1 | — | O | H | $OCH(CH_3)_2$ | $OCH_3$ | $OCH_3$ | N |
| H | A-1 | — | O | H | $OCH(CH_3)_2$ | Cl | $OCH_3$ | CH |
| H | A-1 | — | O | H | $OCH_2CH_2CH_2CH_3$ | $CH_3$ | $CH_3$ | CH |
| H | A-1 | — | O | H | $OCH_2CH_2CH_2CH_3$ | $CH_3$ | $OCH_3$ | CH |
| H | A-1 | — | O | H | $OCH_2CH_2CH_2CH_3$ | $OCH_3$ | $OCH_3$ | CH |
| H | A-1 | — | O | H | $OCH_2-CH(CH_3)_2$ | $CH_3$ | $CH_3$ | N |
| H | A-1 | — | O | H | $OCH_2-CH(CH_3)_2$ | $CH_3$ | $OCH_3$ | N |
| H | A-1 | — | O | H | $OCH_2-CH(CH_3)_2$ | $OCH_3$ | $OCH_3$ | N |
| H | A-1 | — | O | H | $OCH_2-CH(CH_3)_2$ | Cl | $OCH_3$ | CH |
| H | A-1 | — | O | H | $OCF_2H$ | $CH_3$ | $CH_3$ | CH |
| H | A-1 | — | O | H | $OCF_2H$ | $CH_3$ | $OCH_3$ | CH |
| H | A-1 | — | O | H | $OCF_2H$ | $OCH_3$ | $OCH_3$ | CH |
| H | A-1 | — | O | H | $OCF_2H$ | $CH_3$ | $CH_3$ | N |
| H | A-1 | — | O | H | $OCF_2H$ | $CH_3$ | $OCH_3$ | N |
| H | A-1 | — | O | H | $OCF_2H$ | $OCH_3$ | $OCH_3$ | N |
| H | A-1 | — | O | H | $OCF_2H$ | Cl | $OCH_3$ | CH |
| H | A-1 | — | O | H | $OCH_2CH_2Cl$ | $CH_3$ | $CH_3$ | CH |
| H | A-1 | — | O | H | $OCH_2CH_2Cl$ | $CH_3$ | $OCH_3$ | CH |
| H | A-1 | — | O | H | $OCH_2CH_2Cl$ | $OCH_3$ | $OCH_3$ | CH |
| H | A-1 | — | O | H | $OCH_2CH_2Cl$ | $CH_3$ | $CH_3$ | N |
| H | A-1 | — | O | H | $OCH_2CH_2Cl$ | $CH_3$ | $OCH_3$ | N |
| H | A-1 | — | O | H | $OCH_2CH_2Cl$ | $OCH_3$ | $OCH_3$ | N |

TABLE II-continued

| | | | | | | | | |
|---|---|---|---|---|---|---|---|---|
| H | A-1 | — | O | H | OCH$_2$CH$_2$Cl | Cl | OCH$_3$ | CH |
| H | A-1 | — | O | H | OCH$_2$CH$_2$F | CH$_3$ | CH$_3$ | CH |
| H | A-1 | — | O | H | OCH$_2$CH$_2$F | CH$_3$ | OCH$_3$ | CH |
| H | A-1 | — | O | H | OCH$_2$CH$_2$F | OCH$_3$ | OCH$_3$ | CH |
| H | A-1 | — | O | H | OCH$_2$CH$_2$F | CH$_3$ | CH$_3$ | N |
| H | A-1 | — | O | H | OCH$_2$CH$_2$F | CH$_3$ | OCH$_3$ | N |
| H | A-1 | — | O | H | OCH$_2$CH$_2$F | OCH$_3$ | OCH$_3$ | N |
| H | A-1 | — | O | H | OCH$_2$CH$_2$F | Cl | OCH$_3$ | CH |
| H | A-1 | — | O | H | OCH$_2$CF$_3$ | CH$_3$ | CH$_3$ | CH |
| H | A-1 | — | O | H | OCH$_2$CF$_3$ | CH$_3$ | OCH$_3$ | CH |
| H | A-1 | — | O | H | OCH$_2$CF$_3$ | OCH$_3$ | OCH$_3$ | CH |
| H | A-1 | — | O | H | OCH$_2$CF$_3$ | CH$_3$ | CH$_3$ | N |
| H | A-1 | — | O | H | OCH$_2$CF$_3$ | CH$_3$ | OCH$_3$ | N |
| H | A-1 | — | O | H | OCH$_2$CF$_3$ | OCH$_3$ | OCH$_3$ | N |
| H | A-1 | — | O | H | OCH$_2$CF$_3$ | Cl | OCH$_3$ | CH |
| H | A-1 | — | O | H | OCF$_2$CH$_3$ | CH$_3$ | CH$_3$ | CH |
| H | A-1 | — | O | H | OCF$_2$CH$_3$ | CH$_3$ | OCH$_3$ | CH |
| H | A-1 | — | O | H | OCF$_2$CH$_3$ | OCH$_3$ | OCH$_3$ | CH |
| H | A-1 | — | O | H | OCF$_2$CH$_3$ | CH$_3$ | CH$_3$ | N |
| H | A-1 | — | O | H | OCF$_2$CH$_3$ | CH$_3$ | OCH$_3$ | N |
| H | A-1 | — | O | H | OCF$_2$CH$_3$ | OCH$_3$ | OCH$_3$ | N |
| H | A-1 | — | O | H | OCF$_2$CH$_3$ | Cl | OCH$_3$ | CH |
| H | A-1 | — | O | H | OCH$_2$CH$_2$CH$_2$F | CH$_3$ | CH$_3$ | CH |
| H | A-1 | — | O | H | OCH$_2$CH$_2$CH$_2$F | CH$_3$ | OCH$_3$ | CH |
| H | A-1 | — | O | H | OCH$_2$CH$_2$CH$_2$F | OCH$_3$ | OCH$_3$ | CH |
| H | A-1 | — | O | H | OCH$_2$CH$_2$CH$_2$F | CH$_3$ | CH$_3$ | N |
| H | A-1 | — | O | H | OCH$_2$CH$_2$CH$_2$F | CH$_3$ | OCH$_3$ | N |
| H | A-1 | — | O | H | OCH$_2$CH$_2$CH$_2$F | OCH$_3$ | OCH$_3$ | N |
| H | A-1 | — | O | H | OCH$_2$CH$_2$CH$_2$F | Cl | OCH$_3$ | CH |
| H | A-1 | — | O | H | OCH$_2$CH$_2$Cl | CH$_3$ | CH$_3$ | CH |
| H | A-1 | — | O | H | OCH$_2$CH$_2$Cl | CH$_3$ | OCH$_3$ | CH |
| H | A-1 | — | O | H | OCH$_2$CH$_2$Cl | OCH$_3$ | OCH$_3$ | CH |
| H | A-1 | — | O | H | OCH$_2$CH$_2$Br | CH$_3$ | CH$_3$ | N |
| H | A-1 | — | O | H | OCH$_2$CH$_2$Br | CH$_3$ | OCH$_3$ | N |
| H | A-1 | — | O | H | OCH$_2$CH$_2$Br | OCH$_3$ | OCH$_3$ | N |
| H | A-1 | — | O | H | OCH$_2$CH$_2$Br | Cl | OCH$_3$ | CH |
| H | A-1 | — | O | H | OCH$_2$—C≡CH | CH$_3$ | CH$_3$ | CH |
| H | A-1 | — | O | H | OCH$_2$—C≡CH | CH$_3$ | OCH$_3$ | CH |
| H | A-1 | — | O | H | OCH$_2$—C≡CH | OCH$_3$ | OCH$_3$ | CH |
| H | A-1 | — | O | H | OCH$_2$—C≡CH | CH$_3$ | CH$_3$ | N |
| H | A-1 | — | O | H | OCH$_2$—C≡CH | CH$_3$ | OCH$_3$ | N |
| H | A-1 | — | O | H | OCH$_2$—C≡CH | OCH$_3$ | OCH$_3$ | N |
| H | A-1 | — | O | H | OCH$_2$—C≡CH | Cl | OCH$_3$ | CH |
| H | A-1 | — | O | H | OCH$_2$—CH=CH$_2$ | CH$_3$ | CH$_3$ | CH |
| H | A-1 | — | O | H | OCH$_2$—CH=CH$_2$ | CH$_3$ | OCH$_3$ | CH |
| H | A-1 | — | O | H | OCH$_2$—CH=CH$_2$ | OCH$_3$ | OCH$_3$ | CH |
| H | A-1 | — | O | H | OCH$_2$—CH=CH$_2$ | CH$_3$ | CH$_3$ | N |
| H | A-1 | — | O | H | OCH$_2$—CH=CH$_2$ | CH$_3$ | OCH$_3$ | N |
| H | A-1 | — | O | H | OCH$_2$—CH=CH$_2$ | OCH$_3$ | OCH$_3$ | N |
| H | A-1 | — | O | H | OCH$_2$—CH=CH$_2$ | Cl | OCH$_3$ | CH |
| H | A-1 | — | O | H | NO$_2$ | CH$_3$ | CH$_3$ | CH |
| H | A-1 | — | O | H | NO$_2$ | CH$_3$ | OCH$_3$ | CH |
| H | A-1 | — | O | H | NO$_2$ | OCH$_3$ | OCH$_3$ | CH |
| H | A-1 | — | O | H | NO$_2$ | CH$_3$ | CH$_3$ | N |
| H | A-1 | — | O | H | NO$_2$ | OCH$_3$ | OCH$_3$ | N |
| H | A-1 | — | O | H | NO$_2$ | Cl | OCH$_3$ | CH |
| H | A-1 | — | O | H | CO$_2$CH$_3$ | CH$_3$ | CH$_3$ | CH |
| H | A-1 | — | O | H | CO$_2$CH$_3$ | CH$_3$ | OCH$_3$ | CH |
| H | A-1 | — | O | H | CO$_2$CH$_3$ | OCH$_3$ | OCH$_3$ | CH |
| H | A-1 | — | O | H | CO$_2$CH$_3$ | CH$_3$ | CH$_3$ | N |
| H | A-1 | — | O | H | CO$_2$CH$_3$ | CH$_3$ | OCH$_3$ | N |
| H | A-1 | — | O | H | CO$_2$CH$_3$ | OCH$_3$ | OCH$_3$ | N |
| H | A-1 | — | O | H | CO$_2$CH$_3$ | Cl | OCH$_3$ | CH |
| H | A-1 | — | O | H | CO$_2$CH$_2$CH$_3$ | CH$_3$ | CH$_3$ | CH |
| H | A-1 | — | O | H | CO$_2$CH$_2$CH$_3$ | CH$_3$ | OCH$_3$ | CH |
| H | A-1 | — | O | H | CO$_2$CH$_2$CH$_3$ | OCH$_3$ | OCH$_3$ | CH |
| H | A-1 | — | O | H | CO$_2$CH$_2$CH$_3$ | CH$_3$ | CH$_3$ | N |
| H | A-1 | — | O | H | CO$_2$CH$_2$CH$_3$ | CH$_3$ | OCH$_3$ | N |
| H | A-1 | — | O | H | CO$_2$CH$_2$CH$_3$ | OCH$_3$ | OCH$_3$ | N |
| H | A-1 | — | O | H | CO$_2$CH$_2$CH$_3$ | Cl | OCH$_3$ | CH |
| H | A-1 | — | O | H | CO$_2$CH$_2$CH$_2$CH$_3$ | CH$_3$ | CH$_3$ | CH |
| H | A-1 | — | O | H | CO$_2$CH$_2$CH$_2$CH$_3$ | CH$_3$ | OCH$_3$ | CH |
| H | A-1 | — | O | H | CO$_2$CH$_2$CH$_2$CH$_3$ | OCH$_3$ | OCH$_3$ | CH |
| H | A-1 | — | O | H | CO$_2$CH$_2$CH$_2$CH$_3$ | CH$_3$ | CH$_3$ | N |
| H | A-1 | — | O | H | CO$_2$CH$_2$CH$_2$CH$_3$ | CH$_3$ | OCH$_3$ | N |
| H | A-1 | — | O | H | CO$_2$CH$_2$CH$_2$CH$_3$ | OCH$_3$ | OCH$_3$ | N |
| H | A-1 | — | O | H | CO$_2$CH$_2$CH$_2$CH$_3$ | Cl | OCH$_3$ | CH |
| H | A-1 | — | O | H | CO$_2$CH(CH$_3$)$_2$ | CH$_3$ | CH$_3$ | CH |
| H | A-1 | — | O | H | CO$_2$CH(CH$_3$)$_2$ | CH$_3$ | OCH$_3$ | CH |
| H | A-1 | — | O | H | CH$_2$CH(CH$_3$)$_2$ | OCH$_3$ | OCH$_3$ | CH |
| H | A-1 | — | O | H | CO$_2$CH(CH$_3$)$_2$ | CH$_3$ | CH$_3$ | N |

TABLE II-continued

| | | | | | | | | |
|---|---|---|---|---|---|---|---|---|
| H | A-1 | — | O | H | CO₂CH(CH₃)₂ | CH₃ | OCH₃ | N |
| H | A-1 | — | O | H | CO₂CH(CH₃)₂ | OCH₃ | OCH₃ | N |
| H | A-1 | — | O | H | CO₂CH(CH₃)₂ | Cl | OCH₃ | CH |
| H | A-1 | — | O | H | CO₂CH₂CH₂Cl | CH₃ | CH₃ | CH |
| H | A-1 | — | O | H | CO₂CH₂CH₂Cl | CH₃ | OCH₃ | CH |
| H | A-1 | — | O | H | CO₂CH₂CH₂Cl | OCH₃ | OCH₃ | CH |
| H | A-1 | — | O | H | CO₂CH₂CH₂Cl | CH₃ | CH₃ | N |
| H | A-1 | — | O | H | CO₂CH₂CH₂Cl | CH₃ | OCH₃ | N |
| H | A-1 | — | O | H | CO₂CH₂CH₂Cl | OCH₃ | OCH₃ | N |
| H | A-1 | — | O | H | CO₂CH₂CH₂Cl | Cl | OCH₃ | CH |
| H | A-1 | — | O | H | CO₂CH₂CH₂F | CH₃ | CH₃ | CH |
| H | A-1 | — | O | H | CO₂CH₂CH₂F | CH₃ | OCH₃ | CH |
| H | A-1 | — | O | H | CO₂CH₂CH₂F | OCH₃ | OCH₃ | CH |
| H | A-1 | — | O | H | CO₂CH₂CH₂F | CH₃ | CH₃ | N |
| H | A-1 | — | O | H | CO₂CH₂CH₂F | CH₃ | OCH₃ | N |
| H | A-1 | — | O | H | CO₂CH₂CH₂F | OCH₃ | OCH₃ | N |
| H | A-1 | — | O | H | CO₂CH₂CH₂F | Cl | OCH₃ | CH |
| H | A-1 | — | O | H | CO₂CH₂OCH₃ | CH₃ | CH₃ | CH |
| H | A-1 | — | O | H | CO₂CH₂OCH₃ | CH₃ | OCH₃ | CH |
| H | A-1 | — | O | H | CO₂CH₂OCH₃ | OCH₃ | OCH₃ | CH |
| H | A-1 | — | O | H | CO₂CH₂OCH₃ | CH₃ | CH₃ | N |
| H | A-1 | — | O | H | CO₂CH₂OCH₃ | CH₃ | OCH₃ | N |
| H | A-1 | — | O | H | CO₂CH₂OCH₃ | OCH₃ | OCH₃ | N |
| H | A-1 | — | O | H | CO₂CH₂OCH₃ | Cl | OCH₃ | CH |
| H | A-1 | — | O | H | CO₂CH₂CH₂OCH₃ | CH₃ | CH₃ | CH |
| H | A-1 | — | O | H | CO₂CH₂CH₂OCH₃ | CH₃ | OCH₃ | CH |
| H | A-1 | — | O | H | CO₂CH₂CH₂OCH₃ | OCH₃ | OCH₃ | CH |
| H | A-1 | — | O | H | CO₂CH₂CH₂OCH₃ | CH₃ | CH₃ | N |
| H | A-1 | — | O | H | CO₂CH₂CH₂OCH₃ | CH₃ | OCH₃ | N |
| H | A-1 | — | O | H | CO₂CH₂CH₂OCH₃ | OCH₃ | OCH₃ | N |
| H | A-1 | — | O | H | CO₂CH₂CH₂OCH₃ | Cl | OCH₃ | CH |
| H | A-1 | — | O | H | CO₂CH₂CH=CH₂ | CH₃ | CH₃ | CH |
| H | A-1 | — | O | H | CO₂CH₂CH=CH₂ | CH₃ | OCH₃ | CH |
| H | A-1 | — | O | H | CO₂CH₂CH=CH₂ | OCH₃ | OCH₃ | CH |
| H | A-1 | — | O | H | CO₂CH₂CH=CH₂ | CH₃ | CH₃ | N |
| H | A-1 | — | O | H | CO₂CH₂CH=CH₂ | CH₃ | OCH₃ | N |
| H | A-1 | — | O | H | CO₂CH₂CH=CH₂ | OCH₃ | OCH₃ | N |
| H | A-1 | — | O | H | CO₂CH₂CH=CH₂ | Cl | OCH₃ | CH |
| H | A-1 | — | O | H | CO₂CH₂—C≡CH | CH₃ | CH₃ | CH |
| H | A-1 | — | O | H | CO₂CH₂—C≡CH | CH₃ | OCH₃ | CH |
| H | A-1 | — | O | H | CO₂CH₂—C≡CH | OCH₃ | OCH₃ | CH |
| H | A-1 | — | O | H | CO₂CH₂—C≡CH | CH₃ | CH₃ | N |
| H | A-1 | — | O | H | CO₂CH₂—C≡CH | CH₃ | OCH₃ | N |
| H | A-1 | — | O | H | CO₂CH₂—C≡CH | OCH₃ | OCH₃ | N |
| H | A-1 | — | O | H | CO₂CH₂—C≡CH | Cl | OCH₃ | CH |
| H | A-1 | — | O | H | N(CH₃)₂ | CH₃ | CH₃ | CH |
| H | A-1 | — | O | H | N(CH₃)₂ | CH₃ | OCH₃ | CH |
| H | A-1 | — | O | H | N(CH₃)₂ | OCH₃ | OCH₃ | CH |
| H | A-1 | — | O | H | N(CH₃)₂ | CH₃ | CH₃ | N |
| H | A-1 | — | O | H | N(CH₃)₂ | CH₃ | OCH₃ | N |
| H | A-1 | — | O | H | N(CH₃)₂ | OCH₃ | OCH₃ | N |
| H | A-1 | — | O | H | N(CH₃)₂ | Cl | OCH₃ | CH |
| H | A-1 | — | O | H | NCH₂CH₃(CH₃) | CH₃ | CH₃ | CH |
| H | A-1 | — | O | H | NCH₂CH₃(CH₃) | CH₃ | OCH₃ | CH |
| H | A-1 | — | O | H | NCH₂CH₃(CH₃) | OCH₃ | OCH₃ | CH |
| H | A-1 | — | O | H | NCH₂CH₃(CH₃) | CH₃ | CH₃ | N |
| H | A-1 | — | O | H | NCH₂CH₃(CH₃) | CH₃ | OCH₃ | N |
| H | A-1 | — | O | H | NCH₂CH₃(CH₃) | OCH₃ | OCH₃ | N |
| H | A-1 | — | O | H | NCH₂CH₃(CH₃) | Cl | OCH₃ | CH |
| H | A-1 | — | O | H | SCH₃ | CH₃ | CH₃ | CH |
| H | A-1 | — | O | H | SCH₃ | CH₃ | OCH₃ | CH |
| H | A-1 | — | O | H | SCH₃ | OCH₃ | OCH₃ | CH |
| H | A-1 | — | O | H | SCH₃ | CH₃ | CH₃ | N |
| H | A-1 | — | O | H | SCH₃ | CH₃ | OCH₃ | N |
| H | A-1 | — | O | H | SCH₃ | OCH₃ | OCH₃ | N |
| H | A-1 | — | O | H | SCH₃ | Cl | OCH₃ | CH |
| H | A-1 | — | O | H | SCH₂CH₃ | CH₃ | CH₃ | CH |
| H | A-1 | — | O | H | SCH₂CH₃ | CH₃ | OCH₃ | CH |
| H | A-1 | — | O | H | SCH₂CH₃ | OCH₃ | OCH₃ | CH |
| H | A-1 | — | O | H | SCH₂CH₃ | CH₃ | CH₃ | N |
| H | A-1 | — | O | H | SCH₂CH₃ | CH₃ | OCH₃ | N |
| H | A-1 | — | O | H | SCH₂CH₃ | OCH₃ | OCH₃ | N |
| H | A-1 | — | O | H | SCH₂CH₃ | Cl | OCH₃ | CH |
| H | A-1 | — | O | H | SCH₂CH₂CH₃ | CH₃ | CH₃ | CH |
| H | A-1 | — | O | H | SCH₂CH₂CH₃ | CH₃ | OCH₃ | CH |
| H | A-1 | — | O | H | SCH₂CH₂CH₃ | OCH₃ | OCH₃ | CH |
| H | A-1 | — | O | H | SCH₂CH₂CH₃ | CH₃ | CH₃ | N |
| H | A-1 | — | O | H | SCH₂CH₂CH₃ | CH₃ | OCH₃ | N |
| H | A-1 | — | O | H | SCH₂CH₂CH₃ | OCH₃ | OCH₃ | N |
| H | A-1 | — | O | H | SCH₂CH₂CH₃ | Cl | OCH₃ | CH |
| H | A-1 | — | O | H | SCH₂—CH=CH₂ | CH₃ | CH₃ | CH |
| H | A-1 | — | O | H | SCH₂—CH=CH₂ | CH₃ | OCH₃ | CH |

TABLE II-continued

| | | | | | | | | |
|---|---|---|---|---|---|---|---|---|
| H | A-1 | — | O | H | SCH$_2$—CH=CH$_2$ | OCH$_3$ | OCH$_3$ | CH |
| H | A-1 | — | O | H | SCH$_2$—CH=CH$_2$ | CH$_3$ | CH$_3$ | N |
| H | A-1 | — | O | H | SCH$_2$—CH=CH$_2$ | CH$_3$ | OCH$_3$ | N |
| H | A-1 | — | O | H | SCH$_2$—CH=CH$_2$ | OCH$_3$ | OCH$_3$ | N |
| H | A-1 | — | O | H | SCH$_2$—CH=CH$_2$ | Cl | OCH$_3$ | CH |
| H | A-1 | — | O | H | SCH$_2$CH$_2$OCH$_3$ | CH$_3$ | CH$_3$ | CH |
| H | A-1 | — | O | H | SCH$_2$—C≡CH | CH$_3$ | OCH$_3$ | CH |
| H | A-1 | — | O | H | SCH(CH$_3$)$_2$ | OCH$_3$ | OCH$_3$ | CH |
| H | A-1 | — | O | H | SCH(CH$_3$)$_2$ | CH$_3$ | CH$_3$ | N |
| H | A-1 | — | O | H | SCH(CH$_3$)$_2$ | CH$_3$ | OCH$_3$ | N |
| H | A-1 | — | O | H | SCH(CH$_3$)$_2$ | OCH$_3$ | OCH$_3$ | N |
| H | A-1 | — | O | H | SCH(CH$_3$)$_2$ | Cl | OCH$_3$ | CH |
| H | A-1 | — | O | H | SOCH$_3$ | CH$_3$ | CH$_3$ | CH |
| H | A-1 | — | O | H | SOCH$_3$ | CH$_3$ | OCH$_3$ | CH |
| H | A-1 | — | O | H | SOCH$_3$ | OCH$_3$ | OCH$_3$ | CH |
| H | A-1 | — | O | H | SOCH$_3$ | CH$_3$ | CH$_3$ | N |
| H | A-1 | — | O | H | SOCH$_3$ | CH$_3$ | OCH$_3$ | N |
| H | A-1 | — | O | H | SOCH$_3$ | OCH$_3$ | OCH$_3$ | N |
| H | A-1 | — | O | H | SOCH$_3$ | Cl | OCH$_3$ | CH |
| H | A-1 | — | O | H | SO$_2$CH$_3$ | CH$_3$ | CH$_3$ | CH |
| H | A-1 | — | O | H | SO$_2$CH$_3$ | CH$_3$ | OCH$_3$ | CH |
| H | A-1 | — | O | H | SO$_2$CH$_3$ | OCH$_3$ | OCH$_3$ | CH |
| H | A-1 | — | O | H | SO$_2$CH$_3$ | CH$_3$ | CH$_3$ | N |
| H | A-1 | — | O | H | SO$_2$CH$_3$ | CH$_3$ | OCH$_3$ | N |
| H | A-1 | — | O | H | SO$_2$CH$_3$ | OCH$_3$ | OCH$_3$ | N |
| H | A-1 | — | O | H | SO$_2$CH$_3$ | Cl | OCH$_3$ | CH |
| H | A-1 | — | O | H | SOCH$_2$CH$_3$ | CH$_3$ | CH$_3$ | CH |
| H | A-1 | — | O | H | SOCH$_2$CH$_3$ | CH$_3$ | OCH$_3$ | CH |
| H | A-1 | — | O | H | SOCH$_2$CH$_3$ | OCH$_3$ | OCH$_3$ | CH |
| H | A-1 | — | O | H | SOCH$_2$CH$_3$ | CH$_3$ | CH$_3$ | N |
| H | A-1 | — | O | H | SOCH$_2$CH$_3$ | CH$_3$ | OCH$_3$ | N |
| H | A-1 | — | O | H | SOCH$_2$CH$_3$ | OCH$_3$ | OCH$_3$ | N |
| H | A-1 | — | O | H | SOCH$_2$CH$_3$ | Cl | OCH$_3$ | CH |
| H | A-1 | — | O | H | SO$_2$CH$_2$CH$_3$ | CH$_3$ | CH$_3$ | CH |
| H | A-1 | — | O | H | SO$_2$CH$_2$CH$_3$ | CH$_3$ | OCH$_3$ | CH |
| H | A-1 | — | O | H | SO$_2$CH$_2$CH$_3$ | OCH$_3$ | OCH$_3$ | CH |
| H | A-1 | — | O | H | SO$_2$CH$_2$CH$_3$ | CH$_3$ | CH$_3$ | N |
| H | A-1 | — | O | H | SO$_2$CH$_2$CH$_3$ | CH$_3$ | OCH$_3$ | N |
| H | A-1 | — | O | H | SO$_2$CH$_2$CH$_3$ | OCH$_3$ | OCH$_3$ | N |
| H | A-1 | — | O | H | SO$_2$CH$_2$CH$_3$ | Cl | OCH$_3$ | CH |
| H | A-1 | — | O | H | SOCH$_2$CH$_2$CH$_3$ | CH$_3$ | CH$_3$ | CH |
| H | A-1 | — | O | H | SOCH$_2$CH$_2$CH$_3$ | CH$_3$ | OCH$_3$ | CH |
| H | A-1 | — | O | H | SOCH$_2$CH$_2$CH$_3$ | OCH$_3$ | OCH$_3$ | CH |
| H | A-1 | — | O | H | SOCH$_2$CH$_2$CH$_3$ | CH$_3$ | CH$_3$ | N |
| H | A-1 | — | O | H | SOCH$_2$CH$_2$CH$_3$ | CH$_3$ | OCH$_3$ | N |
| H | A-1 | — | O | H | SOCH$_2$CH$_2$CH$_3$ | OCH$_3$ | OCH$_3$ | N |
| H | A-1 | — | O | H | SOCH$_2$CH$_2$CH$_3$ | Cl | OCH$_3$ | CH |
| H | A-1 | — | O | H | SO$_2$CH$_2$CH$_2$CH$_3$ | CH$_3$ | CH$_3$ | CH |
| H | A-1 | — | O | H | SO$_2$CH$_2$CH$_2$CH$_3$ | CH$_3$ | OCH$_3$ | CH |
| H | A-1 | — | O | H | SO$_2$CH$_2$CH$_2$CH$_3$ | OCH$_3$ | OCH$_3$ | CH |
| H | A-1 | — | O | H | SO$_2$CH$_2$CH$_2$CH$_3$ | CH$_3$ | CH$_3$ | N |
| H | A-1 | — | O | H | SO$_2$CH$_2$CH$_2$CH$_3$ | CH$_3$ | OCH$_3$ | N |
| H | A-1 | — | O | H | SO$_2$CH$_2$CH$_2$CH$_3$ | OCH$_3$ | OCH$_3$ | N |
| H | A-1 | — | O | H | SO$_2$CH$_2$CH$_2$CH$_3$ | Cl | OCH$_3$ | CH |
| H | A-1 | — | O | H | SO$_2$N(CH$_3$)$_2$ | CH$_3$ | CH$_3$ | CH |
| H | A-1 | — | O | H | SO$_2$N(CH$_3$)$_2$ | CH$_3$ | OCH$_3$ | CH |
| H | A-1 | — | O | H | SO$_2$N(CH$_3$)$_2$ | OCH$_3$ | OCH$_3$ | CH |
| H | A-1 | — | O | H | SO$_2$N(CH$_3$)$_2$ | CH$_3$ | CH$_3$ | N |
| H | A-1 | — | O | H | SO$_2$N(CH$_3$)$_2$ | CH$_3$ | OCH$_3$ | N |
| H | A-1 | — | O | H | SO$_2$N(CH$_3$)$_2$ | OCH$_3$ | OCH$_3$ | N |
| H | A-1 | — | O | H | SO$_2$N(CH$_3$)$_2$ | Cl | OCH$_3$ | CH |
| H | A-1 | — | O | H | SO$_2$N(CH$_2$CH$_3$)$_2$ | CH$_3$ | CH$_3$ | CH |
| H | A-1 | — | O | H | SO$_2$N(CH$_2$CH$_3$)$_2$ | CH$_3$ | OCH$_3$ | CH |
| H | A-1 | — | O | H | SO$_2$N(CH$_2$CH$_3$)$_2$ | OCH$_3$ | OCH$_3$ | CH |
| H | A-1 | — | O | H | SO$_2$N(CH$_2$CH$_3$)$_2$ | CH$_3$ | CH$_3$ | N |
| H | A-1 | — | O | H | SO$_2$N(CH$_2$CH$_3$)$_2$ | CH$_3$ | OCH$_3$ | N |
| H | A-1 | — | O | H | SO$_2$N(CH$_2$CH$_3$)$_2$ | OCH$_3$ | OCH$_3$ | N |
| H | A-1 | — | O | H | SO$_2$N(CH$_2$CH$_3$)$_2$ | Cl | OCH$_3$ | CH |
| H | A-1 | — | O | H | SO$_2$N(CH$_3$)CH$_2$CH$_3$ | CH$_3$ | CH$_3$ | CH |
| H | A-1 | — | O | H | SO$_2$N(CH$_3$)CH$_2$CH$_3$ | CH$_3$ | OCH$_3$ | CH |
| H | A-1 | — | O | H | SO$_2$N(CH$_3$)CH$_2$CH$_3$ | OCH$_3$ | OCH$_3$ | CH |
| H | A-1 | — | O | H | SO$_2$N(CH$_3$)CH$_2$CH$_3$ | CH$_3$ | CH$_3$ | N |
| H | A-1 | — | O | H | SO$_2$N(CH$_3$)CH$_2$CH$_3$ | CH$_3$ | OCH$_3$ | N |
| H | A-1 | — | O | H | SO$_2$N(CH$_3$)CH$_2$CH$_3$ | OCH$_3$ | OCH$_3$ | N |
| H | A-1 | — | O | H | SO$_2$N(CH$_3$)CH$_2$CH$_3$ | Cl | OCH$_3$ | CH |
| H | A-1 | — | O | H | SO$_2$NHCH$_3$ | CH$_3$ | CH$_3$ | CH |
| H | A-1 | — | O | H | SO$_2$NHCH$_3$ | CH$_3$ | CH$_3$ | CH |
| H | A-1 | — | O | H | SO$_2$NHCH$_3$ | OCH$_3$ | OCH$_3$ | CH |
| H | A-1 | — | O | H | SO$_2$NHCH$_3$ | CH$_3$ | CH$_3$ | N |
| H | A-1 | — | O | H | SO$_2$NHCH$_3$ | CH$_3$ | OCH$_3$ | N |
| H | A-1 | — | O | H | SO$_2$NHCH$_3$ | OCH$_3$ | OCH$_3$ | N |
| H | A-1 | — | O | H | SO$_2$NHCH$_3$ | Cl | OCH$_3$ | CH |

TABLE II-continued

| | | | | | | | | |
|---|---|---|---|---|---|---|---|---|
| H | A-1 | — | O | H | SO$_2$N(OCH$_3$)CH$_3$ | CH$_3$ | CH$_3$ | CH |
| H | A-1 | — | O | H | SO$_2$N(OCH$_3$)CH$_3$ | CH$_3$ | OCH$_3$ | CH |
| H | A-1 | — | O | H | SO$_2$N(OCH$_3$)CH$_3$ | OCH$_3$ | OCH$_3$ | CH |
| H | A-1 | — | O | H | SO$_2$N(OCH$_3$)CH$_3$ | CH$_3$ | CH$_3$ | N |
| H | A-1 | — | O | H | SO$_2$N(OCH$_3$)CH$_3$ | CH$_3$ | OCH$_3$ | N |
| H | A-1 | — | O | H | SO$_2$N(OCH$_3$)CH$_3$ | OCH$_3$ | OCH$_3$ | N |
| H | A-1 | — | O | H | SO$_2$N(OCH$_3$)CH$_3$ | Cl | OCH$_3$ | CH |
| H | A-1 | — | O | H | CON(CH$_3$)$_2$ | CH$_3$ | CH$_3$ | CH |
| H | A-1 | — | O | H | CON(CH$_3$)$_2$ | CH$_3$ | OCH$_3$ | CH |
| H | A-1 | — | O | H | CON(CH$_3$)$_2$ | OCH$_3$ | OCH$_3$ | CH |
| H | A-1 | — | O | H | CON(CH$_3$)$_2$ | CH$_3$ | CH$_3$ | N |
| H | A-1 | — | O | H | CON(CH$_3$)$_2$ | CH$_3$ | OCH$_3$ | N |
| H | A-1 | — | O | H | CON(CH$_3$)$_2$ | OCH$_3$ | OCH$_3$ | N |
| H | A-1 | — | O | H | CON(CH$_3$)$_2$ | Cl | OCH$_3$ | CH |
| H | A-1 | — | O | H | CONHCH$_3$ | CH$_3$ | CH$_3$ | CH |
| H | A-1 | — | O | H | CONHCH$_3$ | CH$_3$ | OCH$_3$ | CH |
| H | A-1 | — | O | H | CONHCH$_3$ | OCH$_3$ | OCH$_3$ | CH |
| H | A-1 | — | O | H | CONHCH$_3$ | CH$_3$ | CH$_3$ | N |
| H | A-1 | — | O | H | CONHCH$_3$ | CH$_3$ | OCH$_3$ | N |
| H | A-1 | — | O | H | CONHCH$_3$ | OCH$_3$ | OCH$_3$ | N |
| H | A-1 | — | O | H | CONHCH$_3$ | Cl | OCH$_3$ | CH |
| H | A-1 | — | O | H | CONHCH$_2$CH$_3$ | CH$_3$ | CH$_3$ | CH |
| H | A-1 | — | O | H | CON(CH$_2$CH$_3$)$_2$ | CH$_3$ | OCH$_3$ | CH |
| H | A-1 | — | O | H | CON(CH$_2$CH$_3$)$_2$ | OCH$_3$ | OCH$_3$ | CH |
| H | A-1 | — | O | H | CON(CH$_2$CH$_3$)$_2$ | CH$_3$ | CH$_3$ | N |
| H | A-1 | — | O | H | CON(CH$_2$CH$_3$)$_2$ | CH$_3$ | OCH$_3$ | N |
| H | A-1 | — | O | H | CON(CH$_2$CH$_3$)$_2$ | OCH$_3$ | OCH$_3$ | N |
| H | A-1 | — | O | H | CON(CH$_2$CH$_3$)$_2$ | Cl | OCH$_3$ | CH |
| H | A-1 | — | O | H | 3,5-dimethyl-1,2,4-oxadiazol-2-yl | CH$_3$ | CH$_3$ | CH |
| H | A-1 | — | O | H | 3,5-dimethyl-1,2,4-oxadiazol-2-yl | CH$_3$ | OCH$_3$ | CH |
| H | A-1 | — | O | H | 3,5-dimethyl-1,2,4-oxadiazol-2-yl | OCH$_3$ | OCH$_3$ | CH |
| H | A-1 | — | O | H | 3,5-dimethyl-1,2,4-oxadiazol-2-yl | CH$_3$ | CH$_3$ | N |
| H | A-1 | — | O | H | 3,5-dimethyl-1,2,4-oxadiazol-2-yl | CH$_3$ | OCH$_3$ | N |
| H | A-1 | — | O | H | 3,5-dimethyl-1,2,4-oxadiazol-2-yl | OCH$_3$ | OCH$_3$ | N |
| H | A-1 | — | O | H | 3,5-dimethyl-1,2,4-oxadiazol-2-yl | Cl | OCH$_3$ | CH |
| H | A-1 | — | O | H | 1-methylpyrazol-3-yl | CH$_3$ | CH$_3$ | CH |
| H | A-1 | — | O | H | 1-methylpyrazol-3-yl | CH$_3$ | OCH$_3$ | CH |

TABLE II-continued

| | | | | | Het | | | |
|---|---|---|---|---|---|---|---|---|
| H | A-1 | — | O | H | 3-methyl-1-methylpyrazol-5-yl | OCH₃ | OCH₃ | CH |
| H | A-1 | — | O | H | 3-methyl-1-methylpyrazol-5-yl | CH₃ | CH₃ | N |
| H | A-1 | — | O | H | 3-methyl-1-methylpyrazol-5-yl | CH₃ | OCH₃ | N |
| H | A-1 | — | O | H | 3-methyl-1-methylpyrazol-5-yl | OCH₃ | OCH₃ | N |
| H | A-1 | — | O | H | 3-methyl-1-methylpyrazol-5-yl | Cl | | CH |
| H | A-1 | — | O | H | 2-thienyl | CH₃ | CH₃ | CH |
| H | A-1 | — | O | H | 2-thienyl | CH₃ | OCH₃ | CH |
| H | A-1 | — | O | H | 2-thienyl | OCH₃ | OCH₃ | CH |
| H | A-1 | — | O | H | 2-thienyl | CH₃ | CH₃ | N |
| H | A-1 | — | O | H | 2-thienyl | CH₃ | OCH₃ | N |
| H | A-1 | — | O | H | 2-thienyl | OCH₃ | OCH₃ | N |
| H | A-1 | — | O | H | 2-thienyl | Cl | OCH₃ | CH |
| H | A-1 | — | O | H | 2-methyl-2H-tetrazol-5-yl | CH₃ | CH₃ | CH |
| H | A-1 | — | O | H | 2-methyl-2H-tetrazol-5-yl | CH₃ | OCH₃ | CH |

TABLE II-continued

| | | | | | | | | |
|---|---|---|---|---|---|---|---|---|
| H | A-1 | — | O | H | N—N—CH₃ tetrazole (N1-CH₃) | OCH₃ | OCH₃ | CH |
| H | A-1 | — | O | H | N—N—CH₃ tetrazole (N1-CH₃) | CH₃ | CH₃ | N |
| H | A-1 | — | O | H | N—N—CH₃ tetrazole (N1-CH₃) | CH₃ | OCH₃ | N |
| H | A-1 | — | O | H | N—N—CH₃ tetrazole (N1-CH₃) | OCH₃ | OCH₃ | N |
| H | A-1 | — | O | H | N—N—CH₃ tetrazole (N1-CH₃) | Cl | OCH₃ | CH |
| H | A-1 | — | O | H | N=N, N—CH₃ tetrazole (N2-CH₃) | CH₃ | CH₃ | CH |
| H | A-1 | — | O | H | N=N, N—CH₃ tetrazole (N2-CH₃) | CH₃ | OCH₃ | CH |
| H | A-1 | — | O | H | N=N, N—CH₃ tetrazole (N2-CH₃) | OCH₃ | OCH₃ | CH |
| H | A-1 | — | O | H | N=N, N—CH₃ tetrazole (N2-CH₃) | CH₃ | CH₃ | N |
| H | A-1 | — | O | H | N=N, N—CH₃ tetrazole (N2-CH₃) | CH₃ | OCH₃ | N |
| H | A-1 | — | O | H | N=N, N—CH₃ tetrazole (N2-CH₃) | OCH₃ | OCH₃ | N |
| H | A-1 | — | O | H | N=N, N—CH₂ tetrazole | Cl | OCH₃ | CH |
| H | A-1 | — | O | H | CH(O—CH₂—CH₂—O) dioxolane | CH₃ | CH₃ | CH |

| | | | | | | | | |
|---|---|---|---|---|---|---|---|---|
| H | A-1 | — | O | H | 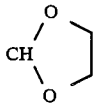 | CH₃ | OCH₃ | CH |
| H | A-1 | — | O | H | 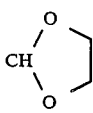 | OCH₃ | OCH₃ | CH |
| H | A-1 | — | O | H | 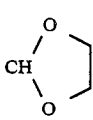 | CH₃ | CH₃ | N |
| H | A-1 | — | O | H | 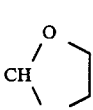 | CH₃ | OCH₃ | N |
| H | A-1 | — | O | H | 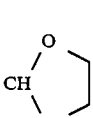 | OCH₃ | OCH₃ | N |
| H | A-1 | — | O | H | 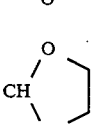 | Cl | OCH₃ | CH |
| H | A-1 | — | O | H | 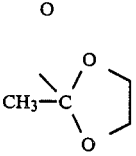 | CH₃ | CH₃ | CH |
| H | A-1 | — | O | H | 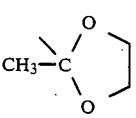 | CH₃ | OCH₃ | CH |
| H | A-1 | — | O | H | 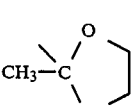 | OCH₃ | OCH₃ | CH |
| H | A-1 | — | O | H | 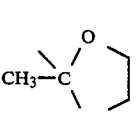 | CH₃ | CH₃ | N |
| H | A-1 | — | O | H | 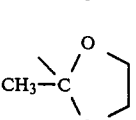 | CH₃ | OCH₃ | N |
| H | A-1 | — | O | H | 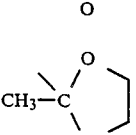 | OCH₃ | OCH₃ | N |
| H | A-1 | — | O | H | 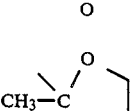 | Cl | OCH₃ | CH |

TABLE II-continued

| | | | | | | | | |
|---|---|---|---|---|---|---|---|---|
| H | A-1 | — | O | H | 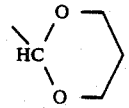 | CH₃ | CH₃ | CH |
| H | A-1 | — | O | H | 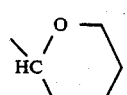 | CH₃ | OCH₃ | CH |
| H | A-1 | — | O | H | 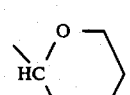 | OCH₃ | OCH₃ | CH |
| H | A-1 | — | O | H | 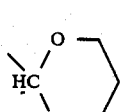 | CH₃ | CH₃ | N |
| H | A-1 | — | O | H | 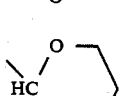 | CH₃ | OCH₃ | N |
| H | A-1 | — | O | H | 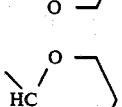 | OCH₃ | OCH₃ | N |
| H | A-1 | — | O | H | 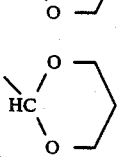 | Cl | OCH₃ | CH |
| CH₃ | A-1 | — | O | H | CH₃ | CH₃ | CH₃ | CH |
| CH₃ | A-1 | — | O | H | CH₃ | CH₃ | OCH₃ | CH |
| CH₃ | A-1 | — | O | H | CH₃ | OCH₃ | OCH₃ | CH |
| CH₃ | A-1 | — | O | H | CH₃ | CH₃ | CH₃ | N |
| CH₃ | A-1 | — | O | H | CH₂CH₃ | CH₃ | OCH₃ | N |
| CH₃ | A-1 | — | O | H | CH₂CH₃ | OCH₃ | OCH₃ | N |
| CH₃ | A-1 | — | O | H | CH₂CH₃ | Cl | OCH₃ | CH |
| CH₃ | A-1 | — | O | H | CH(CH₃)₂ | CH₃ | CH₃ | CH |
| CH₃ | A-1 | — | O | H | CH(CH₃)₂ | CH₃ | OCH₃ | CH |
| CH₃ | A-1 | — | O | H | CH(CH₃)₂ | OCH₃ | OCH₃ | CH |
| CH₃ | A-1 | — | O | H | CH(CH₃)₂ | CH₃ | CH₃ | N |
| CH₃ | A-1 | — | O | H | CH(CH₃)₂ | CH₃ | OCH₃ | N |
| CH₃ | A-1 | — | O | H | CH(CH₃)₂ | OCH₃ | OCH₃ | N |
| CH₃ | A-1 | — | O | H | CH(CH₃)₂ | Cl | OCH₃ | CH |
| CH₃ | A-1 | — | O | H | CH₂CH₂CH₃ | CH₃ | CH₃ | CH |
| CH₃ | A-1 | — | O | H | CH₂CH₂CH₃ | CH₃ | OCH₃ | CH |
| CH₃ | A-1 | — | O | H | CH(CH₃)CH₂CH₃ | OCH₃ | OCH₃ | CH |
| CH₃ | A-1 | — | O | H | CH(CH₃)CH₂CH₃ | CH₃ | CH₃ | N |
| CH₃ | A-1 | — | O | H | CH₂CH(CH₃)₂ | CH₃ | OCH₃ | N |
| CH₃ | A-1 | — | O | H | CH₂CH(CH₃)₂ | OCH₃ | OCH₃ | N |
| CH₃ | A-1 | — | O | H | CH₂CH(CH₃)₂ | Cl | OCH₃ | CH |
| CH₃ | A-1 | — | O | H | cyclopropyl | CH₃ | CH₃ | CH |
| CH₃ | A-1 | — | O | H | cyclopropyl | CH₃ | OCH₃ | CH |
| CH₃ | A-1 | — | O | H | cyclopropyl | OCH₃ | OCH₃ | CH |
| CH₃ | A-1 | — | O | H | cyclopropyl | CH₃ | CH₃ | N |
| CH₃ | A-1 | — | O | H | cyclopropyl | CH₃ | OCH₃ | N |
| CH₃ | A-1 | — | O | H | cyclopropyl | OCH₃ | OCH₃ | N |
| CH₃ | A-1 | — | O | H | cyclopropyl | Cl | OCH₃ | CH |
| CH₃ | A-1 | — | O | H | CH—CF₂—CH₂ | CH₃ | CH₃ | CH |
| CH₃ | A-1 | — | O | H | CH—CF₂—CH₂ | CH₃ | OCH₃ | CH |

TABLE II-continued

| | | | | | | | | |
|---|---|---|---|---|---|---|---|---|
| CH₃ | A-1 | — | O | H | CH—CF₂—CH₂ | OCH₃ | OCH₃ | CH |
| CH₃ | A-1 | — | O | H | CH—CF₂—CH₂ | CH₃ | CH₃ | N |
| CH₃ | A-1 | — | O | H | CH—CF₂—CH₂ | CH₃ | OCH₃ | N |
| CH₃ | A-1 | — | O | H | CH—CF₂—CH₂ | OCH₃ | OCH₃ | N |
| CH₃ | A-1 | — | O | H | CH—CF₂—CH₂ | Cl | OCH₃ | CH |
| CH₃ | A-1 | — | O | H | CH—CHF—CH₂ | CH₃ | CH₃ | CH |
| CH₃ | A-1 | — | O | H | CH—CHF—CH₂ | CH₃ | OCH₃ | CH |
| CH₃ | A-1 | — | O | H | CH—CHF—CH₂ | OCH₃ | OCH₃ | CH |
| CH₃ | A-1 | — | O | H | CH—CHF—CH₂ | CH₃ | CH₃ | N |
| CH₃ | A-1 | — | O | H | CH—CHF—CH₂ | CH₃ | OCH₃ | N |
| CH₃ | A-1 | — | O | H | CH—CHF—CH₂ | OCH₃ | OCH₃ | N |
| CH₃ | A-1 | — | O | H | CH—CHF—CH₂ | Cl | OCH₃ | CH |
| CH₃ | A-1 | — | O | H | CH—CHCl—CH₂ | CH₃ | CH₃ | CH |
| CH₃ | A-1 | — | O | H | CH—CHCl—CH₂ | CH₃ | OCH₃ | CH |
| CH₃ | A-1 | — | O | H | CH—CHCl—CH₂ | OCH₃ | OCH₃ | CH |
| CH₃ | A-1 | — | O | H | CH—CHCl—CH₂ | CH₃ | CH₃ | N |
| CH₃ | A-1 | — | O | H | CH—CHCl—CH₂ | CH₃ | OCH₃ | N |
| CH₃ | A-1 | — | O | H | CH—CHCl—CH₂ | OCH₃ | OCH₃ | N |
| CH₃ | A-1 | — | O | H | CH—CHCl—CH₂ | Cl | OCH₃ | CH |
| CH₃ | A-1 | — | O | H | OCH₂CH₂Cl | CH₃ | CH₃ | CH |
| CH₃ | A-1 | — | O | H | OCH₂CH₂Cl | CH₃ | OCH₃ | CH |
| CH₃ | A-1 | — | O | H | OCH₂CH₂Cl | OCH₃ | OCH₃ | CH |
| CH₃ | A-1 | — | O | H | OCH₂CH₂Cl | CH₃ | CH₃ | N |
| CH₃ | A-1 | — | O | H | OCH₂CH₂Cl | CH₃ | OCH₃ | N |
| CH₃ | A-1 | — | O | H | OCH₂CH₂Cl | OCH₃ | OCH₃ | N |
| CH₃ | A-1 | — | O | H | OCH₂CH₂Cl | Cl | OCH₃ | CH |
| CH₃ | A-1 | — | O | H | OCH₂CH₂F | CH₃ | CH₃ | CH |
| CH₃ | A-1 | — | O | H | OCH₂CH₂F | CH₃ | OCH₃ | CH |

TABLE II-continued

| | | | | | | | | |
|---|---|---|---|---|---|---|---|---|
| CH$_3$ | A-1 | — | O | H | OCH$_2$CH$_2$F | OCH$_3$ | OCH$_3$ | CH |
| CH$_3$ | A-1 | — | O | H | OCH$_2$CH$_2$F | CH$_3$ | CH$_3$ | N |
| CH$_3$ | A-1 | — | O | H | OCH$_2$CH$_2$F | CH$_3$ | OCH$_3$ | N |
| CH$_3$ | A-1 | — | O | H | OCH$_2$CH$_2$F | OCH$_3$ | OCH$_3$ | N |
| CH$_3$ | A-1 | — | O | H | OCH$_2$CH$_2$F | Cl | OCH$_3$ | CH |
| CH$_3$ | A-1 | — | O | H | OCH$_2$CF$_3$ | CH$_3$ | CH$_3$ | CH |
| CH$_3$ | A-1 | — | O | H | OCH$_2$CF$_3$ | CH$_3$ | OCH$_3$ | CH |
| CH$_3$ | A-1 | — | O | H | OCH$_2$CF$_3$ | OCH$_3$ | OCH$_3$ | CH |
| CH$_3$ | A-1 | — | O | H | OCH$_2$CF$_3$ | CH$_3$ | CH$_3$ | N |
| CH$_3$ | A-1 | — | O | H | OCH$_2$CF$_3$ | CH$_3$ | OCH$_3$ | N |
| CH$_3$ | A-1 | — | O | H | OCH$_2$CF$_3$ | OCH$_3$ | OCH$_3$ | N |
| CH$_3$ | A-1 | — | O | H | OCH$_2$CF$_3$ | Cl | OCH$_3$ | CH |
| CH$_3$ | A-1 | — | O | H | OCF$_2$CH$_3$ | CH$_3$ | CH$_3$ | CH |
| CH$_3$ | A-1 | — | O | H | OCF$_2$CH$_3$ | CH$_3$ | OCH$_3$ | CH |
| CH$_3$ | A-1 | — | O | H | OCF$_2$CH$_3$ | OCH$_3$ | OCH$_3$ | CH |
| CH$_3$ | A-1 | — | O | H | OCF$_2$CH$_3$ | CH$_3$ | CH$_3$ | N |
| CH$_3$ | A-1 | — | O | H | OCF$_2$CH$_3$ | CH$_3$ | OCH$_3$ | N |
| CH$_3$ | A-1 | — | O | H | OCF$_2$CH$_3$ | OCH$_3$ | OCH$_3$ | N |
| CH$_3$ | A-1 | — | O | H | OCF$_2$CH$_3$ | Cl | OCH$_3$ | CH |
| CH$_3$ | A-1 | — | O | H | NO$_2$ | CH$_3$ | CH$_3$ | CH |
| CH$_3$ | A-1 | — | O | H | NO$_2$ | CH$_3$ | OCH$_3$ | CH |
| CH$_3$ | A-1 | — | O | H | NO$_2$ | OCH$_3$ | OCH$_3$ | CH |
| CH$_3$ | A-1 | — | O | H | NO$_2$ | CH$_3$ | CH$_3$ | N |
| CH$_3$ | A-1 | — | O | H | NO$_2$ | CH$_3$ | OCH$_3$ | N |
| CH$_3$ | A-1 | — | O | H | NO$_2$ | OCH$_3$ | OCH$_3$ | N |
| CH$_3$ | A-1 | — | O | H | NO$_2$ | Cl | OCH$_3$ | CH |
| CH$_3$ | A-1 | — | O | H | CO$_2$CH$_3$ | CH$_3$ | CH$_3$ | CH |
| CH$_3$ | A-1 | — | O | H | CO$_2$CH$_3$ | CH$_3$ | OCH$_3$ | CH |
| CH$_3$ | A-1 | — | O | H | CO$_2$CH$_3$ | OCH$_3$ | OCH$_3$ | CH |
| CH$_3$ | A-1 | — | O | H | CO$_2$CH$_3$ | CH$_3$ | CH$_3$ | N |
| CH$_3$ | A-1 | — | O | H | CO$_2$CH$_3$ | CH$_3$ | OCH$_3$ | N |
| CH$_3$ | A-1 | — | O | H | CO$_2$CH$_3$ | OCH$_3$ | OCH$_3$ | N |
| CH$_3$ | A-1 | — | O | H | CO$_2$CH$_3$ | Cl | OCH$_3$ | CH |
| CH$_3$ | A-1 | — | O | H | CO$_2$CH$_2$CH$_3$ | CH$_3$ | CH$_3$ | CH |
| CH$_3$ | A-1 | — | O | H | CO$_2$CH$_2$CH$_3$ | CH$_3$ | OCH$_3$ | CH |
| CH$_3$ | A-1 | — | O | H | CO$_2$CH$_2$CH$_3$ | OCH$_3$ | OCH$_3$ | CH |
| CH$_3$ | A-1 | — | O | H | CO$_2$CH$_2$CH$_3$ | CH$_3$ | CH$_3$ | N |
| CH$_3$ | A-1 | — | O | H | CO$_2$CH$_2$CH$_3$ | CH$_3$ | OCH$_3$ | N |
| CH$_3$ | A-1 | — | O | H | CO$_2$CH$_2$CH$_3$ | OCH$_3$ | OCH$_3$ | N |
| CH$_3$ | A-1 | — | O | H | CO$_2$CH$_2$CH$_3$ | Cl | OCH$_3$ | CH |
| CH$_3$ | A-1 | — | O | H | CO$_2$CH$_2$CH$_2$CH$_3$ | CH$_3$ | CH$_3$ | CH |
| CH$_3$ | A-1 | — | O | H | CO$_2$CH$_2$CH$_2$CH$_3$ | CH$_3$ | OCH$_3$ | CH |
| CH$_3$ | A-1 | — | O | H | CO$_2$CH$_2$CH$_2$CH$_3$ | OCH$_3$ | OCH$_3$ | CH |
| CH$_3$ | A-1 | — | O | H | CO$_2$CH$_2$CH$_2$CH$_3$ | CH$_3$ | CH$_3$ | N |
| CH$_3$ | A-1 | — | O | H | CO$_2$CH$_2$CH$_2$CH$_3$ | CH$_3$ | OCH$_3$ | N |
| CH$_3$ | A-1 | — | O | H | CO$_2$CH$_2$CH$_2$CH$_3$ | OCH$_3$ | OCH$_3$ | N |
| CH$_3$ | A-1 | — | O | H | CO$_2$CH$_2$CH$_2$CH$_3$ | Cl | OCH$_3$ | CH |
| CH$_3$ | A-1 | — | O | H | CO$_2$CH$_2$CH$_2$OCH$_3$ | CH$_3$ | CH$_3$ | CH |
| CH$_3$ | A-1 | — | O | H | CO$_2$CH$_2$CH$_2$OCH$_3$ | CH$_3$ | OCH$_3$ | CH |
| CH$_3$ | A-1 | — | O | H | CO$_2$CH$_2$CH$_2$OCH$_3$ | OCH$_3$ | OCH$_3$ | CH |
| CH$_3$ | A-1 | — | O | H | CO$_2$CH$_2$CH$_2$OCH$_3$ | CH$_3$ | CH$_3$ | N |
| CH$_3$ | A-1 | — | O | H | CO$_2$CH$_2$CH$_2$OCH$_3$ | CH$_3$ | OCH$_3$ | N |
| CH$_3$ | A-1 | — | O | H | CO$_2$CH$_2$CH$_2$OCH$_3$ | OCH$_3$ | OCH$_3$ | N |
| CH$_3$ | A-1 | — | O | H | CO$_2$CH$_2$CH$_2$OCH$_3$ | Cl | OCH$_3$ | CH |
| CH$_3$ | A-1 | — | O | H | CO$_2$CH$_2$CH=CH$_2$ | CH$_3$ | CH$_3$ | CH |
| CH$_3$ | A-1 | — | O | H | CO$_2$CH$_2$CH=CH$_2$ | CH$_3$ | OCH$_3$ | CH |
| CH$_3$ | A-1 | — | O | H | CO$_2$CH$_2$CH=CH$_2$ | OCH$_3$ | OCH$_3$ | CH |
| CH$_3$ | A-1 | — | O | H | CO$_2$CH$_2$CH=CH$_2$ | CH$_3$ | CH$_3$ | N |
| CH$_3$ | A-1 | — | O | H | CO$_2$CH$_2$CH=CH$_2$ | CH$_3$ | OCH$_3$ | N |
| CH$_3$ | A-1 | — | O | H | CO$_2$CH$_2$CH=CH$_2$ | OCH$_3$ | OCH$_3$ | N |
| CH$_3$ | A-1 | — | O | H | CO$_2$CH$_2$CH=CH$_2$ | Cl | OCH$_3$ | CH |
| CH$_3$ | A-1 | — | O | H | CO$_2$CH$_2$—C≡CH | CH$_3$ | CH$_3$ | CH |
| CH$_3$ | A-1 | — | O | H | CO$_2$CH$_2$—C≡CH | CH$_3$ | OCH$_3$ | CH |
| CH$_3$ | A-1 | — | O | H | CO$_2$CH$_2$—C≡CH | OCH$_3$ | OCH$_3$ | CH |
| CH$_3$ | A-1 | — | O | H | CO$_2$CH$_2$—C≡CH | CH$_3$ | CH$_3$ | N |
| CH$_3$ | A-1 | — | O | H | CO$_2$CH$_2$—C≡CH | CH$_3$ | OCH$_3$ | N |
| CH$_3$ | A-1 | — | O | H | CO$_2$CH$_2$—C≡CH | OCH$_3$ | OCH$_3$ | N |
| CH$_3$ | A-1 | — | O | H | CO$_2$CH$_2$—C≡CH | Cl | OCH$_3$ | CH |
| CH$_3$ | A-1 | — | O | H | N(CH$_3$)$_2$ | CH$_3$ | CH$_3$ | CH |
| CH$_3$ | A-1 | — | O | H | N(CH$_3$)$_2$ | CH$_3$ | OCH$_3$ | CH |
| CH$_3$ | A-1 | — | O | H | N(CH$_3$)$_2$ | OCH$_3$ | OCH$_3$ | CH |
| CH$_3$ | A-1 | — | O | H | N(CH$_3$)$_2$ | CH$_3$ | CH$_3$ | N |
| CH$_3$ | A-1 | — | O | H | N(CH$_3$)$_2$ | CH$_3$ | OCH$_3$ | N |
| CH$_3$ | A-1 | — | O | H | N(CH$_3$)$_2$ | OCH$_3$ | OCH$_3$ | N |
| CH$_3$ | A-1 | — | O | H | N(CH$_3$)$_2$ | Cl | OCH$_3$ | CH |
| H | A-1 | — | O | 5-F | CH$_3$ | CH$_3$ | CH$_3$ | CH |
| H | A-1 | — | O | 5-F | CH$_3$ | CH$_3$ | OCH$_3$ | CH |
| H | A-1 | — | O | 5-F | CH$_3$ | OCH$_3$ | OCH$_3$ | CH |
| H | A-1 | — | O | 5-F | CH$_3$ | CH$_3$ | CH$_3$ | N |
| H | A-1 | — | O | 5-F | CH$_3$ | CH$_3$ | OCH$_3$ | N |
| H | A-1 | — | O | 5-F | CH$_3$ | OCH$_3$ | OCH$_3$ | N |
| H | A-1 | — | O | 5-F | CH$_3$ | Cl | OCH$_3$ | CH |

TABLE II-continued

| | | | | | | | | |
|---|---|---|---|---|---|---|---|---|
| H | A-1 | — | O | 5-F | CH₂CH₃ | CH₃ | CH₃ | CH |
| H | A-1 | — | O | 5-F | CH₂CH₃ | CH₃ | OCH₃ | CH |
| H | A-1 | — | O | 5-F | CH₂CH₃ | OCH₃ | OCH₃ | CH |
| H | A-1 | — | O | 5-F | CH₂CH₃ | CH₃ | CH₃ | N |
| H | A-1 | — | O | 5-F | CH₂CH₃ | CH₃ | OCH₃ | N |
| H | A-1 | — | O | 5-F | CH₂CH₃ | OCH₃ | OCH₃ | N |
| H | A-1 | — | O | 5-F | CH₂CH₃ | Cl | OCH₃ | CH |
| H | A-1 | — | O | 5-F | CH(CH₃)₂ | CH₃ | CH₃ | CH |
| H | A-1 | — | O | 5-F | CH(CH₃)₂ | CH₃ | OCH₃ | CH |
| H | A-1 | — | O | 5-F | CH(CH₃)₂ | OCH₃ | OCH₃ | CH |
| H | A-1 | — | O | 5-F | CH(CH₃)₂ | CH₃ | CH₃ | N |
| H | A-1 | — | O | 5-F | CH(CH₃)₂ | CH₃ | OCH₃ | N |
| H | A-1 | — | O | 5-F | CH(CH₃)₂ | OCH₃ | OCH₃ | N |
| H | A-1 | — | O | 5-F | CH(CH₃)₂ | Cl | OCH₃ | CH |
| H | A-1 | — | O | 5-F | CH₂CH₂CH₃ | CH₃ | CH₃ | CH |
| H | A-1 | — | O | 5-F | CH₂CH₂CH₃ | CH₃ | OCH₃ | CH |
| H | A-1 | — | O | 5-F | CH(CH₃)CH₂CH₃ | OCH₃ | OCH₃ | CH |
| H | A-1 | — | O | 5-F | CH(CH₃)CH₂CH₃ | CH₃ | CH₃ | N |
| H | A-1 | — | O | 5-F | CH₂CH(CH₃)₂ | CH₃ | OCH₃ | N |
| H | A-1 | — | O | 5-F | CH₂CH(CH₃)₂ | OCH₃ | OCH₃ | N |
| H | A-1 | — | O | 5-F | CH₂CH(CH₃)₂ | Cl | OCH₃ | CH |
| H | A-1 | — | O | 5-Cl | cyclopropyl | CH₃ | CH₃ | CH |
| H | A-1 | — | O | 5-Cl | cyclopropyl | CH₃ | OCH₃ | CH |
| H | A-1 | — | O | 5-Cl | cyclopropyl | OCH₃ | OCH₃ | CH |
| H | A-1 | — | O | 5-Cl | cyclopropyl | CH₃ | CH₃ | N |
| H | A-1 | — | O | 5-Cl | cyclopropyl | CH₃ | OCH₃ | N |
| H | A-1 | — | O | 5-Cl | cyclopropyl | OCH₃ | OCH₃ | N |
| H | A-1 | — | O | 5-Cl | cyclopropyl | Cl | OCH₃ | CH |
| H | A-1 | — | O | 5-Cl | CH—CF₂—CH₂ (ring) | CH₃ | CH₃ | CH |
| H | A-1 | — | O | 5-Cl | CH—CF₂—CH₂ (ring) | CH₃ | OCH₃ | CH |
| H | A-1 | — | O | 5-Cl | CH—CF₂—CH₂ (ring) | OCH₃ | OCH₃ | CH |
| H | A-1 | — | O | 5-Cl | CH—CF₂—CH₂ (ring) | CH₃ | CH₃ | N |
| H | A-1 | — | O | 5-Cl | CH—CF₂—CH₂ (ring) | CH₃ | OCH₃ | N |
| H | A-1 | — | O | 5-Cl | CH—CF₂—CH₂ (ring) | OCH₃ | OCH₃ | N |
| H | A-1 | — | O | 5-Cl | CH—CF₂—CH₂ (ring) | Cl | OCH₃ | CH |
| H | A-1 | — | O | 5-Cl | CH—CHF—CH₂ (ring) | CH₃ | CH₃ | CH |
| H | A-1 | — | O | 5-Cl | CH—CHF—CH₂ (ring) | CH₃ | OCH₃ | CH |
| H | A-1 | — | O | 5-Cl | CH—CHF—CH₂ (ring) | OCH₃ | OCH₃ | CH |
| H | A-1 | — | O | 5-Cl | CH—CHF—CH₂ (ring) | CH₃ | CH₃ | N |
| H | A-1 | — | O | 5-Cl | CH—CHF—CH₂ (ring) | CH₃ | OCH₃ | N |
| H | A-1 | — | O | 5-Cl | CH—CHF—CH₂ (ring) | OCH₃ | OCH₃ | N |
| H | A-1 | — | O | 5-Cl | CH—CHF—CH₂ (ring) | Cl | OCH₃ | CH |

TABLE II-continued

| | | | | | | | | |
|---|---|---|---|---|---|---|---|---|
| H | A-1 | — | O | 5-Cl | CH—CHCl—CH$_2$ | CH$_3$ | CH$_3$ | CH |
| H | A-1 | — | O | 5-Cl | CH—CHCl—CH$_2$ | CH$_3$ | OCH$_3$ | CH |
| H | A-1 | — | O | 5-Cl | CH—CHCl—CH$_2$ | OCH$_3$ | OCH$_3$ | CH |
| H | A-1 | — | O | 5-Cl | CH—CHCl—CH$_2$ | CH$_3$ | CH$_3$ | N |
| H | A-1 | — | O | 5-Cl | CH—CHCl—CH$_2$ | CH$_3$ | OCH$_3$ | N |
| H | A-1 | — | O | 5-Cl | CH—CHCl—CH$_2$ | OCH$_3$ | OCH$_3$ | N |
| H | A-1 | — | O | 5-Cl | CH—CHCl—CH$_2$ | Cl | OCH$_3$ | CH |
| H | A-1 | — | O | 5-CH$_3$ | OCH$_2$CH$_2$CH$_2$F | CH$_3$ | CH$_3$ | CH |
| H | A-1 | — | O | 5-CH$_3$ | OCH$_2$CH$_2$CH$_2$F | CH$_3$ | OCH$_3$ | CH |
| H | A-1 | — | O | 5-CH$_3$ | OCH$_2$CH$_2$CH$_2$F | OCH$_3$ | OCH$_3$ | CH |
| H | A-1 | — | O | 5-CH$_3$ | OCH$_2$CH$_2$CH$_2$F | CH$_3$ | CH$_3$ | N |
| H | A-1 | — | O | 5-CH$_3$ | OCH$_2$CH$_2$CH$_2$F | CH$_3$ | OCH$_3$ | N |
| H | A-1 | — | O | 5-CH$_3$ | OCH$_2$CH$_2$CH$_2$F | OCH$_3$ | OCH$_3$ | N |
| H | A-1 | — | O | 5-CH$_3$ | OCH$_2$CH$_2$CH$_2$F | Cl | OCH$_3$ | CH |
| H | A-1 | — | O | 5-CH$_3$ | OCH$_2$CH$_2$Cl | CH$_3$ | CH$_3$ | CH |
| H | A-1 | — | O | 5-CH$_3$ | OCH$_2$CH$_2$Cl | CH$_3$ | OCH$_3$ | CH |
| H | A-1 | — | O | 5-CH$_3$ | OCH$_2$CH$_2$Cl | OCH$_3$ | OCH$_3$ | CH |
| H | A-1 | — | O | 5-CH$_3$ | OCH$_2$CH$_2$Br | CH$_3$ | CH$_3$ | N |
| H | A-1 | — | O | 5-CH$_3$ | OCH$_2$CH$_2$Br | CH$_3$ | OCH$_3$ | N |
| H | A-1 | — | O | 5-CH$_3$ | OCH$_2$CH$_2$Br | OCH$_3$ | OCH$_3$ | N |
| H | A-1 | — | O | 5-CH$_3$ | OCH$_2$CH$_2$Br | Cl | OCH$_3$ | CH |
| H | A-1 | — | O | 5-CH$_3$ | OCH$_2$—C≡CH | CH$_3$ | CH$_3$ | CH |
| H | A-1 | — | O | 5-CH$_3$ | OCH$_2$—C≡CH | CH$_3$ | OCH$_3$ | CH |
| H | A-1 | — | O | 5-CH$_3$ | OCH$_2$—C≡CH | OCH$_3$ | OCH$_3$ | CH |
| H | A-1 | — | O | 5-CH$_3$ | OCH$_2$—C≡CH | CH$_3$ | CH$_3$ | N |
| H | A-1 | — | O | 5-CH$_3$ | OCH$_2$—C≡CH | CH$_3$ | OCH$_3$ | N |
| H | A-1 | — | O | 5-CH$_3$ | OCH$_2$—C≡CH | OCH$_3$ | OCH$_3$ | N |
| H | A-1 | — | O | 5-CH$_3$ | OCH$_2$—C≡CH | Cl | OCH$_3$ | CH |
| H | A-1 | — | O | 5-CH$_3$ | OCH$_2$—CH=CH$_2$ | CH$_3$ | CH$_3$ | CH |
| H | A-1 | — | O | 5-CH$_3$ | OCH$_2$—CH=CH$_2$ | CH$_3$ | OCH$_3$ | CH |
| H | A-1 | — | O | 5-CH$_3$ | OCH$_2$—CH=CH$_2$ | OCH$_3$ | OCH$_3$ | CH |
| H | A-1 | — | O | 5-CH$_3$ | OCH$_2$—CH=CH$_2$ | CH$_3$ | CH$_3$ | N |
| H | A-1 | — | O | 5-CH$_3$ | OCH$_2$—CH=CH$_2$ | CH$_3$ | OCH$_3$ | N |
| H | A-1 | — | O | 5-CH$_3$ | OCH$_2$—CH=CH$_2$ | OCH$_3$ | OCH$_3$ | N |
| H | A-1 | — | O | 5-CH$_3$ | OCH$_2$—CH=CH$_2$ | Cl | OCH$_3$ | CH |
| H | A-1 | — | O | 5-OCH$_3$ | NO$_2$ | CH$_3$ | CH$_3$ | CH |
| H | A-1 | — | O | 5-OCH$_3$ | NO$_2$ | CH$_3$ | OCH$_3$ | CH |
| H | A-1 | — | O | 5-OCH$_3$ | NO$_2$ | OCH$_3$ | OCH$_3$ | CH |
| H | A-1 | — | O | 5-OCH$_3$ | NO$_2$ | CH$_3$ | CH$_3$ | N |
| H | A-1 | — | O | 5-OCH$_3$ | NO$_2$ | CH$_3$ | OCH$_3$ | N |
| H | A-1 | — | O | 5-OCH$_3$ | NO$_2$ | OCH$_3$ | OCH$_3$ | N |
| H | A-1 | — | O | 5-OCH$_3$ | NO$_2$ | Cl | OCH$_3$ | CH |
| H | A-1 | — | O | 5-OCH$_3$ | CO$_2$CH$_3$ | CH$_3$ | CH$_3$ | CH |
| H | A-1 | — | O | 5-OCH$_3$ | CO$_2$CH$_3$ | CH$_3$ | OCH$_3$ | CH |
| H | A-1 | — | O | 5-OCH$_3$ | CO$_2$CH$_3$ | OCH$_3$ | OCH$_3$ | CH |
| H | A-1 | — | O | 5-OCH$_3$ | CO$_2$CH$_3$ | CH$_3$ | CH$_3$ | N |
| H | A-1 | — | O | 5-OCH$_3$ | CO$_2$CH$_3$ | CH$_3$ | OCH$_3$ | N |
| H | A-1 | — | O | 5-OCH$_3$ | CO$_2$CH$_3$ | OCH$_3$ | OCH$_3$ | N |
| H | A-1 | — | O | 5-OCH$_3$ | CO$_2$CH$_3$ | Cl | OCH$_3$ | CH |
| H | A-1 | — | O | 5-OCH$_3$ | CO$_2$CH$_2$CH$_3$ | CH$_3$ | CH$_3$ | CH |
| H | A-1 | — | O | 5-OCH$_3$ | CO$_2$CH$_2$CH$_3$ | CH$_3$ | OCH$_3$ | CH |
| H | A-1 | — | O | 5-OCH$_3$ | CO$_2$CH$_2$CH$_3$ | OCH$_3$ | OCH$_3$ | CH |
| H | A-1 | — | O | 5-OCH$_3$ | CO$_2$CH$_2$CH$_3$ | CH$_3$ | CH$_3$ | N |
| H | A-1 | — | O | 5-OCH$_3$ | CO$_2$CH$_2$CH$_3$ | CH$_3$ | OCH$_3$ | N |
| H | A-1 | — | O | 5-OCH$_3$ | CO$_2$CH$_2$CH$_3$ | OCH$_3$ | OCH$_3$ | N |
| H | A-1 | — | O | 5-OCH$_3$ | CO$_2$CH$_2$CH$_3$ | Cl | OCH$_3$ | CH |
| H | A-1 | — | O | 5-OCH$_3$ | CO$_2$CH$_2$CH$_2$CH$_3$ | CH$_3$ | CH$_3$ | CH |
| H | A-1 | — | O | 5-OCH$_3$ | CO$_2$CH$_2$CH$_2$CH$_3$ | OCH$_3$ | OCH$_3$ | CH |
| H | A-1 | — | O | 5-OCH$_3$ | CO$_2$CH$_2$CH$_2$CH$_3$ | CH$_3$ | CH$_3$ | N |
| H | A-1 | — | O | 5-OCH$_3$ | CO$_2$CH$_2$CH$_2$CH$_3$ | CH$_3$ | OCH$_3$ | N |

TABLE II-continued

| | | | | | | | | |
|---|---|---|---|---|---|---|---|---|
| H | A-1 | — | O | 5-OCH$_3$ | CO$_2$CH$_2$CH$_2$CH$_3$ | OCH$_3$ | OCH$_3$ | N |
| H | A-1 | — | O | 5-OCH$_3$ | CO$_2$CH$_2$CH$_2$CH$_3$ | Cl | OCH$_3$ | CH |
| H | A-1 | — | O | 5-OCH$_2$CF$_3$ | CO$_2$CH(CH$_3$)$_2$ | CH$_3$ | CH$_3$ | CH |
| H | A-1 | — | O | 5-OCH$_2$CF$_3$ | CO$_2$CH(CH$_3$)$_2$ | CH$_3$ | OCH$_3$ | CH |
| H | A-1 | — | O | 5-OCH$_2$CF$_3$ | CO$_2$CH(CH$_3$)$_2$ | OCH$_3$ | OCH$_3$ | CH |
| H | A-1 | — | O | 5-OCH$_2$CF$_3$ | CO$_2$CH(CH$_3$)$_2$ | CH$_3$ | CH$_3$ | N |
| H | A-1 | — | O | 5-OCH$_2$CF$_3$ | CO$_2$CH(CH$_3$)$_2$ | CH$_3$ | OCH$_3$ | N |
| H | A-1 | — | O | 5-OCH$_2$CF$_3$ | CO$_2$CH(CH$_3$)$_2$ | OCH$_3$ | OCH$_3$ | N |
| H | A-1 | — | O | 5-OCH$_2$CF$_3$ | CO$_2$CH(CH$_3$)$_2$ | Cl | OCH$_3$ | CH |
| H | A-1 | — | O | 5-OCH$_2$CF$_3$ | CO$_2$CH$_2$CH$_2$Cl | CH$_3$ | CH$_3$ | CH |
| H | A-1 | — | O | 5-OCH$_2$CF$_3$ | CO$_2$CH$_2$CH$_2$Cl | CH$_3$ | OCH$_3$ | CH |
| H | A-1 | — | O | 5-OCH$_2$CF$_3$ | CO$_2$CH$_2$CH$_2$Cl | OCH$_3$ | OCH$_3$ | CH |
| H | A-1 | — | O | 5-OCH$_2$CF$_3$ | CO$_2$CH$_2$CH$_2$Cl | CH$_3$ | CH$_3$ | N |
| H | A-1 | — | O | 5-OCH$_2$CF$_3$ | CO$_2$CH$_2$CH$_2$Cl | CH$_3$ | OCH$_3$ | N |
| H | A-1 | — | O | 5-OCH$_2$CF$_3$ | CO$_2$CH$_2$CH$_2$Cl | OCH$_3$ | OCH$_3$ | N |
| H | A-1 | — | O | 5-OCH$_2$CF$_3$ | CO$_2$CH$_2$CH$_2$Cl | Cl | OCH$_3$ | CH |
| H | A-1 | — | O | 5-OCH$_2$CF$_3$ | CO$_2$CH$_2$CH$_2$F | CH$_3$ | CH$_3$ | CH |
| H | A-1 | — | O | 5-OCH$_2$CF$_3$ | CO$_2$CH$_2$CH$_2$F | CH$_3$ | OCH$_3$ | CH |
| H | A-1 | — | O | 5-OCH$_2$CF$_3$ | CO$_2$CH$_2$CH$_2$F | OCH$_3$ | OCH$_3$ | CH |
| H | A-1 | — | O | 5-OCH$_2$CF$_3$ | CO$_2$CH$_2$CH$_2$F | CH$_3$ | CH$_3$ | N |
| H | A-1 | — | O | 5-OCH$_2$CF$_3$ | CO$_2$CH$_2$CH$_2$F | CH$_3$ | OCH$_3$ | N |
| H | A-1 | — | O | 5-OCH$_2$CF$_3$ | CO$_2$CH$_2$CH$_2$F | OCH$_3$ | OCH$_3$ | N |
| H | A-1 | — | O | 5-OCH$_2$CF$_3$ | CO$_2$CH$_2$CH$_2$F | Cl | OCH$_3$ | CH |
| H | A-1 | — | O | 5-OCH$_2$CF$_3$ | CO$_2$CH$_2$OCH$_3$ | CH$_3$ | CH$_3$ | CH |
| H | A-1 | — | O | 5-OCH$_2$CF$_3$ | CO$_2$CH$_2$OCH$_3$ | CH$_3$ | OCH$_3$ | CH |
| H | A-1 | — | O | 5-OCH$_2$CF$_3$ | CO$_2$CH$_2$OCH$_3$ | OCH$_3$ | OCH$_3$ | CH |
| H | A-1 | — | O | 5-OCH$_2$CF$_3$ | CO$_2$CH$_2$OCH$_3$ | CH$_3$ | CH$_3$ | N |
| H | A-1 | — | O | 5-OCH$_2$CF$_3$ | CO$_2$CH$_2$OCH$_3$ | CH$_3$ | OCH$_3$ | N |
| H | A-1 | — | O | 5-OCH$_2$CF$_3$ | CO$_2$CH$_2$OCH$_3$ | OCH$_3$ | OCH$_3$ | N |
| H | A-1 | — | O | 5-OCH$_2$CF$_3$ | CO$_2$CH$_2$OCH$_3$ | Cl | OCH$_3$ | CH |
| H | A-1 | — | O | 4-OCH$_3$ | CO$_2$CH$_3$ | CH$_3$ | CH$_3$ | CH |
| H | A-1 | — | O | 4-OCH$_3$ | CO$_2$CH$_3$ | CH$_3$ | OCH$_3$ | CH |
| H | A-1 | — | O | 4-OCH$_3$ | CO$_2$CH$_3$ | OCH$_3$ | OCH$_3$ | CH |
| H | A-1 | — | O | 4-OCH$_3$ | CO$_2$CH$_3$ | CH$_3$ | CH$_3$ | N |
| H | A-1 | — | O | 4-OCH$_3$ | CO$_2$CH$_3$ | CH$_3$ | OCH$_3$ | N |
| H | A-1 | — | O | 4-OCH$_3$ | CO$_2$CH$_3$ | OCH$_3$ | OCH$_3$ | N |
| H | A-1 | — | O | 4-OCH$_3$ | CO$_2$CH$_3$ | Cl | OCH$_3$ | CH |
| H | A-1 | — | O | 4-OCH$_3$ | CO$_2$CH$_2$CH$_3$ | CH$_3$ | CH$_3$ | CH |
| H | A-1 | — | O | 4-OCH$_3$ | CO$_2$CH$_2$CH$_3$ | CH$_3$ | OCH$_3$ | CH |
| H | A-1 | — | O | 4-OCH$_3$ | CO$_2$CH$_2$CH$_3$ | OCH$_3$ | OCH$_3$ | CH |
| H | A-1 | — | O | 4-OCH$_3$ | CO$_2$CH$_2$CH$_3$ | CH$_3$ | CH$_3$ | N |
| H | A-1 | — | O | 4-OCH$_3$ | CO$_2$CH$_2$CH$_3$ | CH$_3$ | OCH$_3$ | N |
| H | A-1 | — | O | 4-OCH$_3$ | CO$_2$CH$_2$CH$_3$ | OCH$_3$ | OCH$_3$ | N |
| H | A-1 | — | O | 4-OCH$_3$ | CO$_2$CH$_2$CH$_3$ | Cl | OCH$_3$ | CH |
| H | A-1 | — | O | 4-OCH$_3$ | SO$_2$N(CH$_3$)$_2$ | CH$_3$ | CH$_3$ | CH |
| H | A-1 | — | O | 4-OCH$_3$ | SO$_2$N(CH$_3$)$_2$ | CH$_3$ | OCH$_3$ | CH |
| H | A-1 | — | O | 4-OCH$_3$ | SO$_2$N(CH$_3$)$_2$ | OCH$_3$ | OCH$_3$ | CH |
| H | A-1 | — | O | 4-OCH$_3$ | SO$_2$N(CH$_3$)$_2$ | CH$_3$ | CH$_3$ | N |
| H | A-1 | — | O | 4-OCH$_3$ | SO$_2$N(CH$_3$)$_2$ | CH$_3$ | OCH$_3$ | N |
| H | A-1 | — | O | 4-OCH$_3$ | SO$_2$N(CH$_3$)$_2$ | OCH$_3$ | OCH$_3$ | N |
| H | A-1 | — | O | 4-OCH$_3$ | SO$_2$N(CH$_3$)$_2$ | Cl | OCH$_3$ | CH |
| H | A-1 | — | O | 4-OCH$_3$ | SO$_2$CH$_3$ | CH$_3$ | CH$_3$ | CH |
| H | A-1 | — | O | 4-OCH$_3$ | SO$_2$CH$_3$ | CH$_3$ | OCH$_3$ | CH |
| H | A-1 | — | O | 4-OCH$_3$ | SO$_2$CH$_3$ | OCH$_3$ | OCH$_3$ | CH |
| H | A-1 | — | O | 4-OCH$_3$ | SO$_2$CH$_3$ | CH$_3$ | CH$_3$ | N |
| H | A-1 | — | O | 4-OCH$_3$ | SO$_2$CH$_3$ | CH$_3$ | OCH$_3$ | N |
| H | A-1 | — | O | 4-OCH$_3$ | SO$_2$CH$_3$ | OCH$_3$ | OCH$_3$ | N |
| H | A-1 | — | O | 4-OCH$_3$ | SO$_2$CH$_3$ | Cl | OCH$_3$ | CH |
| CH$_3$ | A-1 | — | O | 5-F | SCH$_2$—CH=CH$_2$ | CH$_3$ | CH$_3$ | CH |
| CH$_3$ | A-1 | — | O | 5-F | SCH$_2$—CH=CH$_2$ | CH$_3$ | OCH$_3$ | CH |
| CH$_3$ | A-1 | — | O | 5-F | SCH$_2$—CH=CH$_2$ | OCH$_3$ | OCH$_3$ | CH |
| CH$_3$ | A-1 | — | O | 5-F | SCH$_2$—CH=CH$_2$ | CH$_3$ | CH$_3$ | N |
| CH$_3$ | A-1 | — | O | 5-F | SCH$_2$—CH=CH$_2$ | CH$_3$ | OCH$_3$ | N |
| CH$_3$ | A-1 | — | O | 5-F | SCH$_2$—CH=CH$_2$ | OCH$_3$ | OCH$_3$ | CH |
| CH$_3$ | A-1 | — | O | 5-F | SCH$_2$—CH=CH$_2$ | Cl | OCH$_3$ | CH |
| CH$_3$ | A-1 | — | O | 5-F | SCH$_2$CH$_2$OCH$_3$ | CH$_3$ | CH$_3$ | CH |
| CH$_3$ | A-1 | — | O | 5-F | SCH$_2$—C≡CH | CH$_3$ | OCH$_3$ | CH |
| CH$_3$ | A-1 | — | O | 5-F | SCH(CH$_3$)$_2$ | OCH$_3$ | OCH$_3$ | CH |
| CH$_3$ | A-1 | — | O | 5-F | SCH(CH$_3$)$_2$ | CH$_3$ | CH$_3$ | N |
| CH$_3$ | A-1 | — | O | 5-F | SCH(CH$_3$)$_2$ | CH$_3$ | OCH$_3$ | N |
| CH$_3$ | A-1 | — | O | 5-F | SCH(CH$_3$)$_2$ | OCH$_3$ | OCH$_3$ | N |
| CH$_3$ | A-1 | — | O | 5-F | SCH(CH$_3$)$_2$ | Cl | OCH$_3$ | CH |
| CH$_3$ | A-1 | — | O | 5-F | SOCH$_3$ | CH$_3$ | CH$_3$ | CH |
| CH$_3$ | A-1 | — | O | 5-F | SOCH$_3$ | CH$_3$ | OCH$_3$ | CH |
| CH$_3$ | A-1 | — | O | 5-F | SOCH$_3$ | OCH$_3$ | OCH$_3$ | CH |
| CH$_3$ | A-1 | — | O | 5-F | SOCH$_3$ | CH$_3$ | CH$_3$ | N |
| CH$_3$ | A-1 | — | O | 5-F | SOCH$_3$ | CH$_3$ | OCH$_3$ | N |
| CH$_3$ | A-1 | — | O | 5-F | SOCH$_3$ | OCH$_3$ | OCH$_3$ | N |
| CH$_3$ | A-1 | — | O | 5-F | SOCH$_3$ | Cl | OCH$_3$ | CH |
| CH$_3$ | A-1 | — | O | 5-F | SO$_2$CH$_3$ | CH$_3$ | CH$_3$ | CH |
| CH$_3$ | A-1 | — | O | 5-F | SO$_2$CH$_3$ | CH$_3$ | OCH$_3$ | CH |
| CH$_3$ | A-1 | — | O | 5-F | SO$_2$CH$_3$ | OCH$_3$ | OCH$_3$ | CH |

TABLE II-continued

| R | A | E | W | R₁ | R₂ | | | |
|---|---|---|---|----|----|---|---|---|
| CH₃ | A-1 | — | O | 5-F | SO₂CH₃ | CH₃ | CH₃ | N |
| CH₃ | A-1 | — | O | 5-F | SO₂CH₃ | CH₃ | OCH₃ | N |
| CH₃ | A-1 | — | O | 5-F | SO₂CH₃ | OCH₃ | OCH₃ | N |
| CH₃ | A-1 | — | O | 5-F | SO₂CH₃ | Cl | OCH₃ | CH |

| R | A | E | W | R₁ | R₂ | $X_1$ | $Y_1$ | m.p. (°C.) |
|---|---|---|---|----|----|----|----|------|
| H | A-2 | — | O | H | CO₂CH₃ | CH₃ | O | |
| H | A-2 | — | O | H | CO₂CH₃ | CH₃ | CH₂ | |
| H | A-2 | — | O | H | CO₂CH₃ | OCH₃ | O | |
| H | A-2 | — | O | H | CO₂CH₃ | OCH₃ | CH₂ | |
| H | A-2 | — | O | H | CO₂CH₃ | OCH₂CH₃ | O | |
| H | A-2 | — | O | H | CO₂CH₃ | OCF₂H | CH₂ | |
| H | A-2 | — | O | H | CO₂SO₂N(CH₃)₂ | CH₃ | O | |
| H | A-2 | — | O | H | SO₂N(CH₃)₂ | OCH₃ | O | |
| H | A-2 | — | O | H | SO₂N(CH₃)₂ | OCF₂H | CH₂ | |
| H | A-3 | — | O | H | CO₂CH₃ | CH₃ | | |
| H | A-3 | — | O | H | CO₂CH₃ | OCH₃ | | |
| H | A-3 | — | O | H | CO₂CH₃ | OCH₂CH₃ | | |
| H | A-3 | — | O | H | CO₂CH₃ | OCF₂H | | |
| H | A-3 | — | O | H | Cl | CH₃ | | |
| H | A-3 | — | O | H | Cl | OCH₃ | | |
| H | A-3 | — | O | H | SO₂CH₃ | CH₃ | | |
| H | A-3 | — | O | H | SO₂CH₃ | OCH₃ | | |

| R | A | E | W | R₁ | R₂ | $X_1$ | $Y_3$ | m.p. (°C.) |
|---|---|---|---|----|----|----|----|------|
| H | A-4 | — | O | H | CO₂CH₃ | CH₃ | H | |
| H | A-4 | — | O | H | CO₂CH₃ | OCH₃ | H | |
| H | A-4 | — | O | H | CO₂CH₃ | OCH₂CH₃ | H | |
| H | A-4 | — | O | H | CO₂CH₃ | OCF₂H | H | |
| H | A-4 | — | O | H | CO₂CH₃ | CH₃ | CH₃ | |
| H | A-4 | — | O | H | CO₂CH₃ | OCH₃ | CH₃ | |
| H | A-4 | — | O | H | CO₂CH₃ | OCF₂H | CH₃ | |

| R | A | E | W | R₁ | R₂ | $X_2$ | $Y_2$ | m.p. (°C.) |
|---|---|---|---|----|----|----|----|------|
| H | A-5 | — | O | H | CO₂CH₃ | CH₃ | OCH₃ | |
| H | A-5 | — | O | H | CO₂CH₃ | CH₃ | OCH₂CH₃ | |
| H | A-5 | — | O | H | CO₂CH₃ | CH₃ | SCH₃ | |
| H | A-5 | — | O | H | CO₂CH₃ | CH₃ | SCH₂CH₃ | |
| H | A-5 | — | O | H | CO₂CH₃ | CH₃ | CH₃ | |
| H | A-5 | — | O | H | CO₂CH₃ | CH₃ | CH₂CH₃ | |
| H | A-5 | — | O | H | CO₂CH₃ | CH₂CH₃ | OCH₃ | |
| H | A-5 | — | O | H | CO₂CH₃ | CH₂CH₃ | SCH₃ | |
| H | A-5 | — | O | H | CO₂CH₃ | CH₂CH₃ | OCH₂CH₃ | |
| H | A-5 | — | O | H | CO₂CH₃ | CH₂CF₃ | OCH₃ | |

| R | A | E | W | R₁ | R₂ | $X_3$ | | m.p. (°C.) |
|---|---|---|---|----|----|----|---|------|
| H | A-6 | — | O | H | CO₂CH₃ | CH₃ | | |
| H | A-6 | — | O | H | CO₂CH₃ | OCH₃ | | |
| H | A-6 | — | O | H | NO₂ | CH₃ | | |
| H | A-6 | — | O | H | NO₂ | OCH₃ | | |

| R | A | E | W | R₁ | R₂ | $X_4$ | $Y_4$ | m.p. (°C.) |
|---|---|---|---|----|----|----|----|------|
| H | A-7 | — | O | H | CO₂CH₃ | CH₃ | CH₃ | |
| H | A-7 | — | O | H | CO₂CH₃ | CH₃ | OCH₃ | |
| H | A-7 | — | O | H | CO₂CH₃ | CH₃ | OCH₂CH₃ | |
| H | A-7 | — | O | H | CO₂CH₃ | CH₃ | Cl | |
| H | A-7 | — | O | H | CO₂CH₃ | OCH₃ | CH₃ | |
| H | A-7 | — | O | H | CO₂CH₃ | OCH₃ | OCH₃ | |
| H | A-7 | — | O | H | CO₂CH₃ | OCH₂CH₃ | OCH₃ | |

| R | A | E | W | R₁ | R₂ | X | Y | Z | m.p. (°C.) |
|---|---|---|---|----|----|---|---|---|------|
| H | A-1 | — | O | H | CO₂CH₃ | CH₃ | OCH₂CH₃ | CH | |
| H | A-1 | — | O | H | CO₂CH₃ | CH₃ | OCF₂H | CH | |
| H | A-1 | — | O | H | CO₂CH₃ | CH₃ | SCF₂H | CH | |
| H | A-1 | — | O | H | CO₂CH₃ | CH₃ | SCH₃ | CH | |
| H | A-1 | — | O | H | CO₂CH₃ | CH₃ | CH₂OCH₃ | CH | |
| H | A-1 | — | O | H | CO₂CH₃ | CH₃ | NHCH₃ | N | |
| H | A-1 | — | O | H | CO₂CH₃ | CH₃ | N(CH₃)₂ | N | |
| H | A-1 | — | O | H | CO₂CH₃ | CH₃ | CH₂F | CH | |
| H | A-1 | — | O | H | CO₂CH₃ | CH₃ | C≡CH | CH | |
| H | A-1 | — | O | H | CO₂CH₃ | CH₃ | cyclopropyl | CH | |
| H | A-1 | — | O | H | CO₂CH₃ | CH₃ | CN | CH | |
| H | A-1 | — | O | H | CO₂CH₃ | OCH₃ | CH₂CH₃ | CH | |
| H | A-1 | — | O | H | CO₂CH₃ | OCH₃ | OCH₂CH₃ | CH | |
| H | A-1 | — | O | H | CO₂CH₃ | OCH₃ | SCH₃ | CH | |
| H | A-1 | — | O | H | CO₂CH₃ | OCH₃ | OCF₂H | CH | |
| H | A-1 | — | O | H | CO₂CH₃ | OCH₃ | CH₂F | CH | |
| H | A-1 | — | O | H | CO₂CH₃ | OCH₃ | N(CH₃)₂ | N | |
| H | A-1 | — | O | H | CO₂CH₃ | OCH₃ | NHCH₃ | N | |
| H | A-1 | — | O | H | CO₂CH₃ | OCH₃ | CN | CH | |
| H | A-1 | — | O | H | CO₂CH₃ | OCF₂H | CH₃ | CH | |

TABLE II-continued

| R | A | E | W | R₁ | R₂ | X | Y | Z |
|---|---|---|---|---|---|---|---|---|
| H | A-1 | — | O | H | CO₂CH₃ | OCF₂H | OCH₂CH₃ | CH |
| H | A-1 | — | O | H | CO₂CH₃ | OCF₂H | CH₂CH₃ | CH |
| H | A-1 | — | O | H | CO₂CH₃ | OCF₂H | CH₂F | CH |
| H | A-1 | — | O | H | CO₂CH₃ | OCF₂H | SCH₃ | CH |
| H | A-1 | — | O | H | CO₂CH₃ | OCF₂H | N(CH₃)₂ | CH |
| H | A-1 | — | O | H | CO₂CH₃ | OCF₂H | NHCH₃ | CH |
| H | A-1 | — | O | H | CO₂CH₃ | CH₂OCH₃ | OCH₃ | CH |
| H | A-1 | — | O | H | CO₂CH₃ | CH₂OCH₃ | OCH₂CH₃ | CH |
| H | A-1 | — | O | H | CO₂CH₃ | CH₂OCH₃ | CH₃ | CH |
| H | A-1 | — | O | H | CO₂CH₃ | CH₂OCH₃ | CH₂F | CH |
| H | A-1 | — | O | H | CO₂CH₃ | CH₂OCH₃ | CH₂Cl | CH |
| H | A-1 | — | O | H | CO₂CH₃ | CH₂OCH₃ | CH₂Br | CH |
| H | A-1 | — | O | H | CO₂CH₃ | SCF₂H | OCH₂CH₃ | CH |
| H | A-1 | — | O | H | CO₂CH₃ | SCF₂H | CH₂CH₃ | CH |
| H | A-1 | — | O | H | CO₂CH₃ | SCF₂H | CH₂F | CH |
| H | A-1 | — | O | H | CO₂CH₃ | SCF₂H | NHCH₃ | N |
| H | A-1 | — | O | H | CO₂CH₃ | N(CH₃)₂ | OCH₂CH₃ | N |
| H | A-1 | — | O | H | CO₂CH₃ | N(CH₃)₂ | CH₂CH₃ | N |
| H | A-1 | — | O | H | CO₂CH₃ | N(CH₃)₂ | CH₂F | N |
| H | A-1 | — | O | H | CO₂CH₃ | N(CH₃)₂ | CH₂OCH₃ | N |
| H | A-1 | — | O | H | CO₂CH₃ | N(CH₃)₂ | cyclopropyl | N |
| H | A-1 | — | O | H | CO₂CH₃ | C≡CH | CH₂CH₃ | CH |
| H | A-1 | — | O | H | CO₂CH₃ | C≡CH | OCH₃ | CH |
| H | A-1 | — | O | H | CO₂CH₃ | C≡CH | N(CH₃)₂ | CH |
| H | A-1 | — | O | H | CO₂CH₃ | C≡CH | OCH₂CH₃ | N |

TABLE III

| R | A | E | W | R₁ | R₂ | X | Y | Z | m.p.(°C.) |
|---|---|---|---|---|---|---|---|---|---|
| H | A-1 | — | O | H | H | CH₃ | CH₃ | CH | |
| H | A-1 | — | O | H | H | CH₃ | OCH₃ | CH | |
| H | A-1 | — | O | H | H | OCH₃ | OCH₃ | CH | |
| H | A-1 | — | O | H | H | CH₃ | CH₃ | N | |
| H | A-1 | — | O | H | H | CH₃ | OCH₃ | N | |
| H | A-1 | — | O | H | H | OCH₃ | OCH₃ | N | |
| H | A-1 | — | O | H | H | Cl | OCH₃ | CH | |
| H | A-1 | — | O | H | Cl | CH₃ | CH₃ | CH | |
| H | A-1 | — | O | H | Cl | CH₃ | OCH₃ | CH | |
| H | A-1 | — | O | H | Cl | OCH₃ | OCH₃ | CH | |
| H | A-1 | — | O | H | Cl | CH₃ | CH₃ | N | |
| H | A-1 | — | O | H | Cl | CH₃ | OCH₃ | N | |
| H | A-1 | — | O | H | Cl | OCH₃ | OCH₃ | N | |
| H | A-1 | — | O | H | Cl | Cl | OCH₃ | CH | |
| H | A-1 | — | O | H | Br | CH₃ | CH₃ | CH | |
| H | A-1 | — | O | H | Br | CH₃ | OCH₃ | CH | |
| H | A-1 | — | O | H | Br | OCH₃ | OCH₃ | CH | |
| H | A-1 | — | O | H | Br | CH₃ | CH₃ | N | |
| H | A-1 | — | O | H | Br | CH₃ | OCH₃ | N | |
| H | A-1 | — | O | H | Br | OCH₃ | OCH₃ | N | |
| H | A-1 | — | O | H | Br | Cl | OCH₃ | CH | |
| H | A-1 | — | O | H | F | CH₃ | CH₃ | CH | |
| H | A-1 | — | O | H | F | CH₃ | OCH₃ | CH | |
| H | A-1 | — | O | H | F | OCH₃ | OCH₃ | CH | |
| H | A-1 | — | O | H | F | CH₃ | CH₃ | N | |
| H | A-1 | — | O | H | F | CH₃ | OCH₃ | N | |
| H | A-1 | — | O | H | F | OCH₃ | OCH₃ | N | |
| H | A-1 | — | O | H | F | Cl | OCH₃ | CH | |
| H | A-1 | — | O | H | CH₃ | CH₃ | CH₃ | CH | |
| H | A-1 | — | O | H | CH₃ | CH₃ | OCH₃ | CH | |
| H | A-1 | — | O | H | CH₃ | OCH₃ | OCH₃ | CH | |
| H | A-1 | — | O | H | CH₃ | CH₃ | CH₃ | N | |
| H | A-1 | — | O | H | CH₃ | CH₃ | OCH₃ | N | |
| H | A-1 | — | O | H | CH₃ | OCH₃ | OCH₃ | N | |
| H | A-1 | — | O | H | CH₃ | Cl | OCH₃ | CH | |
| H | A-1 | — | O | H | CH₂CH₃ | CH₃ | CH₃ | CH | |
| H | A-1 | — | O | H | CH₂CH₃ | OCH₃ | OCH₃ | CH | |
| H | A-1 | — | O | H | CH₂CH₃ | CH₃ | CH₃ | N | |
| H | A-1 | — | O | H | CH₂CH₃ | CH₃ | OCH₃ | N | |
| H | A-1 | — | O | H | CH₂CH₃ | OCH₃ | OCH₃ | N | |
| H | A-1 | — | O | H | CH₂CH₃ | Cl | OCH₃ | CH | |
| H | A-1 | — | O | H | CH(CH₃)₂ | CH₃ | CH₃ | CH | |
| H | A-1 | — | O | H | CH(CH₃)₂ | OCH₃ | OCH₃ | CH | |
| H | A-1 | — | O | H | CH(CH₃)₂ | CH₃ | CH₃ | N | |
| H | A-1 | — | O | H | CH(CH₃)₂ | CH₃ | OCH₃ | N | |
| H | A-1 | — | O | H | CH(CH₃)₂ | OCH₃ | OCH₃ | N | |
| H | A-1 | — | O | H | CH(CH₃)₂ | Cl | OCH₃ | CH | |
| H | A-1 | — | O | H | CH₂CH₂CH₃ | CH₃ | CH₃ | CH | |
| H | A-1 | — | O | H | CH₂CH₂CH₃ | CH₃ | OCH₃ | CH | |
| H | A-1 | — | O | H | CH(CH₃)CH₂CH₃ | OCH₃ | OCH₃ | CH | |

TABLE III-continued

| | | | | | | | | |
|---|---|---|---|---|---|---|---|---|
| H | A-1 | — | O | H | CH(CH₃)CH₂CH₃ | CH₃ | CH₃ | N |
| H | A-1 | — | O | H | CH₂CH(CH₃)₂ | CH₃ | OCH₃ | N |
| H | A-1 | — | O | H | CH₂CH(CH₃)₂ | OCH₃ | OCH₃ | N |
| H | A-1 | — | O | H | CH₂CH(CH₃)₂ | Cl | OCH₃ | CH |
| H | A-1 | — | O | H | CH₂Cl | CH₃ | CH₃ | CH |
| H | A-1 | — | O | H | CH₂Cl | CH₃ | OCH₃ | CH |
| H | A-1 | — | O | H | CH₂Cl | OCH₃ | OCH₃ | CH |
| H | A-1 | — | O | H | CH₂Cl | CH₃ | CH₃ | N |
| H | A-1 | — | O | H | CH₂Br | CH₃ | OCH₃ | N |
| H | A-1 | — | O | H | CH₂Br | OCH₃ | OCH₃ | N |
| H | A-1 | — | O | H | CH₂F | Cl | OCH₃ | CH |
| H | A-1 | — | O | H | CH(Cl)CH₃ | CH₃ | CH₃ | CH |
| H | A-1 | — | O | H | CH(Cl)CH₃ | CH₃ | OCH₃ | CH |
| H | A-1 | — | O | H | CH(Cl)CH₃ | OCH₃ | OCH₃ | CH |
| H | A-1 | — | O | H | CH(Cl)CH₃ | CH₃ | CH₃ | N |
| H | A-1 | — | O | H | CH(Cl)CH₃ | CH₃ | OCH₃ | N |
| H | A-1 | — | O | H | CH(Cl)CH₃ | OCH₃ | OCH₃ | N |
| H | A-1 | — | O | H | CH(Cl)CH₃ | Cl | OCH₃ | CH |
| H | A-1 | — | O | H | CH(F)CH₃ | CH₃ | CH₃ | CH |
| H | A-1 | — | O | H | CH(F)CH₃ | CH₃ | OCH₃ | CH |
| H | A-1 | — | O | H | CH(F)CH₃ | OCH₃ | OCH₃ | CH |
| H | A-1 | — | O | H | CH(F)CH₃ | CH₃ | CH₃ | N |
| H | A-1 | — | O | H | CH(F)CH₃ | CH₃ | OCH₃ | N |
| H | A-1 | — | O | H | CH(F)CH₃ | OCH₃ | OCH₃ | N |
| H | A-1 | — | O | H | CH(F)CH₃ | Cl | OCH₃ | CH |
| H | A-1 | — | O | H | CH(F)CH₂CH₃ | CH₃ | CH₃ | CH |
| H | A-1 | — | O | H | CH(F)CH₂CH₃ | CH₃ | OCH₃ | CH |
| H | A-1 | — | O | H | CH(F)CH₂CH₃ | OCH₃ | OCH₃ | CH |
| H | A-1 | — | O | H | CH(F)CH₂CH₃ | CH₃ | CH₃ | N |
| H | A-1 | — | O | H | CH(F)CH₂CH₃ | CH₃ | OCH₃ | N |
| H | A-1 | — | O | H | CH(F)CH₂CH₃ | OCH₃ | OCH₃ | N |
| H | A-1 | — | O | H | CH(F)CH₂CH₃ | Cl | OCH₃ | CH |
| H | A-1 | — | O | H | CF₂CH₃ | CH₃ | CH₃ | CH |
| H | A-1 | — | O | H | CF₂CH₃ | CH₃ | OCH₃ | CH |
| H | A-1 | — | O | H | CF₂CH₃ | OCH₃ | OCH₃ | CH |
| H | A-1 | — | O | H | CF₂CH₃ | CH₃ | CH₃ | N |
| H | A-1 | — | O | H | CF₂CH₃ | CH₃ | OCH₃ | N |
| H | A-1 | — | O | H | CF₂CH₃ | OCH₃ | OCH₃ | N |
| H | A-1 | — | O | H | CF₂CH₃ | Cl | OCH₃ | CH |
| H | A-1 | — | O | H | CF₂H | CH₃ | CH₃ | CH |
| H | A-1 | — | O | H | CF₂H | CH₃ | OCH₃ | CH |
| H | A-1 | — | O | H | CF₂H | OCH₃ | OCH₃ | CH |
| H | A-1 | — | O | H | CF₂H | CH₃ | CH₃ | N |
| H | A-1 | — | O | H | CF₂H | CH₃ | OCH₃ | N |
| H | A-1 | — | O | H | CF₂H | OCH₃ | OCH₃ | N |
| H | A-1 | — | O | H | CF₂H | Cl | OCH₃ | CH |
| H | A-1 | — | O | H | CCl₂H | CH₃ | CH₃ | CH |
| H | A-1 | — | O | H | CCl₂H | CH₃ | OCH₃ | CH |
| H | A-1 | — | O | H | CCl₂H | OCH₃ | OCH₃ | CH |
| H | A-1 | — | O | H | CCl₂H | CH₃ | CH₃ | N |
| H | A-1 | — | O | H | CCl₂H | CH₃ | OCH₃ | N |
| H | A-1 | — | O | H | CCl₂H | OCH₃ | OCH₃ | N |
| H | A-1 | — | O | H | CCl₂H | Cl | OCH₃ | CH |
| H | A-1 | — | O | H | CH₂CH(F)CH₃ | CH₃ | CH₃ | CH |
| H | A-1 | — | O | H | CH₂CH(F)CH₃ | CH₃ | OCH₃ | CH |
| H | A-1 | — | O | H | CH₂CH(F)CH₃ | OCH₃ | OCH₃ | CH |
| H | A-1 | — | O | H | CH(CH₃)CH(Cl)CH₃ | CH₃ | CH₃ | N |
| H | A-1 | — | O | H | CH(CH₃)CH(Cl)CH₃ | CH₃ | OCH₃ | N |
| H | A-1 | — | O | H | CH(CH₃)CH₂Br | OCH₃ | OCH₃ | N |
| H | A-1 | — | O | H | CH(CH₃)CH₂Br | Cl | OCH₃ | CH |
| H | A-1 | — | O | H | cyclopropyl | CH₃ | CH₃ | CH |
| H | A-1 | — | O | H | cyclopropyl | CH₃ | OCH₃ | CH |
| H | A-1 | — | O | H | cyclopropyl | OCH₃ | OCH₃ | CH |
| H | A-1 | — | O | H | cyclopropyl | CH₃ | CH₃ | N |
| H | A-1 | — | O | H | cyclopropyl | CH₃ | OCH₃ | N |
| H | A-1 | — | O | H | cyclopropyl | OCH₃ | OCH₃ | N |
| H | A-1 | — | O | H | cyclopropyl | Cl | OCH₃ | CH |
| H | A-1 | — | O | H | CH—CF₂—CH₂ (ring) | CH₃ | CH₃ | CH |
| H | A-1 | — | O | H | CH—CF₂—CH₂ (ring) | CH₃ | OCH₃ | CH |
| H | A-1 | — | O | H | CH—CF₂—CH₂ (ring) | OCH₃ | OCH₃ | CH |
| H | A-1 | — | O | H | CH—CF₂—CH₂ (ring) | CH₃ | CH₃ | N |

TABLE III-continued

| | | | | | | | | |
|---|---|---|---|---|---|---|---|---|
| H | A-1 | — | O | H | CH—CF$_2$—CH$_2$ | CH$_3$ | OCH$_3$ | N |
| H | A-1 | — | O | H | CH—CF$_2$—CH$_2$ | OCH$_3$ | OCH$_3$ | N |
| H | A-1 | — | O | H | CH—CF$_2$—CH$_2$ | Cl | OCH$_3$ | CH |
| H | A-1 | — | O | H | CH—CHF—CH$_2$ | CH$_3$ | CH$_3$ | CH |
| H | A-1 | — | O | H | CH—CHF—CH$_2$ | CH$_3$ | OCH$_3$ | CH |
| H | A-1 | — | O | H | CH—CHF—CH$_2$ | OCH$_3$ | OCH$_3$ | CH |
| H | A-1 | — | O | H | CH—CHF—CH$_2$ | CH$_3$ | CH$_3$ | N |
| H | A-1 | — | O | H | CH—CHF—CH$_2$ | CH$_3$ | OCH$_3$ | N |
| H | A-1 | — | O | H | CH—CHF—CH$_2$ | OCH$_3$ | OCH$_3$ | N |
| H | A-1 | — | O | H | CH—CHF—CH$_2$ | Cl | OCH$_3$ | CH |
| H | A-1 | — | O | H | CH—CHCl—CH$_2$ | CH$_3$ | CH$_3$ | CH |
| H | A-1 | — | O | H | CH—CHCl—CH$_2$ | CH$_3$ | OCH$_3$ | CH |
| H | A-1 | — | O | H | CH—CHCl—CH$_2$ | OCH$_3$ | OCH$_3$ | CH |
| H | A-1 | — | O | H | CH—CHCl—CH$_2$ | CH$_3$ | CH$_3$ | N |
| H | A-1 | — | O | H | CH—CHCl—CH$_2$ | CH$_3$ | OCH$_3$ | N |
| H | A-1 | — | O | H | CH—CHCl—CH$_2$ | OCH$_3$ | OCH$_3$ | N |
| H | A-1 | — | O | H | CH—CHCl—CH$_2$ | Cl | OCH$_3$ | CH |
| H | A-1 | — | O | H | cyclobutyl | CH$_3$ | CH$_3$ | CH |
| H | A-1 | — | O | H | cyclobutyl | CH$_3$ | OCH$_3$ | CH |
| H | A-1 | — | O | H | cyclobutyl | OCH$_3$ | OCH$_3$ | CH |
| H | A-1 | — | O | H | cyclobutyl | CH$_3$ | CH$_3$ | N |
| H | A-1 | — | O | H | cyclobutyl | CH$_3$ | OCH$_3$ | N |
| H | A-1 | — | O | H | cyclobutyl | OCH$_3$ | OCH$_3$ | N |
| H | A-1 | — | O | H | cyclobutyl | Cl | OCH$_3$ | CH |
| H | A-1 | — | O | H | CH$_2$—CH=CH$_2$ | CH$_3$ | CH$_3$ | CH |
| H | A-1 | — | O | H | CH$_2$—CH=CH$_2$ | CH$_3$ | OCH$_3$ | CH |
| H | A-1 | — | O | H | CH$_2$—CH=CH$_2$ | OCH$_3$ | OCH$_3$ | CH |
| H | A-1 | — | O | H | CH$_2$—CH=CH$_2$ | CH$_3$ | CH$_3$ | N |
| H | A-1 | — | O | H | CH$_2$—CH=CH$_2$ | CH$_3$ | OCH$_3$ | N |
| H | A-1 | — | O | H | CH$_2$—CH=CH$_2$ | OCH$_3$ | OCH$_3$ | N |
| H | A-1 | — | O | H | CH$_2$—CH=CH$_2$ | Cl | OCH$_3$ | CH |
| H | A-1 | — | O | H | CH=CH$_2$ | CH$_3$ | CH$_3$ | CH |

TABLE III-continued

| | | | | | | | | |
|---|---|---|---|---|---|---|---|---|
| H | A-1 | — | O | H | CH=CH$_2$ | CH$_3$ | CH$_3$ | CH |
| H | A-1 | — | O | H | CH=CH$_2$ | CH$_3$ | OCH$_3$ | CH |
| H | A-1 | — | O | H | CH=CH$_2$ | OCH$_3$ | OCH$_3$ | CH |
| H | A-1 | — | O | H | CH=CH$_2$ | CH$_3$ | CH$_3$ | N |
| H | A-1 | — | O | H | CH=CH$_2$ | CH$_3$ | OCH$_3$ | N |
| H | A-1 | — | O | H | CH=CH$_2$ | OCH$_3$ | OCH$_3$ | N |
| H | A-1 | — | O | H | CH=CH$_2$ | Cl | OCH$_3$ | CH |
| H | A-1 | — | O | H | CH$_2$—CF=CH$_2$ | CH$_3$ | CH$_3$ | CH |
| H | A-1 | — | O | H | CH$_2$—CF=CH$_2$ | CH$_3$ | OCH$_3$ | CH |
| H | A-1 | — | O | H | CHF=CH$_2$ | OCH$_3$ | OCH$_3$ | CH |
| H | A-1 | — | O | H | CHF=CH$_2$ | CH$_3$ | CH$_3$ | N |
| H | A-1 | — | O | H | CHF=CH$_2$ | CH$_3$ | OCH$_3$ | N |
| H | A-1 | — | O | H | CHF=CH$_2$ | OCH$_3$ | OCH$_3$ | N |
| H | A-1 | — | O | H | CH$_2$—C=CH—CH$_3$ | Cl | OCH$_3$ | CH |
| H | A-1 | — | O | H | CH$_2$—C≡CH | CH$_3$ | CH$_3$ | CH |
| H | A-1 | — | O | H | CH$_2$—C≡CH | CH$_3$ | OCH$_3$ | CH |
| H | A-1 | — | O | H | CH$_2$—C≡CH | OCH$_3$ | OCH$_3$ | CH |
| H | A-1 | — | O | H | CH$_2$—C≡CH | CH$_3$ | CH$_3$ | N |
| H | A-1 | — | O | H | CH$_2$—C≡CH | CH$_3$ | OCH$_3$ | N |
| H | A-1 | — | O | H | CH$_2$—C≡CH | OCH$_3$ | OCH$_3$ | N |
| H | A-1 | — | O | H | CH$_2$—C≡CH | Cl | OCH$_3$ | CH |
| H | A-1 | — | O | H | C≡CH | CH$_3$ | CH$_3$ | CH |
| H | A-1 | — | O | H | C≡CH | CH$_3$ | OCH$_3$ | CH |
| H | A-1 | — | O | H | C≡CH | OCH$_3$ | OCH$_3$ | CH |
| H | A-1 | — | O | H | C≡CH | CH$_3$ | CH$_3$ | N |
| H | A-1 | — | O | H | C≡CH | CH$_3$ | OCH$_3$ | N |
| H | A-1 | — | O | H | C≡CH | OCH$_3$ | OCH$_3$ | N |
| H | A-1 | — | O | H | C≡C—CH$_2$F | Cl | OCH$_3$ | CH |
| H | A-1 | — | O | H | C≡C—CH$_2$F | CH$_3$ | CH$_3$ | CH |
| H | A-1 | — | O | H | C≡C—CH$_2$F | CH$_3$ | OCH$_3$ | CH |
| H | A-1 | — | O | H | C≡C—CH$_2$F | OCH$_3$ | OCH$_3$ | CH |
| H | A-1 | — | O | H | CH$_2$—C≡C—CH$_2$Cl | CH$_3$ | CH$_3$ | N |
| H | A-1 | — | O | H | CH$_2$—C≡C—CH$_2$Cl | CH$_3$ | OCH$_3$ | N |
| H | A-1 | — | O | H | CH$_2$—C≡C—CH$_2$Cl | OCH$_3$ | OCH$_3$ | N |
| H | A-1 | — | O | H | CH$_2$—C≡C—CH$_2$Cl | Cl | OCH$_3$ | CH |
| H | A-1 | — | O | H | OCH$_3$ | CH$_3$ | CH$_3$ | CH |
| H | A-1 | — | O | H | OCH$_3$ | CH$_3$ | OCH$_3$ | CH |
| H | A-1 | — | O | H | OCH$_3$ | OCH$_3$ | OCH$_3$ | CH |
| H | A-1 | — | O | H | OCH$_3$ | CH$_3$ | CH$_3$ | N |
| H | A-1 | — | O | H | OCH$_3$ | CH$_3$ | OCH$_3$ | N |
| H | A-1 | — | O | H | OCH$_3$ | OCH$_3$ | OCH$_3$ | N |
| H | A-1 | — | O | H | OCH$_3$ | Cl | OCH$_3$ | CH |
| H | A-1 | — | O | H | OCH$_2$CH$_3$ | CH$_3$ | CH$_3$ | CH |
| H | A-1 | — | O | H | OCH$_2$CH$_3$ | CH$_3$ | OCH$_3$ | CH |
| H | A-1 | — | O | H | OCH$_2$CH$_3$ | OCH$_3$ | OCH$_3$ | CH |
| H | A-1 | — | O | H | OCH$_2$CH$_3$ | CH$_3$ | CH$_3$ | N |
| H | A-1 | — | O | H | OCH$_2$CH$_3$ | CH$_3$ | OCH$_3$ | N |
| H | A-1 | — | O | H | OCH$_2$CH$_3$ | OCH$_3$ | OCH$_3$ | N |
| H | A-1 | — | O | H | OCH$_2$CH$_3$ | Cl | OCH$_3$ | CH |
| H | A-1 | — | O | H | OCH(CH$_3$)$_2$ | CH$_3$ | CH$_3$ | CH |
| H | A-1 | — | O | H | OCH(CH$_3$)$_2$ | CH$_3$ | OCH$_3$ | CH |
| H | A-1 | — | O | H | OCH(CH$_3$)$_2$ | OCH$_3$ | OCH$_3$ | CH |
| H | A-1 | — | O | H | OCH(CH$_3$)$_2$ | CH$_3$ | CH$_3$ | N |
| H | A-1 | — | O | H | OCH(CH$_3$)$_2$ | CH$_3$ | OCH$_3$ | N |
| H | A-1 | — | O | H | OCH(CH$_3$)$_2$ | OCH$_3$ | OCH$_3$ | N |
| H | A-1 | — | O | H | OCH(CH$_3$)$_2$ | Cl | OCH$_3$ | CH |
| H | A-1 | — | O | H | OCH$_2$CH$_2$CH$_2$CH$_3$ | CH$_3$ | CH$_3$ | CH |
| H | A-1 | — | O | H | OCH$_2$CH$_2$CH$_2$CH$_3$ | CH$_3$ | OCH$_3$ | CH |
| H | A-1 | — | O | H | OCH$_2$CH$_2$CH$_2$CH$_3$ | OCH$_3$ | OCH$_3$ | CH |
| H | A-1 | — | O | H | OCH$_2$—CH(CH$_3$)$_2$ | CH$_3$ | CH$_3$ | N |
| H | A-1 | — | O | H | OCH$_2$—CH(CH$_3$)$_2$ | CH$_3$ | OCH$_3$ | N |
| H | A-1 | — | O | H | OCH$_2$—CH(CH$_3$)$_2$ | OCH$_3$ | OCH$_3$ | N |
| H | A-1 | — | O | H | OCH$_2$—CH(CH$_3$)$_2$ | Cl | OCH$_3$ | CH |
| H | A-1 | — | O | H | OCF$_2$H | CH$_3$ | CH$_3$ | CH |
| H | A-1 | — | O | H | OCF$_2$H | CH$_3$ | OCH$_3$ | CH |
| H | A-1 | — | O | H | OCF$_2$H | OCH$_3$ | OCH$_3$ | CH |
| H | A-1 | — | O | H | OCF$_2$H | CH$_3$ | CH$_3$ | N |
| H | A-1 | — | O | H | OCF$_2$H | CH$_3$ | OCH$_3$ | N |
| H | A-1 | — | O | H | OCF$_2$H | OCH$_3$ | OCH$_3$ | N |
| H | A-1 | — | O | H | OCF$_2$H | Cl | OCH$_3$ | CH |
| H | A-1 | — | O | H | OCH$_2$CH$_2$Cl | CH$_3$ | CH$_3$ | CH |
| H | A-1 | — | O | H | OCH$_2$CH$_2$Cl | CH$_3$ | OCH$_3$ | CH |
| H | A-1 | — | O | H | OCH$_2$CH$_2$Cl | OCH$_3$ | OCH$_3$ | CH |
| H | A-1 | — | O | H | OCH$_2$CH$_2$Cl | CH$_3$ | CH$_3$ | N |
| H | A-1 | — | O | H | OCH$_2$CH$_2$Cl | CH$_3$ | OCH$_3$ | N |
| H | A-1 | — | O | H | OCH$_2$CH$_2$Cl | OCH$_3$ | OCH$_3$ | N |
| H | A-1 | — | O | H | OCH$_2$CH$_2$Cl | Cl | OCH$_3$ | CH |
| H | A-1 | — | O | H | OCH$_2$CH$_2$F | CH$_3$ | CH$_3$ | CH |
| H | A-1 | — | O | H | OCH$_2$CH$_2$F | CH$_3$ | OCH$_3$ | CH |
| H | A-1 | — | O | H | OCH$_2$CH$_2$F | OCH$_3$ | OCH$_3$ | CH |
| H | A-1 | — | O | H | OCH$_2$CH$_2$F | CH$_3$ | CH$_3$ | N |
| H | A-1 | — | O | H | OCH$_2$CH$_2$F | CH$_3$ | OCH$_3$ | N |
| H | A-1 | — | O | H | OCH$_2$CH$_2$F | OCH$_3$ | OCH$_3$ | N |

TABLE III-continued

| | | | | | | | | |
|---|---|---|---|---|---|---|---|---|
| H | A-1 | — | O | H | OCH$_2$CH$_2$F | Cl | OCH$_3$ | CH |
| H | A-1 | — | O | H | OCH$_2$CF$_3$ | CH$_3$ | CH$_3$ | CH |
| H | A-1 | — | O | H | OCH$_2$CF$_3$ | CH$_3$ | OCH$_3$ | CH |
| H | A-1 | — | O | H | OCH$_2$CF$_3$ | OCH$_3$ | OCH$_3$ | CH |
| H | A-1 | — | O | H | OCH$_2$CF$_3$ | CH$_3$ | CH$_3$ | N |
| H | A-1 | — | O | H | OCH$_2$CF$_3$ | CH$_3$ | OCH$_3$ | N |
| H | A-1 | — | O | H | OCH$_2$CF$_3$ | OCH$_3$ | OCH$_3$ | N |
| H | A-1 | — | O | H | OCH$_2$CF$_3$ | Cl | OCH$_3$ | CH |
| H | A-1 | — | O | H | OCF$_2$CH$_3$ | CH$_3$ | CH$_3$ | CH |
| H | A-1 | — | O | H | OCF$_2$CH$_3$ | CH$_3$ | OCH$_3$ | CH |
| H | A-1 | — | O | H | OCF$_2$CH$_3$ | OCH$_3$ | OCH$_3$ | CH |
| H | A-1 | — | O | H | OCF$_2$CH$_3$ | CH$_3$ | CH$_3$ | N |
| H | A-1 | — | O | H | OCF$_2$CH$_3$ | CH$_3$ | OCH$_3$ | N |
| H | A-1 | — | O | H | OCF$_2$CH$_3$ | OCH$_3$ | OCH$_3$ | N |
| H | A-1 | — | O | H | OCF$_2$CH$_3$ | Cl | OCH$_3$ | CH |
| H | A-1 | — | O | H | OCH$_2$CH$_2$CH$_2$F | CH$_3$ | CH$_3$ | CH |
| H | A-1 | — | O | H | OCH$_2$CH$_2$CH$_2$F | CH$_3$ | OCH$_3$ | CH |
| H | A-1 | — | O | H | OCH$_2$CH$_2$CH$_2$F | OCH$_3$ | OCH$_3$ | CH |
| H | A-1 | — | O | H | OCH$_2$CH$_2$CH$_2$F | CH$_3$ | CH$_3$ | N |
| H | A-1 | — | O | H | OCH$_2$CH$_2$CH$_2$F | CH$_3$ | OCH$_3$ | N |
| H | A-1 | — | O | H | OCH$_2$CH$_2$CH$_2$F | OCH$_3$ | OCH$_3$ | N |
| H | A-1 | — | O | H | OCH$_2$CH$_2$CH$_2$F | Cl | OCH$_3$ | CH |
| H | A-1 | — | O | H | OCH$_2$CH$_2$Cl | CH$_3$ | CH$_3$ | CH |
| H | A-1 | — | O | H | OCH$_2$CH$_2$Cl | CH$_3$ | OCH$_3$ | CH |
| H | A-1 | — | O | H | OCH$_2$CH$_2$Cl | OCH$_3$ | OCH$_3$ | CH |
| H | A-1 | — | O | H | OCH$_2$CH$_2$Br | CH$_3$ | CH$_3$ | N |
| H | A-1 | — | O | H | OCH$_2$CH$_2$Br | CH$_3$ | OCH$_3$ | N |
| H | A-1 | — | O | H | OCH$_2$CH$_2$Br | OCH$_3$ | OCH$_3$ | N |
| H | A-1 | — | O | H | OCH$_2$CH$_2$Br | Cl | OCH$_3$ | CH |
| H | A-1 | — | O | H | OCH$_2$—C≡CH | CH$_3$ | CH$_3$ | CH |
| H | A-1 | — | O | H | OCH$_2$—C≡CH | CH$_3$ | OCH$_3$ | CH |
| H | A-1 | — | O | H | OCH$_2$—C≡CH | OCH$_3$ | OCH$_3$ | CH |
| H | A-1 | — | O | H | OCH$_2$—C≡CH | CH$_3$ | CH$_3$ | N |
| H | A-1 | — | O | H | OCH$_2$—C≡CH | CH$_3$ | OCH$_3$ | N |
| H | A-1 | — | O | H | OCH$_2$—C≡CH | OCH$_3$ | OCH$_3$ | N |
| H | A-1 | — | O | H | OCH$_2$—C≡CH | Cl | OCH$_3$ | CH |
| H | A-1 | — | O | H | OCH$_2$—CH=CH$_2$ | CH$_3$ | CH$_3$ | CH |
| H | A-1 | — | O | H | OCH$_2$—CH=CH$_2$ | CH$_3$ | OCH$_3$ | CH |
| H | A-1 | — | O | H | OCH$_2$—CH=CH$_2$ | OCH$_3$ | OCH$_3$ | CH |
| H | A-1 | — | O | H | OCH$_2$—CH=CH$_2$ | CH$_3$ | CH$_3$ | N |
| H | A-1 | — | O | H | OCH$_2$—CH=CH$_2$ | CH$_3$ | OCH$_3$ | N |
| H | A-1 | — | O | H | OCH$_2$—CH=CH$_2$ | OCH$_3$ | OCH$_3$ | N |
| H | A-1 | — | O | H | OCH$_2$—CH=CH$_2$ | Cl | OCH$_3$ | CH |
| H | A-1 | — | O | H | NO$_2$ | CH$_3$ | CH$_3$ | CH |
| H | A-1 | — | O | H | NO$_2$ | CH$_3$ | OCH$_3$ | CH |
| H | A-1 | — | O | H | NO$_2$ | OCH$_3$ | OCH$_3$ | CH |
| H | A-1 | — | O | H | NO$_2$ | CH$_3$ | CH$_3$ | N |
| H | A-1 | — | O | H | NO$_2$ | CH$_3$ | OCH$_3$ | N |
| H | A-1 | — | O | H | NO$_2$ | OCH$_3$ | OCH$_3$ | N |
| H | A-1 | — | O | H | NO$_2$ | Cl | OCH$_3$ | CH |
| H | A-1 | — | O | H | CO$_2$CH$_3$ | CH$_3$ | CH$_3$ | CH |
| H | A-1 | — | O | H | CO$_2$CH$_3$ | CH$_3$ | OCH$_3$ | CH |
| H | A-1 | — | O | H | CO$_2$CH$_3$ | OCH$_3$ | OCH$_3$ | CH |
| H | A-1 | — | O | H | CO$_2$CH$_3$ | CH$_3$ | CH$_3$ | N |
| H | A-1 | — | O | H | CO$_2$CH$_3$ | CH$_3$ | OCH$_3$ | N |
| H | A-1 | — | O | H | CO$_2$CH$_3$ | OCH$_3$ | OCH$_3$ | N |
| H | A-1 | — | O | H | CO$_2$CH$_3$ | Cl | OCH$_3$ | CH |
| H | A-1 | — | O | H | CO$_2$CH$_2$CH$_3$ | CH$_3$ | CH$_3$ | CH |
| H | A-1 | — | O | H | CO$_2$CH$_2$CH$_3$ | CH$_3$ | OCH$_3$ | CH |
| H | A-1 | — | O | H | CO$_2$CH$_2$CH$_3$ | OCH$_3$ | OCH$_3$ | CH |
| H | A-1 | — | O | H | CO$_2$CH$_2$CH$_3$ | CH$_3$ | CH$_3$ | N |
| H | A-1 | — | O | H | CO$_2$CH$_2$CH$_3$ | CH$_3$ | OCH$_3$ | N |
| H | A-1 | — | O | H | CO$_2$CH$_2$CH$_3$ | OCH$_3$ | OCH$_3$ | N |
| H | A-1 | — | O | H | CO$_2$CH$_2$CH$_3$ | Cl | OCH$_3$ | CH |
| H | A-1 | — | O | H | CO$_2$CH$_2$CH$_2$CH$_3$ | CH$_3$ | CH$_3$ | CH |
| H | A-1 | — | O | H | CO$_2$CH$_2$CH$_2$CH$_3$ | CH$_3$ | OCH$_3$ | CH |
| H | A-1 | — | O | H | CO$_2$CH$_2$CH$_2$CH$_3$ | OCH$_3$ | OCH$_3$ | CH |
| H | A-1 | — | O | H | CO$_2$CH$_2$CH$_2$CH$_3$ | CH$_3$ | CH$_3$ | N |
| H | A-1 | — | O | H | CO$_2$CH$_2$CH$_2$CH$_3$ | CH$_3$ | OCH$_3$ | N |
| H | A-1 | — | O | H | CO$_2$CH$_2$CH$_2$CH$_3$ | OCH$_3$ | OCH$_3$ | N |
| H | A-1 | — | O | H | CO$_2$CH$_2$CH$_2$CH$_3$ | Cl | OCH$_3$ | CH |
| H | A-1 | — | O | H | CO$_2$CH(CH$_3$)$_2$ | CH$_3$ | CH$_3$ | CH |
| H | A-1 | — | O | H | CO$_2$CH(CH$_3$)$_2$ | CH$_3$ | OCH$_3$ | CH |
| H | A-1 | — | O | H | CO$_2$CH(CH$_3$)$_2$ | OCH$_3$ | OCH$_3$ | CH |
| H | A-1 | — | O | H | CO$_2$CH(CH$_3$)$_2$ | CH$_3$ | CH$_3$ | N |
| H | A-1 | — | O | H | CO$_2$CH(CH$_3$)$_2$ | CH$_3$ | OCH$_3$ | N |
| H | A-1 | — | O | H | CO$_2$CH(CH$_3$)$_2$ | OCH$_3$ | OCH$_3$ | N |
| H | A-1 | — | O | H | CO$_2$CH(CH$_3$)$_2$ | Cl | OCH$_3$ | CH |
| H | A-1 | — | O | H | CO$_2$CH$_2$CH$_2$Cl | CH$_3$ | CH$_3$ | CH |
| H | A-1 | — | O | H | CO$_2$CH$_2$CH$_2$Cl | CH$_3$ | OCH$_3$ | CH |
| H | A-1 | — | O | H | CO$_2$CH$_2$CH$_2$Cl | OCH$_3$ | OCH$_3$ | CH |
| H | A-1 | — | O | H | CO$_2$CH$_2$CH$_2$Cl | CH$_3$ | CH$_3$ | N |

TABLE III-continued

| | | | | | | | | |
|---|---|---|---|---|---|---|---|---|
| H | A-1 | — | O | H | CO₂CH₂CH₂Cl | CH₃ | OCH₃ | N |
| H | A-1 | — | O | H | CO₂CH₂CH₂Cl | OCH₃ | OCH₃ | N |
| H | A-1 | — | O | H | CO₂CH₂CH₂Cl | Cl | OCH₃ | CH |
| H | A-1 | — | O | H | CO₂CH₂CH₂F | CH₃ | CH₃ | CH |
| H | A-1 | — | O | H | CO₂CH₂CH₂F | CH₃ | OCH₃ | CH |
| H | A-1 | — | O | H | CO₂CH₂CH₂F | OCH₃ | OCH₃ | CH |
| H | A-1 | — | O | H | CO₂CH₂CH₂F | CH₃ | CH₃ | N |
| H | A-1 | — | O | H | CO₂CH₂CH₂F | CH₃ | OCH₃ | N |
| H | A-1 | — | O | H | CO₂CH₂CH₂F | OCH₃ | OCH₃ | N |
| H | A-1 | — | O | H | CO₂CH₂CH₂F | Cl | OCH₃ | CH |
| H | A-1 | — | O | H | CO₂CH₂OCH₃ | CH₃ | CH₃ | CH |
| H | A-1 | — | O | H | CO₂CH₂OCH₃ | CH₃ | OCH₃ | CH |
| H | A-1 | — | O | H | CO₂CH₂OCH₃ | OCH₃ | OCH₃ | CH |
| H | A-1 | — | O | H | CO₂CH₂OCH₃ | CH₃ | CH₃ | N |
| H | A-1 | — | O | H | CO₂CH₂OCH₃ | CH₃ | OCH₃ | N |
| H | A-1 | — | O | H | CO₂CH₂OCH₃ | OCH₃ | OCH₃ | N |
| H | A-1 | — | O | H | CO₂CH₂OCH₃ | Cl | OCH₃ | CH |
| H | A-1 | — | O | H | CO₂CH₂CH₂OCH₃ | CH₃ | CH₃ | CH |
| H | A-1 | — | O | H | CO₂CH₂CH₂OCH₃ | CH₃ | OCH₃ | CH |
| H | A-1 | — | O | H | CO₂CH₂CH₂OCH₃ | OCH₃ | OCH₃ | CH |
| H | A-1 | — | O | H | CO₂CH₂CH₂OCH₃ | CH₃ | CH₃ | N |
| H | A-1 | — | O | H | CO₂CH₂CH₂OCH₃ | CH₃ | OCH₃ | N |
| H | A-1 | — | O | H | CO₂CH₂CH₂OCH₃ | OCH₃ | OCH₃ | N |
| H | A-1 | — | O | H | CO₂CH₂CH₂OCH₃ | Cl | OCH₃ | CH |
| H | A-1 | — | O | H | CO₂CH₂CH=CH₂ | CH₃ | CH₃ | CH |
| H | A-1 | — | O | H | CO₂CH₂CH=CH₂ | CH₃ | OCH₃ | CH |
| H | A-1 | — | O | H | CO₂CH₂CH=CH₂ | OCH₃ | OCH₃ | CH |
| H | A-1 | — | O | H | CO₂CH₂CH=CH₂ | CH₃ | CH₃ | N |
| H | A-1 | — | O | H | CO₂CH₂CH=CH₂ | CH₃ | OCH₃ | N |
| H | A-1 | — | O | H | CO₂CH₂CH=CH₂ | OCH₃ | OCH₃ | N |
| H | A-1 | — | O | H | CO₂CH₂CH=CH₂ | Cl | OCH₃ | CH |
| H | A-1 | — | O | H | CO₂CH₂—C≡CH | CH₃ | CH₃ | CH |
| H | A-1 | — | O | H | CO₂CH₂—C≡CH | CH₃ | OCH₃ | CH |
| H | A-1 | — | O | H | CO₂CH₂—C≡CH | OCH₃ | OCH₃ | CH |
| H | A-1 | — | O | H | CO₂CH₂—C≡CH | CH₃ | CH₃ | N |
| H | A-1 | — | O | H | CO₂CH₂—C≡CH | CH₃ | OCH₃ | N |
| H | A-1 | — | O | H | CO₂CH₂—C≡CH | OCH₃ | OCH₃ | N |
| H | A-1 | — | O | H | CO₂CH₂—C≡CH | Cl | OCH₃ | CH |
| H | A-1 | — | O | H | N(CH₃)₂ | CH₃ | CH₃ | CH |
| H | A-1 | — | O | H | N(CH₃)₂ | CH₃ | OCH₃ | CH |
| H | A-1 | — | O | H | N(CH₃)₂ | OCH₃ | OCH₃ | CH |
| H | A-1 | — | O | H | N(CH₃)₂ | CH₃ | CH₃ | N |
| H | A-1 | — | O | H | N(CH₃)₂ | CH₃ | OCH₃ | N |
| H | A-1 | — | O | H | N(CH₃)₂ | OCH₃ | OCH₃ | N |
| H | A-1 | — | O | H | N(CH₃)₂ | Cl | OCH₃ | CH |
| H | A-1 | — | O | H | NCH₂CH₃(CH₃) | CH₃ | CH₃ | CH |
| H | A-1 | — | O | H | NCH₂CH₃(CH₃) | CH₃ | OCH₃ | CH |
| H | A-1 | — | O | H | NCH₂CH₃(CH₃) | OCH₃ | OCH₃ | CH |
| H | A-1 | — | O | H | NCH₂CH₃(CH₃) | CH₃ | CH₃ | N |
| H | A-1 | — | O | H | NCH₂CH₃(CH₃) | CH₃ | OCH₃ | N |
| H | A-1 | — | O | H | NCH₂CH₃(CH₃) | OCH₃ | OCH₃ | N |
| H | A-1 | — | O | H | NCH₂CH₃(CH₃) | Cl | OCH₃ | CH |
| H | A-1 | — | O | H | SCH₃ | CH₃ | CH₃ | CH |
| H | A-1 | — | O | H | SCH₃ | CH₃ | OCH₃ | CH |
| H | A-1 | — | O | H | SCH₃ | OCH₃ | OCH₃ | CH |
| H | A-1 | — | O | H | SCH₃ | CH₃ | CH₃ | N |
| H | A-1 | — | O | H | SCH₃ | CH₃ | OCH₃ | N |
| H | A-1 | — | O | H | SCH₃ | OCH₃ | OCH₃ | N |
| H | A-1 | — | O | H | SCH₃ | Cl | OCH₃ | CH |
| H | A-1 | — | O | H | SCH₂CH₃ | CH₃ | CH₃ | CH |
| H | A-1 | — | O | H | SCH₂CH₃ | CH₃ | OCH₃ | CH |
| H | A-1 | — | O | H | SCH₂CH₃ | OCH₃ | OCH₃ | CH |
| H | A-1 | — | O | H | SCH₂CH₃ | CH₃ | CH₃ | N |
| H | A-1 | — | O | H | SCH₂CH₃ | CH₃ | OCH₃ | N |
| H | A-1 | — | O | H | SCH₂CH₃ | OCH₃ | OCH₃ | N |
| H | A-1 | — | O | H | SCH₂CH₃ | Cl | OCH₃ | CH |
| H | A-1 | — | O | H | SCH₂CH₂CH₃ | CH₃ | CH₃ | CH |
| H | A-1 | — | O | H | SCH₂CH₂CH₃ | CH₃ | OCH₃ | CH |
| H | A-1 | — | O | H | SCH₂CH₂CH₃ | OCH₃ | OCH₃ | CH |
| H | A-1 | — | O | H | SCH₂CH₂CH₃ | CH₃ | CH₃ | N |
| H | A-1 | — | O | H | SCH₂CH₂CH₃ | CH₃ | OCH₃ | N |
| H | A-1 | — | O | H | SCH₂CH₂CH₃ | OCH₃ | OCH₃ | N |
| H | A-1 | — | O | H | SCH₂CH₂CH₃ | Cl | OCH₃ | CH |
| H | A-1 | — | O | H | SCH₂—CH=CH₂ | CH₃ | CH₃ | CH |
| H | A-1 | — | O | H | SCH₂—CH=CH₂ | CH₃ | OCH₃ | CH |
| H | A-1 | — | O | H | SCH₂—CH=CH₂ | OCH₃ | OCH₃ | CH |
| H | A-1 | — | O | H | SCH₂—CH=CH₂ | CH₃ | CH₃ | N |
| H | A-1 | — | O | H | SCH₂—CH=CH₂ | CH₃ | OCH₃ | N |
| H | A-1 | — | O | H | SCH₂—CH=CH₂ | OCH₃ | OCH₃ | N |
| H | A-1 | — | O | H | SCH₂—CH=CH₂ | Cl | OCH₃ | CH |
| H | A-1 | — | O | H | SCH₂CH₂OCH₃ | CH₃ | CH₃ | CH |
| H | A-1 | — | O | H | SCH₂—C≡CH | CH₃ | OCH₃ | CH |

TABLE III-continued

| | | | | | | | | |
|---|---|---|---|---|---|---|---|---|
| H | A-1 | — | O | H | SCH(CH$_3$)$_2$ | OCH$_3$ | OCH$_3$ | CH |
| H | A-1 | — | O | H | SCH(CH$_3$)$_2$ | CH$_3$ | CH$_3$ | N |
| H | A-1 | — | O | H | SCH(CH$_3$)$_2$ | CH$_3$ | OCH$_3$ | N |
| H | A-1 | — | O | H | SCH(CH$_3$)$_2$ | OCH$_3$ | OCH$_3$ | N |
| H | A-1 | — | O | H | SCH(CH$_3$)$_2$ | Cl | OCH$_3$ | CH |
| H | A-1 | — | O | H | SOCH$_3$ | CH$_3$ | CH$_3$ | CH |
| H | A-1 | — | O | H | SOCH$_3$ | CH$_3$ | OCH$_3$ | CH |
| H | A-1 | — | O | H | SOCH$_3$ | OCH$_3$ | OCH$_3$ | CH |
| H | A-1 | — | O | H | SOCH$_3$ | CH$_3$ | CH$_3$ | N |
| H | A-1 | — | O | H | SOCH$_3$ | CH$_3$ | OCH$_3$ | N |
| H | A-1 | — | O | H | SOCH$_3$ | OCH$_3$ | OCH$_3$ | N |
| H | A-1 | — | O | H | SOCH$_3$ | Cl | OCH$_3$ | CH |
| H | A-1 | — | O | H | SO$_2$CH$_3$ | CH$_3$ | CH$_3$ | CH |
| H | A-1 | — | O | H | SO$_2$CH$_3$ | CH$_3$ | OCH$_3$ | CH |
| H | A-1 | — | O | H | SO$_2$CH$_3$ | OCH$_3$ | OCH$_3$ | CH |
| H | A-1 | — | O | H | SO$_2$CH$_3$ | CH$_3$ | CH$_3$ | N |
| H | A-1 | — | O | H | SO$_2$CH$_3$ | CH$_3$ | OCH$_3$ | N |
| H | A-1 | — | O | H | SO$_2$CH$_3$ | OCH$_3$ | OCH$_3$ | N |
| H | A-1 | — | O | H | SO$_2$CH$_3$ | Cl | OCH$_3$ | CH |
| H | A-1 | — | O | H | SOCH$_2$CH$_3$ | CH$_3$ | CH$_3$ | CH |
| H | A-1 | — | O | H | SOCH$_2$CH$_3$ | CH$_3$ | OCH$_3$ | CH |
| H | A-1 | — | O | H | SOCH$_2$CH$_3$ | OCH$_3$ | OCH$_3$ | CH |
| H | A-1 | — | O | H | SOCH$_2$CH$_3$ | CH$_3$ | CH$_3$ | N |
| H | A-1 | — | O | H | SOCH$_2$CH$_3$ | CH$_3$ | OCH$_3$ | N |
| H | A-1 | — | O | H | SOCH$_2$CH$_3$ | OCH$_3$ | OCH$_3$ | N |
| H | A-1 | — | O | H | SOCH$_2$CH$_3$ | Cl | OCH$_3$ | CH |
| H | A-1 | — | O | H | SO$_2$CH$_2$CH$_3$ | CH$_3$ | CH$_3$ | CH |
| H | A-1 | — | O | H | SO$_2$CH$_2$CH$_3$ | CH$_3$ | OCH$_3$ | CH |
| H | A-1 | — | O | H | SO$_2$CH$_2$CH$_3$ | OCH$_3$ | OCH$_3$ | CH |
| H | A-1 | — | O | H | SO$_2$CH$_2$CH$_3$ | CH$_3$ | CH$_3$ | N |
| H | A-1 | — | O | H | SO$_2$CH$_2$CH$_3$ | CH$_3$ | OCH$_3$ | N |
| H | A-1 | — | O | H | SO$_2$CH$_2$CH$_3$ | OCH$_3$ | OCH$_3$ | N |
| H | A-1 | — | O | H | SO$_2$CH$_2$CH$_3$ | Cl | OCH$_3$ | CH |
| H | A-1 | — | O | H | SOCH$_2$CH$_2$CH$_3$ | CH$_3$ | CH$_3$ | CH |
| H | A-1 | — | O | H | SOCH$_2$CH$_2$CH$_3$ | CH$_3$ | OCH$_3$ | CH |
| H | A-1 | — | O | H | SOCH$_2$CH$_2$CH$_3$ | OCH$_3$ | OCH$_3$ | CH |
| H | A-1 | — | O | H | SOCH$_2$CH$_2$CH$_3$ | CH$_3$ | CH$_3$ | N |
| H | A-1 | — | O | H | SOCH$_2$CH$_2$CH$_3$ | CH$_3$ | OCH$_3$ | N |
| H | A-1 | — | O | H | SOCH$_2$CH$_2$CH$_3$ | OCH$_3$ | OCH$_3$ | N |
| H | A-1 | — | O | H | SOCH$_2$CH$_2$CH$_3$ | Cl | OCH$_3$ | CH |
| H | A-1 | — | O | H | SO$_2$CH$_2$CH$_2$CH$_3$ | CH$_3$ | CH$_3$ | CH |
| H | A-1 | — | O | H | SO$_2$CH$_2$CH$_2$CH$_3$ | CH$_3$ | OCH$_3$ | CH |
| H | A-1 | — | O | H | SO$_2$CH$_2$CH$_2$CH$_3$ | OCH$_3$ | OCH$_3$ | CH |
| H | A-1 | — | O | H | SO$_2$CH$_2$CH$_2$CH$_3$ | CH$_3$ | CH$_3$ | N |
| H | A-1 | — | O | H | SO$_2$CH$_2$CH$_2$CH$_3$ | CH$_3$ | OCH$_3$ | N |
| H | A-1 | — | O | H | SO$_2$CH$_2$CH$_2$CH$_3$ | OCH$_3$ | OCH$_3$ | N |
| H | A-1 | — | O | H | SO$_2$CH$_2$CH$_2$CH$_3$ | Cl | OCH$_3$ | CH |
| H | A-1 | — | O | H | SO$_2$N(CH$_3$)$_2$ | CH$_3$ | CH$_3$ | CH |
| H | A-1 | — | O | H | SO$_2$N(CH$_3$)$_2$ | CH$_3$ | OCH$_3$ | CH |
| H | A-1 | — | O | H | SO$_2$N(CH$_3$)$_2$ | OCH$_3$ | OCH$_3$ | CH |
| H | A-1 | — | O | H | SO$_2$N(CH$_3$)$_2$ | CH$_3$ | CH$_3$ | N |
| H | A-1 | — | O | H | SO$_2$N(CH$_3$)$_2$ | CH$_3$ | OCH$_3$ | N |
| H | A-1 | — | O | H | SO$_2$N(CH$_3$)$_2$ | OCH$_3$ | OCH$_3$ | N |
| H | A-1 | — | O | H | SO$_2$N(CH$_3$)$_2$ | Cl | OCH$_3$ | CH |
| H | A-1 | — | O | H | SO$_2$N(CH$_2$CH$_3$)$_2$ | CH$_3$ | CH$_3$ | CH |
| H | A-1 | — | O | H | SO$_2$N(CH$_2$CH$_3$)$_2$ | CH$_3$ | OCH$_3$ | CH |
| H | A-1 | — | O | H | SO$_2$N(CH$_2$CH$_3$)$_2$ | OCH$_3$ | OCH$_3$ | CH |
| H | A-1 | — | O | H | SO$_2$N(CH$_2$CH$_3$)$_2$ | CH$_3$ | CH$_3$ | N |
| H | A-1 | — | O | H | SO$_2$N(CH$_2$CH$_3$)$_2$ | CH$_3$ | OCH$_3$ | N |
| H | A-1 | — | O | H | SO$_2$N(CH$_2$CH$_3$)$_2$ | OCH$_3$ | OCH$_3$ | N |
| H | A-1 | — | O | H | SO$_2$N(CH$_2$CH$_3$)$_2$ | Cl | OCH$_3$ | CH |
| H | A-1 | — | O | H | SO$_2$N(CH$_3$)CH$_2$CH$_3$ | CH$_3$ | CH$_3$ | CH |
| H | A-1 | — | O | H | SO$_2$N(CH$_3$)CH$_2$CH$_3$ | CH$_3$ | OCH$_3$ | CH |
| H | A-1 | — | O | H | SO$_2$N(CH$_3$)CH$_2$CH$_3$ | OCH$_3$ | OCH$_3$ | CH |
| H | A-1 | — | O | H | SO$_2$N(CH$_3$)CH$_2$CH$_3$ | CH$_3$ | CH$_3$ | N |
| H | A-1 | — | O | H | SO$_2$N(CH$_3$)CH$_2$CH$_3$ | CH$_3$ | OCH$_3$ | N |
| H | A-1 | — | O | H | SO$_2$N(CH$_3$)CH$_2$CH$_3$ | OCH$_3$ | OCH$_3$ | N |
| H | A-1 | — | O | H | SO$_2$N(CH$_3$)CH$_2$CH$_3$ | Cl | OCH$_3$ | CH |
| H | A-1 | — | O | H | SO$_2$NHCH$_3$ | CH$_3$ | CH$_3$ | CH |
| H | A-1 | — | O | H | SO$_2$NHCH$_3$ | CH$_3$ | OCH$_3$ | CH |
| H | A-1 | — | O | H | SO$_2$NHCH$_3$ | OCH$_3$ | OCH$_3$ | CH |
| H | A-1 | — | O | H | SO$_2$NHCH$_3$ | CH$_3$ | CH$_3$ | N |
| H | A-1 | — | O | H | SO$_2$NHCH$_3$ | CH$_3$ | OCH$_3$ | N |
| H | A-1 | — | O | H | SO$_2$NHCH$_3$ | OCH$_3$ | OCH$_3$ | N |
| H | A-1 | — | O | H | SO$_2$NHCH$_3$ | Cl | OCH$_3$ | CH |
| H | A-1 | — | O | H | SO$_2$N(OCH$_3$)CH$_3$ | CH$_3$ | CH$_3$ | CH |
| H | A-1 | — | O | H | SO$_2$N(OCH$_3$)CH$_3$ | CH$_3$ | OCH$_3$ | CH |
| H | A-1 | — | O | H | SO$_2$N(OCH$_3$)CH$_3$ | OCH$_3$ | OCH$_3$ | CH |
| H | A-1 | — | O | H | SO$_2$N(OCH$_3$)CH$_3$ | CH$_3$ | CH$_3$ | N |
| H | A-1 | — | O | H | SO$_2$N(OCH$_3$)CH$_3$ | CH$_3$ | OCH$_3$ | N |
| H | A-1 | — | O | H | SO$_2$N(OCH$_3$)CH$_3$ | OCH$_3$ | OCH$_3$ | N |
| H | A-1 | — | O | H | SO$_2$N(OCH$_3$)CH$_3$ | Cl | OCH$_3$ | CH |

TABLE III-continued

| | | | | | | | | |
|---|---|---|---|---|---|---|---|---|
| H | A-1 | — | O | H | CON(CH$_3$)$_2$ | CH$_3$ | CH$_3$ | CH |
| H | A-1 | — | O | H | CON(CH$_3$)$_2$ | CH$_3$ | OCH$_3$ | CH |
| H | A-1 | — | O | H | CON(CH$_3$)$_2$ | OCH$_3$ | OCH$_3$ | CH |
| H | A-1 | — | O | H | CON(CH$_3$)$_2$ | CH$_3$ | CH$_3$ | N |
| H | A-1 | — | O | H | CON(CH$_3$)$_2$ | CH$_3$ | OCH$_3$ | N |
| H | A-1 | — | O | H | CON(CH$_3$)$_2$ | OCH$_3$ | OCH$_3$ | N |
| H | A-1 | — | O | H | CON(CH$_3$)$_2$ | Cl | OCH$_3$ | CH |
| H | A-1 | — | O | H | CONHCH$_3$ | CH$_3$ | CH$_3$ | CH |
| H | A-1 | — | O | H | CONHCH$_3$ | CH$_3$ | OCH$_3$ | CH |
| H | A-1 | — | O | H | CONHCH$_3$ | OCH$_3$ | OCH$_3$ | CH |
| H | A-1 | — | O | H | CONHCH$_3$ | CH$_3$ | CH$_3$ | N |
| H | A-1 | — | O | H | CONHCH$_3$ | CH$_3$ | OCH$_3$ | N |
| H | A-1 | — | O | H | CONHCH$_3$ | OCH$_3$ | OCH$_3$ | N |
| H | A-1 | — | O | H | CONHCH$_3$ | Cl | OCH$_3$ | CH |
| H | A-1 | — | O | H | CONHCH$_2$CH$_3$ | CH$_3$ | CH$_3$ | CH |
| H | A-1 | — | O | H | CON(CH$_2$CH$_3$)$_2$ | CH$_3$ | OCH$_3$ | CH |
| H | A-1 | — | O | H | CON(CH$_2$CH$_3$)$_2$ | OCH$_3$ | OCH$_3$ | CH |
| H | A-1 | — | O | H | CON(CH$_2$CH$_3$)$_2$ | CH$_3$ | CH$_3$ | N |
| H | A-1 | — | O | H | CON(CH$_2$CH$_3$)$_2$ | CH$_3$ | OCH$_3$ | N |
| H | A-1 | — | O | H | CON(CH$_2$CH$_3$)$_2$ | OCH$_3$ | OCH$_3$ | N |
| H | A-1 | — | O | H | CON(CH$_2$CH$_3$)$_2$ | Cl | OCH$_3$ | CH |
| H | A-1 | — | O | H | (N=N, O, CH$_3$ oxadiazole) | CH$_3$ | CH$_3$ | CH |
| H | A-1 | — | O | H | (N=N, O, CH$_3$ oxadiazole) | CH$_3$ | OCH$_3$ | CH |
| H | A-1 | — | O | H | (N=N, O, CH$_3$ oxadiazole) | OCH$_3$ | OCH$_3$ | CH |
| H | A-1 | — | O | H | (N=N, O, CH$_3$ oxadiazole) | CH$_3$ | CH$_3$ | N |
| H | A-1 | — | O | H | (N=N, O, CH$_3$ oxadiazole) | CH$_3$ | OCH$_3$ | N |
| H | A-1 | — | O | H | (N=N, O, CH$_3$ oxadiazole) | OCH$_3$ | OCH$_3$ | N |
| H | A-1 | — | O | H | (N=N, O, CH$_3$ oxadiazole) | Cl | OCH$_3$ | CH |
| H | A-1 | — | O | H | (N-methylpyrazole) | CH$_3$ | CH$_3$ | CH |
| H | A-1 | — | O | H | (N-methylpyrazole) | CH$_3$ | OCH$_3$ | CH |
| H | A-1 | — | O | H | (N-methylpyrazole) | OCH$_3$ | OCH$_3$ | CH |
| H | A-1 | — | O | H | (N-methylpyrazole) | CH$_3$ | CH$_3$ | N |

TABLE III-continued
| | | | | | | | | |
|---|---|---|---|---|---|---|---|---|
| H | A-1 | — | O | H | 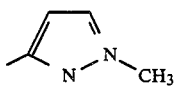 | CH₃ | OCH₃ | N |
| H | A-1 | — | O | H | 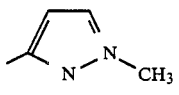 | OCH₃ | OCH₃ | N |
| H | A-1 | — | O | H | 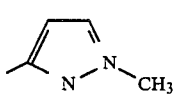 | Cl | OCH₃ | CH |
| H | A-1 | — | O | H | 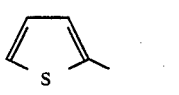 | CH₃ | CH₃ | CH |
| H | A-1 | — | O | H | 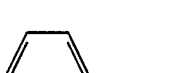 | CH₃ | OCH₃ | CH |
| H | A-1 | — | O | H | 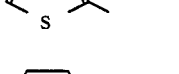 | OCH₃ | OCH₃ | CH |
| H | A-1 | — | O | H | 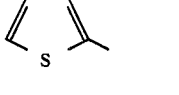 | CH₃ | CH₃ | N |
| H | A-1 | — | O | H | 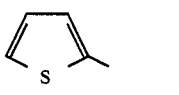 | CH₃ | OCH₃ | N |
| H | A-1 | — | O | H | 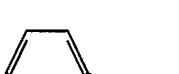 | OCH₃ | OCH₃ | N |
| H | A-1 | — | O | H | 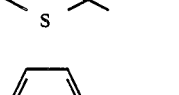 | Cl | OCH₃ | CH |
| H | A-1 | — | O | H | 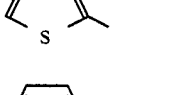 | CH₃ | CH₃ | CH |
| H | A-1 | — | O | H | 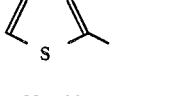 | CH₃ | OCH₃ | CH |
| H | A-1 | — | O | H | 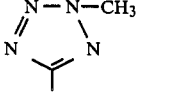 | OCH₃ | OCH₃ | CH |
| H | A-1 | — | O | H | 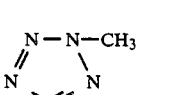 | CH₃ | CH₃ | N |
| H | A-1 | — | O | H | 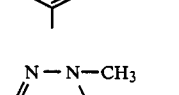 | CH₃ | OCH₃ | N |

TABLE III-continued
| | | | | | | | |
|---|---|---|---|---|---|---|---|
| H | A-1 | — | O | H | 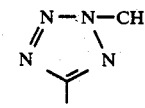 | OCH$_3$ | OCH$_3$ | N |
| H | A-1 | — | O | H | 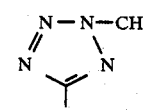 | Cl | OCH$_3$ | CH |
| H | A-1 | — | O | H |  | CH$_3$ | CH$_3$ | CH |
| H | A-1 | — | O | H | 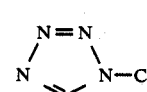 | CH$_3$ | OCH$_3$ | CH |
| H | A-1 | — | O | H | 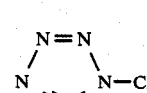 | OCH$_3$ | OCH$_3$ | CH |
| H | A-1 | — | O | H | 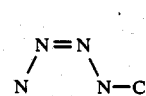 | CH$_3$ | CH$_3$ | N |
| H | A-1 | — | O | H | 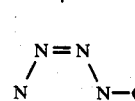 | CH$_3$ | OCH$_3$ | N |
| H | A-1 | — | O | H | 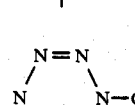 | OCH$_3$ | OCH$_3$ | N |
| H | A-1 | — | O | H | 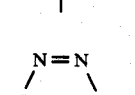 | Cl | OCH$_3$ | CH |
| H | A-1 | — | O | H |  | CH$_3$ | CH$_3$ | CH |
| H | A-1 | — | O | H |  | CH$_3$ | OCH$_3$ | CH |
| H | A-1 | — | O | H |  | OCH$_3$ | OCH$_3$ | CH |
| H | A-1 | — | O | H |  | CH$_3$ | CH$_3$ | N |

TABLE III-continued

| | | | | | | | | |
|---|---|---|---|---|---|---|---|---|
| H | A-1 | — | O | H | (1,3-dioxolan-2-yl, CH) | CH₃ | OCH₃ | N |
| H | A-1 | — | O | H | (1,3-dioxolan-2-yl, CH) | OCH₃ | OCH₃ | N |
| H | A-1 | — | O | H | (1,3-dioxolan-2-yl, CH) | Cl | OCH₃ | CH |
| H | A-1 | — | O | H | (2-methyl-1,3-dioxolan-2-yl) | CH₃ | CH₃ | CH |
| H | A-1 | — | O | H | (2-methyl-1,3-dioxolan-2-yl) | CH₃ | OCH₃ | CH |
| H | A-1 | — | O | H | (2-methyl-1,3-dioxolan-2-yl) | OCH₃ | OCH₃ | CH |
| H | A-1 | — | O | H | (2-methyl-1,3-dioxolan-2-yl) | CH₃ | CH₃ | N |
| H | A-1 | — | O | H | (2-methyl-1,3-dioxolan-2-yl) | CH₃ | OCH₃ | N |
| H | A-1 | — | O | H | (2-methyl-1,3-dioxolan-2-yl) | OCH₃ | OCH₃ | N |
| H | A-1 | — | O | H | (2-methyl-1,3-dioxolan-2-yl) | Cl | OCH₃ | CH |
| H | A-1 | — | O | H | (1,3-dioxan-2-yl) | CH₃ | CH₃ | CH |
| H | A-1 | — | O | H | (1,3-dioxan-2-yl) | CH₃ | OCH₃ | CH |
| H | A-1 | — | O | H | (1,3-dioxan-2-yl) | OCH₃ | OCH₃ | CH |

TABLE III-continued

| | | | | | | | | |
|---|---|---|---|---|---|---|---|---|
| H | A-1 | — | O | H | ![O-CH-O ring with CH2CH2] | CH₃ | CH₃ | N |
| H | A-1 | — | O | H | ![O-CH-O ring with CH2CH2] | CH₃ | OCH₃ | N |
| H | A-1 | — | O | H | ![O-CH-O ring with CH2CH2] | OCH₃ | OCH₃ | N |
| H | A-1 | — | O | H | ![O-CH-O ring with CH2CH2] | Cl | OCH₃ | CH |
| CH₃ | A-1 | — | O | H | CH₃ | CH₃ | CH₃ | CH |
| CH₃ | A-1 | — | O | H | CH₃ | CH₃ | OCH₃ | CH |
| CH₃ | A-1 | — | O | H | CH₃ | OCH₃ | OCH₃ | CH |
| CH₃ | A-1 | — | O | H | CH₃ | CH₃ | CH₃ | N |
| CH₃ | A-1 | — | O | H | CH₃ | CH₃ | OCH₃ | N |
| CH₃ | A-1 | — | O | H | CH₃ | OCH₃ | OCH₃ | N |
| CH₃ | A-1 | — | O | H | CH₃ | Cl | OCH₃ | CH |
| CH₃ | A-1 | — | O | H | CH₂CH₃ | CH₃ | CH₃ | CH |
| CH₃ | A-1 | — | O | H | CH₂CH₃ | CH₃ | OCH₃ | CH |
| CH₃ | A-1 | — | O | H | CH₂CH₃ | OCH₃ | OCH₃ | CH |
| CH₃ | A-1 | — | O | H | CH₂CH₃ | CH₃ | CH₃ | N |
| CH₃ | A-1 | — | O | H | CH₂CH₃ | CH₃ | OCH₃ | N |
| CH₃ | A-1 | — | O | H | CH₂CH₃ | OCH₃ | OCH₃ | N |
| CH₃ | A-1 | — | O | H | CH₂CH₃ | Cl | OCH₃ | CH |
| CH₃ | A-1 | — | O | H | CH(CH₃)₂ | CH₃ | CH₃ | CH |
| CH₃ | A-1 | — | O | H | CH(CH₃)₂ | CH₃ | OCH₃ | CH |
| CH₃ | A-1 | — | O | H | CH(CH₃)₂ | OCH₃ | OCH₃ | CH |
| CH₃ | A-1 | — | O | H | CH(CH₃)₂ | CH₃ | CH₃ | N |
| CH₃ | A-1 | — | O | H | CH(CH₃)₂ | CH₃ | OCH₃ | N |
| CH₃ | A-1 | — | O | H | CH(CH₃)₂ | OCH₃ | OCH₃ | N |
| CH₃ | A-1 | — | O | H | CH(CH₃)₂ | Cl | OCH₃ | CH |
| CH₃ | A-1 | — | O | H | CH₂CH₂CH₃ | CH₃ | CH₃ | CH |
| CH₃ | A-1 | — | O | H | CH₂CH₂CH₃ | CH₃ | OCH₃ | CH |
| CH₃ | A-1 | — | O | H | CH(CH₃)CH₂CH₃ | OCH₃ | OCH₃ | CH |
| CH₃ | A-1 | — | O | H | CH(CH₃)CH₂CH₃ | CH₃ | CH₃ | N |
| CH₃ | A-1 | — | O | H | CH₂CH(CH₃)₂ | CH₃ | OCH₃ | N |
| CH₃ | A-1 | — | O | H | CH₂CH(CH₃)₂ | OCH₃ | OCH₃ | N |
| CH₃ | A-1 | — | O | H | CH₂CH(CH₃)₂ | Cl | OCH₃ | CH |
| CH₃ | A-1 | — | O | H | cyclopropyl | CH₃ | CH₃ | CH |
| CH₃ | A-1 | — | O | H | cyclopropyl | CH₃ | OCH₃ | CH |
| CH₃ | A-1 | — | O | H | cyclopropyl | OCH₃ | OCH₃ | CH |
| CH₃ | A-1 | — | O | H | cyclopropyl | CH₃ | CH₃ | N |
| CH₃ | A-1 | — | O | H | cyclopropyl | CH₃ | OCH₃ | N |
| CH₃ | A-1 | — | O | H | cyclopropyl | OCH₃ | OCH₃ | N |
| CH₃ | A-1 | — | O | H | cyclopropyl | Cl | OCH₃ | CH |
| CH₃ | A-1 | — | O | H | CH—CF₂—CH₂ (ring) | CH₃ | CH₃ | CH |
| CH₃ | A-1 | — | O | H | CH—CF₂—CH₂ (ring) | CH₃ | OCH₃ | CH |
| CH₃ | A-1 | — | O | H | CH—CF₂—CH₂ (ring) | OCH₃ | OCH₃ | CH |
| CH₃ | A-1 | — | O | H | CH—CF₂—CH₂ (ring) | CH₃ | CH₃ | N |
| CH₃ | A-1 | — | O | H | CH—CF₂—CH₂ (ring) | CH₃ | OCH₃ | N |

TABLE III-continued

| | | | | | | | |
|---|---|---|---|---|---|---|---|
| CH₃ | A-1 | — | O | H | CH—CF₂—CH₂ | OCH₃ | OCH₃ | N |
| CH₃ | A-1 | — | O | H | CH—CF₂—CH₂ | Cl | OCH₃ | CH |
| CH₃ | A-1 | — | O | H | CH—CHF—CH₂ | CH₃ | CH₃ | CH |
| CH₃ | A-1 | — | O | H | CH—CHF—CH₂ | CH₃ | OCH₃ | CH |
| CH₃ | A-1 | — | O | H | CH—CHF—CH₂ | OCH₃ | OCH₃ | CH |
| CH₃ | A-1 | — | O | H | CH—CHF—CH₂ | CH₃ | CH₃ | N |
| CH₃ | A-1 | — | O | H | CH—CHF—CH₂ | CH₃ | OCH₃ | N |
| CH₃ | A-1 | — | O | H | CH—CHF—CH₂ | OCH₃ | OCH₃ | N |
| CH₃ | A-1 | — | O | H | CH—CHF—CH₂ | Cl | OCH₃ | CH |
| CH₃ | A-1 | — | O | H | CH—CHCl—CH₂ | CH₃ | CH₃ | CH |
| CH₃ | A-1 | — | O | H | CH—CHCl—CH₂ | CH₃ | OCH₃ | CH |
| CH₃ | A-1 | — | O | H | CH—CHCl—CH₂ | OCH₃ | OCH₃ | CH |
| CH₃ | A-1 | — | O | H | CH—CHCl—CH₂ | CH₃ | CH₃ | N |
| CH₃ | A-1 | — | O | H | CH—CHCl—CH₂ | CH₃ | OCH₃ | N |
| CH₃ | A-1 | — | O | H | CH—CHCl—CH₂ | OCH₃ | OCH₃ | N |
| CH₃ | A-1 | — | O | H | CH—CHCl—CH₂ | Cl | OCH₃ | CH |
| CH₃ | A-1 | — | O | H | OCH₂CH₂Cl | CH₃ | CH₃ | CH |
| CH₃ | A-1 | — | O | H | OCH₂CH₂Cl | CH₃ | OCH₃ | CH |
| CH₃ | A-1 | — | O | H | OCH₂CH₂Cl | OCH₃ | OCH₃ | CH |
| CH₃ | A-1 | — | O | H | OCH₂CH₂Cl | CH₃ | CH₃ | N |
| CH₃ | A-1 | — | O | H | OCH₂CH₂Cl | CH₃ | OCH₃ | N |
| CH₃ | A-1 | — | O | H | OCH₂CH₂Cl | OCH₃ | OCH₃ | N |
| CH₃ | A-1 | — | O | H | OCH₂CH₂Cl | Cl | OCH₃ | CH |
| CH₃ | A-1 | — | O | H | OCH₂CH₂F | CH₃ | CH₃ | CH |
| CH₃ | A-1 | — | O | H | OCH₂CH₂F | CH₃ | OCH₃ | CH |
| CH₃ | A-1 | — | O | H | OCH₂CH₂F | OCH₃ | OCH₃ | CH |
| CH₃ | A-1 | — | O | H | OCH₂CH₂F | CH₃ | CH₃ | N |
| CH₃ | A-1 | — | O | H | OCH₂CH₂F | CH₃ | OCH₃ | N |
| CH₃ | A-1 | — | O | H | OCH₂CH₂F | OCH₃ | OCH₃ | N |
| CH₃ | A-1 | — | O | H | OCH₂CH₂F | Cl | OCH₃ | CH |
| CH₃ | A-1 | — | O | H | OCH₂CF₃ | CH₃ | CH₃ | CH |
| CH₃ | A-1 | — | O | H | OCH₂CF₃ | CH₃ | OCH₃ | CH |
| CH₃ | A-1 | — | O | H | OCH₂CF₃ | OCH₃ | OCH₃ | CH |
| CH₃ | A-1 | — | O | H | OCH₂CF₃ | CH₃ | CH₃ | N |
| CH₃ | A-1 | — | O | H | OCH₂CF₃ | CH₃ | OCH₃ | N |

TABLE III-continued

| | | | | | | | | |
|---|---|---|---|---|---|---|---|---|
| CH$_3$ | A-1 | — | O | H | OCH$_2$CF$_3$ | OCH$_3$ | OCH$_3$ | N |
| CH$_3$ | A-1 | — | O | H | OCH$_2$CF$_3$ | Cl | OCH$_3$ | CH |
| CH$_3$ | A-1 | — | O | H | OCF$_2$CH$_3$ | CH$_3$ | CH$_3$ | CH |
| CH$_3$ | A-1 | — | O | H | OCF$_2$CH$_3$ | CH$_3$ | OCH$_3$ | CH |
| CH$_3$ | A-1 | — | O | H | OCF$_2$CH$_3$ | OCH$_3$ | OCH$_3$ | CH |
| CH$_3$ | A-1 | — | O | H | OCF$_2$CH$_3$ | CH$_3$ | CH$_3$ | N |
| CH$_3$ | A-1 | — | O | H | OCF$_2$CH$_3$ | CH$_3$ | OCH$_3$ | N |
| CH$_3$ | A-1 | — | O | H | OCF$_2$CH$_3$ | OCH$_3$ | OCH$_3$ | N |
| CH$_3$ | A-1 | — | O | H | OCF$_2$CH$_3$ | Cl | OCH$_3$ | CH |
| CH$_3$ | A-1 | — | O | H | NO$_2$ | CH$_3$ | CH$_3$ | CH |
| CH$_3$ | A-1 | — | O | H | NO$_2$ | CH$_3$ | OCH$_3$ | CH |
| CH$_3$ | A-1 | — | O | H | NO$_2$ | OCH$_3$ | OCH$_3$ | CH |
| CH$_3$ | A-1 | — | O | H | NO$_2$ | CH$_3$ | CH$_3$ | N |
| CH$_3$ | A-1 | — | O | H | NO$_2$ | CH$_3$ | OCH$_3$ | N |
| CH$_3$ | A-1 | — | O | H | NO$_2$ | OCH$_3$ | OCH$_3$ | N |
| CH$_3$ | A-1 | — | O | H | NO$_2$ | Cl | OCH$_3$ | CH |
| CH$_3$ | A-1 | — | O | H | CO$_2$CH$_3$ | CH$_3$ | CH$_3$ | CH |
| CH$_3$ | A-1 | — | O | H | CO$_2$CH$_3$ | CH$_3$ | OCH$_3$ | CH |
| CH$_3$ | A-1 | — | O | H | CO$_2$CH$_3$ | OCH$_3$ | OCH$_3$ | CH |
| CH$_3$ | A-1 | — | O | H | CO$_2$CH$_3$ | CH$_3$ | CH$_3$ | N |
| CH$_3$ | A-1 | — | O | H | CO$_2$CH$_3$ | CH$_3$ | OCH$_3$ | N |
| CH$_3$ | A-1 | — | O | H | CO$_2$CH$_3$ | OCH$_3$ | OCH$_3$ | N |
| CH$_3$ | A-1 | — | O | H | CO$_2$CH$_3$ | Cl | OCH$_3$ | CH |
| CH$_3$ | A-1 | — | O | H | CO$_2$CH$_2$CH$_3$ | CH$_3$ | CH$_3$ | CH |
| CH$_3$ | A-1 | — | O | H | CO$_2$CH$_2$CH$_3$ | CH$_3$ | OCH$_3$ | CH |
| CH$_3$ | A-1 | — | O | H | CO$_2$CH$_2$CH$_3$ | OCH$_3$ | OCH$_3$ | CH |
| CH$_3$ | A-1 | — | O | H | CO$_2$CH$_2$CH$_3$ | CH$_3$ | CH$_3$ | N |
| CH$_3$ | A-1 | — | O | H | CO$_2$CH$_2$CH$_3$ | CH$_3$ | OCH$_3$ | N |
| CH$_3$ | A-1 | — | O | H | CO$_2$CH$_2$CH$_3$ | OCH$_3$ | OCH$_3$ | N |
| CH$_3$ | A-1 | — | O | H | CO$_2$CH$_2$CH$_3$ | Cl | OCH$_3$ | CH |
| CH$_3$ | A-1 | — | O | H | CO$_2$CH$_2$CH$_2$CH$_3$ | CH$_3$ | CH$_3$ | CH |
| CH$_3$ | A-1 | — | O | H | CO$_2$CH$_2$CH$_2$CH$_3$ | CH$_3$ | OCH$_3$ | CH |
| CH$_3$ | A-1 | — | O | H | CO$_2$CH$_2$CH$_2$CH$_3$ | OCH$_3$ | OCH$_3$ | CH |
| CH$_3$ | A-1 | — | O | H | CO$_2$CH$_2$CH$_2$CH$_3$ | CH$_3$ | CH$_3$ | N |
| CH$_3$ | A-1 | — | O | H | CO$_2$CH$_2$CH$_2$CH$_3$ | CH$_3$ | OCH$_3$ | N |
| CH$_3$ | A-1 | — | O | H | CO$_2$CH$_2$CH$_2$CH$_3$ | OCH$_3$ | OCH$_3$ | N |
| CH$_3$ | A-1 | — | O | H | CO$_2$CH$_2$CH$_2$CH$_3$ | Cl | OCH$_3$ | CH |
| CH$_3$ | A-1 | — | O | H | CO$_2$CH$_2$CH$_2$OCH$_3$ | CH$_3$ | CH$_3$ | CH |
| CH$_3$ | A-1 | — | O | H | CO$_2$CH$_2$CH$_2$OCH$_3$ | CH$_3$ | OCH$_3$ | CH |
| CH$_3$ | A-1 | — | O | H | CO$_2$CH$_2$CH$_2$OCH$_3$ | OCH$_3$ | OCH$_3$ | CH |
| CH$_3$ | A-1 | — | O | H | CO$_2$CH$_2$CH$_2$OCH$_3$ | CH$_3$ | CH$_3$ | N |
| CH$_3$ | A-1 | — | O | H | CO$_2$CH$_2$CH$_2$OCH$_3$ | CH$_3$ | OCH$_3$ | N |
| CH$_3$ | A-1 | — | O | H | CO$_2$CH$_2$CH$_2$OCH$_3$ | OCH$_3$ | OCH$_3$ | N |
| CH$_3$ | A-1 | — | O | H | CO$_2$CH$_2$CH$_2$OCH$_3$ | Cl | OCH$_3$ | CH |
| CH$_3$ | A-1 | — | O | H | CO$_2$CH$_2$CH=CH$_2$ | CH$_3$ | CH$_3$ | CH |
| CH$_3$ | A-1 | — | O | H | CO$_2$CH$_2$CH=CH$_2$ | CH$_3$ | OCH$_3$ | CH |
| CH$_3$ | A-1 | — | O | H | CO$_2$CH$_2$CH=CH$_2$ | OCH$_3$ | OCH$_3$ | CH |
| CH$_3$ | A-1 | — | O | H | CO$_2$CH$_2$CH=CH$_2$ | CH$_3$ | CH$_3$ | N |
| CH$_3$ | A-1 | — | O | H | CO$_2$CH$_2$CH=CH$_2$ | CH$_3$ | OCH$_3$ | N |
| CH$_3$ | A-1 | — | O | H | CO$_2$CH$_2$CH=CH$_2$ | OCH$_3$ | OCH$_3$ | N |
| CH$_3$ | A-1 | — | O | H | CO$_2$CH$_2$CH=CH$_2$ | Cl | OCH$_3$ | CH |
| CH$_3$ | A-1 | — | O | H | CO$_2$CH$_2$—C≡CH | CH$_3$ | CH$_3$ | CH |
| CH$_3$ | A-1 | — | O | H | CO$_2$CH$_2$—C≡CH | CH$_3$ | OCH$_3$ | CH |
| CH$_3$ | A-1 | — | O | H | CO$_2$CH$_2$—C≡CH | OCH$_3$ | OCH$_3$ | CH |
| CH$_3$ | A-1 | — | O | H | CO$_2$CH$_2$—C≡CH | CH$_3$ | CH$_3$ | N |
| CH$_3$ | A-1 | — | O | H | CO$_2$CH$_2$—C≡CH | CH$_3$ | OCH$_3$ | N |
| CH$_3$ | A-1 | — | O | H | CO$_2$CH$_2$—C≡CH | OCH$_3$ | OCH$_3$ | N |
| CH$_3$ | A-1 | — | O | H | CO$_2$CH$_2$—C≡CH | Cl | OCH$_3$ | CH |
| CH$_3$ | A-1 | — | O | H | N(CH$_3$)$_2$ | CH$_3$ | CH$_3$ | CH |
| CH$_3$ | A-1 | — | O | H | N(CH$_3$)$_2$ | CH$_3$ | OCH$_3$ | CH |
| CH$_3$ | A-1 | — | O | H | N(CH$_3$)$_2$ | OCH$_3$ | OCH$_3$ | CH |
| CH$_3$ | A-1 | — | O | H | N(CH$_3$)$_2$ | CH$_3$ | CH$_3$ | N |
| CH$_3$ | A-1 | — | O | H | N(CH$_3$)$_2$ | CH$_3$ | OCH$_3$ | N |
| CH$_3$ | A-1 | — | O | H | N(CH$_3$)$_2$ | OCH$_3$ | OCH$_3$ | N |
| CH$_3$ | A-1 | — | O | H | N(CH$_3$)$_2$ | Cl | OCH$_3$ | CH |
| H | A-1 | — | O | 2-F | CH$_3$ | CH$_3$ | CH$_3$ | CH |
| H | A-1 | — | O | 2-F | CH$_3$ | CH$_3$ | OCH$_3$ | CH |
| H | A-1 | — | O | 2-F | CH$_3$ | OCH$_3$ | OCH$_3$ | CH |
| H | A-1 | — | O | 2-F | CH$_3$ | CH$_3$ | CH$_3$ | N |
| H | A-1 | — | O | 2-F | CH$_3$ | CH$_3$ | OCH$_3$ | N |
| H | A-1 | — | O | 2-F | CH$_3$ | OCH$_3$ | OCH$_3$ | N |
| H | A-1 | — | O | 2-F | CH$_3$ | Cl | OCH$_3$ | CH |
| H | A-1 | — | O | 2-F | CH$_2$CH$_3$ | CH$_3$ | CH$_3$ | CH |
| H | A-1 | — | O | 2-F | CH$_2$CH$_3$ | CH$_3$ | OCH$_3$ | CH |
| H | A-1 | — | O | 2-F | CH$_2$CH$_3$ | OCH$_3$ | OCH$_3$ | CH |
| H | A-1 | — | O | 2-F | CH$_2$CH$_3$ | CH$_3$ | CH$_3$ | N |
| H | A-1 | — | O | 2-F | CH$_2$CH$_3$ | CH$_3$ | OCH$_3$ | N |
| H | A-1 | — | O | 2-F | CH$_2$CH$_3$ | OCH$_3$ | OCH$_3$ | N |
| H | A-1 | — | O | 2-F | CH$_2$CH$_3$ | Cl | OCH$_3$ | CH |
| H | A-1 | — | O | 2-F | CH(CH$_3$)$_2$ | CH$_3$ | CH$_3$ | CH |
| H | A-1 | — | O | 2-F | CH(CH$_3$)$_2$ | CH$_3$ | OCH$_3$ | CH |
| H | A-1 | — | O | 2-F | CH(CH$_3$)$_2$ | OCH$_3$ | OCH$_3$ | CH |

TABLE III-continued

| | | | | | | | | |
|---|---|---|---|---|---|---|---|---|
| H | A-1 | — | O | 2-F | CH(CH$_3$)$_2$ | CH$_3$ | CH$_3$ | N |
| H | A-1 | — | O | 2-F | CH(CH$_3$)$_2$ | CH$_3$ | OCH$_3$ | N |
| H | A-1 | — | O | 2-F | CH(CH$_3$)$_2$ | OCH$_3$ | OCH$_3$ | N |
| H | A-1 | — | O | 2-F | CH(CH$_3$)$_2$ | Cl | OCH$_3$ | CH |
| H | A-1 | — | O | 2-F | CH$_2$CH$_2$CH$_3$ | CH$_3$ | CH$_3$ | CH |
| H | A-1 | — | O | 2-F | CH$_2$CH$_2$CH$_3$ | CH$_3$ | OCH$_3$ | CH |
| H | A-1 | — | O | 2-F | CH(CH$_3$)CH$_2$CH$_3$ | OCH$_3$ | OCH$_3$ | CH |
| H | A-1 | — | O | 2-F | CH(CH$_3$)CH$_2$CH$_3$ | CH$_3$ | CH$_3$ | N |
| H | A-1 | — | O | 2-F | CH$_2$CH(CH$_3$)$_2$ | CH$_3$ | OCH$_3$ | N |
| H | A-1 | — | O | 2-F | CH$_2$CH(CH$_3$)$_2$ | OCH$_3$ | OCH$_3$ | N |
| H | A-1 | — | O | 2-F | CH$_2$CH(CH$_3$)$_2$ | Cl | OCH$_3$ | CH |
| H | A-1 | — | O | 2-Cl | cyclopropyl | CH$_3$ | CH$_3$ | CH |
| H | A-1 | — | O | 2-Cl | cyclopropyl | CH$_3$ | OCH$_3$ | CH |
| H | A-1 | — | O | 2-Cl | cyclopropyl | OCH$_3$ | OCH$_3$ | CH |
| H | A-1 | — | O | 2-Cl | cyclopropyl | CH$_3$ | CH$_3$ | N |
| H | A-1 | — | O | 2-Cl | cyclopropyl | CH$_3$ | OCH$_3$ | N |
| H | A-1 | — | O | 2-Cl | cyclopropyl | OCH$_3$ | OCH$_3$ | N |
| H | A-1 | — | O | 2-Cl | cyclopropyl | Cl | OCH$_3$ | CH |
| H | A-1 | — | O | 2-Cl | $\overline{CH-CF_2-CH_2}$ | CH$_3$ | CH$_3$ | CH |
| H | A-1 | — | O | 2-Cl | $\overline{CH-CF_2-CH_2}$ | CH$_3$ | OCH$_3$ | CH |
| H | A-1 | — | O | 2-Cl | $\overline{CH-CF_2-CH_2}$ | OCH$_3$ | OCH$_3$ | CH |
| H | A-1 | — | O | 2-Cl | $\overline{CH-CF_2-CH_2}$ | CH$_3$ | CH$_3$ | N |
| H | A-1 | — | O | 2-Cl | $\overline{CH-CF_2-CH_2}$ | CH$_3$ | OCH$_3$ | N |
| H | A-1 | — | O | 2-Cl | $\overline{CH-CF_2-CH_2}$ | OCH$_3$ | OCH$_3$ | N |
| H | A-1 | — | O | 2-Cl | $\overline{CH-CF_2-CH_2}$ | Cl | OCH$_3$ | CH |
| H | A-1 | — | O | 2-Cl | $\overline{CH-CHF-CH_2}$ | CH$_3$ | CH$_3$ | CH |
| H | A-1 | — | O | 2-Cl | $\overline{CH-CHF-CH_2}$ | CH$_3$ | OCH$_3$ | CH |
| H | A-1 | — | O | 2-Cl | $\overline{CH-CHF-CH_2}$ | OCH$_3$ | OCH$_3$ | CH |
| H | A-1 | — | O | 2-Cl | $\overline{CH-CHF-CH_2}$ | CH$_3$ | CH$_3$ | N |
| H | A-1 | — | O | 2-Cl | $\overline{CH-CHF-CH_2}$ | CH$_3$ | OCH$_3$ | N |
| H | A-1 | — | O | 2-Cl | $\overline{CH-CHF-CH_2}$ | OCH$_3$ | OCH$_3$ | N |
| H | A-1 | — | O | 2-Cl | $\overline{CH-CHF-CH_2}$ | Cl | OCH$_3$ | CH |
| H | A-1 | — | O | 2-Cl | $\overline{CH-CHCl-CH_2}$ | CH$_3$ | CH$_3$ | CH |
| H | A-1 | — | O | 2-Cl | $\overline{CH-CHCl-CH_2}$ | CH$_3$ | OCH$_3$ | CH |

TABLE III-continued

| | | | | | | | |
|---|---|---|---|---|---|---|---|
| H | A-1 | — | O | 2-Cl | CH—CHCl—CH₂ (cyclic) | OCH₃ | OCH₃ | CH |
| H | A-1 | — | O | 2-Cl | CH—CHCl—CH₂ (cyclic) | CH₃ | CH₃ | N |
| H | A-1 | — | O | 2-Cl | CH—CHCl—CH₂ (cyclic) | CH₃ | OCH₃ | N |
| H | A-1 | — | O | 2-Cl | CH—CHCl—CH₂ (cyclic) | OCH₃ | OCH₃ | N |
| H | A-1 | — | O | 2-Cl | CH—CHCl—CH₂ (cyclic) | Cl | OCH₃ | CH |
| H | A-1 | — | O | 6-CH₃ | OCH₂CH₂CH₂F | CH₃ | CH₃ | CH |
| H | A-1 | — | O | 6-CH₃ | OCH₂CH₂CH₂F | CH₃ | OCH₃ | CH |
| H | A-1 | — | O | 6-CH₃ | OCH₂CH₂CH₂F | OCH₃ | OCH₃ | CH |
| H | A-1 | — | O | 6-CH₃ | OCH₂CH₂CH₂F | CH₃ | CH₃ | N |
| H | A-1 | — | O | 6-CH₃ | OCH₂CH₂CH₂F | CH₃ | OCH₃ | N |
| H | A-1 | — | O | 6-CH₃ | OCH₂CH₂CH₂F | OCH₃ | OCH₃ | N |
| H | A-1 | — | O | 6-CH₃ | OCH₂CH₂CH₂F | Cl | OCH₃ | CH |
| H | A-1 | — | O | 6-CH₃ | OCH₂CH₂Cl | CH₃ | CH₃ | CH |
| H | A-1 | — | O | 6-CH₃ | OCH₂CH₂Cl | CH₃ | OCH₃ | CH |
| H | A-1 | — | O | 6-CH₃ | OCH₂CH₂Cl | OCH₃ | OCH₃ | CH |
| H | A-1 | — | O | 6-CH₃ | OCH₂CH₂Br | CH₃ | CH₃ | N |
| H | A-1 | — | O | 6-CH₃ | OCH₂CH₂Br | CH₃ | OCH₃ | N |
| H | A-1 | — | O | 6-CH₃ | OCH₂CH₂Br | OCH₃ | OCH₃ | N |
| H | A-1 | — | O | 6-CH₃ | OCH₂CH₂Br | Cl | OCH₃ | CH |
| H | A-1 | — | O | 6-CH₃ | OCH₂—C≡CH | CH₃ | CH₃ | CH |
| H | A-1 | — | O | 6-CH₃ | OCH₂—C≡CH | CH₃ | OCH₃ | CH |
| H | A-1 | — | O | 6-CH₃ | OCH₂—C≡CH | OCH₃ | OCH₃ | CH |
| H | A-1 | — | O | 6-CH₃ | OCH₂—C≡CH | CH₃ | CH₃ | N |
| H | A-1 | — | O | 6-CH₃ | OCH₂—C≡CH | CH₃ | OCH₃ | N |
| H | A-1 | — | O | 6-CH₃ | OCH₂—C≡CH | OCH₃ | OCH₃ | N |
| H | A-1 | — | O | 6-CH₃ | OCH₂—C≡CH | Cl | OCH₃ | CH |
| H | A-1 | — | O | 6-CH₃ | OCH₂—CH=CH₂ | CH₃ | CH₃ | CH |
| H | A-1 | — | O | 6-CH₃ | OCH₂—CH=CH₂ | CH₃ | OCH₃ | CH |
| H | A-1 | — | O | 6-CH₃ | OCH₂—CH=CH₂ | OCH₃ | OCH₃ | CH |
| H | A-1 | — | O | 6-CH₃ | OCH₂—CH=CH₂ | CH₃ | CH₃ | N |
| H | A-1 | — | O | 6-CH₃ | OCH₂—CH=CH₂ | CH₃ | OCH₃ | N |
| H | A-1 | — | O | 6-CH₃ | OCH₂—CH=CH₂ | OCH₃ | OCH₃ | N |
| H | A-1 | — | O | 6-CH₃ | OCH₂—CH=CH₂ | Cl | OCH₃ | CH |
| H | A-1 | — | O | 2-OCH₃ | NO₂ | CH₃ | CH₃ | CH |
| H | A-1 | — | O | 2-OCH₃ | NO₂ | CH₃ | OCH₃ | CH |
| H | A-1 | — | O | 2-OCH₃ | NO₂ | OCH₃ | OCH₃ | CH |
| H | A-1 | — | O | 2-OCH₃ | NO₂ | CH₃ | CH₃ | N |
| H | A-1 | — | O | 2-OCH₃ | NO₂ | CH₃ | OCH₃ | N |
| H | A-1 | — | O | 2-OCH₃ | NO₂ | OCH₃ | OCH₃ | N |
| H | A-1 | — | O | 2-OCH₃ | NO₂ | Cl | OCH₃ | CH |
| H | A-1 | — | O | 2-OCH₃ | CO₂CH₃ | CH₃ | CH₃ | CH |
| H | A-1 | — | O | 2-OCH₃ | CO₂CH₃ | CH₃ | OCH₃ | CH |
| H | A-1 | — | O | 2-OCH₃ | CO₂CH₃ | OCH₃ | OCH₃ | CH |
| H | A-1 | — | O | 2-OCH₃ | CO₂CH₃ | CH₃ | CH₃ | N |
| H | A-1 | — | O | 2-OCH₃ | CO₂CH₃ | CH₃ | OCH₃ | N |
| H | A-1 | — | O | 2-OCH₃ | CO₂CH₃ | OCH₃ | OCH₃ | N |
| H | A-1 | — | O | 2-OCH₃ | CO₂CH₃ | Cl | OCH₃ | CH |
| H | A-1 | — | O | 2-OCH₃ | CO₂CH₂CH₃ | CH₃ | CH₃ | CH |
| H | A-1 | — | O | 2-OCH₃ | CO₂CH₂CH₃ | CH₃ | OCH₃ | CH |
| H | A-1 | — | O | 2-OCH₃ | CO₂CH₂CH₃ | OCH₃ | OCH₃ | CH |
| H | A-1 | — | O | 2-OCH₃ | CO₂CH₂CH₃ | CH₃ | CH₃ | N |
| H | A-1 | — | O | 2-OCH₃ | CO₂CH₂CH₃ | CH₃ | OCH₃ | N |
| H | A-1 | — | O | 2-OCH₃ | CO₂CH₂CH₃ | OCH₃ | OCH₃ | N |
| H | A-1 | — | O | 2-OCH₃ | CO₂CH₂CH₃ | Cl | OCH₃ | CH |
| H | A-1 | — | O | 2-OCH₃ | CO₂CH₂CH₂CH₃ | CH₃ | CH₃ | CH |
| H | A-1 | — | O | 2-OCH₃ | CO₂CH₂CH₂CH₃ | CH₃ | OCH₃ | CH |
| H | A-1 | — | O | 2-OCH₃ | CO₂CH₂CH₂CH₃ | OCH₃ | OCH₃ | CH |
| H | A-1 | — | O | 2-OCH₃ | CO₂CH₂CH₂CH₃ | CH₃ | CH₃ | N |
| H | A-1 | — | O | 2-OCH₃ | CO₂CH₂CH₂CH₃ | CH₃ | OCH₃ | N |
| H | A-1 | — | O | 2-OCH₃ | CO₂CH₂CH₂CH₃ | OCH₃ | OCH₃ | N |
| H | A-1 | — | O | 2-OCH₃ | CO₂CH₂CH₂CH₃ | Cl | OCH₃ | CH |
| H | A-1 | — | O | 2-OCH₂CF₃ | CO₂CH(CH₃)₂ | CH₃ | CH₃ | CH |
| H | A-1 | — | O | 2-OCH₂CF₃ | CO₂CH(CH₃)₂ | CH₃ | OCH₃ | CH |
| H | A-1 | — | O | 2-OCH₂CF₃ | CO₂CH(CH₃)₂ | OCH₃ | OCH₃ | CH |
| H | A-1 | — | O | 2-OCH₂CF₃ | CO₂CH(CH₃)₂ | CH₃ | CH₃ | N |
| H | A-1 | — | O | 2-OCH₂CF₃ | CO₂CH(CH₃)₂ | CH₃ | OCH₃ | N |
| H | A-1 | — | O | 2-OCH₂CF₃ | CO₂CH(CH₃)₂ | OCH₃ | OCH₃ | N |
| H | A-1 | — | O | 2-OCH₂CF₃ | CO₂CH(CH₃)₂ | Cl | OCH₃ | CH |

TABLE III-continued

| R | A | E | W | R₁ | R₂ | X₁ | Y₁ | Z |
|---|---|---|---|---|---|---|---|---|
| H | A-1 | — | O | 2-OCH₂CF₃ | CO₂CH₂CH₂Cl | CH₃ | CH₃ | CH |
| H | A-1 | — | O | 2-OCH₂CF₃ | CO₂CH₂CH₂Cl | CH₃ | OCH₃ | CH |
| H | A-1 | — | O | 2-OCH₂CF₃ | CO₂CH₂CH₂Cl | OCH₃ | OCH₃ | CH |
| H | A-1 | — | O | 2-OCH₂CF₃ | CO₂CH₂CH₂Cl | CH₃ | CH₃ | N |
| H | A-1 | — | O | 2-OCH₂CF₃ | CO₂CH₂CH₂Cl | CH₃ | OCH₃ | N |
| H | A-1 | — | O | 2-OCH₂CF₃ | CO₂CH₂CH₂Cl | OCH₃ | OCH₃ | N |
| H | A-1 | — | O | 2-OCH₂CF₃ | CO₂CH₂CH₂Cl | Cl | OCH₃ | CH |
| H | A-1 | — | O | 2-OCH₂CF₃ | CO₂CH₂CH₂F | CH₃ | CH₃ | CH |
| H | A-1 | — | O | 2-OCH₂CF₃ | CO₂CH₂CH₂F | CH₃ | OCH₃ | CH |
| H | A-1 | — | O | 2-OCH₂CF₃ | CO₂CH₂CH₂F | OCH₃ | OCH₃ | CH |
| H | A-1 | — | O | 2-OCH₂CF₃ | CO₂CH₂CH₂F | CH₃ | CH₃ | N |
| H | A-1 | — | O | 2-OCH₂CF₃ | CO₂CH₂CH₂F | CH₃ | OCH₃ | N |
| H | A-1 | — | O | 2-OCH₂CF₃ | CO₂CH₂CH₂F | OCH₃ | OCH₃ | N |
| H | A-1 | — | O | 2-OCH₂CF₃ | CO₂CH₂CH₂F | Cl | OCH₃ | CH |
| H | A-1 | — | O | 2-OCH₂CF₃ | CO₂CH₂OCH₃ | CH₃ | CH₃ | CH |
| H | A-1 | — | O | 2-OCH₂CF₃ | CO₂CH₂OCH₃ | CH₃ | OCH₃ | CH |
| H | A-1 | — | O | 2-OCH₂CF₃ | CO₂CH₂OCH₃ | OCH₃ | OCH₃ | CH |
| H | A-1 | — | O | 2-OCH₂CF₃ | CO₂CH₂OCH₃ | CH₃ | CH₃ | N |
| H | A-1 | — | O | 2-OCH₂CF₃ | CO₂CH₂OCH₃ | CH₃ | OCH₃ | N |
| H | A-1 | — | O | 2-OCH₂CF₃ | CO₂CH₂OCH₃ | OCH₃ | OCH₃ | N |
| H | A-1 | — | O | 2-OCH₂CF₃ | CO₂CH₂OCH₃ | Cl | OCH₃ | CH |
| H | A-1 | — | O | 5-OCH₃ | CO₂CH₃ | CH₃ | CH₃ | CH |
| H | A-1 | — | O | 5-OCH₃ | CO₂CH₃ | CH₃ | OCH₃ | CH |
| H | A-1 | — | O | 5-OCH₃ | CO₂CH₃ | OCH₃ | OCH₃ | CH |
| H | A-1 | — | O | 5-OCH₃ | CO₂CH₃ | CH₃ | CH₃ | N |
| H | A-1 | — | O | 5-OCH₃ | CO₂CH₃ | CH₃ | OCH₃ | N |
| H | A-1 | — | O | 5-OCH₃ | CO₂CH₃ | OCH₃ | OCH₃ | N |
| H | A-1 | — | O | 5-OCH₃ | CO₂CH₃ | Cl | OCH₃ | CH |
| H | A-1 | — | O | 5-OCH₃ | CO₂CH₂CH₃ | CH₃ | CH₃ | CH |
| H | A-1 | — | O | 5-OCH₃ | CO₂CH₂CH₃ | CH₃ | OCH₃ | CH |
| H | A-1 | — | O | 5-OCH₃ | CO₂CH₂CH₃ | OCH₃ | OCH₃ | CH |
| H | A-1 | — | O | 5-OCH₃ | CO₂CH₂CH₃ | CH₃ | CH₃ | N |
| H | A-1 | — | O | 5-OCH₃ | CO₂CH₂CH₃ | CH₃ | OCH₃ | N |
| H | A-1 | — | O | 5-OCH₃ | CO₂CH₂CH₃ | OCH₃ | OCH₃ | N |
| H | A-1 | — | O | 5-OCH₃ | CO₂CH₂CH₃ | Cl | OCH₃ | CH |
| H | A-1 | — | O | 5-OCH₃ | SO₂N(CH₃)₂ | CH₃ | CH₃ | CH |
| H | A-1 | — | O | 5-OCH₃ | SO₂N(CH₃)₂ | CH₃ | OCH₃ | CH |
| H | A-1 | — | O | 5-OCH₃ | SO₂N(CH₃)₂ | OCH₃ | OCH₃ | CH |
| H | A-1 | — | O | 5-OCH₃ | SO₂N(CH₃)₂ | CH₃ | CH₃ | N |
| H | A-1 | — | O | 5-OCH₃ | SO₂N(CH₃)₂ | CH₃ | OCH₃ | N |
| H | A-1 | — | O | 5-OCH₃ | SO₂N(CH₃)₂ | OCH₃ | OCH₃ | N |
| H | A-1 | — | O | 5-OCH₃ | SO₂N(CH₃)₂ | Cl | OCH₃ | CH |
| H | A-1 | — | O | 5-OCH₃ | SO₂CH₃ | CH₃ | CH₃ | CH |
| H | A-1 | — | O | 5-OCH₃ | SO₂CH₃ | CH₃ | OCH₃ | CH |
| H | A-1 | — | O | 5-OCH₃ | SO₂CH₃ | OCH₃ | OCH₃ | CH |
| H | A-1 | — | O | 5-OCH₃ | SO₂CH₃ | CH₃ | CH₃ | N |
| H | A-1 | — | O | 5-OCH₃ | SO₂CH₃ | CH₃ | OCH₃ | N |
| H | A-1 | — | O | 5-OCH₃ | SO₂CH₃ | OCH₃ | OCH₃ | N |
| H | A-1 | — | O | 5-OCH₃ | SO₂CH₃ | Cl | OCH₃ | CH |
| CH₃ | A-1 | — | O | 2-F | SCH₂—CH=CH₂ | CH₃ | CH₃ | CH |
| CH₃ | A-1 | — | O | 2-F | SCH₂—CH=CH₂ | CH₃ | OCH₃ | CH |
| CH₃ | A-1 | — | O | 2-F | SCH₂—CH=CH₂ | OCH₃ | OCH₃ | CH |
| CH₃ | A-1 | — | O | 2-F | SCH₂—CH=CH₂ | CH₃ | CH₃ | N |
| CH₃ | A-1 | — | O | 2-F | SCH₂—CH=CH₂ | CH₃ | OCH₃ | N |
| CH₃ | A-1 | — | O | 2-F | SCH₂—CH=CH₂ | OCH₃ | OCH₃ | N |
| CH₃ | A-1 | — | O | 2-F | SCH₂—CH=CH₂ | Cl | OCH₃ | CH |
| CH₃ | A-1 | — | O | 2-F | SCH₂CH₂OCH₃ | CH₃ | CH₃ | CH |
| CH₃ | A-1 | — | O | 2-F | SCH₂—C≡CH | CH₃ | OCH₃ | CH |
| CH₃ | A-1 | — | O | 2-F | SCH(CH₃)₂ | OCH₃ | OCH₃ | CH |
| CH₃ | A-1 | — | O | 2-F | SCH(CH₃)₂ | CH₃ | CH₃ | N |
| CH₃ | A-1 | — | O | 2-F | SCH(CH₃)₂ | CH₃ | OCH₃ | N |
| CH₃ | A-1 | — | O | 2-F | SCH(CH₃)₂ | OCH₃ | OCH₃ | N |
| CH₃ | A-1 | — | O | 2-F | SCH(CH₃)₂ | Cl | OCH₃ | CH |
| CH₃ | A-1 | — | O | 2-F | SOCH₃ | CH₃ | CH₃ | CH |
| CH₃ | A-1 | — | O | 2-F | SOCH₃ | CH₃ | OCH₃ | CH |
| CH₃ | A-1 | — | O | 2-F | SOCH₃ | OCH₃ | OCH₃ | CH |
| CH₃ | A-1 | — | O | 2-F | SOCH₃ | CH₃ | CH₃ | N |
| CH₃ | A-1 | — | O | 2-F | SOCH₃ | CH₃ | OCH₃ | N |
| CH₃ | A-1 | — | O | 2-F | SOCH₃ | OCH₃ | OCH₃ | N |
| CH₃ | A-1 | — | O | 2-F | SOCH₃ | Cl | OCH₃ | CH |
| CH₃ | A-1 | — | O | 2-F | SO₂CH₃ | CH₃ | CH₃ | CH |
| CH₃ | A-1 | — | O | 2-F | SO₂CH₃ | CH₃ | OCH₃ | CH |
| CH₃ | A-1 | — | O | 2-F | SO₂CH₃ | OCH₃ | OCH₃ | CH |
| CH₃ | A-1 | — | O | 2-F | SO₂CH₃ | CH₃ | CH₃ | N |
| CH₃ | A-1 | — | O | 2-F | SO₂CH₃ | CH₃ | OCH₃ | N |
| CH₃ | A-1 | — | O | 2-F | SO₂CH₃ | OCH₃ | OCH₃ | N |
| CH₃ | A-1 | — | O | 2-F | SO₂CH₃ | Cl | OCH₃ | CH |

| R | A | E | W | R₁ | R₂ | X₁ | Y₁ | m.p.(°C.) |
|---|---|---|---|---|---|---|---|---|
| H | A-2 | — | O | H | CO₂CH₃ | CH₃ | O | |
| H | A-2 | — | O | H | CO₂CH₃ | CH₃ | CH₂ | |
| H | A-2 | — | O | H | CO₂CH₃ | OCH₃ | O | |

TABLE III-continued

| R | A | E | W | R₁ | R₂ | | | m.p.(°C.) |
|---|---|---|---|---|---|---|---|---|
| H | A-2 | — | O | H | CO₂CH₃ | OCH₃ | CH₂ | |
| H | A-2 | — | O | H | CO₂CH₃ | OCH₂CH₃ | O | |
| H | A-2 | — | O | H | CO₂CH₃ | OCF₂H | CH₂ | |
| H | A-2 | — | O | H | SO₂N(CH₃)₂ | CH₃ | O | |
| H | A-2 | — | O | H | SO₂N(CH₃)₂ | OCH₃ | O | |
| H | A-2 | — | O | H | SO₂N(CH₃)₂ | OCF₂H | CH₂ | |

| R | A | E | W | R₁ | R₂ | X₁ | m.p.(°C.) |
|---|---|---|---|---|---|---|---|
| H | A-3 | — | O | H | CO₂CH₃ | CH₃ | |
| H | A-3 | — | O | H | CO₂CH₃ | OCH₃ | |
| H | A-3 | — | O | H | CO₂CH₃ | OCH₂CH₃ | |
| H | A-3 | — | O | H | CO₂CH₃ | OCF₂H | |
| H | A-3 | — | O | H | Cl | CH₃ | |
| H | A-3 | — | O | H | Cl | OCH₃ | |
| H | A-3 | — | O | H | SO₂CH₃ | CH₃ | |
| H | A-3 | — | O | H | SO₂CH₃ | OCH₃ | |

| R | A | E | W | R₁ | R₂ | X₁ | Y₃ | m.p.(°C.) |
|---|---|---|---|---|---|---|---|---|
| H | A-4 | — | O | H | CO₂CH₃ | CH₃ | H | |
| H | A-4 | — | O | H | CO₂CH₃ | OCH₃ | H | |
| H | A-4 | — | O | H | CO₂CH₃ | OCH₂CH₃ | H | |
| H | A-4 | — | O | H | CO₂CH₃ | OCF₂H | H | |
| H | A-4 | — | O | H | CO₂CH₃ | CH₃ | CH₃ | |
| H | A-4 | — | O | H | CO₂CH₃ | OCH₃ | CH₃ | |
| H | A-4 | — | O | H | CO₂CH₃ | OCF₂H | CH₃ | |

| R | A | E | W | R₁ | R₂ | X₂ | Y₂ | m.p.(°C.) |
|---|---|---|---|---|---|---|---|---|
| H | A-5 | — | O | H | CO₂CH₃ | CH₃ | OCH₃ | |
| H | A-5 | — | O | H | CO₂CH₃ | CH₃ | OCH₂CH₃ | |
| H | A-5 | — | O | H | CO₂CH₃ | CH₃ | SCH₃ | |
| H | A-5 | — | O | H | CO₂CH₃ | CH₃ | SCH₂CH₃ | |
| H | A-5 | — | O | H | CO₂CH₃ | CH₃ | CH₃ | |
| H | A-5 | — | O | H | CO₂CH₃ | CH₃ | CH₂CH₃ | |
| H | A-5 | — | O | H | CO₂CH₃ | CH₂CH₃ | OCH₃ | |
| H | A-5 | — | O | H | CO₂CH₃ | CH₂CH₃ | SCH₃ | |
| H | A-5 | — | O | H | CO₂CH₃ | CH₂CH₃ | OCH₂CH₃ | |
| H | A-5 | — | O | H | CO₂CH₃ | CH₂CF₃- | OCH₃ | |

| R | A | E | W | R₁ | R₂ | X₃ | m.p.(°C.) |
|---|---|---|---|---|---|---|---|
| H | A-6 | — | O | H | CO₂CH₃ | CH₃ | |
| H | A-6 | — | O | H | CO₂CH₃ | OCH₃ | |
| H | A-6 | — | O | H | NO₂ | CH₃ | |
| H | A-6 | — | O | H | NO₂ | OCH₃ | |

| R | A | E | W | R₁ | R₂ | X₄ | Y₄ | m.p.(°C.) |
|---|---|---|---|---|---|---|---|---|
| H | A-7 | — | O | H | CO₂CH₃ | CH₃ | CH₃ | |
| H | A-7 | — | O | H | CO₂CH₃ | CH₃ | OCH₃ | |
| H | A-7 | — | O | H | CO₂CH₃ | CH₃ | OCH₂CH₃ | |
| H | A-7 | — | O | H | CO₂CH₃ | CH₃ | Cl | |
| H | A-7 | — | O | H | CO₂CH₃ | OCH₃ | CH₃ | |
| H | A-7 | — | O | H | CO₂CH₃ | OCH₃ | OCH₃ | |
| H | A-7 | — | O | H | CO₂CH₃ | OCH₂CH₃ | OCH₃ | |

| R | A | E | W | R₁ | R₂ | X | Y | Z | m.p.(°C.) |
|---|---|---|---|---|---|---|---|---|---|
| H | A-1 | — | O | H | CO₂CH₃ | CH₃ | OCH₂CH₃ | CH | |
| H | A-1 | — | O | H | CO₂CH₃ | CH₃ | OCF₂H | CH | |
| H | A-1 | — | O | H | CO₂CH₃ | CH₃ | SCF₂H | CH | |
| H | A-1 | — | O | H | CO₂CH₃ | CH₃ | SCH₃ | CH | |
| H | A-1 | — | O | H | CO₂CH₃ | CH₃ | CH₂OCH₃ | N | |
| H | A-1 | — | O | H | CO₂CH₃ | CH₃ | NHCH₃ | N | |
| H | A-1 | — | O | H | CO₂CH₃ | CH₃ | N(CH₃)₂ | N | |
| H | A-1 | — | O | H | CO₂CH₃ | CH₃ | CH₂F | CH | |
| H | A-1 | — | O | H | CO₂CH₃ | CH₃ | C≡CH | CH | |
| H | A-1 | — | O | H | CO₂CH₃ | CH₃ | cyclopropyl | CH | |
| H | A-1 | — | O | H | CO₂CH₃ | CH₃ | CN | CH | |
| H | A-1 | — | O | H | CO₂CH₃ | OCH₃ | CH₂CH₃ | CH | |
| H | A-1 | — | O | H | CO₂CH₃ | OCH₃ | OCH₂CH₃ | N | |
| H | A-1 | — | O | H | CO₂CH₃ | OCH₃ | SCH₃ | N | |
| H | A-1 | — | O | H | CO₂CH₃ | OCH₃ | OCF₂H | CH | |
| H | A-1 | — | O | H | CO₂CH₃ | OCH₃ | CH₂F | CH | |
| H | A-1 | — | O | H | CO₂CH₃ | OCH₃ | N(CH₃)₂ | N | |
| H | A-1 | — | O | H | CO₂CH₃ | OCH₃ | NHCH₃ | N | |
| H | A-1 | — | O | H | CO₂CH₃ | OCH₃ | CN | CH | |
| H | A-1 | — | O | H | CO₂CH₃ | OCF₂H | CH₃ | CH | |
| H | A-1 | — | O | H | CO₂CH₃ | OCF₂H | OCH₂CH₃ | CH | |
| H | A-1 | — | O | H | CO₂CH₃ | OCF₂H | CH₂CH₃ | N | |
| H | A-1 | — | O | H | CO₂CH₃ | OCF₂H | CH₂F | N | |
| H | A-1 | — | O | H | CO₂CH₃ | OCF₂H | SCH₃ | CH | |
| H | A-1 | — | O | H | CO₂CH₃ | OCF₂H | N(CH₃)₂ | CH | |
| H | A-1 | — | O | H | CO₂CH₃ | OCF₂H | NHCH₃ | N | |
| H | A-1 | — | O | H | CO₂CH₃ | CH₂OCH₃ | OCH₃ | N | |
| H | A-1 | — | O | H | CO₂CH₃ | CH₂OCH₃ | OCH₂CH₃ | CH | |

TABLE III-continued

| R | A | E | W | R₁ | R₂ | X | Y | Z |
|---|---|---|---|---|---|---|---|---|
| H | A-1 | — | O | H | CO₂CH₃ | CH₂OCH₃ | CH₃ | CH |
| H | A-1 | — | O | H | CO₂CH₃ | CH₂OCH₃ | CH₂F | CH |
| H | A-1 | — | O | H | CO₂CH₃ | CH₂OCH₃ | CH₂Cl | CH |
| H | A-1 | — | O | H | CO₂CH₃ | CH₂OCH₃ | CH₂Br | N |
| H | A-1 | — | O | H | CO₂CH₃ | SCF₂H | OCH₂CH₃ | CH |
| H | A-1 | — | O | H | CO₂CH₃ | SCF₂H | CH₂CH₃ | CH |
| H | A-1 | — | O | H | CO₂CH₃ | SCF₂H | CH₂F | CH |
| H | A-1 | — | O | H | CO₂CH₃ | SCF₂H | NHCH₃ | N |
| H | A-1 | — | O | H | CO₂CH₃ | N(CH₃)₂ | OCH₂CH₃ | N |
| H | A-1 | — | O | H | CO₂CH₃ | N(CH₃)₂ | CH₂CH₃ | N |
| H | A-1 | — | O | H | CO₂CH₃ | N(CH₃)₂ | CH₂F | CH |
| H | A-1 | — | O | H | CO₂CH₃ | N(CH₃)₂ | CH₂OCH₃ | N |
| H | A-1 | — | O | H | CO₂CH₃ | N(CH₃)₂ | cyclopropyl | CH |
| H | A-1 | — | O | H | CO₂CH₃ | C≡CH | CH₂CH₃ | CH |
| H | A-1 | — | O | H | CO₂CH₃ | C≡CH | OCH₃ | CH |
| H | A-1 | — | O | H | CO₂CH₃ | C≡CH | N(CH₃)₂ | CH |
| H | A-1 | — | O | H | CO₂CH₃ | C≡CH | OCH₂CH₃ | CH |

TABLE IV

| R | A | E | W | R₁ | R₂ | X | Y | Z | m.p. (°C.) |
|---|---|---|---|---|---|---|---|---|---|
| H | A-1 | — | O | H | H | CH₃ | CH₃ | CH | |
| H | A-1 | — | O | H | H | CH₃ | OCH₃ | CH | |
| H | A-1 | — | O | H | H | OCH₃ | OCH₃ | CH | |
| H | A-1 | — | O | H | H | CH₃ | CH₃ | N | |
| H | A-1 | — | O | H | H | CH₃ | OCH₃ | N | |
| H | A-1 | — | O | H | H | OCH₃ | OCH₃ | N | |
| H | A-1 | — | O | H | H | Cl | OCH₃ | CH | |
| H | A-1 | — | O | H | Cl | CH₃ | CH₃ | CH | |
| H | A-1 | — | O | H | Cl | CH₃ | OCH₃ | CH | |
| H | A-1 | — | O | H | Cl | OCH₃ | OCH₃ | CH | |
| H | A-1 | — | O | H | Cl | CH₃ | CH₃ | N | |
| H | A-1 | — | O | H | Cl | CH₃ | OCH₃ | N | |
| H | A-1 | — | O | H | Cl | OCH₃ | OCH₃ | N | |
| H | A-1 | — | O | H | Cl | Cl | OCH₃ | CH | |
| H | A-1 | — | O | H | Br | CH₃ | CH₃ | CH | |
| H | A-1 | — | O | H | Br | CH₃ | OCH₃ | CH | |
| H | A-1 | — | O | H | Br | OCH₃ | OCH₃ | CH | |
| H | A-1 | — | O | H | Br | CH₃ | CH₃ | N | |
| H | A-1 | — | O | H | Br | CH₃ | OCH₃ | N | |
| H | A-1 | — | O | H | Br | OCH₃ | OCH₃ | N | |
| H | A-1 | — | O | H | Br | Cl | OCH₃ | CH | |
| H | A-1 | — | O | H | F | CH₃ | CH₃ | CH | |
| H | A-1 | — | O | H | F | CH₃ | OCH₃ | CH | |
| H | A-1 | — | O | H | F | OCH₃ | OCH₃ | CH | |
| H | A-1 | — | O | H | F | CH₃ | CH₃ | N | |
| H | A-1 | — | O | H | F | CH₃ | OCH₃ | N | |
| H | A-1 | — | O | H | F | OCH₃ | OCH₃ | N | |
| H | A-1 | — | O | H | F | Cl | OCH₃ | CH | |
| H | A-1 | — | O | H | CH₃ | CH₃ | CH₃ | CH | |
| H | A-1 | — | O | H | CH₃ | CH₃ | OCH₃ | CH | |
| H | A-1 | — | O | H | CH₃ | OCH₃ | OCH₃ | CH | |
| H | A-1 | — | O | H | CH₃ | CH₃ | CH₃ | N | |
| H | A-1 | — | O | H | CH₃ | CH₃ | OCH₃ | N | |
| H | A-1 | — | O | H | CH₃ | OCH₃ | OCH₃ | N | |
| H | A-1 | — | O | H | CH₃ | Cl | OCH₃ | CH | |
| H | A-1 | — | O | H | CH₂CH₃ | CH₃ | CH₃ | CH | |
| H | A-1 | — | O | H | CH₂CH₃ | CH₃ | OCH₃ | CH | |
| H | A-1 | — | O | H | CH₂CH₃ | OCH₃ | OCH₃ | CH | |
| H | A-1 | — | O | H | CH₂CH₃ | CH₃ | CH₃ | N | |
| H | A-1 | — | O | H | CH₂CH₃ | CH₃ | OCH₃ | N | |
| H | A-1 | — | O | H | CH₂CH₃ | OCH₃ | OCH₃ | N | |
| H | A-1 | — | O | H | CH₂CH₃ | Cl | OCH₃ | CH | |
| H | A-1 | — | O | H | CH(CH₃)₂ | CH₃ | CH₃ | CH | |
| H | A-1 | — | O | H | CH(CH₃)₂ | CH₃ | OCH₃ | CH | |
| H | A-1 | — | O | H | CH(CH₃)₂ | OCH₃ | OCH₃ | CH | |
| H | A-1 | — | O | H | CH(CH₃)₂ | CH₃ | CH₃ | N | |
| H | A-1 | — | O | H | CH(CH₃)₂ | CH₃ | OCH₃ | N | |
| H | A-1 | — | O | H | CH(CH₃)₂ | OCH₃ | OCH₃ | N | |
| H | A-1 | — | O | H | CH(CH₃)₂ | Cl | OCH₃ | CH | |
| H | A-1 | — | O | H | CH₂CH₂CH₃ | CH₃ | CH₃ | CH | |
| H | A-1 | — | O | H | CH₂CH₂CH₃ | CH₃ | OCH₃ | CH | |
| H | A-1 | — | O | H | CH(CH₃)CH₂CH₃ | OCH₃ | OCH₃ | CH | |
| H | A-1 | — | O | H | CH(CH₃)CH₂CH₃ | CH₃ | CH₃ | N | |
| H | A-1 | — | O | H | CH₂CH(CH₃)₂ | CH₃ | OCH₃ | N | |
| H | A-1 | — | O | H | CH₂CH(CH₃)₂ | OCH₃ | OCH₃ | N | |
| H | A-1 | — | O | H | CH₂CH(CH₃)₂ | Cl | OCH₃ | CH | |
| H | A-1 | — | O | H | CH₂Cl | CH₃ | CH₃ | CH | |
| H | A-1 | — | O | H | CH₂Cl | CH₃ | OCH₃ | CH | |
| H | A-1 | — | O | H | CH₂Cl | OCH₃ | OCH₃ | CH | |
| H | A-1 | — | O | H | CH₂Cl | CH₃ | CH₃ | N | |

TABLE IV-continued

| | | | | | | | |
|---|---|---|---|---|---|---|---|
| H | A-1 | —O | H | CH$_2$Br | CH$_3$ | OCH$_3$ | N |
| H | A-1 | —O | H | CH$_2$Br | OCH$_3$ | OCH$_3$ | N |
| H | A-1 | —O | H | CH$_2$F | Cl | OCH$_3$ | CH |
| H | A-1 | —O | H | CH(Cl)CH$_3$ | CH$_3$ | CH$_3$ | CH |
| H | A-1 | —O | H | CH(Cl)CH$_3$ | CH$_3$ | OCH$_3$ | CH |
| H | A-1 | —O | H | CH(Cl)CH$_3$ | OCH$_3$ | OCH$_3$ | CH |
| H | A-1 | —O | H | CH(Cl)CH$_3$ | CH$_3$ | CH$_3$ | N |
| H | A-1 | —O | H | CH(Cl)CH$_3$ | CH$_3$ | OCH$_3$ | N |
| H | A-1 | —O | H | CH(Cl)CH$_3$ | OCH$_3$ | OCH$_3$ | N |
| H | A-1 | —O | H | CH(Cl)CH$_3$ | Cl | OCH$_3$ | CH |
| H | A-1 | —O | H | CH(F)CH$_3$ | CH$_3$ | CH$_3$ | CH |
| H | A-1 | —O | H | CH(F)CH$_3$ | CH$_3$ | OCH$_3$ | CH |
| H | A-1 | —O | H | CH(F)CH$_3$ | OCH$_3$ | OCH$_3$ | CH |
| H | A-1 | —O | H | CH(F)CH$_3$ | CH$_3$ | CH$_3$ | N |
| H | A-1 | —O | H | CH(F)CH$_3$ | CH$_3$ | OCH$_3$ | N |
| H | A-1 | —O | H | CH(F)CH$_3$ | OCH$_3$ | OCH$_3$ | N |
| H | A-1 | —O | H | CH(F)CH$_3$ | Cl | OCH$_3$ | CH |
| H | A-1 | —O | H | CH(F)CH$_2$CH$_3$ | CH$_3$ | CH$_3$ | CH |
| H | A-1 | —O | H | CH(F)CH$_2$CH$_3$ | CH$_3$ | OCH$_3$ | CH |
| H | A-1 | —O | H | CH(F)CH$_2$CH$_3$ | OCH$_3$ | OCH$_3$ | CH |
| H | A-1 | —O | H | CH(F)CH$_2$CH$_3$ | CH$_3$ | CH$_3$ | N |
| H | A-1 | —O | H | CH(F)CH$_2$CH$_3$ | CH$_3$ | OCH$_3$ | N |
| H | A-1 | —O | H | CH(F)CH$_2$CH$_3$ | OCH$_3$ | OCH$_3$ | N |
| H | A-1 | —O | H | CH(F)CH$_2$CH$_3$ | Cl | OCH$_3$ | CH |
| H | A-1 | —O | H | CF$_2$CH$_3$ | CH$_3$ | CH$_3$ | CH |
| H | A-1 | —O | H | CF$_2$CH$_3$ | CH$_3$ | OCH$_3$ | CH |
| H | A-1 | —O | H | CF$_2$CH$_3$ | OCH$_3$ | OCH$_3$ | CH |
| H | A-1 | —O | H | CF$_2$CH$_3$ | CH$_3$ | CH$_3$ | N |
| H | A-1 | —O | H | CF$_2$CH$_3$ | CH$_3$ | OCH$_3$ | N |
| H | A-1 | —O | H | CF$_2$CH$_3$ | OCH$_3$ | OCH$_3$ | N |
| H | A-1 | —O | H | CF$_2$CH$_3$ | Cl | OCH$_3$ | CH |
| H | A-1 | —O | H | CF$_2$H | CH$_3$ | CH$_3$ | CH |
| H | A-1 | —O | H | CF$_2$H | CH$_3$ | OCH$_3$ | CH |
| H | A-1 | —O | H | CF$_2$H | OCH$_3$ | OCH$_3$ | CH |
| H | A-1 | —O | H | CF$_2$H | CH$_3$ | CH$_3$ | N |
| H | A-1 | —O | H | CF$_2$H | CH$_3$ | OCH$_3$ | N |
| H | A-1 | —O | H | CF$_2$H | OCH$_3$ | OCH$_3$ | N |
| H | A-1 | —O | H | CF$_2$H | Cl | OCH$_3$ | CH |
| H | A-1 | —O | H | CCl$_2$H | CH$_3$ | CH$_3$ | CH |
| H | A-1 | —O | H | CCl$_2$H | CH$_3$ | OCH$_3$ | CH |
| H | A-1 | —O | H | CCl$_2$H | OCH$_3$ | OCH$_3$ | CH |
| H | A-1 | —O | H | CCl$_2$H | CH$_3$ | CH$_3$ | N |
| H | A-1 | —O | H | CCl$_2$H | CH$_3$ | OCH$_3$ | N |
| H | A-1 | —O | H | CCl$_2$H | OCH$_3$ | OCH$_3$ | N |
| H | A-1 | —O | H | CCl$_2$H | Cl | OCH$_3$ | CH |
| H | A-1 | —O | H | CH$_2$CH(F)CH$_3$ | CH$_3$ | CH$_3$ | CH |
| H | A-1 | —O | H | CH$_2$CH(F)CH$_3$ | CH$_3$ | OCH$_3$ | CH |
| H | A-1 | —O | H | CH$_2$CH(F)CH$_3$ | OCH$_3$ | OCH$_3$ | CH |
| H | A-1 | —O | H | CH(CH$_3$)CH(Cl)CH$_3$ | CH$_3$ | CH$_3$ | N |
| H | A-1 | —O | H | CH(CH$_3$)CH(Cl)CH$_3$ | CH$_3$ | OCH$_3$ | N |
| H | A-1 | —O | H | CH(CH$_3$)CH$_2$Br | OCH$_3$ | OCH$_3$ | N |
| H | A-1 | —O | H | CH(CH$_3$)CH$_2$Br | Cl | OCH$_3$ | CH |
| H | A-1 | —O | H | cyclopropyl | CH$_3$ | CH$_3$ | CH |
| H | A-1 | —O | H | cyclopropyl | CH$_3$ | OCH$_3$ | CH |
| H | A-1 | —O | H | cyclopropyl | OCH$_3$ | OCH$_3$ | CH |
| H | A-1 | —O | H | cyclopropyl | CH$_3$ | CH$_3$ | N |
| H | A-1 | —O | H | cyclopropyl | CH$_3$ | OCH$_3$ | N |
| H | A-1 | —O | H | cyclopropyl | OCH$_3$ | OCH$_3$ | N |
| H | A-1 | —O | H | cyclopropyl | Cl | OCH$_3$ | CH |
| H | A-1 | —O | H | CH—CF$_2$—CH$_2$ (ring) | CH$_3$ | CH$_3$ | CH |
| H | A-1 | —O | H | CH—CF$_2$—CH$_2$ (ring) | CH$_3$ | OCH$_3$ | CH |
| H | A-1 | —O | H | CH—CF$_2$—CH$_2$ (ring) | OCH$_3$ | OCH$_3$ | CH |
| H | A-1 | —O | H | CH—CF$_2$—CH$_2$ (ring) | CH$_3$ | CH$_3$ | N |
| H | A-1 | —O | H | CH—CF$_2$—CH$_2$ (ring) | CH$_3$ | OCH$_3$ | N |
| H | A-1 | —O | H | CH—CF$_2$—CH$_2$ (ring) | OCH$_3$ | OCH$_3$ | N |

TABLE IV-continued

| | | | | | | | | |
|---|---|---|---|---|---|---|---|---|
| H | A-1 | — | O | H | CH—CF$_2$—CH$_2$ (cyclic) | Cl | OCH$_3$ | CH |
| H | A-1 | — | O | H | CH—CHF—CH$_2$ (cyclic) | CH$_3$ | CH$_3$ | CH |
| H | A-1 | — | O | H | CH—CHF—CH$_2$ (cyclic) | CH$_3$ | OCH$_3$ | CH |
| H | A-1 | — | O | H | CH—CHF—CH$_2$ (cyclic) | OCH$_3$ | OCH$_3$ | CH |
| H | A-1 | — | O | H | CH—CHF—CH$_2$ (cyclic) | CH$_3$ | CH$_3$ | N |
| H | A-1 | — | O | H | CH—CHF—CH$_2$ (cyclic) | CH$_3$ | OCH$_3$ | N |
| H | A-1 | — | O | H | CH—CHF—CH$_2$ (cyclic) | OCH$_3$ | OCH$_3$ | N |
| H | A-1 | — | O | H | CH—CHF—CH$_2$ (cyclic) | Cl | OCH$_3$ | CH |
| H | A-1 | — | O | H | CH—CHCl—CH$_2$ (cyclic) | CH$_3$ | CH$_3$ | CH |
| H | A-1 | — | O | H | CH—CHCl—CH$_2$ (cyclic) | CH$_3$ | OCH$_3$ | CH |
| H | A-1 | — | O | H | CH—CHCl—CH$_2$ (cyclic) | OCH$_3$ | OCH$_3$ | CH |
| H | A-1 | — | O | H | CH—CHCl—CH$_2$ (cyclic) | CH$_3$ | CH$_3$ | N |
| H | A-1 | — | O | H | CH—CHCl—CH$_2$ (cyclic) | CH$_3$ | OCH$_3$ | N |
| H | A-1 | — | O | H | CH—CHCl—CH$_2$ (cyclic) | OCH$_3$ | OCH$_3$ | N |
| H | A-1 | — | O | H | CH—CHCl—CH$_2$ (cyclic) | Cl | OCH$_3$ | CH |
| H | A-1 | — | O | H | cyclobutyl | CH$_3$ | CH$_3$ | CH |
| H | A-1 | — | O | H | cyclobutyl | CH$_3$ | OCH$_3$ | CH |
| H | A-1 | — | O | H | cyclobutyl | OCH$_3$ | OCH$_3$ | CH |
| H | A-1 | — | O | H | cyclobutyl | CH$_3$ | CH$_3$ | N |
| H | A-1 | — | O | H | cyclobutyl | CH$_3$ | OCH$_3$ | N |
| H | A-1 | — | O | H | cyclobutyl | OCH$_3$ | OCH$_3$ | N |
| H | A-1 | — | O | H | cyclobutyl | Cl | OCH$_3$ | CH |
| H | A-1 | — | O | H | CH$_2$—CH=CH$_2$ | CH$_3$ | CH$_3$ | CH |
| H | A-1 | — | O | H | CH$_2$—CH=CH$_2$ | CH$_3$ | OCH$_3$ | CH |
| H | A-1 | — | O | H | CH$_2$—CH=CH$_2$ | OCH$_3$ | OCH$_3$ | CH |
| H | A-1 | — | O | H | CH$_2$—CH=CH$_2$ | CH$_3$ | CH$_3$ | N |
| H | A-1 | — | O | H | CH$_2$—CH=CH$_2$ | CH$_3$ | OCH$_3$ | N |
| H | A-1 | — | O | H | CH$_2$—CH=CH$_2$ | OCH$_3$ | OCH$_3$ | N |
| H | A-1 | — | O | H | CH$_2$—CH=CH$_2$ | Cl | OCH$_3$ | CH |
| H | A-1 | — | O | H | CH=CH$_2$ | CH$_3$ | CH$_3$ | CH |
| H | A-1 | — | O | H | CH=CH$_2$ | CH$_3$ | OCH$_3$ | CH |
| H | A-1 | — | O | H | CH=CH$_2$ | OCH$_3$ | OCH$_3$ | CH |
| H | A-1 | — | O | H | CH=CH$_2$ | CH$_3$ | CH$_3$ | N |
| H | A-1 | — | O | H | CH=CH$_2$ | CH$_3$ | OCH$_3$ | N |
| H | A-1 | — | O | H | CH=CH$_2$ | OCH$_3$ | OCH$_3$ | N |
| H | A-1 | — | O | H | CH=CH$_2$ | Cl | OCH$_3$ | CH |
| H | A-1 | — | O | H | CH$_2$—CF=CH$_2$ | CH$_3$ | CH$_3$ | CH |

TABLE IV-continued

| | | | | | | | |
|---|---|---|---|---|---|---|---|
| H | A-1 | — | O | H | CH$_2$—CF=CH$_2$ | CH$_3$ | OCH$_3$ | CH |
| H | A-1 | — | O | H | CHF=CH$_2$ | OCH$_3$ | OCH$_3$ | CH |
| H | A-1 | — | O | H | CHF=CH$_2$ | CH$_3$ | CH$_3$ | N |
| H | A-1 | — | O | H | CHF=CH$_2$ | CH$_3$ | OCH$_3$ | N |
| H | A-1 | — | O | H | CHF=CH$_2$ | OCH$_3$ | OCH$_3$ | N |
| H | A-1 | — | O | H | CH$_2$—C=CH—CH$_3$ | Cl | OCH$_3$ | CH |
| H | A-1 | — | O | H | CH$_2$—C≡CH | CH$_3$ | CH$_3$ | CH |
| H | A-1 | — | O | H | CH$_2$—C≡CH | CH$_3$ | OCH$_3$ | CH |
| H | A-1 | — | O | H | CH$_2$—C≡CH | OCH$_3$ | OCH$_3$ | CH |
| H | A-1 | — | O | H | CH$_2$—C≡CH | CH$_3$ | CH$_3$ | N |
| H | A-1 | — | O | H | CH$_2$—C≡CH | CH$_3$ | OCH$_3$ | N |
| H | A-1 | — | O | H | CH$_2$—C≡CH | OCH$_3$ | OCH$_3$ | N |
| H | A-1 | — | O | H | CH$_2$—C≡CH | Cl | OCH$_3$ | CH |
| H | A-1 | — | O | H | C≡CH | CH$_3$ | CH$_3$ | CH |
| H | A-1 | — | O | H | C≡CH | CH$_3$ | OCH$_3$ | CH |
| H | A-1 | — | O | H | C≡CH | OCH$_3$ | OCH$_3$ | CH |
| H | A-1 | — | O | H | C≡CH | CH$_3$ | CH$_3$ | N |
| H | A-1 | — | O | H | C≡CH | CH$_3$ | OCH$_3$ | N |
| H | A-1 | — | O | H | C≡CH | OCH$_3$ | OCH$_3$ | N |
| H | A-1 | — | O | H | C≡C—CH$_2$F | Cl | OCH$_3$ | CH |
| H | A-1 | — | O | H | C≡C—CH$_2$F | CH$_3$ | CH$_3$ | CH |
| H | A-1 | — | O | H | C≡C—CH$_2$F | CH$_3$ | OCH$_3$ | CH |
| H | A-1 | — | O | H | C≡C—CH$_2$F | OCH$_3$ | OCH$_3$ | CH |
| H | A-1 | — | O | H | CH$_2$—C≡C—CH$_2$Cl | CH$_3$ | CH$_3$ | N |
| H | A-1 | — | O | H | CH$_2$—C≡C—CH$_2$Cl | CH$_3$ | OCH$_3$ | N |
| H | A-1 | — | O | H | CH$_2$—C≡C—CH$_2$Cl | OCH$_3$ | OCH$_3$ | N |
| H | A-1 | — | O | H | CH$_2$—C≡C—CH$_2$Cl | Cl | OCH$_3$ | CH |
| H | A-1 | — | O | H | OCH$_3$ | CH$_3$ | CH$_3$ | CH |
| H | A-1 | — | O | H | OCH$_3$ | CH$_3$ | OCH$_3$ | CH |
| H | A-1 | — | O | H | OCH$_3$ | OCH$_3$ | OCH$_3$ | CH |
| H | A-1 | — | O | H | OCH$_3$ | CH$_3$ | CH$_3$ | N |
| H | A-1 | — | O | H | OCH$_3$ | CH$_3$ | OCH$_3$ | N |
| H | A-1 | — | O | H | OCH$_3$ | OCH$_3$ | OCH$_3$ | N |
| H | A-1 | — | O | H | OCH$_3$ | Cl | OCH$_3$ | CH |
| H | A-1 | — | O | H | OCH$_2$CH$_3$ | CH$_3$ | CH$_3$ | CH |
| H | A-1 | — | O | H | OCH$_2$CH$_3$ | CH$_3$ | OCH$_3$ | CH |
| H | A-1 | — | O | H | OCH$_2$CH$_3$ | OCH$_3$ | OCH$_3$ | CH |
| H | A-1 | — | O | H | OCH$_2$CH$_3$ | CH$_3$ | CH$_3$ | N |
| H | A-1 | — | O | H | OCH$_2$CH$_3$ | CH$_3$ | OCH$_3$ | N |
| H | A-1 | — | O | H | OCH$_2$CH$_3$ | OCH$_3$ | OCH$_3$ | N |
| H | A-1 | — | O | H | OCH$_2$CH$_3$ | Cl | OCH$_3$ | CH |
| H | A-1 | — | O | H | OCH(CH$_3$)$_2$ | CH$_3$ | CH$_3$ | CH |
| H | A-1 | — | O | H | OCH(CH$_3$)$_2$ | CH$_3$ | OCH$_3$ | CH |
| H | A-1 | — | O | H | OCH(CH$_3$)$_2$ | OCH$_3$ | OCH$_3$ | CH |
| H | A-1 | — | O | H | OCH(CH$_3$)$_2$ | CH$_3$ | CH$_3$ | N |
| H | A-1 | — | O | H | OCH(CH$_3$)$_2$ | CH$_3$ | OCH$_3$ | N |
| H | A-1 | — | O | H | OCH(CH$_3$)$_2$ | OCH$_3$ | OCH$_3$ | N |
| H | A-1 | — | O | H | OCH(CH$_3$)$_2$ | Cl | OCH$_3$ | CH |
| H | A-1 | — | O | H | OCH$_2$CH$_2$CH$_2$CH$_3$ | CH$_3$ | CH$_3$ | CH |
| H | A-1 | — | O | H | OCH$_2$CH$_2$CH$_2$CH$_3$ | CH$_3$ | OCH$_3$ | CH |
| H | A-1 | — | O | H | OCH$_2$CH$_2$CH$_2$CH$_3$ | OCH$_3$ | OCH$_3$ | CH |
| H | A-1 | — | O | H | OCH$_2$—CH(CH$_3$)$_2$ | CH$_3$ | CH$_3$ | N |
| H | A-1 | — | O | H | OCH$_2$—CH(CH$_3$)$_2$ | CH$_3$ | OCH$_3$ | N |
| H | A-1 | — | O | H | OCH$_2$—CH(CH$_3$)$_2$ | OCH$_3$ | OCH$_3$ | N |
| H | A-1 | — | O | H | OCH$_2$—CH(CH$_3$)$_2$ | Cl | OCH$_3$ | CH |
| H | A-1 | — | O | H | OCF$_2$H | CH$_3$ | CH$_3$ | CH |
| H | A-1 | — | O | H | OCF$_2$H | CH$_3$ | OCH$_3$ | CH |
| H | A-1 | — | O | H | OCF$_2$H | OCH$_3$ | OCH$_3$ | CH |
| H | A-1 | — | O | H | OCF$_2$H | CH$_3$ | CH$_3$ | N |
| H | A-1 | — | O | H | OCF$_2$H | CH$_3$ | OCH$_3$ | N |
| H | A-1 | — | O | H | OCF$_2$H | OCH$_3$ | OCH$_3$ | N |
| H | A-1 | — | O | H | OCF$_2$H | Cl | OCH$_3$ | CH |
| H | A-1 | — | O | H | OCH$_2$CH$_2$Cl | CH$_3$ | CH$_3$ | CH |
| H | A-1 | — | O | H | OCH$_2$CH$_2$Cl | CH$_3$ | OCH$_3$ | CH |
| H | A-1 | — | O | H | OCH$_2$CH$_2$Cl | OCH$_3$ | OCH$_3$ | CH |
| H | A-1 | — | O | H | OCH$_2$CH$_2$Cl | CH$_3$ | CH$_3$ | N |
| H | A-1 | — | O | H | OCH$_2$CH$_2$Cl | CH$_3$ | OCH$_3$ | N |
| H | A-1 | — | O | H | OCH$_2$CH$_2$Cl | OCH$_3$ | OCH$_3$ | N |
| H | A-1 | — | O | H | OCH$_2$CH$_2$Cl | Cl | OCH$_3$ | CH |
| H | A-1 | — | O | H | OCH$_2$CH$_2$F | CH$_3$ | CH$_3$ | CH |
| H | A-1 | — | O | H | OCH$_2$CH$_2$F | CH$_3$ | OCH$_3$ | CH |
| H | A-1 | — | O | H | OCH$_2$CH$_2$F | OCH$_3$ | OCH$_3$ | CH |
| H | A-1 | — | O | H | OCH$_2$CH$_2$F | CH$_3$ | CH$_3$ | N |
| H | A-1 | — | O | H | OCH$_2$CH$_2$F | CH$_3$ | OCH$_3$ | N |
| H | A-1 | — | O | H | OCH$_2$CH$_2$F | OCH$_3$ | OCH$_3$ | N |
| H | A-1 | — | O | H | OCH$_2$CH$_2$F | Cl | OCH$_3$ | CH |
| H | A-1 | — | O | H | OCH$_2$CF$_3$ | CH$_3$ | CH$_3$ | CH |
| H | A-1 | — | O | H | OCH$_2$CF$_3$ | CH$_3$ | OCH$_3$ | CH |
| H | A-1 | — | O | H | OCH$_2$CF$_3$ | OCH$_3$ | OCH$_3$ | CH |
| H | A-1 | — | O | H | OCH$_2$CF$_3$ | CH$_3$ | CH$_3$ | N |
| H | A-1 | — | O | H | OCH$_2$CF$_3$ | CH$_3$ | OCH$_3$ | N |
| H | A-1 | — | O | H | OCH$_2$CF$_3$ | OCH$_3$ | OCH$_3$ | N |

TABLE IV-continued

| | | | | | | | | |
|---|---|---|---|---|---|---|---|---|
| H | A-1 | — | O | H | OCH$_2$CF$_3$ | Cl | OCH$_3$ | CH |
| H | A-1 | — | O | H | OCF$_2$CH$_3$ | CH$_3$ | CH$_3$ | CH |
| H | A-1 | — | O | H | OCF$_2$CH$_3$ | CH$_3$ | OCH$_3$ | CH |
| H | A-1 | — | O | H | OCF$_2$CH$_3$ | OCH$_3$ | OCH$_3$ | CH |
| H | A-1 | — | O | H | OCF$_2$CH$_3$ | CH$_3$ | CH$_3$ | N |
| H | A-1 | — | O | H | OCF$_2$CH$_3$ | CH$_3$ | OCH$_3$ | N |
| H | A-1 | — | O | H | OCF$_2$CH$_3$ | OCH$_3$ | OCH$_3$ | N |
| H | A-1 | — | O | H | OCF$_2$CH$_3$ | Cl | OCH$_3$ | CH |
| H | A-1 | — | O | H | OCH$_2$CH$_2$CH$_2$F | CH$_3$ | CH$_3$ | CH |
| H | A-1 | — | O | H | OCH$_2$CH$_2$CH$_2$F | CH$_3$ | OCH$_3$ | CH |
| H | A-1 | — | O | H | OCH$_2$CH$_2$CH$_2$F | OCH$_3$ | OCH$_3$ | CH |
| H | A-1 | — | O | H | OCH$_2$CH$_2$CH$_2$F | CH$_3$ | CH$_3$ | N |
| H | A-1 | — | O | H | OCH$_2$CH$_2$CH$_2$F | CH$_3$ | OCH$_3$ | N |
| H | A-1 | — | O | H | OCH$_2$CH$_2$CH$_2$F | OCH$_3$ | OCH$_3$ | N |
| H | A-1 | — | O | H | OCH$_2$CH$_2$CH$_2$F | Cl | OCH$_3$ | CH |
| H | A-1 | — | O | H | OCH$_2$CH$_2$Cl | CH$_3$ | CH$_3$ | CH |
| H | A-1 | — | O | H | OCH$_2$CH$_2$Cl | CH$_3$ | OCH$_3$ | CH |
| H | A-1 | — | O | H | OCH$_2$CH$_2$Cl | OCH$_3$ | OCH$_3$ | CH |
| H | A-1 | — | O | H | OCH$_2$CH$_2$Br | CH$_3$ | CH$_3$ | N |
| H | A-1 | — | O | H | OCH$_2$CH$_2$Br | CH$_3$ | OCH$_3$ | N |
| H | A-1 | — | O | H | OCH$_2$CH$_2$Br | OCH$_3$ | OCH$_3$ | N |
| H | A-1 | — | O | H | OCH$_2$CH$_2$Br | Cl | OCH$_3$ | CH |
| H | A-1 | — | O | H | OCH$_2$—C≡CH | CH$_3$ | CH$_3$ | CH |
| H | A-1 | — | O | H | OCH$_2$—C≡CH | CH$_3$ | OCH$_3$ | CH |
| H | A-1 | — | O | H | OCH$_2$—C≡CH | OCH$_3$ | OCH$_3$ | CH |
| H | A-1 | — | O | H | OCH$_2$—C≡CH | CH$_3$ | CH$_3$ | N |
| H | A-1 | — | O | H | OCH$_2$—C≡CH | CH$_3$ | OCH$_3$ | N |
| H | A-1 | — | O | H | OCH$_2$—C≡CH | OCH$_3$ | OCH$_3$ | N |
| H | A-1 | — | O | H | OCH$_2$—C≡CH | Cl | OCH$_3$ | CH |
| H | A-1 | — | O | H | OCH$_2$—CH=CH$_2$ | CH$_3$ | CH$_3$ | CH |
| H | A-1 | — | O | H | OCH$_2$—CH=CH$_2$ | CH$_3$ | OCH$_3$ | CH |
| H | A-1 | — | O | H | OCH$_2$—CH=CH$_2$ | OCH$_3$ | OCH$_3$ | CH |
| H | A-1 | — | O | H | OCH$_2$—CH=CH$_2$ | CH$_3$ | CH$_3$ | N |
| H | A-1 | — | O | H | OCH$_2$—CH=CH$_2$ | CH$_3$ | OCH$_3$ | N |
| H | A-1 | — | O | H | OCH$_2$—CH=CH$_2$ | OCH$_3$ | OCH$_3$ | N |
| H | A-1 | — | O | H | OCH$_2$—CH=CH$_2$ | Cl | OCH$_3$ | CH |
| H | A-1 | — | O | H | NO$_2$ | CH$_3$ | CH$_3$ | CH |
| H | A-1 | — | O | H | NO$_2$ | OCH$_3$ | OCH$_3$ | CH |
| H | A-1 | — | O | H | NO$_2$ | CH$_3$ | CH$_3$ | N |
| H | A-1 | — | O | H | NO$_2$ | CH$_3$ | OCH$_3$ | N |
| H | A-1 | — | O | H | NO$_2$ | OCH$_3$ | OCH$_3$ | N |
| H | A-1 | — | O | H | NO$_2$ | Cl | OCH$_3$ | CH |
| H | A-1 | — | O | H | CO$_2$CH$_3$ | CH$_3$ | CH$_3$ | CH |
| H | A-1 | — | O | H | CO$_2$CH$_3$ | CH$_3$ | OCH$_3$ | CH |
| H | A-1 | — | O | H | CO$_2$CH$_3$ | OCH$_3$ | OCH$_3$ | CH |
| H | A-1 | — | O | H | CO$_2$CH$_3$ | CH$_3$ | CH$_3$ | N |
| H | A-1 | — | O | H | CO$_2$CH$_3$ | CH$_3$ | OCH$_3$ | N |
| H | A-1 | — | O | H | CO$_2$CH$_3$ | OCH$_3$ | OCH$_3$ | N |
| H | A-1 | — | O | H | CO$_2$CH$_3$ | Cl | OCH$_3$ | CH |
| H | A-1 | — | O | H | CO$_2$CH$_2$CH$_3$ | CH$_3$ | CH$_3$ | CH |
| H | A-1 | — | O | H | CO$_2$CH$_2$CH$_3$ | CH$_3$ | OCH$_3$ | CH |
| H | A-1 | — | O | H | CO$_2$CH$_2$CH$_3$ | OCH$_3$ | OCH$_3$ | CH |
| H | A-1 | — | O | H | CO$_2$CH$_2$CH$_3$ | CH$_3$ | CH$_3$ | N |
| H | A-1 | — | O | H | CO$_2$CH$_2$CH$_3$ | CH$_3$ | OCH$_3$ | N |
| H | A-1 | — | O | H | CO$_2$CH$_2$CH$_3$ | OCH$_3$ | OCH$_3$ | N |
| H | A-1 | — | O | H | CO$_2$CH$_2$CH$_3$ | Cl | OCH$_3$ | CH |
| H | A-1 | — | O | H | CO$_2$CH$_2$CH$_2$CH$_3$ | CH$_3$ | CH$_3$ | CH |
| H | A-1 | — | O | H | CO$_2$CH$_2$CH$_2$CH$_3$ | CH$_3$ | OCH$_3$ | CH |
| H | A-1 | — | O | H | CO$_2$CH$_2$CH$_2$CH$_3$ | OCH$_3$ | OCH$_3$ | CH |
| H | A-1 | — | O | H | CO$_2$CH$_2$CH$_2$CH$_3$ | CH$_3$ | CH$_3$ | N |
| H | A-1 | — | O | H | CO$_2$CH$_2$CH$_2$CH$_3$ | CH$_3$ | OCH$_3$ | N |
| H | A-1 | — | O | H | CO$_2$CH$_2$CH$_2$CH$_3$ | OCH$_3$ | OCH$_3$ | N |
| H | A-1 | — | O | H | CO$_2$CH$_2$CH$_2$CH$_3$ | Cl | OCH$_3$ | CH |
| H | A-1 | — | O | H | CO$_2$CH(CH$_3$)$_2$ | CH$_3$ | CH$_3$ | CH |
| H | A-1 | — | O | H | CO$_2$CH(CH$_3$)$_2$ | CH$_3$ | OCH$_3$ | CH |
| H | A-1 | — | O | H | CO$_2$CH(CH$_3$)$_2$ | OCH$_3$ | OCH$_3$ | CH |
| H | A-1 | — | O | H | CO$_2$CH(CH$_3$)$_2$ | CH$_3$ | CH$_3$ | N |
| H | A-1 | — | O | H | CO$_2$CH(CH$_3$)$_2$ | CH$_3$ | OCH$_3$ | N |
| H | A-1 | — | O | H | CO$_2$CH(CH$_3$)$_2$ | OCH$_3$ | OCH$_3$ | N |
| H | A-1 | — | O | H | CO$_2$CH(CH$_3$)$_2$ | Cl | OCH$_3$ | CH |
| H | A-1 | — | O | H | CO$_2$CH$_2$CH$_2$Cl | CH$_3$ | CH$_3$ | CH |
| H | A-1 | — | O | H | CO$_2$CH$_2$CH$_2$Cl | CH$_3$ | OCH$_3$ | CH |
| H | A-1 | — | O | H | CO$_2$CH$_2$CH$_2$Cl | OCH$_3$ | OCH$_3$ | CH |
| H | A-1 | — | O | H | CO$_2$CH$_2$CH$_2$Cl | CH$_3$ | CH$_3$ | N |
| H | A-1 | — | O | H | CO$_2$CH$_2$CH$_2$Cl | CH$_3$ | OCH$_3$ | N |
| H | A-1 | — | O | H | CO$_2$CH$_2$CH$_2$Cl | OCH$_3$ | OCH$_3$ | N |
| H | A-1 | — | O | H | CO$_2$CH$_2$CH$_2$Cl | Cl | OCH$_3$ | CH |
| H | A-1 | — | O | H | CO$_2$CH$_2$CH$_2$F | CH$_3$ | CH$_3$ | CH |
| H | A-1 | — | O | H | CO$_2$CH$_2$CH$_2$F | CH$_3$ | OCH$_3$ | CH |
| H | A-1 | — | O | H | CO$_2$CH$_2$CH$_2$F | OCH$_3$ | OCH$_3$ | CH |
| H | A-1 | — | O | H | CO$_2$CH$_2$CH$_2$F | CH$_3$ | CH$_3$ | N |

TABLE IV-continued

| | | | | | | | |
|---|---|---|---|---|---|---|---|
| H | A-1 | — O | H | $CO_2CH_2CH_2F$ | $CH_3$ | $OCH_3$ | N |
| H | A-1 | — O | H | $CO_2CH_2CH_2F$ | $OCH_3$ | $OCH_3$ | N |
| H | A-1 | — O | H | $CO_2CH_2CH_2F$ | Cl | $OCH_3$ | CH |
| H | A-1 | — O | H | $CO_2CH_2OCH_3$ | $CH_3$ | $CH_3$ | CH |
| H | A-1 | — O | H | $CO_2CH_2OCH_3$ | $CH_3$ | $OCH_3$ | CH |
| H | A-1 | — O | H | $CO_2CH_2OCH_3$ | $OCH_3$ | $OCH_3$ | CH |
| H | A-1 | — O | H | $CO_2CH_2OCH_3$ | $CH_3$ | $CH_3$ | N |
| H | A-1 | — O | H | $CO_2CH_2OCH_3$ | $CH_3$ | $OCH_3$ | N |
| H | A-1 | — O | H | $CO_2CH_2OCH_3$ | $OCH_3$ | $OCH_3$ | N |
| H | A-1 | — O | H | $CO_2CH_2OCH_3$ | Cl | $OCH_3$ | CH |
| H | A-1 | — O | H | $CO_2CH_2CH_2OCH_3$ | $CH_3$ | $CH_3$ | CH |
| H | A-1 | — O | H | $CO_2CH_2CH_2OCH_3$ | $CH_3$ | $OCH_3$ | CH |
| H | A-1 | — O | H | $CO_2CH_2CH_2OCH_3$ | $OCH_3$ | $OCH_3$ | CH |
| H | A-1 | — O | H | $CO_2CH_2CH_2OCH_3$ | $CH_3$ | $CH_3$ | N |
| H | A-1 | — O | H | $CO_2CH_2CH_2OCH_3$ | $CH_3$ | $OCH_3$ | N |
| H | A-1 | — O | H | $CO_2CH_2CH_2OCH_3$ | $OCH_3$ | $OCH_3$ | N |
| H | A-1 | — O | H | $CO_2CH_2CH_2OCH_3$ | Cl | $OCH_3$ | CH |
| H | A-1 | — O | H | $CO_2CH_2CH=CH_2$ | $CH_3$ | $CH_3$ | CH |
| H | A-1 | — O | H | $CO_2CH_2CH=CH_2$ | $CH_3$ | $OCH_3$ | CH |
| H | A-1 | — O | H | $CO_2CH_2CH=CH_2$ | $OCH_3$ | $OCH_3$ | CH |
| H | A-1 | — O | H | $CO_2CH_2CH=CH_2$ | $CH_3$ | $CH_3$ | N |
| H | A-1 | — O | H | $CO_2CH_2CH=CH_2$ | $CH_3$ | $OCH_3$ | N |
| H | A-1 | — O | H | $CO_2CH_2CH=CH_2$ | $OCH_3$ | $OCH_3$ | N |
| H | A-1 | — O | H | $CO_2CH_2CH=CH_2$ | Cl | $OCH_3$ | CH |
| H | A-1 | — O | H | $CO_2CH_2-C\equiv CH$ | $CH_3$ | $CH_3$ | CH |
| H | A-1 | — O | H | $CO_2CH_2-C\equiv CH$ | $CH_3$ | $OCH_3$ | CH |
| H | A-1 | — O | H | $CO_2CH_2-C\equiv CH$ | $OCH_3$ | $OCH_3$ | CH |
| H | A-1 | — O | H | $CO_2CH_2-C\equiv CH$ | $CH_3$ | $CH_3$ | N |
| H | A-1 | — O | H | $CO_2CH_2-C\equiv CH$ | $CH_3$ | $OCH_3$ | N |
| H | A-1 | — O | H | $CO_2CH_2-C\equiv CH$ | $OCH_3$ | $OCH_3$ | N |
| H | A-1 | — O | H | $CO_2CH_2-C\equiv CH$ | $OCH_3$ | CH | |
| H | A-1 | — O | H | $N(CH_3)_2$ | $CH_3$ | $CH_3$ | CH |
| H | A-1 | — O | H | $N(CH_3)_2$ | $CH_3$ | $OCH_3$ | CH |
| H | A-1 | — O | H | $N(CH_3)_2$ | $OCH_3$ | $OCH_3$ | CH |
| H | A-1 | — O | H | $N(CH_3)_2$ | $CH_3$ | $CH_3$ | N |
| H | A-1 | — O | H | $N(CH_3)_2$ | $CH_3$ | $OCH_3$ | N |
| H | A-1 | — O | H | $N(CH_3)_2$ | $OCH_3$ | $OCH_3$ | N |
| H | A-1 | — O | H | $N(CH_3)_2$ | Cl | $OCH_3$ | CH |
| H | A-1 | — O | H | $NCH_2CH_3(CH_3)$ | $CH_3$ | $CH_3$ | CH |
| H | A-1 | — O | H | $NCH_2CH_3(CH_3)$ | $CH_3$ | $OCH_3$ | CH |
| H | A-1 | — O | H | $NCH_2CH_3(CH_3)$ | $OCH_3$ | $OCH_3$ | CH |
| H | A-1 | — O | H | $NCH_2CH_3(CH_3)$ | $CH_3$ | $CH_3$ | N |
| H | A-1 | — O | H | $NCH_2CH_3(CH_3)$ | $CH_3$ | $OCH_3$ | N |
| H | A-1 | — O | H | $NCH_2CH_3(CH_3)$ | $OCH_3$ | $OCH_3$ | N |
| H | A-1 | — O | H | $NCH_2CH_3(CH_3)$ | Cl | $OCH_3$ | CH |
| H | A-1 | — O | H | $SCH_3$ | $CH_3$ | $CH_3$ | CH |
| H | A-1 | — O | H | $SCH_3$ | $CH_3$ | $OCH_3$ | CH |
| H | A-1 | — O | H | $SCH_3$ | $OCH_3$ | $OCH_3$ | CH |
| H | A-1 | — O | H | $SCH_3$ | $CH_3$ | $CH_3$ | N |
| H | A-1 | — O | H | $SCH_3$ | $CH_3$ | $OCH_3$ | N |
| H | A-1 | — O | H | $SCH_3$ | $OCH_3$ | $OCH_3$ | N |
| H | A-1 | — O | H | $SCH_3$ | Cl | $OCH_3$ | CH |
| H | A-1 | — O | H | $SCH_2CH_3$ | $CH_3$ | $CH_3$ | CH |
| H | A-1 | — O | H | $SCH_2CH_3$ | $CH_3$ | $OCH_3$ | CH |
| H | A-1 | — O | H | $SCH_2CH_3$ | $OCH_3$ | $OCH_3$ | CH |
| H | A-1 | — O | H | $SCH_2CH_3$ | $CH_3$ | $CH_3$ | N |
| H | A-1 | — O | H | $SCH_2CH_3$ | $CH_3$ | $OCH_3$ | N |
| H | A-1 | — O | H | $SCH_2CH_3$ | $OCH_3$ | $OCH_3$ | N |
| H | A-1 | — O | H | $SCH_2CH_3$ | Cl | $OCH_3$ | CH |
| H | A-1 | — O | H | $SCH_2CH_2CH_3$ | $CH_3$ | $CH_3$ | CH |
| H | A-1 | — O | H | $SCH_2CH_2CH_3$ | $CH_3$ | $OCH_3$ | CH |
| H | A-1 | — O | H | $SCH_2CH_2CH_3$ | $OCH_3$ | $OCH_3$ | CH |
| H | A-1 | — O | H | $SCH_2CH_2CH_3$ | $CH_3$ | $CH_3$ | N |
| H | A-1 | — O | H | $SCH_2CH_2CH_3$ | $CH_3$ | $OCH_3$ | N |
| H | A-1 | — O | H | $SCH_2CH_2CH_3$ | $OCH_3$ | $OCH_3$ | N |
| H | A-1 | — O | H | $SCH_2CH_2CH_3$ | Cl | $OCH_3$ | CH |
| H | A-1 | — O | H | $SCH_2-CH=CH_2$ | $CH_3$ | $CH_3$ | CH |
| H | A-1 | — O | H | $SCH_2-CH=CH_2$ | $CH_3$ | $OCH_3$ | CH |
| H | A-1 | — O | H | $SCH_2-CH=CH_2$ | $OCH_3$ | $OCH_3$ | CH |
| H | A-1 | — O | H | $SCH_2-CH=CH_2$ | $CH_3$ | $CH_3$ | N |
| H | A-1 | — O | H | $SCH_2-CH=CH_2$ | $CH_3$ | $OCH_3$ | N |
| H | A-1 | — O | H | $SCH_2-CH=CH_2$ | $OCH_3$ | $OCH_3$ | N |
| H | A-1 | — O | H | $SCH_2-CH=CH_2$ | Cl | $OCH_3$ | CH |
| H | A-1 | — O | H | $SCH_2CH_2OCH_3$ | $CH_3$ | $CH_3$ | CH |
| H | A-1 | — O | H | $SCH_2-C\equiv CH$ | $CH_3$ | $OCH_3$ | CH |
| H | A-1 | — O | H | $SCH(CH_3)_2$ | $OCH_3$ | $OCH_3$ | CH |
| H | A-1 | — O | H | $SCH(CH_3)_2$ | $CH_3$ | $CH_3$ | N |
| H | A-1 | — O | H | $SCH(CH_3)_2$ | $CH_3$ | $OCH_3$ | N |
| H | A-1 | — O | H | $SCH(CH_3)_2$ | $OCH_3$ | $OCH_3$ | N |
| H | A-1 | — O | H | $SCH(CH_3)_2$ | Cl | $OCH_3$ | CH |
| H | A-1 | — O | H | $SOCH_3$ | $CH_3$ | $CH_3$ | CH |
| H | A-1 | — O | H | $SOCH_3$ | $CH_3$ | $OCH_3$ | CH |

TABLE IV-continued

| | | | | | | | | |
|---|---|---|---|---|---|---|---|---|
| H | A-1 | — | O | H | SOCH$_3$ | OCH$_3$ | OCH$_3$ | CH |
| H | A-1 | — | O | H | SOCH$_3$ | CH$_3$ | CH$_3$ | N |
| H | A-1 | — | O | H | SOCH$_3$ | CH$_3$ | OCH$_3$ | N |
| H | A-1 | — | O | H | SOCH$_3$ | OCH$_3$ | OCH$_3$ | N |
| H | A-1 | — | O | H | SOCH$_3$ | Cl | OCH$_3$ | CH |
| H | A-1 | — | O | H | SO$_2$CH$_3$ | CH$_3$ | CH$_3$ | CH |
| H | A-1 | — | O | H | SO$_2$CH$_3$ | CH$_3$ | OCH$_3$ | CH |
| H | A-1 | — | O | H | SO$_2$CH$_3$ | OCH$_3$ | OCH$_3$ | CH |
| H | A-1 | — | O | H | SO$_2$CH$_3$ | CH$_3$ | CH$_3$ | N |
| H | A-1 | — | O | H | SO$_2$CH$_3$ | CH$_3$ | OCH$_3$ | N |
| H | A-1 | — | O | H | SO$_2$CH$_3$ | OCH$_3$ | OCH$_3$ | N |
| H | A-1 | — | O | H | SO$_2$CH$_3$ | Cl | OCH$_3$ | CH |
| H | A-1 | — | O | H | SOCH$_2$CH$_3$ | CH$_3$ | CH$_3$ | CH |
| H | A-1 | — | O | H | SOCH$_2$CH$_3$ | CH$_3$ | OCH$_3$ | CH |
| H | A-1 | — | O | H | SOCH$_2$CH$_3$ | OCH$_3$ | OCH$_3$ | CH |
| H | A-1 | — | O | H | SOCH$_2$CH$_3$ | CH$_3$ | CH$_3$ | N |
| H | A-1 | — | O | H | SOCH$_2$CH$_3$ | CH$_3$ | OCH$_3$ | N |
| H | A-1 | — | O | H | SOCH$_2$CH$_3$ | OCH$_3$ | OCH$_3$ | N |
| H | A-1 | — | O | H | SOCH$_2$CH$_3$ | Cl | OCH$_3$ | CH |
| H | A-1 | — | O | H | SO$_2$CH$_2$CH$_3$ | CH$_3$ | CH$_3$ | CH |
| H | A-1 | — | O | H | SO$_2$CH$_2$CH$_3$ | CH$_3$ | OCH$_3$ | CH |
| H | A-1 | — | O | H | SO$_2$CH$_2$CH$_3$ | OCH$_3$ | OCH$_3$ | CH |
| H | A-1 | — | O | H | SO$_2$CH$_2$CH$_3$ | CH$_3$ | CH$_3$ | N |
| H | A-1 | — | O | H | SO$_2$CH$_2$CH$_3$ | CH$_3$ | OCH$_3$ | N |
| H | A-1 | — | O | H | SO$_2$CH$_2$CH$_3$ | OCH$_3$ | OCH$_3$ | N |
| H | A-1 | — | O | H | SO$_2$CH$_2$CH$_3$ | Cl | OCH$_3$ | CH |
| H | A-1 | — | O | H | SOCH$_2$CH$_2$CH$_3$ | CH$_3$ | CH$_3$ | CH |
| H | A-1 | — | O | H | SOCH$_2$CH$_2$CH$_3$ | CH$_3$ | OCH$_3$ | CH |
| H | A-1 | — | O | H | SOCH$_2$CH$_2$CH$_3$ | OCH$_3$ | OCH$_3$ | CH |
| H | A-1 | — | O | H | SOCH$_2$CH$_2$CH$_3$ | CH$_3$ | CH$_3$ | N |
| H | A-1 | — | O | H | SOCH$_2$CH$_2$CH$_3$ | CH$_3$ | OCH$_3$ | N |
| H | A-1 | — | O | H | SOCH$_2$CH$_2$CH$_3$ | OCH$_3$ | OCH$_3$ | N |
| H | A-1 | — | O | H | SOCH$_2$CH$_2$CH$_3$ | Cl | OCH$_3$ | CH |
| H | A-1 | — | O | H | SO$_2$CH$_2$CH$_2$CH$_3$ | CH$_3$ | CH$_3$ | CH |
| H | A-1 | — | O | H | SO$_2$CH$_2$CH$_2$CH$_3$ | CH$_3$ | OCH$_3$ | CH |
| H | A-1 | — | O | H | SO$_2$CH$_2$CH$_2$CH$_3$ | OCH$_3$ | OCH$_3$ | CH |
| H | A-1 | — | O | H | SO$_2$CH$_2$CH$_2$CH$_3$ | CH$_3$ | CH$_3$ | N |
| H | A-1 | — | O | H | SO$_2$CH$_2$CH$_2$CH$_3$ | CH$_3$ | OCH$_3$ | N |
| H | A-1 | — | O | H | SO$_2$CH$_2$CH$_2$CH$_3$ | OCH$_3$ | OCH$_3$ | N |
| H | A-1 | — | O | H | SO$_2$CH$_2$CH$_2$CH$_3$ | Cl | OCH$_3$ | CH |
| H | A-1 | — | O | H | SO$_2$N(CH$_3$)$_2$ | CH$_3$ | CH$_3$ | CH |
| H | A-1 | — | O | H | SO$_2$N(CH$_3$)$_2$ | CH$_3$ | OCH$_3$ | CH |
| H | A-1 | — | O | H | SO$_2$N(CH$_3$)$_2$ | OCH$_3$ | OCH$_3$ | CH |
| H | A-1 | — | O | H | SO$_2$N(CH$_3$)$_2$ | CH$_3$ | CH$_3$ | N |
| H | A-1 | — | O | H | SO$_2$N(CH$_3$)$_2$ | CH$_3$ | OCH$_3$ | N |
| H | A-1 | — | O | H | SO$_2$N(CH$_3$)$_2$ | OCH$_3$ | OCH$_3$ | N |
| H | A-1 | — | O | H | SO$_2$N(CH$_3$)$_2$ | Cl | OCH$_3$ | CH |
| H | A-1 | — | O | H | SO$_2$N(CH$_2$CH$_3$)$_2$ | CH$_3$ | CH$_3$ | CH |
| H | A-1 | — | O | H | SO$_2$N(CH$_2$CH$_3$)$_2$ | CH$_3$ | OCH$_3$ | CH |
| H | A-1 | — | O | H | SO$_2$N(CH$_2$CH$_3$)$_2$ | OCH$_3$ | OCH$_3$ | CH |
| H | A-1 | — | O | H | SO$_2$N(CH$_2$CH$_3$)$_2$ | CH$_3$ | CH$_3$ | N |
| H | A-1 | — | O | H | SO$_2$N(CH$_2$CH$_3$)$_2$ | CH$_3$ | OCH$_3$ | N |
| H | A-1 | — | O | H | SO$_2$N(CH$_2$CH$_3$)$_2$ | OCH$_3$ | OCH$_3$ | N |
| H | A-1 | — | O | H | SO$_2$N(CH$_2$CH$_3$)$_2$ | Cl | OCH$_3$ | CH |
| H | A-1 | — | O | H | SO$_2$N(CH$_3$)CH$_2$CH$_3$ | CH$_3$ | CH$_3$ | CH |
| H | A-1 | — | O | H | SO$_2$N(CH$_3$)CH$_2$CH$_3$ | CH$_3$ | OCH$_3$ | CH |
| H | A-1 | — | O | H | SO$_2$N(CH$_3$)CH$_2$CH$_3$ | OCH$_3$ | OCH$_3$ | CH |
| H | A-1 | — | O | H | SO$_2$N(CH$_3$)CH$_2$CH$_3$ | CH$_3$ | CH$_3$ | N |
| H | A-1 | — | O | H | SO$_2$N(CH$_3$)CH$_2$CH$_3$ | CH$_3$ | OCH$_3$ | N |
| H | A-1 | — | O | H | SO$_2$N(CH$_3$)CH$_2$CH$_3$ | OCH$_3$ | OCH$_3$ | N |
| H | A-1 | — | O | H | SO$_2$N(CH$_3$)CH$_2$CH$_3$ | Cl | OCH$_3$ | CH |
| H | A-1 | — | O | H | SO$_2$NHCH$_3$ | CH$_3$ | CH$_3$ | CH |
| H | A-1 | — | O | H | SO$_2$NHCH$_3$ | CH$_3$ | OCH$_3$ | CH |
| H | A-1 | — | O | H | SO$_2$NHCH$_3$ | OCH$_3$ | OCH$_3$ | CH |
| H | A-1 | — | O | H | SO$_2$NHCH$_3$ | CH$_3$ | CH$_3$ | N |
| H | A-1 | — | O | H | SO$_2$NHCH$_3$ | CH$_3$ | OCH$_3$ | N |
| H | A-1 | — | O | H | SO$_2$NHCH$_3$ | OCH$_3$ | OCH$_3$ | N |
| H | A-1 | — | O | H | SO$_2$NHCH$_3$ | Cl | OCH$_3$ | CH |
| H | A-1 | — | O | H | SO$_2$N(OCH$_3$)CH$_3$ | CH$_3$ | CH$_3$ | CH |
| H | A-1 | — | O | H | SO$_2$N(OCH$_3$)CH$_3$ | CH$_3$ | OCH$_3$ | CH |
| H | A-1 | — | O | H | SO$_2$N(OCH$_3$)CH$_3$ | OCH$_3$ | OCH$_3$ | CH |
| H | A-1 | — | O | H | SO$_2$N(OCH$_3$)CH$_3$ | CH$_3$ | CH$_3$ | N |
| H | A-1 | — | O | H | SO$_2$N(OCH$_3$)CH$_3$ | CH$_3$ | OCH$_3$ | N |
| H | A-1 | — | O | H | SO$_2$N(OCH$_3$)CH$_3$ | OCH$_3$ | OCH$_3$ | N |
| H | A-1 | — | O | H | SO$_2$N(OCH$_3$)CH$_3$ | Cl | OCH$_3$ | CH |
| H | A-1 | — | O | H | CON(CH$_3$)$_2$ | CH$_3$ | CH$_3$ | CH |
| H | A-1 | — | O | H | CON(CH$_3$)$_2$ | CH$_3$ | OCH$_3$ | CH |
| H | A-1 | — | O | H | CON(CH$_3$)$_2$ | OCH$_3$ | OCH$_3$ | CH |
| H | A-1 | — | O | H | CON(CH$_3$)$_2$ | CH$_3$ | CH$_3$ | N |
| H | A-1 | — | O | H | CON(CH$_3$)$_2$ | CH$_3$ | OCH$_3$ | N |
| H | A-1 | — | O | H | CON(CH$_3$)$_2$ | OCH$_3$ | OCH$_3$ | N |
| H | A-1 | — | O | H | CON(CH$_3$)$_2$ | Cl | OCH$_3$ | CH |

TABLE IV-continued

| | | | | | | | |
|---|---|---|---|---|---|---|---|
| H | A-1 | — O | H | CONHCH₃ | CH₃ | CH₃ | CH |
| H | A-1 | — O | H | CONHCH₃ | CH₃ | OCH₃ | CH |
| H | A-1 | — O | H | CONHCH₃ | OCH₃ | OCH₃ | CH |
| H | A-1 | — O | H | CONHCH₃ | CH₃ | CH₃ | N |
| H | A-1 | — O | H | CONHCH₃ | CH₃ | OCH₃ | N |
| H | A-1 | — O | H | CONHCH₃ | OCH₃ | OCH₃ | N |
| H | A-1 | — O | H | CONHCH₃ | Cl | OCH₃ | CH |
| H | A-1 | — O | H | CON(CH₂CH₃)₂ | CH₃ | CH₃ | CH |
| H | A-1 | — O | H | CON(CH₂CH₃)₂ | CH₃ | OCH₃ | CH |
| H | A-1 | — O | H | CON(CH₂CH₃)₂ | OCH₃ | OCH₃ | CH |
| H | A-1 | — O | H | CON(CH₂CH₃)₂ | CH₃ | CH₃ | N |
| H | A-1 | — O | H | CON(CH₂CH₃)₂ | CH₃ | OCH₃ | N |
| H | A-1 | — O | H | CON(CH₂CH₃)₂ | OCH₃ | OCH₃ | N |
| H | A-1 | — O | H | CON(CH₂CH₃)₂ | Cl | OCH₃ | CH |
| H | A-1 | — O | H | (N—N oxadiazole with two CH₃) | CH₃ | CH₃ | CH |
| H | A-1 | — O | H | (N—N oxadiazole with two CH₃) | CH₃ | OCH₃ | CH |
| H | A-1 | — O | H | (N—N oxadiazole with two CH₃) | OCH₃ | OCH₃ | CH |
| H | A-1 | — O | H | (N—N oxadiazole with two CH₃) | CH₃ | CH₃ | N |
| H | A-1 | — O | H | (N—N oxadiazole with two CH₃) | CH₃ | OCH₃ | N |
| H | A-1 | — O | H | (N—N oxadiazole with two CH₃) | OCH₃ | OCH₃ | N |
| H | A-1 | — O | H | (N—N oxadiazole with two CH₃) | Cl | OCH₃ | CH |
| H | A-1 | — O | H | (N-methylpyrazole) | CH₃ | CH₃ | CH |
| H | A-1 | — O | H | (N-methylpyrazole) | CH₃ | OCH₃ | CH |
| H | A-1 | — O | H | (N-methylpyrazole) | OCH₃ | OCH₃ | CH |
| H | A-1 | — O | H | (N-methylpyrazole) | CH₃ | CH₃ | N |
| H | A-1 | — O | H | (N-methylpyrazole) | CH₃ | OCH₃ | N |

TABLE IV-continued

| | | | | | Het | | | |
|---|---|---|---|---|---|---|---|---|
| H | A-1 | — | O | H | 3-methyl-1-methylpyrazol-5-yl | OCH₃ | OCH₃ | N |
| H | A-1 | — | O | H | 3-methyl-1-methylpyrazol-5-yl | Cl | OCH₃ | CH |
| H | A-1 | — | O | H | thien-2-yl | CH₃ | CH₃ | CH |
| H | A-1 | — | O | H | thien-2-yl | CH₃ | OCH₃ | CH |
| H | A-1 | — | O | H | thien-2-yl | OCH₃ | OCH₃ | CH |
| H | A-1 | — | O | H | thien-2-yl | CH₃ | CH₃ | N |
| H | A-1 | — | O | H | thien-2-yl | CH₃ | OCH₃ | N |
| H | A-1 | — | O | H | thien-2-yl | OCH₃ | OCH₃ | N |
| H | A-1 | — | O | H | thien-2-yl | Cl | OCH₃ | CH |
| H | A-1 | — | O | H | 2-methyltetrazol-5-yl | CH₃ | CH₃ | CH |
| H | A-1 | — | O | H | 2-methyltetrazol-5-yl | CH₃ | OCH₃ | CH |
| H | A-1 | — | O | H | 2-methyltetrazol-5-yl | OCH₃ | OCH₃ | CH |
| H | A-1 | — | O | H | 2-methyltetrazol-5-yl | CH₃ | CH₃ | N |
| H | A-1 | — | O | H | 2-methyltetrazol-5-yl | CH₃ | OCH₃ | N |

TABLE IV-continued

| | | | | | | | |
|---|---|---|---|---|---|---|---|
| H | A-1 | — | O | H | [N-N(CH₃)-N=N ring with CH₃] tetrazole | OCH₃ | OCH₃ | N |
| H | A-1 | — | O | H | [N-N(CH₃)-N=N ring with CH₃] tetrazole | Cl | OCH₃ | CH |
| H | A-1 | — | O | H | [N=N-N=N, N-CH₃ tetrazole] | CH₃ | CH₃ | CH |
| H | A-1 | — | O | H | [N=N-N=N, N-CH₃ tetrazole] | CH₃ | OCH₃ | CH |
| H | A-1 | — | O | H | [N=N-N=N, N-CH₃ tetrazole] | OCH₃ | OCH₃ | CH |
| H | A-1 | — | O | H | [N=N-N=N, N-CH₃ tetrazole] | CH₃ | CH₃ | N |
| H | A-1 | — | O | H | [N=N-N=N, N-CH₃ tetrazole] | CH₃ | OCH₃ | N |
| H | A-1 | — | O | H | [N=N-N=N, N-CH₃ tetrazole] | OCH₃ | OCH₃ | N |
| H | A-1 | — | O | H | [N=N-N=N, N-CH₃ tetrazole] | Cl | OCH₃ | CH |
| H | A-1 | — | O | H | 1,3-dioxolan-2-yl | CH₃ | CH₃ | CH |
| H | A-1 | — | O | H | 1,3-dioxolan-2-yl | CH₃ | OCH₃ | CH |
| H | A-1 | — | O | H | 1,3-dioxolan-2-yl | OCH₃ | OCH₃ | CH |
| H | A-1 | — | O | H | 1,3-dioxolan-2-yl | CH₃ | CH₃ | N |

TABLE IV-continued

| | | | | | | | |
|---|---|---|---|---|---|---|---|
| H | A-1 | — O | H | 1,3-dioxolane (CH) | CH$_3$ | OCH$_3$ | N |
| H | A-1 | — O | H | 1,3-dioxolane (CH) | OCH$_3$ | OCH$_3$ | N |
| H | A-1 | — O | H | 1,3-dioxolane (CH) | Cl | OCH$_3$ | CH |
| H | A-1 | — O | H | 2-methyl-1,3-dioxolane (CH$_3$–C) | CH$_3$ | CH$_3$ | CH |
| H | A-1 | — O | H | 2-methyl-1,3-dioxolane (CH$_3$–C) | CH$_3$ | OCH$_3$ | CH |
| H | A-1 | — O | H | 2-methyl-1,3-dioxolane (CH$_3$–C) | OCH$_3$ | OCH$_3$ | CH |
| H | A-1 | — O | H | 2-methyl-1,3-dioxolane (CH$_3$–C) | CH$_3$ | CH$_3$ | N |
| H | A-1 | — O | H | 2-methyl-1,3-dioxolane (CH$_3$–C) | CH$_3$ | OCH$_3$ | N |
| H | A-1 | — O | H | 2-methyl-1,3-dioxolane (CH$_3$–C) | OCH$_3$ | OCH$_3$ | N |
| H | A-1 | — O | H | 2-methyl-1,3-dioxolane (CH$_3$–C) | Cl | OCH$_3$ | CH |
| H | A-1 | — O | H | 1,3-dioxane (HC) | CH$_3$ | CH$_3$ | CH |
| H | A-1 | — O | H | 1,3-dioxane (HC) | CH$_3$ | OCH$_3$ | CH |
| H | A-1 | — O | H | 1,3-dioxane (HC) | OCH$_3$ | OCH$_3$ | CH |

TABLE IV-continued

| | | | | | | | | |
|---|---|---|---|---|---|---|---|---|
| H | A-1 | — | O | H | (1,3-dioxolan-2-yl: HC(O-CH2-CH2-O)) | CH3 | CH3 | N |
| H | A-1 | — | O | H | (1,3-dioxolan-2-yl) | CH3 | OCH3 | N |
| H | A-1 | — | O | H | (1,3-dioxolan-2-yl) | OCH3 | OCH3 | N |
| H | A-1 | — | O | H | (1,3-dioxolan-2-yl) | Cl | OCH3 | CH |
| CH3 | A-1 | — | O | H | CH3 | CH3 | CH3 | CH |
| CH3 | A-1 | — | O | H | CH3 | CH3 | OCH3 | CH |
| CH3 | A-1 | — | O | H | CH3 | OCH3 | OCH3 | CH |
| CH3 | A-1 | — | O | H | CH3 | CH3 | CH3 | N |
| CH3 | A-1 | — | O | H | CH3 | CH3 | OCH3 | N |
| CH3 | A-1 | — | O | H | CH3 | OCH3 | OCH3 | N |
| CH3 | A-1 | — | O | H | CH3 | Cl | OCH3 | CH |
| CH3 | A-1 | — | O | H | CH2CH3 | CH3 | CH3 | CH |
| CH3 | A-1 | — | O | H | CH2CH3 | CH3 | OCH3 | CH |
| CH3 | A-1 | — | O | H | CH2CH3 | OCH3 | OCH3 | CH |
| CH3 | A-1 | — | O | H | CH2CH3 | CH3 | CH3 | N |
| CH3 | A-1 | — | O | H | CH2CH3 | CH3 | OCH3 | N |
| CH3 | A-1 | — | O | H | CH2CH3 | OCH3 | OCH3 | N |
| CH3 | A-1 | — | O | H | CH2CH3 | Cl | OCH3 | CH |
| CH3 | A-1 | — | O | H | CH(CH3)2 | CH3 | CH3 | CH |
| CH3 | A-1 | — | O | H | CH(CH3)2 | CH3 | OCH3 | CH |
| CH3 | A-1 | — | O | H | CH(CH3)2 | OCH3 | OCH3 | CH |
| CH3 | A-1 | — | O | H | CH(CH3)2 | CH3 | CH3 | N |
| CH3 | A-1 | — | O | H | CH(CH3)2 | CH3 | OCH3 | N |
| CH3 | A-1 | — | O | H | CH(CH3)2 | OCH3 | OCH3 | N |
| CH3 | A-1 | — | O | H | CH(CH3)2 | Cl | OCH3 | CH |
| CH3 | A-1 | — | O | H | CH2CH2CH3 | CH3 | CH3 | CH |
| CH3 | A-1 | — | O | H | CH2CH2CH3 | CH3 | OCH3 | CH |
| CH3 | A-1 | — | O | H | CH(CH3)CH2CH3 | OCH3 | OCH3 | CH |
| CH3 | A-1 | — | O | H | CH(CH3)CH2CH3 | CH3 | CH3 | N |
| CH3 | A-1 | — | O | H | CH2CH(CH3)2 | CH3 | OCH3 | N |
| CH3 | A-1 | — | O | H | CH2CH(CH3)2 | OCH3 | OCH3 | N |
| CH3 | A-1 | — | O | H | CH2CH(CH3)2 | Cl | OCH3 | CH |
| CH3 | A-1 | — | O | H | cyclopropyl | CH3 | CH3 | CH |
| CH3 | A-1 | — | O | H | cyclopropyl | CH3 | OCH3 | CH |
| CH3 | A-1 | — | O | H | cyclopropyl | OCH3 | OCH3 | CH |
| CH3 | A-1 | — | O | H | cyclopropyl | CH3 | CH3 | N |
| CH3 | A-1 | — | O | H | cyclopropyl | CH3 | OCH3 | N |
| CH3 | A-1 | — | O | H | cyclopropyl | OCH3 | OCH3 | N |
| CH3 | A-1 | — | O | H | cyclopropyl | Cl | OCH3 | CH |
| CH3 | A-1 | — | O | H | CH—CF2—CH2 (cyclic) | CH3 | CH3 | CH |
| CH3 | A-1 | — | O | H | CH—CF2—CH2 (cyclic) | CH3 | OCH3 | CH |
| CH3 | A-1 | — | O | H | CH—CF2—CH2 (cyclic) | OCH3 | OCH3 | CH |
| CH3 | A-1 | — | O | H | CH—CF2—CH2 (cyclic) | CH3 | CH3 | N |
| CH3 | A-1 | — | O | H | CH—CF2—CH2 (cyclic) | CH3 | OCH3 | N |

TABLE IV-continued

| | | | | | | | | |
|---|---|---|---|---|---|---|---|---|
| CH₃ | A-1 | — | O | H | CH—CF₂—CH₂ | OCH₃ | OCH₃ | N |
| CH₃ | A-1 | — | O | H | CH—CF₂—CH₂ | Cl | OCH₃ | CH |
| CH₃ | A-1 | — | O | H | CH—CHF—CH₂ | CH₃ | CH₃ | CH |
| CH₃ | A-1 | — | O | H | CH—CHF—CH₂ | CH₃ | OCH₃ | CH |
| CH₃ | A-1 | — | O | H | CH—CHF—CH₂ | OCH₃ | OCH₃ | CH |
| CH₃ | A-1 | — | O | H | CH—CHF—CH₂ | CH₃ | CH₃ | N |
| CH₃ | A-1 | — | O | H | CH—CHF—CH₂ | CH₃ | OCH₃ | N |
| CH₃ | A-1 | — | O | H | CH—CHF—CH₂ | OCH₃ | OCH₃ | N |
| CH₃ | A-1 | — | O | H | CH—CHF—CH₂ | Cl | OCH₃ | CH |
| CH₃ | A-1 | — | O | H | CH—CHCl—CH₂ | CH₃ | CH₃ | CH |
| CH₃ | A-1 | — | O | H | CH—CHCl—CH₂ | CH₃ | OCH₃ | CH |
| CH₃ | A-1 | — | O | H | CH—CHCl—CH₂ | OCH₃ | OCH₃ | CH |
| CH₃ | A-1 | — | O | H | CH—CHCl—CH₂ | CH₃ | CH₃ | N |
| CH₃ | A-1 | — | O | H | CH—CHCl—CH₂ | CH₃ | OCH₃ | N |
| CH₃ | A-1 | — | O | H | CH—CHCl—CH₂ | OCH₃ | OCH₃ | N |
| CH₃ | A-1 | — | O | H | CH—CHCl—CH₂ | Cl | OCH₃ | CH |
| CH₃ | A-1 | — | O | H | OCH₂CH₂Cl | CH₃ | CH₃ | CH |
| CH₃ | A-1 | — | O | H | OCH₂CH₂Cl | CH₃ | OCH₃ | CH |
| CH₃ | A-1 | — | O | H | OCH₂CH₂Cl | OCH₃ | OCH₃ | CH |
| CH₃ | A-1 | — | O | H | OCH₂CH₂Cl | CH₃ | CH₃ | N |
| CH₃ | A-1 | — | O | H | OCH₂CH₂Cl | CH₃ | OCH₃ | N |
| CH₃ | A-1 | — | O | H | OCH₂CH₂Cl | OCH₃ | OCH₃ | N |
| CH₃ | A-1 | — | O | H | OCH₂CH₂Cl | Cl | OCH₃ | CH |
| CH₃ | A-1 | — | O | H | OCH₂CH₂F | CH₃ | CH₃ | CH |
| CH₃ | A-1 | — | O | H | OCH₂CH₂F | CH₃ | OCH₃ | CH |
| CH₃ | A-1 | — | O | H | OCH₂CH₂F | OCH₃ | OCH₃ | CH |
| CH₃ | A-1 | — | O | H | OCH₂CH₂F | CH₃ | CH₃ | N |
| CH₃ | A-1 | — | O | H | OCH₂CH₂F | CH₃ | OCH₃ | N |
| CH₃ | A-1 | — | O | H | OCH₂CH₂F | OCH₃ | OCH₃ | N |
| CH₃ | A-1 | — | O | H | OCH₂CH₂F | Cl | OCH₃ | CH |
| CH₃ | A-1 | — | O | H | OCH₂CF₃ | CH₃ | CH₃ | CH |
| CH₃ | A-1 | — | O | H | OCH₂CF₃ | CH₃ | OCH₃ | CH |
| CH₃ | A-1 | — | O | H | OCH₂CF₃ | OCH₃ | OCH₃ | CH |
| CH₃ | A-1 | — | O | H | OCH₂CF₃ | CH₃ | CH₃ | N |
| CH₃ | A-1 | — | O | H | OCH₂CF₃ | CH₃ | OCH₃ | N |

TABLE IV-continued

| | | | | | | | |
|---|---|---|---|---|---|---|---|
| CH₃ | A-1 | — | O | H | OCH₂CF₃ | OCH₃ | OCH₃ | N |
| CH₃ | A-1 | — | O | H | OCH₂CF₃ | Cl | OCH₃ | CH |
| CH₃ | A-1 | — | O | H | OCF₂CH₃ | CH₃ | CH₃ | CH |
| CH₃ | A-1 | — | O | H | OCF₂CH₃ | CH₃ | OCH₃ | CH |
| CH₃ | A-1 | — | O | H | OCF₂CH₃Cl | OCH₃ | OCH₃ | CH |
| CH₃ | A-1 | — | O | H | OCF₂CH₃ | CH₃ | CH₃ | N |
| CH₃ | A-1 | — | O | H | OCF₂CH₃ | OCH₃ | OCH₃ | N |
| CH₃ | A-1 | — | O | H | OCF₂CH₃ | Cl | OCH₃ | CH |
| CH₃ | A-1 | — | O | H | NO₂ | CH₃ | CH₃ | CH |
| CH₃ | A-1 | — | O | H | NO₂ | CH₃ | OCH₃ | CH |
| CH₃ | A-1 | — | O | H | NO₂ | OCH₃ | OCH₃ | CH |
| CH₃ | A-1 | — | O | H | NO₂ | CH₃ | CH₃ | N |
| CH₃ | A-1 | — | O | H | NO₂ | CH₃ | OCH₃ | N |
| CH₃ | A-1 | — | O | H | NO₂ | OCH₃ | OCH₃ | N |
| CH₃ | A-1 | — | O | H | NO₂ | Cl | OCH₃ | CH |
| CH₃ | A-1 | — | O | H | CO₂CH₃ | CH₃ | CH₃ | CH |
| CH₃ | A-1 | — | O | H | CO₂CH₃ | CH₃ | OCH₃ | CH |
| CH₃ | A-1 | — | O | H | CO₂CH₃ | OCH₃ | OCH₃ | CH |
| CH₃ | A-1 | — | O | H | CO₂CH₃ | CH₃ | CH₃ | N |
| CH₃ | A-1 | — | O | H | CO₂CH₃ | CH₃ | OCH₃ | N |
| CH₃ | A-1 | — | O | H | CO₂CH₃ | OCH₃ | OCH₃ | N |
| CH₃ | A-1 | — | O | H | CO₂CH₃ | Cl | OCH₃ | CH |
| CH₃ | A-1 | — | O | H | CO₂CH₂CH₃ | CH₃ | CH₃ | CH |
| CH₃ | A-1 | — | O | H | CO₂CH₂CH₃ | CH₃ | OCH₃ | CH |
| CH₃ | A-1 | — | O | H | CO₂CH₂CH₃ | OCH₃ | OCH₃ | CH |
| CH₃ | A-1 | — | O | H | CO₂CH₂CH₃ | CH₃ | CH₃ | N |
| CH₃ | A-1 | — | O | H | CO₂CH₂CH₃ | CH₃ | OCH₃ | N |
| CH₃ | A-1 | — | O | H | CO₂CH₂CH₃ | OCH₃ | OCH₃ | N |
| CH₃ | A-1 | — | O | H | CO₂CH₂CH₃ | Cl | OCH₃ | CH |
| CH₃ | A-1 | — | O | H | CO₂CH₂CH₂OCH₃ | CH₃ | CH₃ | CH |
| CH₃ | A-1 | — | O | H | CO₂CH₂CH₂OCH₃ | CH₃ | OCH₃ | CH |
| CH₃ | A-1 | — | O | H | CO₂CH₂CH₂OCH₃ | OCH₃ | OCH₃ | CH |
| CH₃ | A-1 | — | O | H | CO₂CH₂CH₂OCH₃ | CH₃ | CH₃ | N |
| CH₃ | A-1 | — | O | H | CO₂CH₂CH₂OCH₃ | CH₃ | OCH₃ | N |
| CH₃ | A-1 | — | O | H | CO₂CH₂CH₂OCH₃ | OCH₃ | OCH₃ | N |
| CH₃ | A-1 | — | O | H | CO₂CH₂CH₂OCH₃ | Cl | OCH₃ | CH |
| CH₃ | A-1 | — | O | H | CO₂CH₂CH=CH₂ | CH₃ | CH₃ | CH |
| CH₃ | A-1 | — | O | H | CO₂CH₂CH=CH₂ | CH₃ | OCH₃ | CH |
| CH₃ | A-1 | — | O | H | CO₂CH₂CH=CH₂ | OCH₃ | OCH₃ | CH |
| CH₃ | A-1 | — | O | H | CO₂CH₂CH=CH₂ | CH₃ | CH₃ | N |
| CH₃ | A-1 | — | O | H | CO₂CH₂CH=CH₂ | CH₃ | OCH₃ | N |
| CH₃ | A-1 | — | O | H | CO₂CH₂CH=CH₂ | OCH₃ | OCH₃ | N |
| CH₃ | A-1 | — | O | H | CO₂CH₂CH=CH₂ | Cl | OCH₃ | CH |
| CH₃ | A-1 | — | O | H | CO₂CH₂—C≡CH | CH₃ | CH₃ | CH |
| CH₃ | A-1 | — | O | H | CO₂CH₂—C≡CH | CH₃ | OCH₃ | CH |
| CH₃ | A-1 | — | O | H | CO₂CH₂—C≡CH | OCH₃ | OCH₃ | CH |
| CH₃ | A-1 | — | O | H | CO₂CH₂—C≡CH | CH₃ | CH₃ | N |
| CH₃ | A-1 | — | O | H | CO₂CH₂—C≡CH | CH₃ | OCH₃ | N |
| CH₃ | A-1 | — | O | H | CO₂CH₂—C≡CH | OCH₃ | OCH₃ | N |
| CH₃ | A-1 | — | O | H | CO₂CH₂—C≡CH | Cl | OCH₃ | CH |
| CH₃ | A-1 | — | O | H | N(CH₃)₂ | CH₃ | CH₃ | CH |
| CH₃ | A-1 | — | O | H | N(CH₃)₂ | CH₃ | OCH₃ | CH |
| CH₃ | A-1 | — | O | H | N(CH₃)₂ | OCH₃ | OCH₃ | CH |
| CH₃ | A-1 | — | O | H | N(CH₃)₂ | CH₃ | CH₃ | N |
| CH₃ | A-1 | — | O | H | N(CH₃)₂ | CH₃ | OCH₃ | N |
| CH₃ | A-1 | — | O | H | N(CH₃)₂ | OCH₃ | OCH₃ | N |
| CH₃ | A-1 | — | O | H | N(CH₃)₂ | Cl | OCH₃ | CH |
| H | A-1 | — | O | 5-F | CH₃ | CH₃ | CH₃ | CH |
| H | A-1 | — | O | 5-F | CH₃ | CH₃ | OCH₃ | CH |
| H | A-1 | — | O | 5-F | CH₃ | OCH₃ | OCH₃ | CH |
| H | A-1 | — | O | 5-F | CH₃ | CH₃ | CH₃ | N |
| H | A-1 | — | O | 5-F | CH₃ | CH₃ | OCH₃ | N |
| H | A-1 | — | O | 5-F | CH₃ | OCH₃ | OCH₃ | N |
| H | A-1 | — | O | 5-F | CH₃ | Cl | OCH₃ | CH |
| H | A-1 | — | O | 5-F | CH₂CH₃ | CH₃ | CH₃ | CH |
| H | A-1 | — | O | 5-F | CH₂CH₃ | CH₃ | OCH₃ | CH |
| H | A-1 | — | O | 5-F | CH₂CH₃ | OCH₃ | OCH₃ | CH |
| H | A-1 | — | O | 5-F | CH₂CH₃ | CH₃ | CH₃ | N |
| H | A-1 | — | O | 5-F | CH₂CH₃ | CH₃ | OCH₃ | N |
| H | A-1 | — | O | 5-F | CH₂CH₃ | OCH₃ | OCH₃ | N |
| H | A-1 | — | O | 5-F | CH₂CH₃ | Cl | OCH₃ | CH |
| H | A-1 | — | O | 5-F | CH(CH₃)₂ | CH₃ | CH₃ | CH |
| H | A-1 | — | O | 5-F | CH(CH₃)₂ | CH₃ | OCH₃ | CH |
| H | A-1 | — | O | 5-F | CH(CH₃)₂ | OCH₃ | OCH₃ | CH |
| H | A-1 | — | O | 5-F | CH(CH₃)₂ | CH₃ | CH₃ | N |
| H | A-1 | — | O | 5-F | CH(CH₃)₂ | CH₃ | OCH₃ | N |
| H | A-1 | — | O | 5-F | CH(CH₃)₂ | OCH₃ | OCH₃ | N |
| H | A-1 | — | O | 5-F | CH(CH₃)₂ | Cl | OCH₃ | CH |
| H | A-1 | — | O | 5-F | CH₂CH₂CH₃ | CH₃ | CH₃ | CH |
| H | A-1 | — | O | 5-F | CH₂CH₂CH₃ | CH₃ | OCH₃ | CH |
| H | A-1 | — | O | 5-F | CH(CH₃)CH₂CH₃ | OCH₃ | OCH₃ | CH |

TABLE IV-continued

| | | | | | | | |
|---|---|---|---|---|---|---|---|
| H | A-1 | — | O | 5-F | CH(CH₃)CH₂CH₃ | CH₃ | CH₃ | N |
| H | A-1 | — | O | 5-F | CH₂CH(CH₃)₂ | CH₃ | OCH₃ | N |
| H | A-1 | — | O | 5-F | CH(CH₃)₂ | OCH₃ | OCH₃ | N |
| H | A-1 | — | O | 5-F | CH(CH₃)₂ | Cl | OCH₃ | CH |
| H | A-1 | — | O | 5-Cl | cyclopropyl | CH₃ | CH₃ | CH |
| H | A-1 | — | O | 5-Cl | cyclopropyl | CH₃ | OCH₃ | CH |
| H | A-1 | — | O | 5-Cl | cyclopropyl | OCH₃ | OCH₃ | CH |
| H | A-1 | — | O | 5-Cl | cyclopropyl | CH₃ | CH₃ | N |
| H | A-1 | — | O | 5-Cl | cyclopropyl | CH₃ | OCH₃ | N |
| H | A-1 | — | O | 5-Cl | cyclopropyl | OCH₃ | OCH₃ | N |
| H | A-1 | — | O | 5-Cl | cyclopropyl | Cl | OCH₃ | CH |
| H | A-1 | — | O | 5-Cl | CH—CF₂—CH₂ (ring) | CH₃ | CH₃ | CH |
| H | A-1 | — | O | 5-Cl | CH—CF₂—CH₂ (ring) | CH₃ | OCH₃ | CH |
| H | A-1 | — | O | 5-Cl | CH—CF₂—CH₂ (ring) | OCH₃ | OCH₃ | CH |
| H | A-1 | — | O | 5-Cl | CH—CF₂—CH₂ (ring) | CH₃ | CH₃ | N |
| H | A-1 | — | O | 5-Cl | CH—CF₂—CH₂ (ring) | CH₃ | OCH₃ | N |
| H | A-1 | — | O | 5-Cl | CH—CF₂—CH₂ (ring) | OCH₃ | OCH₃ | N |
| H | A-1 | — | O | 5-Cl | CH—CF₂—CH₂ (ring) | Cl | OCH₃ | CH |
| H | A-1 | — | O | 5-Cl | CH—CHF—CH₂ (ring) | CH₃ | CH₃ | CH |
| H | A-1 | — | O | 5-Cl | CH—CHF—CH₂ (ring) | CH₃ | OCH₃ | CH |
| H | A-1 | — | O | 5-Cl | CH—CHF—CH₂ (ring) | OCH₃ | OCH₃ | CH |
| H | A-1 | — | O | 5-Cl | CH—CHF—CH₂ (ring) | CH₃ | CH₃ | N |
| H | A-1 | — | O | 5-Cl | CH—CHF—CH₂ (ring) | CH₃ | OCH₃ | N |
| H | A-1 | — | O | 5-Cl | CH—CHF—CH₂ (ring) | OCH₃ | OCH₃ | N |
| H | A-1 | — | O | 5-Cl | CH—CHF—CH₂ (ring) | Cl | OCH₃ | CH |
| H | A-1 | — | O | 5-Cl | CH—CHCl—CH₂ (ring) | CH₃ | CH₃ | CH |
| H | A-1 | — | O | 5-Cl | CH—CHCl—CH₂ (ring) | CH₃ | OCH₃ | CH |
| H | A-1 | — | O | 5-Cl | CH—CHCl—CH₂ (ring) | OCH₃ | OCH₃ | CH |
| H | A-1 | — | O | 5-Cl | CH—CHCl—CH₂ (ring) | CH₃ | CH₃ | N |

TABLE IV-continued

| | | | | | | | | |
|---|---|---|---|---|---|---|---|---|
| H | A-1 | — | O | 5-Cl | CH—CHCl—CH$_2$ | CH$_3$ | OCH$_3$ | N |
| H | A-1 | — | O | 5-Cl | CH—CHCl—CH$_2$ | OCH$_3$ | OCH$_3$ | N |
| H | A-1 | — | O | 5-Cl | CH—CHCl—CH$_2$ | Cl | OCH$_3$ | CH |
| H | A-1 | — | O | 5-CH$_3$ | OCH$_2$CH$_2$CH$_2$F | CH$_3$ | CH$_3$ | CH |
| H | A-1 | — | O | 5-CH$_3$ | OCH$_2$CH$_2$CH$_2$F | CH$_3$ | OCH$_3$ | CH |
| H | A-1 | — | O | 5-CH$_3$ | OCH$_2$CH$_2$CH$_2$F | OCH$_3$ | OCH$_3$ | CH |
| H | A-1 | — | O | 5-CH$_3$ | OCH$_2$CH$_2$CH$_2$F | CH$_3$ | CH$_3$ | N |
| H | A-1 | — | O | 5-CH$_3$ | OCH$_2$CH$_2$CH$_2$F | CH$_3$ | OCH$_3$ | N |
| H | A-1 | — | O | 5-CH$_3$ | OCH$_2$CH$_2$CH$_2$F | OCH$_3$ | OCH$_3$ | N |
| H | A-1 | — | O | 5-CH$_3$ | OCH$_2$CH$_2$CH$_2$F | Cl | OCH$_3$ | CH |
| H | A-1 | — | O | 5-CH$_3$ | OCH$_2$CH$_2$Cl | CH$_3$ | CH$_3$ | CH |
| H | A-1 | — | O | 5-CH$_3$ | OCH$_2$CH$_2$Cl | CH$_3$ | OCH$_3$ | CH |
| H | A-1 | — | O | 5-CH$_3$ | OCH$_2$CH$_2$Cl | OCH$_3$ | OCH$_3$ | CH |
| H | A-1 | — | O | 5-CH$_3$ | OCH$_2$CH$_2$Br | CH$_3$ | CH$_3$ | N |
| H | A-1 | — | O | 5-CH$_3$ | OCH$_2$CH$_2$Br | CH$_3$ | OCH$_3$ | N |
| H | A-1 | — | O | 5-CH$_3$ | OCH$_2$CH$_2$Br | OCH$_3$ | OCH$_3$ | N |
| H | A-1 | — | O | 5-CH$_3$ | OCH$_2$CH$_2$Br | Cl | OCH$_3$ | CH |
| H | A-1 | — | O | 5-CH$_3$ | OCH$_2$—C≡CH | CH$_3$ | CH$_3$ | CH |
| H | A-1 | — | O | 5-CH$_3$ | OCH$_2$—C≡CH | CH$_3$ | OCH$_3$ | CH |
| H | A-1 | — | O | 5-CH$_3$ | OCH$_2$—C≡CH | OCH$_3$ | OCH$_3$ | CH |
| H | A-1 | — | O | 5-CH$_3$ | OCH$_2$—C≡CH | CH$_3$ | CH$_3$ | N |
| H | A-1 | — | O | 5-CH$_3$ | OCH$_2$—C≡CH | CH$_3$ | OCH$_3$ | N |
| H | A-1 | — | O | 5-CH$_3$ | OCH$_2$—C≡CH | OCH$_3$ | OCH$_3$ | N |
| H | A-1 | — | O | 5-CH$_3$ | OCH$_2$—C≡CH | Cl | OCH$_3$ | CH |
| H | A-1 | — | O | 5-OCH$_3$ | NO$_2$ | CH$_3$ | CH$_3$ | CH |
| H | A-1 | — | O | 5-OCH$_3$ | NO$_2$ | CH$_3$ | OCH$_3$ | CH |
| H | A-1 | — | O | 5-OCH$_3$ | NO$_2$ | OCH$_3$ | OCH$_3$ | CH |
| H | A-1 | — | O | 5-OCH$_3$ | NO$_2$ | CH$_3$ | CH$_3$ | N |
| H | A-1 | — | O | 5-OCH$_3$ | NO$_2$ | CH$_3$ | OCH$_3$ | N |
| H | A-1 | — | O | 5-OCH$_3$ | NO$_2$ | OCH$_3$ | OCH$_3$ | N |
| H | A-1 | — | O | 5-OCH$_3$ | NO$_2$ | Cl | OCH$_3$ | CH |
| H | A-1 | — | O | 5-OCH$_3$ | CO$_2$CH$_3$ | CH$_3$ | CH$_3$ | CH |
| H | A-1 | — | O | 5-OCH$_3$ | CO$_2$CH$_3$ | CH$_3$ | OCH$_3$ | CH |
| H | A-1 | — | O | 5-OCH$_3$ | CO$_2$CH$_3$ | OCH$_3$ | OCH$_3$ | CH |
| H | A-1 | — | O | 5-OCH$_3$ | CO$_2$CH$_3$ | CH$_3$ | CH$_3$ | N |
| H | A-1 | — | O | 5-OCH$_3$ | CO$_2$CH$_3$ | CH$_3$ | OCH$_3$ | N |
| H | A-1 | — | O | 5-OCH$_3$ | CO$_2$CH$_3$ | OCH$_3$ | OCH$_3$ | N |
| H | A-1 | — | O | 5-OCH$_3$ | CO$_2$CH$_3$ | Cl | OCH$_3$ | CH |
| H | A-1 | — | O | 5-OCH$_3$ | CO$_2$CH$_2$CH$_3$ | CH$_3$ | CH$_3$ | CH |
| H | A-1 | — | O | 5-OCH$_3$ | CO$_2$CH$_2$CH$_3$ | CH$_3$ | OCH$_3$ | CH |
| H | A-1 | — | O | 5-OCH$_3$ | CO$_2$CH$_2$CH$_3$ | OCH$_3$ | OCH$_3$ | CH |
| H | A-1 | — | O | 5-OCH$_3$ | CO$_2$CH$_2$CH$_3$ | CH$_3$ | CH$_3$ | N |
| H | A-1 | — | O | 5-OCH$_3$ | CO$_2$CH$_2$CH$_3$ | CH$_3$ | OCH$_3$ | N |
| H | A-1 | — | O | 5-OCH$_3$ | CO$_2$CH$_2$CH$_3$ | OCH$_3$ | OCH$_3$ | N |
| H | A-1 | — | O | 5-OCH$_3$ | CO$_2$CH$_2$CH$_3$ | Cl | OCH$_3$ | CH |
| H | A-1 | — | O | 5-OCH$_3$ | CO$_2$CH$_2$CH$_2$CH$_3$ | CH$_3$ | CH$_3$ | CH |
| H | A-1 | — | O | 5-OCH$_3$ | CO$_2$CH$_2$CH$_2$CH$_3$ | CH$_3$ | OCH$_3$ | CH |
| H | A-1 | — | O | 5-OCH$_3$ | CO$_2$CH$_2$CH$_2$CH$_3$ | OCH$_3$ | OCH$_3$ | CH |
| H | A-1 | — | O | 5-OCH$_3$ | CO$_2$CH$_2$CH$_2$CH$_3$ | CH$_3$ | CH$_3$ | N |
| H | A-1 | — | O | 5-OCH$_3$ | CO$_2$CH$_2$CH$_2$CH$_3$ | CH$_3$ | OCH$_3$ | N |
| H | A-1 | — | O | 5-OCH$_3$ | CO$_2$CH$_2$CH$_2$CH$_3$ | OCH$_3$ | OCH$_3$ | N |
| H | A-1 | — | O | 5-OCH$_3$ | CO$_2$CH$_2$CH$_2$CH$_3$ | Cl | OCH$_3$ | CH |
| H | A-1 | — | O | 5-OCH$_2$CF$_3$ | CO$_2$CH(CH$_3$)$_2$ | CH$_3$ | CH$_3$ | CH |
| H | A-1 | — | O | 5-OCH$_2$CF$_3$ | CO$_2$CH(CH$_3$)$_2$ | CH$_3$ | OCH$_3$ | CH |
| H | A-1 | — | O | 5-OCH$_2$CF$_3$ | CO$_2$CH(CH$_3$)$_2$ | OCH$_3$ | OCH$_3$ | CH |
| H | A-1 | — | O | 5-OCH$_2$CF$_3$ | CO$_2$CH(CH$_3$)$_2$ | CH$_3$ | CH$_3$ | N |
| H | A-1 | — | O | 5-OCH$_2$CF$_3$ | CO$_2$CH(CH$_3$)$_2$ | OCH$_3$ | OCH$_3$ | N |
| H | A-1 | — | O | 5-OCH$_2$CF$_3$ | CO$_2$CH(CH$_3$)$_2$ | Cl | OCH$_3$ | CH |
| H | A-1 | — | O | 5-OCH$_2$CF$_3$ | CO$_2$CH$_2$CH$_2$Cl | CH$_3$ | CH$_3$ | CH |
| H | A-1 | — | O | 5-OCH$_2$CF$_3$ | CO$_2$CH$_2$CH$_2$Cl | CH$_3$ | OCH$_3$ | CH |
| H | A-1 | — | O | 5-OCH$_2$CF$_3$ | CO$_2$CH$_2$CH$_2$Cl | OCH$_3$ | OCH$_3$ | CH |
| H | A-1 | — | O | 5-OCH$_2$CF$_3$ | CO$_2$CH$_2$CH$_2$Cl | CH$_3$ | CH$_3$ | N |
| H | A-1 | — | O | 5-OCH$_2$CF$_3$ | CO$_2$CH$_2$CH$_2$Cl | OCH$_3$ | OCH$_3$ | N |
| H | A-1 | — | O | 5-OCH$_2$CF$_3$ | CO$_2$CH$_2$CH$_2$Cl | Cl | OCH$_3$ | CH |
| H | A-1 | — | O | 5-OCH$_2$CF$_3$ | CO$_2$CH$_2$CH$_2$F | CH$_3$ | CH$_3$ | CH |
| H | A-1 | — | O | 5-OCH$_2$CF$_3$ | CO$_2$CH$_2$CH$_2$F | CH$_3$ | OCH$_3$ | CH |
| H | A-1 | — | O | 5-OCH$_2$CF$_3$ | CO$_2$CH$_2$CH$_2$F | OCH$_3$ | OCH$_3$ | CH |
| H | A-1 | — | O | 5-OCH$_2$CF$_3$ | CO$_2$CH$_2$CH$_2$F | CH$_3$ | CH$_3$ | N |
| H | A-1 | — | O | 5-OCH$_2$CF$_3$ | CO$_2$CH$_2$CH$_2$F | CH$_3$ | OCH$_3$ | N |
| H | A-1 | — | O | 5-OCH$_2$CF$_3$ | CO$_2$CH$_2$CH$_2$F | OCH$_3$ | OCH$_3$ | N |
| H | A-1 | — | O | 5-OCH$_2$CF$_3$ | CO$_2$CH$_2$CH$_2$F | Cl | OCH$_3$ | CH |

TABLE IV-continued

| R | A | E | W | R₁ | R₂ | X | Y | Z |
|---|---|---|---|---|---|---|---|---|
| H | A-1 | — | O | 5-OCH₂CF₃ | CO₂CH₂OCH₃ | CH₃ | CH₃ | CH |
| H | A-1 | — | O | 5-OCH₂CF₃ | CO₂CH₂OCH₃ | CH₃ | OCH₃ | CH |
| H | A-1 | — | O | 5-OCH₂CF₃ | CO₂CH₂OCH₃ | OCH₃ | OCH₃ | CH |
| H | A-1 | — | O | 5-OCH₂CF₃ | CO₂CH₂OCH₃ | CH₃ | CH₃ | N |
| H | A-1 | — | O | 5-OCH₂CF₃ | CO₂CH₂OCH₃ | CH₃ | OCH₃ | N |
| H | A-1 | — | O | 5-OCH₂CF₃ | CO₂CH₂OCH₃ | OCH₃ | OCH₃ | N |
| H | A-1 | — | O | 5-OCH₂CF₃ | CO₂CH₂OCH₃ | Cl | OCH₃ | CH |
| H | A-1 | — | O | 6-OCH₃ | CO₂CH₃ | CH₃ | CH₃ | CH |
| H | A-1 | — | O | 6-OCH₃ | CO₂CH₃ | CH₃ | OCH₃ | CH |
| H | A-1 | — | O | 6-OCH₃ | CO₂CH₃ | OCH₃ | OCH₃ | CH |
| H | A-1 | — | O | 6-OCH₃ | CO₂CH₃ | CH₃ | CH₃ | N |
| H | A-1 | — | O | 6-OCH₃ | CO₂CH₃ | CH₃ | OCH₃ | N |
| H | A-1 | — | O | 6-OCH₃ | CO₂CH₃ | OCH₃ | OCH₃ | N |
| H | A-1 | — | O | 6-OCH₃ | CO₂CH₃ | Cl | OCH₃ | CH |
| H | A-1 | — | O | 6-OCH₃ | CO₂CH₂CH₃ | CH₃ | CH₃ | CH |
| H | A-1 | — | O | 6-OCH₃ | CO₂CH₂CH₃ | OCH₃ | OCH₃ | CH |
| H | A-1 | — | O | 6-OCH₃ | CO₂CH₂CH₃ | CH₃ | CH₃ | N |
| H | A-1 | — | O | 6-OCH₃ | CO₂CH₂CH₃ | CH₃ | OCH₃ | N |
| H | A-1 | — | O | 6-OCH₃ | CO₂CH₂CH₃ | OCH₃ | OCH₃ | N |
| H | A-1 | — | O | 6-OCH₃ | CO₂CH₂CH₃ | Cl | OCH₃ | CH |
| H | A-1 | — | O | 6-OCH₃ | SO₂N(CH₃)₂ | CH₃ | CH₃ | CH |
| H | A-1 | — | O | 6-OCH₃ | SO₂N(CH₃)₂ | CH₃ | OCH₃ | CH |
| H | A-1 | — | O | 6-OCH₃ | SO₂N(CH₃)₂ | OCH₃ | OCH₃ | CH |
| H | A-1 | — | O | 6-OCH₃ | SO₂N(CH₃)₂ | CH₃ | CH₃ | N |
| H | A-1 | — | O | 6-OCH₃ | SO₂N(CH₃)₂ | CH₃ | OCH₃ | N |
| H | A-1 | — | O | 6-OCH₃ | SO₂N(CH₃)₂ | OCH₃ | OCH₃ | N |
| H | A-1 | — | O | 6-OCH₃ | SO₂N(CH₃)₂ | Cl | OCH₃ | CH |
| H | A-1 | — | O | 6-OCH₃ | SO₂CH₃ | CH₃ | CH₃ | CH |
| H | A-1 | — | O | 6-OCH₃ | SO₂CH₃ | CH₃ | OCH₃ | CH |
| H | A-1 | — | O | 6-OCH₃ | SO₂CH₃ | OCH₃ | OCH₃ | CH |
| H | A-1 | — | O | 6-OCH₃ | SO₂CH₃ | CH₃ | CH₃ | N |
| H | A-1 | — | O | 6-OCH₃ | SO₂CH₃ | CH₃ | OCH₃ | N |
| H | A-1 | — | O | 6-OCH₃ | SO₂CH₃ | OCH₃ | OCH₃ | N |
| H | A-1 | — | O | 6-OCH₃ | SO₂CH₃ | Cl | OCH₃ | CH |
| CH₃ | A-1 | — | O | 6-F | SCH₂—CH=CH₂ | CH₃ | CH₃ | CH |
| CH₃ | A-1 | — | O | 6-F | SCH₂—CH=CH₂ | CH₃ | OCH₃ | CH |
| CH₃ | A-1 | — | O | 6-F | SCH₂—CH=CH₂ | OCH₃ | OCH₃ | CH |
| CH₃ | A-1 | — | O | 6-F | SCH₂—CH=CH₂ | CH₃ | CH₃ | N |
| CH₃ | A-1 | — | O | 6-F | SCH₂—CH=CH₂ | CH₃ | OCH₃ | N |
| CH₃ | A-1 | — | O | 6-F | SCH₂—CH=CH₂ | OCH₃ | OCH₃ | N |
| CH₃ | A-1 | — | O | 6-F | SCH₂—CH=CH₂ | Cl | OCH₃ | CH |
| CH₃ | A-1 | — | O | 6-F | SCH₂CH₂OCH₃ | CH₃ | CH₃ | CH |
| CH₃ | A-1 | — | O | 6-F | SCH₂—C≡CH | CH₃ | OCH₃ | CH |
| CH₃ | A-1 | — | O | 6-F | SCH(CH₃)₂ | CH₃ | CH₃ | CH |
| CH₃ | A-1 | — | O | 6-F | SCH(CH₃)₂ | OCH₃ | OCH₃ | N |
| CH₃ | A-1 | — | O | 6-F | SCH(CH₃)₂ | CH₃ | OCH₃ | N |
| CH₃ | A-1 | — | O | 6-F | SCH(CH₃)₂ | OCH₃ | OCH₃ | N |
| CH₃ | A-1 | — | O | 6-F | SCH(CH₃)₂ | Cl | OCH₃ | CH |
| CH₃ | A-1 | — | O | 6-F | SOCH₃ | CH₃ | CH₃ | CH |
| CH₃ | A-1 | — | O | 6-F | SOCH₃ | CH₃ | OCH₃ | CH |
| CH₃ | A-1 | — | O | 6-F | SOCH₃ | OCH₃ | OCH₃ | CH |
| CH₃ | A-1 | — | O | 6-F | SOCH₃ | CH₃ | CH₃ | N |
| CH₃ | A-1 | — | O | 6-F | SOCH₃ | CH₃ | OCH₃ | N |
| CH₃ | A-1 | — | O | 6-F | SOCH₃ | OCH₃ | OCH₃ | N |
| CH₃ | A-1 | — | O | 6-F | SOCH₃ | Cl | OCH₃ | CH |
| CH₃ | A-1 | — | O | 6-F | SO₂CH₃ | CH₃ | CH₃ | CH |
| CH₃ | A-1 | — | O | 6-F | SO₂CH₃ | CH₃ | OCH₃ | CH |
| CH₃ | A-1 | — | O | 6-F | SO₂CH₃ | OCH₃ | OCH₃ | CH |
| CH₃ | A-1 | — | O | 6-F | SO₂CH₃ | CH₃ | CH₃ | N |
| CH₃ | A-1 | — | O | 6-F | SO₂CH₃ | CH₃ | OCH₃ | N |
| CH₃ | A-1 | — | O | 6-F | SO₂CH₃ | OCH₃ | OCH₃ | N |
| CH₃ | A-1 | — | O | 6-F | SO₂CH₃ | Cl | OCH₃ | CH |

| R | A | E | W | R₁ | R₂ | X₁ | Y₁ | m.p. (°C.) |
|---|---|---|---|---|---|---|---|---|
| H | A-2 | — | O | H | CO₂CH₃ | CH₃ | O | |
| H | A-2 | — | O | H | CO₂CH₃ | CH₃ | CH₂ | |
| H | A-2 | — | O | H | CO₂CH₃ | OCH₃ | O | |
| H | A-2 | — | O | H | CO₂CH₃ | OCH₃ | CH₂ | |
| H | A-2 | — | O | H | CO₂CH₃ | OCH₂CH₃ | O | |
| H | A-2 | — | O | H | CO₂CH₃ | OCF₂H | CH₂ | |
| H | A-2 | — | O | H | SO₂N(CH₃)₂ | CH₃ | O | |
| H | A-2 | — | O | H | SO₂N(CH₃)₂ | OCH₃ | O | |
| H | A-2 | — | O | H | SO₂N(CH₃)₂ | OCF₂H | CH₂ | |

| R | A | E | W | R₁ | R₂ | X₁ | | m.p. (°C.) |
|---|---|---|---|---|---|---|---|---|
| H | A-3 | — | O | H | CO₂CH₃ | CH₃ | | |
| H | A-3 | — | O | H | CO₂CH₃ | OCH₃ | | |
| H | A-3 | — | O | H | CO₂CH₃ | OCH₂CH₃ | | |
| H | A-3 | — | O | H | CO₂CH₃ | OCF₂H | | |
| H | A-3 | — | O | H | Cl | CH₃ | | |
| H | A-3 | — | O | H | Cl | OCH₃ | | |

TABLE IV-continued

| R | A | E | W | R₁ | R₂ | | | m.p. (°C.) |
|---|---|---|---|---|---|---|---|---|
| H | A-3 | — | O | H | SO$_2$CH$_3$ | CH$_3$ | | |
| H | A-3 | — | O | H | SO$_2$CH$_3$ | OCH$_3$ | | |

| R | A | E | W | R$_1$ | R$_2$ | X$_1$ | Y$_3$ | m.p. (°C.) |
|---|---|---|---|---|---|---|---|---|
| H | A-4 | — | O | H | CO$_2$CH$_3$ | CH$_3$ | H | |
| H | A-4 | — | O | H | CO$_2$CH$_3$ | OCH$_3$ | H | |
| H | A-4 | — | O | H | CO$_2$CH$_3$ | OCH$_2$CH$_3$ | H | |
| H | A-4 | — | O | H | CO$_2$CH$_3$ | OCF$_2$H | H | |
| H | A-4 | — | O | H | CO$_2$CH$_3$ | CH$_3$ | CH$_3$ | |
| H | A-4 | — | O | H | CO$_2$CH$_3$ | OCH$_3$ | CH$_3$ | |
| H | A-4 | — | O | H | CO$_2$CH$_3$ | OCF$_2$H | CH$_3$ | |

| R | A | E | W | R$_1$ | R$_2$ | X$_2$ | Y$_2$ | m.p. (°C.) |
|---|---|---|---|---|---|---|---|---|
| H | A-5 | — | O | H | CO$_2$CH$_3$ | CH$_3$ | OCH$_3$ | |
| H | A-5 | — | O | H | CO$_2$CH$_3$ | CH$_3$ | OCH$_2$CH$_3$ | |
| H | A-5 | — | O | H | CO$_2$CH$_3$ | CH$_3$ | SCH$_3$ | |
| H | A-5 | — | O | H | CO$_2$CH$_3$ | CH$_3$ | SCH$_2$CH$_3$ | |
| H | A-5 | — | O | H | CO$_2$CH$_3$ | CH$_3$ | CH$_3$ | |
| H | A-5 | — | O | H | CO$_2$CH$_3$ | CH$_3$ | CH$_2$CH$_3$ | |
| H | A-5 | — | O | H | CO$_2$CH$_3$ | CH$_2$CH$_3$ | OCH$_3$ | |
| H | A-5 | — | O | H | CO$_2$CH$_3$ | CH$_2$CH$_3$ | SCH$_3$ | |
| H | A-5 | — | O | H | CO$_2$CH$_3$ | CH$_2$CH$_3$ | OCH$_2$CH$_3$ | |
| H | A-5 | — | O | H | CO$_2$CH$_3$ | CH$_2$CH$_3$ | OCH$_3$ | |

| R | A | E | W | R$_1$ | R$_2$ | X$_3$ | | m.p. (°C.) |
|---|---|---|---|---|---|---|---|---|
| H | A-6 | — | O | H | CO$_2$CH$_3$ | CH$_3$ | | |
| H | A-6 | — | O | H | CO$_2$CH$_3$ | OCH$_3$ | | |
| H | A-6 | — | O | H | NO$_2$ | CH$_3$ | | |
| H | A-6 | — | O | H | NO$_2$ | OCH$_3$ | | |

| R | A | E | W | R$_1$ | R$_2$ | X$_4$ | Y$_4$ | m.p. (°C.) |
|---|---|---|---|---|---|---|---|---|
| H | A-7 | — | O | H | CO$_2$CH$_3$ | CH$_3$ | CH$_3$ | |
| H | A-7 | — | O | H | CO$_2$CH$_3$ | CH$_3$ | OCH$_3$ | |
| H | A-7 | — | O | H | CO$_2$CH$_3$ | CH$_3$ | OCH$_2$CH$_3$ | |
| H | A-7 | — | O | H | CO$_2$CH$_3$ | CH$_3$ | Cl | |
| H | A-7 | — | O | H | CO$_2$CH$_3$ | OCH$_3$ | CH$_3$ | |
| H | A-7 | — | O | H | CO$_2$CH$_3$ | OCH$_3$ | OCH$_3$ | |
| H | A-7 | — | O | H | CO$_2$CH$_3$ | OCH$_2$CH$_3$ | OCH$_3$ | |

| R | A | E | W | R$_1$ | R$_2$ | X | Y | Z | m.p. (°C.) |
|---|---|---|---|---|---|---|---|---|---|
| H | A-1 | — | O | H | CO$_2$CH$_3$ | CH$_3$ | OCH$_2$CH$_3$ | CH | |
| H | A-1 | — | O | H | CO$_2$CH$_3$ | CH$_3$ | OCF$_2$H | CH | |
| H | A-1 | — | O | H | CO$_2$CH$_3$ | CH$_3$ | SCF$_2$H | CH | |
| H | A-1 | — | O | H | CO$_2$CH$_3$ | CH$_3$ | SCH$_3$ | CH | |
| H | A-1 | — | O | H | CO$_2$CH$_3$ | CH$_3$ | CH$_2$OCH$_3$ | CH | |
| H | A-1 | — | O | H | CO$_2$CH$_3$ | CH$_3$ | NHCH$_3$ | N | |
| H | A-1 | — | O | H | CO$_2$CH$_3$ | CH$_3$ | N(CH$_3$)$_2$ | N | |
| H | A-1 | — | O | H | CO$_2$CH$_3$ | CH$_3$ | CH$_2$F | CH | |
| H | A-1 | — | O | H | CO$_2$CH$_3$ | CH$_3$ | C≡CH | CH | |
| H | A-1 | — | O | H | CO$_2$CH$_3$ | CH$_3$ | cyclopropyl | N | |
| H | A-1 | — | O | H | CO$_2$CH$_3$ | CH$_3$ | CN | CH | |
| H | A-1 | — | O | H | CO$_2$CH$_3$ | OCH$_3$ | CH$_2$CH$_3$ | CH | |
| H | A-1 | — | O | H | CO$_2$CH$_3$ | OCH$_3$ | OCH$_2$CH$_3$ | CH | |
| H | A-1 | — | O | H | CO$_2$CH$_3$ | OCH$_3$ | SCH$_3$ | N | |
| H | A-1 | — | O | H | CO$_2$CH$_3$ | OCH$_3$ | OCF$_2$H | CH | |
| H | A-1 | — | O | H | CO$_2$CH$_3$ | OCH$_3$ | CH$_2$F | CH | |
| H | A-1 | — | O | H | CO$_2$CH$_3$ | OCH$_3$ | N(CH$_3$)$_2$ | N | |
| H | A-1 | — | O | H | CO$_2$CH$_3$ | OCH$_3$ | NHCH$_3$ | N | |
| H | A-1 | — | O | H | CO$_2$CH$_3$ | OCH$_3$ | CN | N | |
| H | A-1 | — | O | H | CO$_2$CH$_3$ | OCF$_2$H | CH$_3$ | CH | |
| H | A-1 | — | O | H | CO$_2$CH$_3$ | OCF$_2$H | OCH$_2$CH$_3$ | CH | |
| H | A-1 | — | O | H | CO$_2$CH$_3$ | OCF$_2$H | CH$_2$CH$_3$ | N | |
| H | A-1 | — | O | H | CO$_2$CH$_3$ | OCF$_2$H | CH$_2$F | CH | |
| H | A-1 | — | O | H | CO$_2$CH$_3$ | OCF$_2$H | SCH$_3$ | CH | |
| H | A-1 | — | O | H | CO$_2$CH$_3$ | OCF$_2$H | N(CH$_3$)$_2$ | N | |
| H | A-1 | — | O | H | CO$_2$CH$_3$ | OCF$_2$H | NHCH$_3$ | N | |
| H | A-1 | — | O | H | CO$_2$CH$_3$ | CH$_2$OCH$_3$ | OCH$_3$ | CH | |
| H | A-1 | — | O | H | CO$_2$CH$_3$ | CH$_2$OCH$_3$ | OCH$_2$CH$_3$ | CH | |
| H | A-1 | — | O | H | CO$_2$CH$_3$ | CH$_2$OCH$_3$ | CH$_3$ | N | |
| H | A-1 | — | O | H | CO$_2$CH$_3$ | CH$_2$OCH$_3$ | CH$_2$F | CH | |
| H | A-1 | — | O | H | CO$_2$CH$_3$ | CH$_2$OCH$_3$ | CH$_2$Cl | CH | |
| H | A-1 | — | O | H | CO$_2$CH$_3$ | CH$_2$OCH$_3$ | CH$_2$Br | CH | |
| H | A-1 | — | O | H | CO$_2$CH$_3$ | SCF$_2$H | OCH$_2$CH$_3$ | CH | |
| H | A-1 | — | O | H | CO$_2$CH$_3$ | SCF$_2$H | CH$_2$CH$_3$ | CH | |
| H | A-1 | — | O | H | CO$_2$CH$_3$ | SCF$_2$H | CH$_2$F | CH | |
| H | A-1 | — | O | H | CO$_2$CH$_3$ | SCF$_2$H | NHCH$_3$ | N | |
| H | A-1 | — | O | H | CO$_2$CH$_3$ | N(CH$_3$)$_2$ | OCH$_2$CH$_3$ | N | |
| H | A-1 | — | O | H | CO$_2$CH$_3$ | N(CH$_3$)$_2$ | CH$_2$CH$_3$ | N | |
| H | A-1 | — | O | H | CO$_2$CH$_3$ | N(CH$_3$)$_2$ | CH$_2$F | N | |
| H | A-1 | — | O | H | CO$_2$CH$_3$ | N(CH$_3$)$_2$ | CH$_2$OCH$_3$ | N | |
| H | A-1 | — | O | H | CO$_2$CH$_3$ | N(CH$_3$)$_2$ | cyclopropyl | N | |
| H | A-1 | — | O | H | CO$_2$CH$_3$ | C≡CH | CH$_2$CH$_3$ | N | |

TABLE IV-continued

| H | A-1 | — | O | H | CO₂CH₃ | C≡CH | OCH₃ | CH |
| H | A-1 | — | O | H | CO₂CH₃ | C≡CH | N(CH₃)₂ | CH |
| H | A-1 | — | O | H | CO₂CH₃ | C≡CH | OCH₂CH₃ | N |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

|  | Active Ingredient | Weight Percent* Diluent(s) | Surfactant(s) |
| --- | --- | --- | --- |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example: H. M. Loux, U.S. Pat. No. 3,235,361, Feb. 15, 1966, col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following Examples, all parts are by weight unless otherwise indicated.

EXAMPLE 9

| Wettable Powder | |
| --- | --- |
| N—[(4-methoxy-6-methyl-1,3,5-triazin-2-yl)aminocarbonyl]-2-pyridinesulfonamide-1-oxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 10

| Wettable Powder | |
| --- | --- |
| N—[(4,6-dimethoxypyrimidin-2-yl)aminocarbonyl]-3-methyl-2-pyridinesulfonamide-1-oxide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

| Granule | |
| --- | --- |
| Wettable powder of Example 10 | 5% |
| attapulgite granules (U.S.S. 20 to 40 mesh; 0.84–0.42 mm) | 95% |

A slurry of wettable powder containing 25% solids is sprayed on the surface of attapulgite granules in a double-cone blender. The granules are dried and packaged.

EXAMPLE 12

| Extruded Pellet | |
|---|---|
| N—[(4-methoxy-6-methyl-1,3,5-triazin-2-yl)aminocarbonyl]-2-pyridinesulfonamide-1-oxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

| Low Strength Granule | |
|---|---|
| N—[(4,6-dimethoxypyrimidin-2-yl)aminocarbonyl]-3-methyl-2-pyridinesulfonamide-1-oxide | 0.1% |
| attapulgite granules (U.S.S. 20 to 40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 14

| Granule | |
|---|---|
| N—[(4-methoxy-6-methyl-1,3,5-triazin-2-yl)aminocarbonyl]-2-pyridinesulfonamide-1-oxide | 80% |
| wetting agent | 1% |
| crude ligninsulfonate salt (containing 5 to 20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14 to 100 mesh (1410 to 149 microns), and packaged for use.

EXAMPLE 15

| Low Strength Granule | |
|---|---|
| N—[(4,6-dimethoxypyrimidin-2-yl)aminocarbonyl]-3-methyl-2-pyridinesulfonamide-1-oxide | 1% |
| N,N—dimethylformamide | 9% |

—continued

| Low Strength Granule | |
|---|---|
| attapulgite granules (U.S.S. 20 to 40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

| Aqueous Suspension | |
|---|---|
| N—[(4-methoxy-6-methyl-1,3,5-triazin-2-yl)aminocarbonyl]-2-pyridinesulfonamide-1-oxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 17

| Solution | |
|---|---|
| N—[(4,6-dimethoxypyrimidin-2-yl)aminocarbonyl]-3-methyl-2-pyridinesulfonamide-1-oxide, ammonium salt | 5% |
| water | 95% |

The salt is added directly to the water with stirring to produce the solution, which may then be packaged for use.

EXAMPLE 18

| High Strength Concentrate | |
|---|---|
| N—[(4-methoxy-6-methyl-1,3,5-triazin-2-yl)aminocarbonyl]-2-pyridinesulfonamide-1-oxide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
|---|---|
| N—[(4,6-dimethoxypyrimidin-2-yl)aminocarbonyl]-3-methyl-2-pyridinesulfonamide-1-oxide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 20

| Wettable Powder | |
|---|---|
| N—[(4-methoxy-6-methyl-1,3,5-triazin-2-yl)amino-carbonyl]-2-pyridinesulfonamide-1-oxide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

| Oil Suspension | |
|---|---|
| N—[(4,6-dimethoxypyrimidin-2-yl)aminocarbonyl]-3-methyl-2-pyridinesulfonamide-1-oxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 22

| Dust | |
|---|---|
| N—[(4-methoxy-6-methyl-1,3,5-triazin-2-yl)amino-carbonyl]-2-pyridinesulfonamide-1-oxide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 23

| Oil Suspension | |
|---|---|
| N—[(4,6-dimethoxypyrimidin-2-yl)aminocarbonyl]-3-methyl-2-pyridinesulfonamide-1-oxide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 24

| Wettable Powder | |
|---|---|
| N—[(4-methoxy-6-methyl-1,3,5-triazin-2-yl)amino-carbonyl]-2-pyridinesulfonamide-1-oxide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve 0.3 mm opening) and packaged.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, industrial storage areas, parking lots, drive-in theaters, around billboards, highway and railroad structures. Some of the compounds have utility for selective weed control in crops such as wheat, barley and corn. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate and bipyridylium, imidazolinone types.

The herbicidal properties of the subject compounds were discovered in a number of greenhouse tests. The test procedures and results follow.

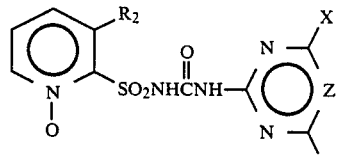

| Compound | $R_1$ | $R_2$ | X | Y | Z |
|---|---|---|---|---|---|
| 1 | H | $CH_3$ | $CH_3$ | CH | |
| 2 | H | $CH_3$ | $OCH_3$ | CH | |
| 3 | H | $OCH_3$ | $OCH_3$ | CH | |
| 4 | H | $CH_3$ | $CH_3$ | N | |
| 5 | H | $CH_3$ | $OCH_3$ | N | |
| 6 | H | $OCH_3$ | $OCH_3$ | N | |
| 7 | $CH_3$ | $CH_3$ | $CH_3$ | CH | |
| 8 | $CH_3$ | $CH_3$ | $OCH_3$ | CH | |
| 9 | $CH_3$ | $OCH_3$ | $OCH_3$ | CH | |
| 10 | $CH_3$ | $CH_3$ | $OCH_3$ | N | |
| 11 | $CH_3$ | $OCH_3$ | $OCH_3$ | N | |
| 12 | $CH_3$ | Cl | $OCH_3$ | CH | |
| 13 | cyclopropyl | $CH_3$ | $CH_3$ | CH | |
| 14 | cyclopropyl | $CH_3$ | $OCH_3$ | CH | |
| 15 | cyclopropyl | $OCH_3$ | $OCH_3$ | CH | |
| 16 | cyclopropyl | $OCH_3$ | $OCH_3$ | N | |
| 17 | $CH(CH_3)_2$ | $CH_3$ | $CH_3$ | CH | |
| 18 | $CH(CH_3)_2$ | $OCH_3$ | $OCH_3$ | CH | |

| Compound | R₁ | R₂ | X | Y | Z |
|---|---|---|---|---|---|

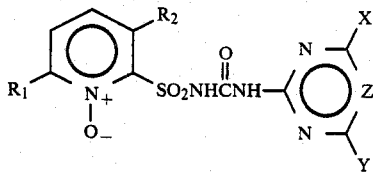

| Compound | R₁ | R₂ | X | Y | Z |
|---|---|---|---|---|---|
| 19 | SCH₃ | H | CH₃ | CH₃ | CH |
| 20 | SCH₃ | H | CH₃ | OCH₃ | CH |
| 21 | SCH₃ | H | OCH₃ | OCH₃ | CH |
| 22 | SCH₃ | H | CH₃ | OCH₃ | N |
| 23 | SCH₃ | H | OCH₃ | OCH₃ | N |
| 24 | SCH₃ | H | Cl | OCH₃ | CH |
| 25 | H | OC₂H₅ | OCH₃ | OCH₃ | CH |
| 26 | H | OC₂H₅ | CH₃ | OCH₃ | N |
| 27 | H | OC₂H₅ | Cl | OCH₃ | CH |
| 28 | SCH₃ | SCH₃ | CH₃ | OCH₃ | CH |

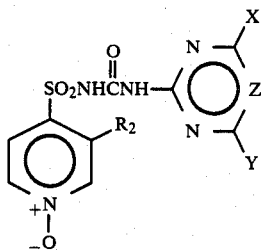

| Compound | | R₂ | X | Y | Z |
|---|---|---|---|---|---|
| 29 | | CH₃ | OCH₃ | OCH₃ | CH |
| 30 | | CH₃ | CH₃ | OCH₃ | CH |
| 31 | | CH₃ | CH₃ | OCH₃ | N |

Test A

Seeds of crabgrass (Digitaria spp.), barnyardgrass (Echinochloa crusgalli), giant foxtail (Setaria faberi), wild oats (Avena fatua), cheatgrass (Bromus secalinus), velvetleaf (Abutilon theophrasti), morningglory (Ipomoea spp.), cocklebur (Xanthium pensylvanicum), sorghum, corn, soybean, sugarbeet, cotton, rice, wheat, barley and purple nutsedge (Cyperus rotundus) tubers were planted and treated preemergence with the test chemicals dissolved in a non-phytotoxic solvent. At the same time, these crop and weed species were treated with a soil-foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols gave the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

A dash (—) response means no test. Response ratings are contained in Table A.

TABLE A

POSTEMERGENCE

| RATE = KG/HA | CMPD 1 0.05 | CMPD 1 0.01 | CMPD 2 0.05 | CMPD 2 0.01 | CMPD 3 0.05 | CMPD 3 0.01 | CMPD 4 0.05 | CMPD 4 0.01 | CMPD 5 0.05 | CMPD 5 0.01 | CMPD 6 0.05 | CMPD 6 0.01 | CMPD 7 0.05 | CMPD 7 0.01 | CMPD 8 0.05 | CMPD 8 0.01 | CMPD 9 0.05 | CMPD 9 0.01 | CMPD 10 0.05 | CMPD 10 0.01 | CMPD 11 0.05 | CMPD 11 0.01 |
|---|---|---|---|---|---|---|---|---|---|---|---|---|---|---|---|---|---|---|---|---|---|---|
| COTTON | 0 | — | 4C,9G | — | — | — | 0 | — | 0 | — | — | — | 3C,7H | 2C | 9H | 2C,8G | 3C,9G | 2C,9H | 9H | 1C | 4C,9H | 3C,6G |
| MORNING GLORY | 2H | — | 5C,9G | — | 6G | — | 0 | — | — | — | — | — | 4C,8H | 2C,2H | 4C,9G | 2C,7G | 10C | 9C | 5C,9G | 3C,8H | 5C,9G | 3C,8H |
| COCKLEBUR | 0 | — | 4C,9G | — | 3C,6G | — | 0 | — | 3C,5H | — | — | — | 4C,8G | 2C,4G | 8G | 2C,7G | 10C | 7G | 4C,9H | 6G | 6H | 3G |
| NUTSEDGE | 0 | — | 2C,9G | — | 10C | — | 0 | — | 0 | — | — | — | 4C,8G | 0 | 5G | 8G | 4C,9G | 9G | 2G | 3G | 0 | 0 |
| CRABGRASS | 0 | — | 2G | — | 7G | — | 0 | — | 0 | — | — | — | 7G | — | 8G | 4C,9H | 10C | 9G | 9C | 3G | 0 | — |
| BARNYARD GRASS | 0 | — | 4C,9H | — | 4G | — | 3C,8H | 2H | 2G | — | — | — | 3C,6H | 3C,6H | 5C,9G | 3C,6G | 2C,8G | 3C,7G | 3G | 3C,7H | 5C,9G | 3C,7H |
| WILD OATS | — | — | — | — | 9H | — | 0 | — | 2C,8H | — | — | — | 2G | 4G | 6G | 5G | 4C,9G | 4C,9H | 0 | 0 | 1C | 0 |
| WHEAT | 0 | — | 2C,3G | — | 3C,7G | — | 0 | — | 0 | — | — | — | 7G | 1C,3G | 4C,9G | 2C,9G | 4C,9G | 3C,9G | 4C,9G | 4C,9G | 5C,9G | 4C,9G |
| CORN | 0 | — | 4C,9G | — | 8G | — | 2H | 0 | 3C,9H | — | — | — | 3C,9H | 3C,3H | 2C,9G | 3C,8G | 5C,9G | 3C,9G | 2C,4G | 2C,4G | 5C,9G | 2C,2H |
| SOYBEAN | 6G | — | 9C | — | — | — | — | — | 4H | — | — | — | 5C,9G | 3C,8G | 3C,9G | 3C,8G | 5C,9G | 5C,9G | 5C,9G | 4C,9G | 5C,9G | 4C,9G |
| RICE | 0 | — | 5C,9G | — | — | — | — | — | 2C,4G | — | — | — | 3C,9H | 2C,5G | 3C,9G | 3C,8G | 3C,9G | 3C,5G | 6C,9G | 4C,9H | 4C,9G | 3C,9G |
| SORGHUM | 6G | — | 9C | — | — | — | — | — | 3C,9H | — | — | — | 4C,9G | 5G | 9G | 7G | 9C | 4C,9G | 3C,7G | 3C,5H | 8G | 0 |
| CHEATGRASS | 2G | — | 9G | — | — | — | — | — | 2C,4G | — | — | — | 9G | 3C,7H | 4C,9H | 5C,9G | 4C,9G | 9C | 5C,9H | 3C,7H | 9C | 4C,9G |
| SUGAR BEETS | 1H | — | 4C,8G | — | — | — | — | — | 4H | — | — | — | 4C,9G | 3C,3H | 9C | 4C,9G | 9C | 4C,9G | 4C,9H | 2C,3G | 4C,9H | 3C,6H |
| VELVETLEAF | 0 | — | 9C | — | — | — | 2H | 0 | 1C | — | — | — | 4C,9H | 2G | 4C,9G | 3C,7H | 5C,9G | 3C,8H | 3C,7G | 2G | 0 | — |
| GIANT FOXTAIL | — | — | 5C,9G | — | — | — | 0 | — | — | — | — | — | 3C,7G | 5G | 8G | — | 9C | — | 9C | — | 3G | — |
| BARLEY | — | — | — | — | — | — | — | — | — | — | — | — | — | — | — | — | — | — | — | — | — | — |
| DOWNY BROME | — | — | — | — | — | — | — | — | — | — | — | — | — | — | — | — | — | — | — | — | — | — |

PREEMERGENCE

| RATE = KG/HA | CMPD 1 0.05 | CMPD 1 0.01 | CMPD 2 0.05 | CMPD 2 0.01 | CMPD 3 0.05 | CMPD 3 0.01 | CMPD 4 0.05 | CMPD 4 0.01 | CMPD 5 0.05 | CMPD 5 0.01 | CMPD 6 0.05 | CMPD 6 0.01 | CMPD 7 0.05 | CMPD 7 0.01 | CMPD 8 0.05 | CMPD 8 0.01 | CMPD 9 0.05 | CMPD 9 0.01 | CMPD 10 0.05 | CMPD 10 0.01 | CMPD 11 0.05 | CMPD 11 0.01 |
|---|---|---|---|---|---|---|---|---|---|---|---|---|---|---|---|---|---|---|---|---|---|---|
| COTTON | — | — | — | — | — | — | — | — | — | — | — | — | 0 | 0 | 2G | 0 | 7G | 3G | 2G | 0 | 0 | 0 |
| MORNING GLORY | — | — | — | — | — | — | — | — | — | — | — | — | 0 | 0 | 0 | 0 | 7G | 3C,3H | 1H | 0 | 0 | 0 |
| COCKLEBUR | — | — | — | — | — | — | — | — | — | — | — | — | — | — | 1C | 0 | 3C,3G | 2C,2H | 3G | 2G | 2G | 0 |
| NUTSEDGE | — | — | — | — | — | — | — | — | — | — | — | — | 0 | 0 | 0 | 0 | 2C,3G | 3G | 0 | 0 | 0 | 0 |
| CRABGRASS | — | — | — | — | — | — | — | — | — | — | — | — | 0 | 0 | 3G | 0 | 4G | 2G | 0 | 0 | 0 | 0 |
| BARNYARD GRASS | — | — | — | — | — | — | — | — | — | — | — | — | 0 | 0 | 2G | 0 | 3C,8H | 2G | 2C,3G | 0 | 0 | 0 |
| WILD OATS | — | — | — | — | — | — | — | — | — | — | — | — | 0 | 0 | 0 | 0 | 3G | 0 | 0 | 0 | 0 | 0 |
| WHEAT | — | — | — | — | — | — | — | — | — | — | — | — | 0 | 0 | 2C | 0 | 0 | 4G | 0 | 0 | 0 | 0 |
| CORN | — | — | — | — | — | — | — | — | — | — | — | — | 2G | 0 | 2C | 0 | 3C,5G | 2H | 0 | 0 | 1C | 0 |
| SOYBEAN | — | — | — | — | — | — | — | — | — | — | — | — | 2G | 0 | 3C | 0 | 2C,6G | 3G | 0 | 0 | 0 | 0 |
| RICE | — | — | — | — | — | — | — | — | — | — | — | — | 3C | 0 | 3C | 0 | 3C,8G | 3G | 0 | 0 | 3C,3G | 0 |
| SORGHUM | — | — | — | — | — | — | — | — | — | — | — | — | — | — | 0 | 0 | 3C,8G | 3C,5G | 3G | 0 | 0 | 0 |
| CHEATGRASS | — | — | — | — | — | — | — | — | — | — | — | — | 5H | 0 | 1H | 0 | 8G | 5G | 5G | 3G | 3H | 0 |
| SUGAR BEETS | — | — | — | — | — | — | — | — | — | — | — | — | 2C | 0 | 2C | 0 | 2C,6H | 2H | 2C | 0 | 2C | 0 |
| VELVETLEAF | — | — | — | — | — | — | — | — | — | — | — | — | 0 | 0 | 6G | 0 | 7G | 7H | 0 | 0 | 0 | 0 |
| GIANT FOXTAIL | — | — | — | — | — | — | — | — | — | — | — | — | 0 | 0 | 2G | 0 | 3C,6G | 0 | 0 | 0 | 0 | 0 |
| BARLEY | — | — | — | — | — | — | — | — | — | — | — | — | 0 | 0 | 0 | 0 | 2G | 0 | 0 | 0 | 0 | — |
| DOWNY BROME | — | — | — | — | — | — | — | — | — | — | — | — | — | — | — | — | — | — | — | — | — | — |

POSTEMERGENCE

| RATE = KG/HA | CMPD 12 0.05 | CMPD 12 0.01 | CMPD 13 0.05 | CMPD 13 0.01 | CMPD 14 0.05 | CMPD 14 0.01 | CMPD 15 0.05 | CMPD 15 0.01 | CMPD 16 0.05 | CMPD 16 0.01 | CMPD 17 0.05 | CMPD 17 0.01 | CMPD 18 0.05 | CMPD 18 0.01 | CMPD 19 0.05 | CMPD 19 0.01 | CMPD 20 0.05 | CMPD 20 0.01 | CMPD 21 0.05 | CMPD 21 0.01 |
|---|---|---|---|---|---|---|---|---|---|---|---|---|---|---|---|---|---|---|---|---|
| COTTON | 3C,8G | 3G | 3C,7G | 2C,4G | 9G | 2C,6G | 3C,9H | 2C,5G | 4C,9G | 2C,4G | 2C,7G | 2C,4G | 3C,9G | 5C,9G | 7G | 0 | 6G | 2G | 2C,2G | 3C,6G |
| MORNING GLORY | 4C,8G | 2C,6G | 2C,7G | 1H | 4C,9G | 3C,8G | 9C | 4C,9G | 9C | 3C,7G | 2C,8G | 3C,7G | 1C | 10C | 3C,3H | 0 | 2C,3H | 2C,4G | 1C | 3C,7G |
| COCKLEBUR | 7G | 1C | 9C | 2C,5G | 4C,8H | 10C | 10C | 9C | 10C | 2C,7G | 3C,9H | 5C,9H | 5C,9H | 10C | 2C,3G | 0 | 3C,5G | 4C,9G | 3C,8H | 3C,9H |
| NUTSEDGE | 4C,8G | — | 3C,5G | 2C,5G | 3C,8G | 10C | 7G | 9C | 8G | 10C | 9G | 0 | 9G | 3C,9G | 0 | 0 | 0 | 2C,8G | 5G | 3C,9G |
| CRABGRASS | 0 | 0 | 6G | 6G | 6G | 5G | 9C | 3C,7G | 10C | 4C,8H | 5G | 4C,8H | 5G | 8G | 2G | 0 | 0 | 5G | 0 | 4C,8G |
| BARNYARD GRASS | 3C,9H | 5H | 5C,9H | 10C | 9C | 5C,9H | 5C,9G | 5C,9H | 10C | 9G | 5C,9H | 3C,9G | 9C | 5C,9G | 2C | 0 | 0 | 0 | 0 | 3C,5G |
| WILD OATS | 0 | 0 | 4C,9G | 3C,7G | 2C,9G | 5C,9G | 5C,9G | 5C,9G | 9C | 9G | 4C,9G | 3C,9G | 9G | 5C,9G | 7H | 0 | 8G | 0 | 0 | 3G |
| WHEAT | 0 | 0 | 9G | 4C,9G | 3C,9G | 2C,9G | 5C,9G | 5C,9G | 9C | 9G | 3C,9G | 9G | 9G | | 0 | 0 | 0 | 0 | 0 | 0 |

TABLE A-continued

| | CMPD 22 | | CMPD 23 | | CMPD 24 | | CMPD 25 | | CMPD 26 | | CMPD 27 | | CMPD 28 | | CMPD 29 | | CMPD 30 | | CMPD 31 | |
|---|---|---|---|---|---|---|---|---|---|---|---|---|---|---|---|---|---|---|---|---|---|
| RATE = KG/HA | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| CORN | 3C,7G | 2G | 3C,9G | 2C,9G | 9C | 3C,9G | 9C | 3C,9G | 3C,8G | 8G | 3C,9G | 6U,9G | 0 | 0 | 0 | 0 | 0 | 4C,9H | 0 | 3C,9G |
| SOYBEAN | 3H | 0 | 4C,8G | 4C,9G | 9C | 5C,9G | 5C,9G | 5C,9G | 3C,8G | 5C,9G | 5C,9G | 5C,9G | 0 | 3C,8G | 0 | 2H | 0 | 3C,8G | 0 | 4C,9H |
| RICE | 5C,9G | 3C,6G | 5C,9G | 9G | 9C | 9C | 10C | 9C | 8G | 4C,8G | 4C,9G | 5C,9G | 0 | 5C,9G | 0 | 3G | 0 | 3C,5G | 0 | 5C,9G |
| SORGHUM | 4C,9H | 3C,7H | 2C,9G | 3C,7G | 9C | 3C,9G | 9C | 3C,9G | 9G | 9G | 3C,9G | 6C,9G | 0 | 3G | 0 | 0 | 0 | 4C,9H | 0 | 4C,9H |
| CHEATGRASS | 2C,5G | 0 | 8G | 0 | 9C | 4C,9G | 10C | 5C,9G | 3C,8H | 9G | 3C,9G | 9C | 0 | 3C,7H | 0 | 0 | 0 | 2C,8G | 0 | 7G |
| SUGAR BEETS | 9C | 4C,8G | 5C,9G | 5C,9G | 10C | 5C,9G | 10C | 9C | 3C,8H | 3C,8H | 5C,9G | 10C | 3G | 3C,7H | 0 | 3C,6H | 0 | 10C | 0 | 5C,9G |
| VELVETLEAF | 8H | 2C,5G | 3C,9G | 9C | 10C | 10C | 5C,9H | 5C,9H | 3C,8H | 5C,9G | 5C,9H | 10C | 3G | 3G | 0 | 3C,5G | 0 | 4C,9G | 0 | 3C,7H |
| GIANT FOXTAIL | 2C,5G | 3G | 3C,5G | 3C,6G | 9C | 4C,8G | 9C | 3C,7G | 5C,9G | 9C | 5C,9G | 9C | 0 | 3C,9G | 0 | 0 | 0 | 3C,6G | 0 | 0 |
| BARLEY | 0 | 0 | 9G | 2C,8G | 9H | 2C,9G | 9C | 2C,8G | 3C,8H | 3C,8G | 4C,9G | 9C | 0 | 2G | 0 | 0 | 0 | 0 | 0 | 5C,5G |
| DOWNY BROME | 0 | 0 | 3C,7G | 3C,9G | 5C,9G | 2C,9G | 9C | 3C,8G | 9G | 9G | 3C,8G | 3C,8G | 0 | 0 | 0 | 0 | 0 | 0 | 0 | 3C,5G |

PREEMERGENCE

| | | | | | | | | | | | | | | | | | | | | |
|---|---|---|---|---|---|---|---|---|---|---|---|---|---|---|---|---|---|---|---|---|
| COTTON | 5G | 0 | 0 | 3G | 0 | 3G | 2G | 3G | 3C,5G | 3G | 4G | 3C,6G | 0 | 0 | 0 | 0 | 0 | 0 | 0 | 0 |
| MORNING GLORY | 3G | 0 | 0 | 2G | 0 | 9G | 2C,2G | 8G | 4C,8G | 0 | 0 | 5C,9G | 3C,8H | 2H | 0 | 0 | 0 | 0 | 0 | 0 |
| COCKLEBUR | 3G | — | 2H | 0 | 0 | 9G | 1C | 2C,2H | 4C,8G | 0 | 8G | 9H | 5C,9G | 3G | 0 | 1C | 0 | 0 | 0 | 0 |
| NUTSEDGE | 0 | 0 | 0 | 0 | 3G | 9H | 10E | 0 | 10C | 0 | 5G | 10E | 0 | 0 | 0 | 0 | 0 | 0 | 0 | 0 |
| CRABGRASS | 0 | 0 | 0 | 0 | 0 | 2G | 3C,6G | 3C,5G | 4C,8G | 0 | 7G | 8G | 3G | 0 | 0 | 0 | 0 | 0 | 0 | 0 |
| BARNYARD GRASS | 3G | 0 | 0 | 2G | 0 | 3G | 3C,6G | 3C,6G | 10C | 0 | 3C,8H | 9H | 3C,8H | 0 | 0 | 0 | 0 | 0 | 0 | 0 |
| WILD OATS | 0 | 0 | 0 | 2G | 0 | 3G | 3C,8G | 3C,8G | 3C,8H | 0 | 3G | 8G | 3G | 0 | 0 | 0 | 0 | 0 | 0 | 0 |
| WHEAT | 0 | 0 | 0 | 3G | 0 | 7G | 2C,8H | 2C,8H | 9G | 0 | 8G | 9G | 3G | 0 | 0 | 0 | 0 | 0 | 0 | 0 |
| CORN | 3G | 0 | 0 | 3C,4G | 0 | 8G | 3G | 3C,9G | 5C,9G | 2C,3G | 8G | 9G | 3C,9G | 0 | 0 | 0 | 0 | 0 | 0 | 0 |
| SOYBEAN | 2G | 0 | 0 | 1C | 0 | 3C,6G | 3C,5G | 3C,7G | 4C,9G | 1C | 3C,8H | 9G | 3C,7H | 0 | 0 | 0 | 0 | 0 | 2C,3G | 0 |
| RICE | 6G | 0 | 0 | 0 | 0 | 3C,7G | 4C,4G | 3C,8G | 4C,8G | 2C | 1C,3G | 4C,8G | 3G | 0 | 0 | 0 | 0 | 0 | 2C | 0 |
| SORGHUM | 3C,6G | 0 | 0 | 2C,3G | 0 | 3C,9H | 3G | 4C,9G | 4C,9G | 1C,2G | 2C,8G | 10H | 3C,9G | 0 | 0 | 0 | 0 | 0 | 2C | 0 |
| CHEATGRASS | 0 | 0 | 0 | 3G | 0 | 3C,9H | 3C,5G | 3C,9G | 3C,9G | 0 | 9G | 5C,9H | 0 | 0 | 0 | 0 | 0 | 0 | 2C | 2C,4G |
| SUGAR BEETS | 0 | 0 | 0 | 4G | 0 | 7G | 5G | 3C,8G | 5C,9G | 1C,2G | 7G | 4C,9H | 4C,9H | 0 | 0 | 0 | 0 | 0 | 0 | 0 |
| VELVETLEAF | 2G | 0 | 0 | 3H | 0 | 8G | 2G | 3C,6G | 9C | 2G | 2G | 9G | 9G | 0 | 0 | 0 | 2G | 0 | 2H | 3H |
| GIANT FOXTAIL | 0 | 0 | 4G | 0 | 0 | 7G | 5G | 2C,5H | 4C,9G | 1C,3G | 8G | 4C,9G | 4C,9G | 0 | 0 | 0 | 0 | 0 | 0 | 0 |
| BARLEY | 2G | 0 | 0 | 3H | 0 | 8G | 9G | 2C,2G | 3C,6G | 2C,3H | 2C,8G | 3C,9G | 2G | 0 | 0 | 0 | 0 | 0 | 0 | 0 |
| DOWNY BROME | 0 | 2G | 0 | 0 | 0 | 6G | 2C,2G | 8G | 3C,8G | 3G | 9G | 9G | 3G | 0 | 0 | 0 | 0 | 0 | 0 | 0 |

POSTEMERGENCE

| | CMPD 22 | | CMPD 23 | | CMPD 24 | | CMPD 25 | | CMPD 26 | | CMPD 27 | | CMPD 28 | | CMPD 29 | | CMPD 30 | | CMPD 31 | |
|---|---|---|---|---|---|---|---|---|---|---|---|---|---|---|---|---|---|---|---|---|---|
| | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 |
| COTTON | 0 | 0 | 0 | 3C,4G | 0 | 0 | 2G | 5C,9G | 3C,5G | 4G | 4G | 3C,6G | 0 | 0 | 0 | 0 | 0 | 0 | 0 | 0 |
| MORNING GLORY | 3C,6G | 3C,8G | 0 | 1H | 0 | 0 | 9C | 10C | 4C,8G | 3C,5G | 3C,5G | 5C,9G | 2C,5G | 3C,8H | 0 | 0 | 0 | 2H | 0 | 3H |
| COCKLEBUR | 3C,8G | 2H | 2H | 3C,8H | 3G | 3G | 10C | 10C | 4C,8G | 4C,8G | 4G | 4C,9G | 3C,8H | 5C,9G | 0 | 0 | 0 | 0 | 0 | 0 |
| NUTSEDGE | 0 | 0 | 0 | 0 | 0 | 0 | 10C | 10C | 7G | 4C,8G | 4G | 5C,9G | 3G | 0 | 0 | 0 | 0 | 0 | 0 | 0 |
| CRABGRASS | 0 | 0 | 0 | 2G | 0 | 0 | 3C,7G | 10C | 0 | 0 | 3G | 5C,9G | 0 | 3G | 0 | 0 | 0 | 0 | 0 | 0 |
| BARNYARD GRASS | 0 | 3G | 0 | 2G | 0 | 0 | 5C,9G | 10C | 4C,8G | 4C,8G | 3C,7H | 5C,9G | 0 | 3C,7H | 0 | 0 | 0 | 0 | 0 | 0 |
| WILD OATS | 0 | 0 | 0 | 2G | 0 | 0 | 5C,9G | 10C | 10C | 5C,9G | 0 | 5 | 0 | 3G | 0 | 0 | 0 | 0 | 0 | 0 |
| WHEAT | 0 | 0 | 0 | 0 | 0 | 0 | 8G | 9C | 5C,9G | 4C,9G | 5G | 9C | 0 | 3C,9G | 0 | 0 | 0 | 0 | 0 | 0 |
| CORN | 0 | 4G | 0 | 3C,4H | 0 | 3G | 9C | 10C | 9C | 5G | 9G | 5G | 0 | 3G | 0 | 0 | 0 | 0 | 0 | 0 |
| SOYBEAN | 0 | 3C,3H | 0 | 4G | 0 | 0 | 5C,9G | 5C,9G | 5C,9G | 5G | 4C,9G | 5G | 1H | 3C,9G | 2G | 9C | 0 | 0 | 0 | 0 |
| RICE | 0 | 3C,4G | 0 | 2G | 0 | 4G | 5C,9G | 5C,9G | 4C,9G | 4C,9G | 4C,9G | 9C | 0 | 8G | 0 | 10C | 0 | 0 | 0 | 0 |
| SORGHUM | 0 | 3C,7G | 0 | 0 | 0 | 0 | 5C,9G | 10C | 5C,9G | 4C,9G | 9C | 5G | 2G | 3C,9G | 0 | 0 | 0 | 0 | 0 | 0 |
| CHEATGRASS | 3C,6G | 6G | 0 | 5C,9G | 3C,8H | 9C | 5C,9G | 9C | 4C,9H | 0 | 7G | 5G | 3G | 2G | 0 | 0 | 0 | 0 | 0 | 0 |
| SUGAR BEETS | 0 | 2H | 0 | 3C,8G | 0 | 5C,9G | 9C | 5C,9G | 0 | 3C,8G | 9C | 9C | 3C,5G | 9C | 2G | 9C | 0 | 0 | 0 | 0 |
| VELVETLEAF | 3C,4G | 7H | 0 | 3G | 0 | 9C | 4C,9G | 9C | 4C,9G | 3C,6G | 9C | 0 | 2G | 4C,9G | 0 | 10C | 0 | 0 | 0 | 0 |
| GIANT FOXTAIL | 0 | 0 | 4G | 0 | 0 | 0 | 3C,9G | 3C,9G | 7G | 0 | 0 | 5G | 3G | 2G | 0 | 5G | 0 | 0 | 0 | 0 |
| BARLEY | 0 | 2G | 0 | 3G | 0 | 0 | 4C,9G | 3C,5G | 7G | 3G | 5G | 7G | 2G | 3G | 0 | 0 | 0 | 0 | 0 | 0 |
| DOWNY BROME | | | | | | | | | | | | | | | | | | | | |

PREEMERGENCE

TABLE A-continued

| | | | | | | | | | | | | | | | | | | | | | | | | |
|---|---|---|---|---|---|---|---|---|---|---|---|---|---|---|---|---|---|---|---|---|---|---|---|---|
| COTTON | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| MORNING GLORY | 0 | 0 | 0 | 0 | 0 | 0 | 0 | 0 | 0 | 0 | 7G | 7G | 0 | 0 | 5G | 5G | 0 | 0 | 0 | 0 | 0 | 0 | 0 | 0 |
| COCKLEBUR | 0 | 0 | 0 | 0 | 0 | 0 | 0 | 0 | 0 | 0 | 6G | 9G | 0 | 0 | 3G | 8G | 0 | 0 | 0 | 0 | 0 | 0 | 0 | 0 |
| NUTSEDGE | 0 | 0 | 0 | 0 | 0 | 0 | 0 | 0 | 0 | 0 | 10E | 3C,8H | 0 | 0 | 1H | 3C,7G | 0 | 0 | 0 | 0 | 0 | 0 | 0 | 0 |
| CRABGRASS | 0 | 0 | 0 | 0 | 0 | 0 | 0 | 0 | 0 | 0 | 3C,6G | 10E | 0 | 0 | 0 | 9G | 0 | 0 | 0 | 0 | 0 | 0 | 0 | 0 |
| BARNYARD GRASS | 0 | 0 | 0 | 0 | 0 | 0 | 0 | 0 | 0 | 0 | 3C,5G | 3C,9G | 2G | 0 | 2G | 3C,7G | 0 | 0 | 0 | 0 | 0 | 0 | 0 | 0 |
| WILD OATS | 0 | 0 | 0 | 0 | 0 | 0 | 0 | 0 | 0 | 0 | 3C,3G | 9H | 3C,7H | 0 | 2C | 7G | 0 | 0 | 0 | 0 | 0 | 0 | 0 | 0 |
| WHEAT | 0 | 0 | 0 | 0 | 0 | 0 | 0 | 0 | 0 | 0 | 2C,6G | 3C,8H | 0 | 0 | 0 | 0 | 0 | 0 | 0 | 0 | 0 | 0 | 0 | 0 |
| CORN | 0 | 0 | 0 | 0 | 0 | 0 | 0 | 0 | 0 | 0 | 3C,7H | 3C,9G | 0 | 0 | 2G | 3C,8G | 0 | 0 | 0 | 0 | 0 | 0 | 0 | 0 |
| SOYBEAN | 0 | 0 | 0 | 0 | 0 | 0 | 0 | 0 | 0 | 0 | 3C,8G | 3C,8H | 0 | 0 | 2G | 3C,6H | 0 | 0 | 0 | 0 | 0 | 0 | 0 | 0 |
| RICE | 0 | 0 | 0 | 0 | 0 | 0 | 0 | 0 | 0 | 0 | 8H | 9H | 0 | 0 | 3G | 9H | 0 | 0 | 0 | 0 | 0 | 0 | 0 | 0 |
| SORGHUM | 0 | 0 | 0 | 0 | 0 | 0 | 0 | 0 | 0 | 0 | 3C,8H | 10H | 3C,8H | 0 | 5G | 3C,9G | 0 | 0 | 0 | 0 | 0 | 0 | 0 | 0 |
| CHEATGRASS | 0 | 0 | 0 | 0 | 0 | 0 | 0 | 0 | 0 | 0 | 8G | 7G | 2H | 0 | 4G | 5G | 0 | 0 | 0 | 0 | 0 | 0 | 0 | 0 |
| SUGAR BEETS | 0 | 0 | 0 | 0 | 0 | 0 | 0 | 0 | 0 | 0 | 6H | 3C,9G | 0 | 0 | 0 | 2C,4H | 0 | 0 | 0 | 0 | 0 | 0 | 0 | 0 |
| VELVETLEAF | 0 | 0 | 0 | 0 | 0 | 0 | 0 | 0 | 0 | 0 | 3C,5G | 3C,9H | 0 | 0 | 0 | 2G | 0 | 0 | 0 | 0 | 0 | 0 | 0 | 0 |
| GIANT FOXTAIL | 0 | 0 | 0 | 0 | 0 | 0 | 0 | 0 | 0 | 0 | 3C,6G | 2C,8G | 0 | 0 | 0 | 2G | 0 | 0 | 0 | 0 | 0 | 0 | 0 | 0 |
| BARLEY | 0 | 0 | 0 | 0 | 0 | 0 | 0 | 0 | 0 | 0 | 8G | 3C,8H | 0 | 0 | 2G | 5G | 0 | 0 | 0 | 0 | 0 | 0 | 0 | 0 |
| DOWNY BROME | 0 | 0 | 0 | 0 | 0 | 0 | 0 | 0 | 0 | 0 | | | | | | | | | | | | | | |

Test B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*) and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*) and giant foxtail (*Setaria faberia*). The third pot was planted with wheat (*Triticum aestivum*), barley (*Hordeum vulgare*), wild buckwheat (*Polgonum convolvulus L.*), cheatgrass (*Bromus secalinus L.*), sugarbeet (*Beta vulgaris*), wild oat (*Avena fatua*), viola (*Viola arvensis*), blackgrass (*Alpercurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheatgrass, sugarbeet, wild oat, viola, blackgrass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 where 0=no effect and 100=complete control. A dash (−) response means no test.

Response ratings are contained in Table B.

TABLE B

PREEMERGENCE

| RATE = G/HA | CMPD 2 | | | | CMPD 3 | | | | | CMPD 9 | | | CMPD 10 | | | CMPD 15 | | | CMPD 16 | | | CMPD 18 | | |
|---|---|---|---|---|---|---|---|---|---|---|---|---|---|---|---|---|---|---|---|---|---|---|---|---|
| | 1. | 4. | 16. | 62. | 250. | 1. | 4. | 16. | 62. | 250. | 0250 | 0062 | 0016 | 0004 | 0016 | 0004 | 0004 | 0016 | 0062 | 0004 | 0016 | 0062 | 0001 | 0004 | 0016 | 0062 |
| GIANT FOXTAIL | — | 0 | 0 | 0.0 | 50 | — | — | 50 | 90 | 100 | 90 | 80 | 0 | 0 | 0 | 0 | | 50 | 80 | | 0 | 30 | | 20 | 80 | 100 |
| VELVETLEAF | — | 20 | 70 | 100.30 | 90 | — | — | 30 | 90 | 90 | 90 | 90 | 80 | 0 | 40 | 0 | 60 | 90 | 100 | 30 | 50 | 70 | 30 | 70 | 100 | 100 |
| SUGAR BEETS | — | 50 | 100 | 100.0 | 50 | — | — | 0 | 70 | 90 | 90 | — | 50 | 0 | 70 | 0 | | 90 | 80 | | 30 | 70 | 20 | 20 | 70 | 80 |
| CRABGRASS | — | 0 | 0 | 30.20 | 40 | — | — | 20 | 50 | 90 | 90 | 0 | 0 | 0 | 0 | 0 | 50 | 70 | 90 | 0 | 30 | 60 | 30 | 60 | 80 | 80 |
| TEAWEED | — | 0 | 40 | 80.20 | 50 | — | — | 0 | 30 | 80 | 100 | 0 | 0 | 0 | 0 | 0 | 50 | 50 | 90 | 0 | 30 | 50 | 50 | 20 | 80 | 80 |
| JIMSONWEED | — | 20 | 70 | 80.0 | 60 | — | — | 0 | 40 | 70 | 80 | 0 | 0 | 0 | 0 | 0 | 30 | 70 | 70 | 30 | 30 | 80 | 40 | 80 | 40 | 100 |
| RICE | — | 20 | 80 | 100.50 | 90 | — | — | 60 | 90 | 100 | 100 | 70 | 50 | 30 | 0 | 30 | 90 | 100 | 90 | 0 | 50 | 60 | 0 | 30 | 30 | 80 |
| COCKLEBUR | — | 0 | 0 | 0.0 | 0 | — | — | 0 | 0 | 20 | 80 | 40 | 40 | 0 | 30 | 0 | 0 | 60 | 70 | 0 | 30 | 80 | 20 | 20 | 50 | 100 |
| COTTON | — | 30 | 40 | 100.0 | 40 | — | — | 0 | 20 | 60 | 60 | 20 | 20 | 20 | 0 | 0 | 30 | 20 | 0 | 0 | 30 | 30 | 0 | 30 | 30 | 80 |
| SOYBEAN | — | 30 | 90 | 100.0 | 0 | — | — | 0 | 50 | 80 | 80 | 50 | 30 | 30 | 20 | 0 | 40 | 30 | 30 | 0 | 0 | 0 | 20 | 20 | 40 | 70 |
| BARNYARD GRASS | — | 0 | 0 | 30.0 | 80 | — | — | 20 | 30 | 60 | 90 | 40 | 20 | 0 | 0 | 0 | 0 | 30 | 100 | 0 | 30 | 60 | 30 | 40 | 100 | 100 |
| WILD OATS | — | 0 | 0 | 0.0 | 50 | | | 0 | 0 | 40 | 50 | 40 | 0 | 0 | 0 | 0 | 0 | 30 | 50 | | 0 | 30 | 20 | 40 | 70 | 90 |
| MORNINGGLORY | — | 0 | 50 | 100.0 | 90 | | | 0 | 0 | 50 | 80 | 50 | 0 | 20 | 0 | 20 | 0 | 30 | 50 | 0 | 0 | 30 | 0 | 0 | 20 | 50 |
| WHEAT | — | 0 | 0 | 0.0 | 50 | | | 0 | 80 | 90 | 30 | 0 | 0 | 30 | 20 | 0 | | 30 | 60 | | 0 | 30 | 20 | 40 | 80 | 90 |
| CASSIA | — | 20 | 80 | 100.50 | 80 | | | 0 | 80 | 90 | | 70 | 30 | 0 | 0 | 0 | 80 | 90 | 100 | | 50 | 100 | | 30 | 70 | 100 |
| JOHNSONGRASS | | | | | | | | 20 | 80 | 90 | 80 | 60 | 0 | 0 | 0 | 0 | 60 | 90 | 100 | 50 | 70 | 80 | 30 | 50 | 70 | 80 |
| NUTSEDGE | | | | | | | | 20 | 70 | 70 | 50 | 20 | 30 | 0 | 20 | 0 | 30 | 50 | 60 | 0 | 0 | 30 | 0 | 0 | 30 | 90 |
| CORN | | | | | | | | 0 | 10 | 30 | | 20 | 0 | 0 | 0 | 0 | | 0 | 60 | | 0 | 30 | 20 | 20 | 100 | 100 |
| WILD BUCKWHEAT | | | | | | | | 0 | 50 | 80 | | 40 | 0 | 0 | 0 | 0 | 50 | 70 | 70 | 30 | 30 | 50 | 70 | 80 | 90 | 100 |
| BLACK GRASS | | | | | | | | 30 | 80 | 90 | 90 | 50 | 0 | 0 | 0 | 0 | 80 | | 70 | | 50 | 70 | 40 | 60 | 80 | 80 |
| RAPESEED | | | | | | | | 0 | 0 | 80 | 80 | 70 | 30 | 0 | 0 | 0 | 50 | 50 | 50 | | 30 | 50 | 30 | 70 | 100 | 100 |
| BARLEY | | | | | | | | | | | | 0 | 0 | 0 | 20 | 0 | 30 | 30 | 30 | | 0 | 30 | 20 | 40 | 70 | 80 |
| GREEN FOXTAIL | | | | | | | | | | | | 70 | 30 | 30 | 0 | 0 | 70 | 70 | 60 | 0 | 30 | 50 | 30 | 50 | 100 | 100 |
| CHEAT GRASS | | | | | | | | | | | | 60 | 0 | 0 | 0 | 0 | 60 | 100 | 100 | | 50 | 70 | 30 | 80 | 100 | 90 |
| BUCKWHEAT | | | | | | | | | | | | 20 | 0 | 20 | 0 | 0 | | 30 | 90 | | 0 | | | 0 | 30 | |
| VIOLA | | | | | | | | | | | | | | | | | | | | | | | | | | |
| LAMBSQUARTER | | | | | | | | | | | 90 | 80 | 0 | 0 | 20 | 0 | 100 | 100 | 100 | 50 | 50 | 90 | 20 | 60 | 70 | 100 |
| CHICK WEED | | | | | | | | | | | 100 | 70 | 60 | 70 | 70 | 0 | | 70 | 80 | | 80 | | 50 | 70 | 90 | 90 |

POSTEMERGENCE

| RATE = G/HA | 1. | 4. | 16. | 62. | 250. | 1. | 4. | 16. | 62. | 250. | 0250 | 0062 | 0016 | 0004 | 0016 | 0004 | 0001 | 0004 | 0016 | 0062 | 0001 | 0004 | 0016 | 0062 | 0001 | 0004 | 0016 | 0062 |
|---|---|---|---|---|---|---|---|---|---|---|---|---|---|---|---|---|---|---|---|---|---|---|---|---|---|---|---|---|
| GIANT FOXTAIL | 0 | 0 | 0 | 0.0 | 50 | — | — | 0 | 40 | — | 100 | 80 | 70 | 50 | 30 | 20 | 20 | 40 | 60 | 90 | 50 | 90 | 100 | 90 | 20 | 30 | 80 | 100 |
| VELVETLEAF | 0 | 0 | 30 | 0.0 | 90 | — | — | 90 | 100 | — | 100 | 100 | 100 | 80 | 70 | 40 | 60 | 80 | 90 | 100 | 90 | 100 | 100 | 100 | 30 | 60 | 100 | 100 |
| SUGAR BEETS | 50 | 30 | 90 | 100.0 | 50 | — | — | 100 | 100 | — | 100 | 100 | 100 | 60 | 80 | 70 | 0 | 70 | 90 | 100 | 50 | 80 | 100 | 80 | 20 | 40 | 70 | 80 |
| CRABGRASS | 0 | 0 | 0 | 0.0 | 40 | — | — | 30 | 90 | — | 90 | 80 | 70 | 40 | 50 | 60 | 20 | 20 | 40 | 60 | 40 | 80 | 80 | 100 | 20 | 40 | 70 | 100 |
| TEAWEED | 50 | 0 | 40 | 30.20 | 50 | — | — | 40 | 70 | — | 100 | 90 | 50 | 20 | 50 | 40 | 0 | 20 | 40 | 80 | 30 | 90 | 100 | 90 | 20 | 40 | 80 | 80 |
| JIMSONWEED | 0 | 0 | 70 | 80.0 | 60 | — | — | 30 | 70 | — | 90 | 70 | 70 | 40 | 90 | 80 | 80 | 30 | 90 | 100 | 40 | 100 | 100 | 90 | 20 | 80 | 80 | 100 |
| RICE | 20 | 50 | 80 | 100.50 | 90 | — | — | 100 | 100 | — | 100 | 100 | 100 | 80 | 90 | 70 | 30 | 60 | 80 | 70 | 90 | 100 | 100 | 100 | 50 | 30 | 100 | 100 |
| COCKLEBUR | 0 | 0 | 20 | 0.0 | 0 | — | — | 20 | 30 | — | 100 | 50 | 70 | 30 | 30 | 50 | 80 | 30 | 90 | 100 | 30 | 80 | 100 | 90 | 0 | 50 | 50 | 100 |
| COTTON | 0 | 20 | 40 | 100.0 | 40 | — | — | 60 | 90 | — | 100 | 70 | 70 | 20 | 50 | 20 | 20 | 0 | 50 | 90 | 30 | 80 | 100 | 100 | 20 | 20 | 80 | 100 |
| SOYBEAN | 30 | 50 | 90 | 100.0 | 0 | — | — | 100 | 100 | — | 80 | 80 | 50 | 60 | 70 | 30 | 50 | 40 | 50 | 90 | 30 | 30 | 40 | 90 | 40 | 50 | 100 | 100 |
| BARNYARD GRASS | 0 | 0 | 0 | 30.0 | 80 | — | — | 30 | 60 | — | 100 | 90 | 100 | 60 | 30 | 50 | 40 | 70 | 90 | 100 | 50 | 80 | 90 | 100 | 60 | 20 | 100 | 100 |
| WILD OATS | 0 | 0 | 0 | 0.0 | 0 | — | — | 0 | 30 | — | 90 | 70 | 40 | 30 | 30 | 0 | 0 | 40 | 0 | 30 | 100 | 100 | 100 | 100 | 0 | 70 | 100 | 100 |
| MORNINGGLORY | 0 | 0 | 50 | 100.0 | 50 | — | — | 60 | 80 | — | 100 | 100 | 90 | 30 | 0 | 30 | 40 | 0 | 60 | 40 | 100 | 60 | 90 | 100 | 50 | 20 | 80 | 90 |
| WHEAT | 0 | 0 | 0 | 0.0 | 0 | — | — | 0 | 0 | — | 60 | 40 | 10 | 0 | 40 | 0 | | 40 | 50 | 90 | 90 | 50 | 90 | 100 | 40 | 80 | 100 | 100 |
| CASSIA | 20 | 20 | 80 | 100.50 | 80 | — | — | 80 | 100 | — | | | | 50 | 70 | 50 | 60 | 50 | 90 | 100 | 85 | 90 | 90 | 100 | 40 | 90 | 100 | 100 |

TABLE B-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| JOHNSONGRASS | 0 | 0 | 40.40 | 80 | 0 | 30 | 80 | 100 | — | 100 | 80 | 50 | 30 | 60 | 50 | 20 | 50 | 85 | 100 | 100 | 30 | 60 | 90 | 100 | 30 | 90 | 100 |
| NUTSEDGE | 0 | 0 | 20.20 | 50 | 0 | 0 | 40 | 100 | — | 100 | 80 | 60 | 30 | 0 | 0 | 0 | 40 | 90 | 100 | 100 | 0 | 0 | 20 | 40 | 20 | 100 | 100 |
| CORN | 50 | 100 | 100.0 | 30 | 30 | 90 | 100 | 100 | — | 100 | 90 | 80 | 60 | 80 | 60 | 20 | 80 | 90 | 100 | 100 | 90 | 100 | 100 | 100 | 80 | 90 | 100 |
| WILD | — | — | — | — | — | — | — | — | — | 90 | 90 | 70 | 60 | — | — | — | 30 | 50 | 90 | 100 | 30 | 80 | 100 | 100 | 30 | 40 | 100 |
| BUCKWHEAT | | | | | | | | | | | | | | | | | | | | | | | | | | | |
| BLACK GRASS | 0 | 0 | 0.50 | 80 | 0 | 0 | 0 | 80 | — | 70 | 60 | 40 | 40 | 30 | 0 | 0 | 40 | 90 | 100 | 100 | 40 | 70 | 100 | 100 | | 60 | 100 |
| RAPESEED | 50 | 90 | 100.0 | 80 | 50 | 70 | 100 | 100 | — | 100 | 100 | 100 | 100 | 100 | 100 | 70 | 60 | 100 | 100 | 100 | 60 | 100 | 100 | 100 | | 100 | 100 |
| BARLEY | — | — | — | — | — | — | — | — | — | 70 | 60 | 10 | 0 | 10 | 0 | 0 | 50 | 60 | 80 | 90 | 60 | 90 | 80 | 100 | 40 | 80 | 90 |
| GREEN FOXTAIL | — | — | — | — | — | — | — | — | — | 100 | 80 | 80 | 70 | 90 | 80 | 40 | 40 | 60 | 80 | 90 | 0 | 40 | 100 | 100 | 30 | 50 | 90 |
| CHEAT GRASS | — | — | — | — | — | — | — | — | — | 90 | 80 | 70 | 60 | 60 | 50 | 40 | 30 | 50 | 90 | 100 | 0 | 40 | 80 | 100 | 50 | 70 | 100 |
| BUCKWHEAT | | | | | | | | | | | | | | | | | | | | | | | | | | | |
| VIOLA | — | — | — | — | — | — | — | — | — | 100 | — | — | 0 | — | — | 70 | 40 | | 100 | 100 | 0 | 50 | 70 | 90 | 30 | 60 | 100 |
| LAMBSQUARTER | — | — | — | — | — | — | — | — | — | 100 | 100 | 100 | 100 | 100 | 90 | 80 | 0 | 30 | 80 | 100 | 30 | 70 | 90 | 100 | | 50 | 80 |
| CHICK WEED | — | — | — | — | — | — | — | — | — | | | | | | | | | | | | | | | | | | 70 |

What is claimed is:
1. A compound of the formula:

$$JSO_2NHCNRA \overset{W}{\underset{\|}{}}$$

wherein
J is

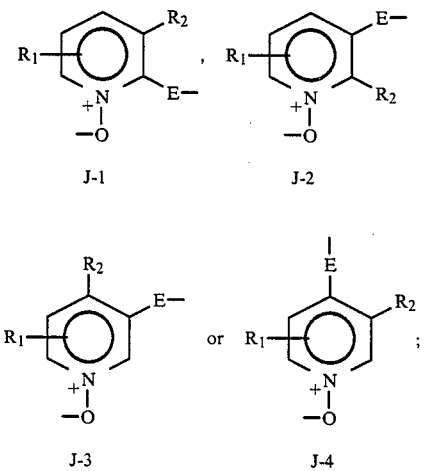

wherein
R is H or $CH_3$;
E is a single bond or $CH_2$;
W is O, S or $NR_x$;
$R_x$ is H, $C_1$-$C_3$ alkyl or $C_1$-$C_3$ alkoxy;
$R_1$ is H, F, Cl, Br, $C_1$-$C_3$ alkyl, $C_1$-$C_3$ haloalkyl, $C_1$-$C_3$ alkoxy, $C_1$-$C_3$ haloalkoxy or $C_1$-$C_3$ thioalkyl;
$R_2$ is H, Cl, Br, F, $C_1$-$C_4$ alkyl, $C_1$-$C_4$ haloalkyl, cyclopropyl optionally substituted by 1-4 halogen, cyclobutyl optionally substituted by 1-4 halogen, $C_2$-$C_4$ alkenyl optionally substituted by halogen, $C_2$-$C_4$ alkynyl optionally substituted by halogen, $C_1$-$C_4$ alkoxy, $C_1$-$C_4$ haloalkoxy, $C_3$-$C_4$ alkenyloxy, $C_3$-$C_4$ alkynyloxy, $NO_2$, $CO_2R_3$, $NR_4R_5$, $S(O)_nR_6$, $SO_2NR_7R_8$, $C(O)NR_9R_{10}$,

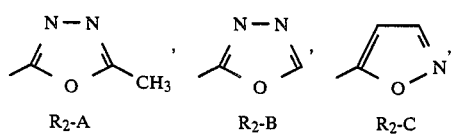
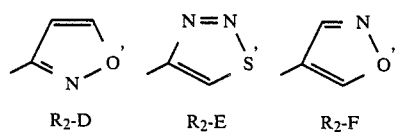
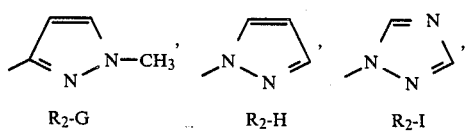
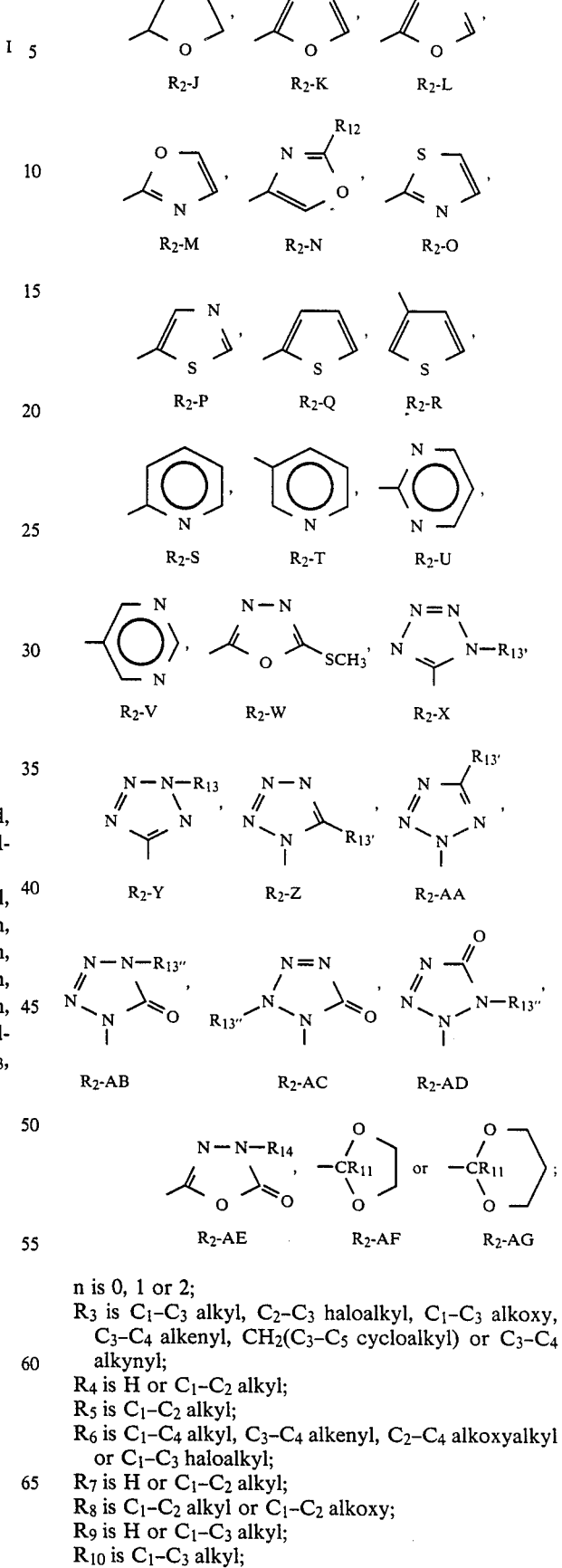

n is 0, 1 or 2;
$R_3$ is $C_1$-$C_3$ alkyl, $C_2$-$C_3$ haloalkyl, $C_1$-$C_3$ alkoxy, $C_3$-$C_4$ alkenyl, $CH_2(C_3$-$C_5$ cycloalkyl) or $C_3$-$C_4$ alkynyl;
$R_4$ is H or $C_1$-$C_2$ alkyl;
$R_5$ is $C_1$-$C_2$ alkyl;
$R_6$ is $C_1$-$C_4$ alkyl, $C_3$-$C_4$ alkenyl, $C_2$-$C_4$ alkoxyalkyl or $C_1$-$C_3$ haloalkyl;
$R_7$ is H or $C_1$-$C_2$ alkyl;
$R_8$ is $C_1$-$C_2$ alkyl or $C_1$-$C_2$ alkoxy;
$R_9$ is H or $C_1$-$C_3$ alkyl;
$R_{10}$ is $C_1$-$C_3$ alkyl;

$R_{11}$ is H or $CH_3$;
$R_{12}$ is H or $CH_3$;
$R_{13}$ is H, $C_1$–$C_3$ alkyl, allyl, $C_1$–$C_3$ haloalkyl or $C_1$–$C_3$ alkyl substituted with $C_1$–$C_2$ alkoxy;
$R_{13}'$ is H, $C_1$–$C_3$ alkyl, $C_1$–$C_3$ haloalkyl, allyl, $C_1$–$C_2$ alkoxy, $C_1$–$C_2$ haloalkoxy or $C_1$–$C_2$ alkylthio;
$R_{13}''$ is H, $C_1$–$C_3$ alkyl, allyl or $C_1$–$C_3$ haloalkyl;
$R_{14}$ is $C_1$–$C_3$ alkyl, $CH_2OCH_3$ or $CH_2CN$;

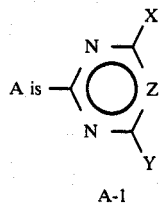

A-1

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

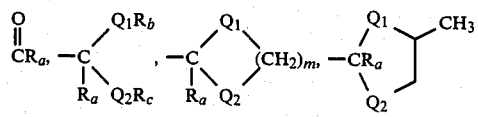

or
$N(OCH_3)CH_3$;
m is 2 or 3;
$Q_1$ and $Q_2$ are independently O or S;
$R_a$ is H or $C_1$–$C_3$ alkyl;
$R_b$ and $R_c$ are independently $C_1$–$C_3$ alkyl; and
Z is CH, $CCH_3$, $CC_2H_5$, CCl or CBr;
and their agriculturally suitable salts; provided that
(1) when X is halogen, then Z is CH and Y is $OCH_3$, $OC_2H_5$, $NH_2$, $NHCH_3$, $N(CH_3)_2$, $OCF_2H$, $OCF_2Br$ or $N(OCH_3)CH_3$;
(2) when W is S, then R is H, E is a single bond, Z is CH and Y is $CH_3$, $OCH_3$, $OC_2H_5$, $CHHd 2OCH_3$, $C_2H_5$, $CF_3$, $SCH_3$, $OCH_2CH=CH_2$, $OCH_2\equiv CH$, $OCH_2CH_2OCH_3$, $CH(OCH_3)_2$ or

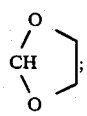

nd
(3) when the total number of carbon atoms of X and Y is greater than four, then the combined number of carbons of $R_1$ and $R_2$ is less than or equal to six and
(4) when X or Y is $C_1$ haloalkoxy, then Z is CH.
2. A compound of claim 1 where X is $C_1$–$C_2$ alkyl, $C_1$–$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $C(O)R_a$,

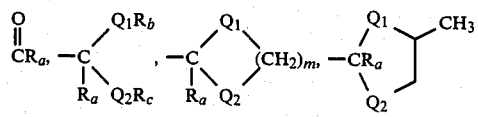

$OCF_2H$, $SCF_2H$, $OCF_2Br$, cyclopropyl, $C\equiv CH$ or $C\equiv CCH_3$;

Z is CH; and
$R_a$ is H or $CH_3$.
3. A compound of claim 2 where
E is a single bond;
W is O; and
$R_1$ is H, F, Cl, Br, $CH_3$, $C_1$ haloalkyl or $OCH_3$.
4. A compound of claim 2 where
E is $CH_2$;
W is O; and
$R_1$ is H, F, Cl, Br, $CH_3$ or $OCH_3$.
5. A compound of claim 3 where
$R_2$ is H, Cl, Br, F, $C_1$–$C_2$ alkyl, $C_1$–$C_2$ haloalkyl, cyclopropyl, $C_1$–$C_2$ alkoxy, $C_1$–$C_2$ haloalkoxy, $CF=CFCl$, $CF=CFCF_3$, $NO_2$, $CO_2R_3$, $NR_4R_5$, $S(O)_nR_6$, $SO_2NR_7R_8$, $SO_2N(OCH_3)CH_3$, $C(O)NR_9R_{10}$, $R_2$-A, $R_2$-B, $R_2$-E, $R_2$-J, $R_2$-N, $R_2$-Q, $R_2$-R, $R_2$-X, $R_2$-Y, $R_2$-AB, $R_2$-AC or $R_2$-AD;
$R_3$ is $CH_3$, $CH_2CH_3$, $CH_2CH_2OCH_3$ or $CH_2CH_2Cl$;
$R_4$ is H or $CH_3$;
$R_6$ is $C_1$–$C_3$ alkyl, $C_1$–$C_3$ haloalkyl or allyl;
$R_7$ is H or $CH_3$;
$R_8$ is $C_1$–$C_2$ alkyl
$R_9$ is H or $CH_3$;
$R_{10}$ is $CH_3$ or $CH_2CH_3$;
$R_{13}$ is H, $CH_3$, $CH_2CH_3$ or $CH_2CH_2OCH_3$; and
$R_{13}''$ is H, $CH_3$ or $CH_2CH_3$.
6. A compound of claim 5 where
X is $CH_3$, $OCH_3$, $OCH_2CH_3$, Cl, $OCF_2H$ or $OCH_2CF_3$;
Y is $CH_3$, $OCH_3$, $CH_2CH_3$, $CH_2OCH_3$, $NHCH_3$ or $CH(OCH_3)_2$.
7. A compound of claim 6 where J is J-1.
8. A compound of claim 6 where J is J-2.
9. A compound of claim 6 where J is J-3.
10. A compound of claim 6 where J is J-4.
11. The compound of claim 1 which is N-[(4,6-dimethoxypyrimidin-2-yl)aminocarbonyl]-3-methyl-2-pyridinesulfonamide-1-oxide.
12. A composition suitable for controlling the growth of undesired vegetation which comprises an effective amount of the compound of claim 1 and at least one of the following: surfactant, solid or liquid diluent.
13. A composition suitable for controlling the growth of undesired vegetation which comprises an effective amount of the compound of claim 2 and at least one of the following: surfactant, solid or liquid diluent.
14. A composition suitable for controlling the growth of undesired vegetation which comprises an effective amount of the compound of claim 3 and at least one of the following: surfactant, solid or liquid diluent.
15. A composition suitable for controlling the growth of undesired vegetation which comprises an effective amount of the compound of claim 4 and at least one of the following: surfactant, solid or liquid diluent.

16. A composition suitable for controlling the growth of undesired vegetation which comprises an effective amount of the compound of claim 5 and at least one of the following: surfactant, solid or liquid diluent.

17. A composition suitable for controlling the growth of undesired vegetation which comprises an effective amount of the compound of claim 6 and at least one of the following: surfactant, solid or liquid diluent.

18. A composition suitable for controlling the growth of undesired vegetation which comprises an effective amount of the compound of claim 11 and at least one of the following: surfactant, solid or liquid diluent.

19. A method for controlling the growth of undesired vegetation which comprises applying to the locus to be protected an effective amount of the compound of claim 1.

20. A method for controlling the growth of undesired vegetation which comprises applying to the locus to be protected an effective amount of the compound of claim 2.

21. A method for controlling the growth of undesired vegetation which comprises applying to the locus to be protected an effective amount of the compound of claim 3.

22. A method for controlling the growth of undesired vegetation which comprises applying to the locus to be protected an effective amount of the compound of claim 4.

23. A method for controlling the growth of undesired vegetation which comprises applying to the locus to be protected an effective amount of the compound of claim 5.

24. A method for controlling the growth of undesired vegetation which comprises applying to the locus to be protected an effective amount of the compound of claim 6.

25. A method for controlling the growth of undesired vegetation which comprises applying to the locus to be protected an effective amount of the compound of claim 11.

* * * * *